(12) United States Patent
Suzuki et al.

(10) Patent No.: US 9,745,274 B2
(45) Date of Patent: Aug. 29, 2017

(54) COMPOUND, ORGANIC CATION TRANSPORTER 3 DETECTION AGENT, AND ORGANIC CATION TRANSPORTER 3 ACTIVITY INHIBITOR

(71) Applicant: SHIN NIPPON BIOMEDICAL LABORATORIES, LTD., Kagoshima-shi, Kagoshima (JP)

(72) Inventors: Nobuyuki Suzuki, Kagoshima (JP); Hidetoshi Yamashita, Kagoshima (JP)

(73) Assignee: SHIN NIPPON BIOMEDICAL LABORATORIES, LTD., Kagoshima (JP)

(*) Notice: Subject to any disclaimer, the term of this patent is extended or adjusted under 35 U.S.C. 154(b) by 0 days.

(21) Appl. No.: 14/902,005

(22) PCT Filed: Jun. 30, 2014

(86) PCT No.: PCT/JP2014/067441
§ 371 (c)(1),
(2) Date: Dec. 30, 2015

(87) PCT Pub. No.: WO2015/002150
PCT Pub. Date: Jan. 8, 2015

(65) Prior Publication Data
US 2016/0318886 A1 Nov. 3, 2016

(30) Foreign Application Priority Data

Jul. 3, 2013 (JP) .................. 2013-139807

(51) Int. Cl.
| | | |
|---|---|---|
| C07D 213/74 | (2006.01) | |
| C07D 213/75 | (2006.01) | |
| C07D 401/12 | (2006.01) | |
| C07D 403/12 | (2006.01) | |
| C07C 279/16 | (2006.01) | |
| C07C 279/18 | (2006.01) | |
| C07D 277/48 | (2006.01) | |
| C07D 417/06 | (2006.01) | |
| C07C 323/60 | (2006.01) | |
| C07D 417/12 | (2006.01) | |
| C07D 417/14 | (2006.01) | |
| C07D 277/26 | (2006.01) | |
| C07D 207/42 | (2006.01) | |
| C07D 277/36 | (2006.01) | |
| C07D 277/42 | (2006.01) | |
| C07D 307/71 | (2006.01) | |
| C07C 317/28 | (2006.01) | |
| C07D 307/72 | (2006.01) | |

(52) U.S. Cl.
CPC .......... *C07D 277/48* (2013.01); *C07C 317/28* (2013.01); *C07C 323/60* (2013.01); *C07D 207/42* (2013.01); *C07D 213/74* (2013.01); *C07D 213/75* (2013.01); *C07D 277/26* (2013.01); *C07D 277/36* (2013.01); *C07D 277/42* (2013.01); *C07D 307/71* (2013.01); *C07D 307/72* (2013.01); *C07D 401/12* (2013.01); *C07D 403/12* (2013.01); *C07D 417/06* (2013.01); *C07D 417/12* (2013.01); *C07D 417/14* (2013.01)

(58) Field of Classification Search
CPC .. C07D 213/74; C07D 213/75; C07D 401/12; C07D 403/12; C07C 279/16; C07C 279/18
See application file for complete search history.

(56) References Cited

U.S. PATENT DOCUMENTS

| 6,403,645 B2 | 6/2002 | Schildkraut et al. |
| 2007/0136828 A1 | 6/2007 | Kitaichi |

FOREIGN PATENT DOCUMENTS

| EP | 0869120 A1 | 3/1998 |
|---|---|---|
| EP | WO 98/42690 A1 | 10/1998 |
| JP | 53-147069 A | 12/1978 |
| JP | 55-118476 A | 9/1980 |
| JP | 57-54177 A | 3/1982 |
| JP | 57-167969 A | 10/1982 |
| JP | 58-140088 A | 8/1983 |
| JP | 1990288860 A | 11/1990 |
| JP | 1991157308 A | 7/1991 |
| JP | 1991291267 A | 12/1991 |
| JP | 1993009173 A | 1/1993 |
| JP | 1997067342 A | 3/1997 |
| JP | 1997095477 A | 4/1997 |
| JP | 1997278767 A | 10/1997 |
| JP | 1998120666 A | 5/1998 |
| JP | 1998158233 A | 6/1998 |
| JP | 1998237073 A | 9/1998 |
| JP | 2000281665 A | 10/2000 |
| JP | WO 01/93868 A1 | 12/2001 |

(Continued)

OTHER PUBLICATIONS

Extended European Search Report of European patent application No. 14819450.9 dated Oct. 28, 2016 (6 pages).

(Continued)

*Primary Examiner* — Kendra D Carter
(74) *Attorney, Agent, or Firm* — Pyprus Pte Ltd

(57) ABSTRACT

[Problem] The present invention addresses the problem of providing a novel compound. The present invention also addresses the problem of providing an OCT3 detection agent or an OCT3 activity inhibitor, which comprises the novel compound.

[Solution] A compound represented by formula (A), a pharmaceutically acceptable salt thereof, or a pharmaceutically acceptable solvate thereof.

$$R^1\text{-}R^2\text{-}R^3\text{-}R^4 \qquad (A)$$

2 Claims, No Drawings

(56) References Cited

FOREIGN PATENT DOCUMENTS

| JP | 2004285073 A | 10/2004 |
|---|---|---|
| JP | 2005029479 A | 2/2005 |
| JP | WO2005/084707 A1 | 9/2005 |
| JP | 2008507571 A | 3/2006 |
| JP | 2007504176 A | 3/2007 |
| JP | 2007523113 A | 8/2007 |
| JP | 2009050352 A | 3/2009 |
| JP | 2011513477 A | 4/2011 |
| WO | WO 2009/134877 A1 | 5/2009 |

OTHER PUBLICATIONS

International Search Report of International Application No. PCT/JP2014/067441 completed Aug. 12, 2014 and mailed Aug. 19, 2014 (6 pages).

Bourdet. D. L. et al, "Differential Substrate and Inhibitory Activities of Ranitidine and Famotidine toward Human Organic Cation Transporter 1 (hOCT1; SLC22A1), hOCT2 (SLC22A2), and hOCT3 (SLC22A3)", The Journal of Pharmacology and Experimental Therapeutics, 2005, vol. 315, No. 3, p. 1288-1297.

Nies et al, "Organic Cation Transporters (OCTs, MATEs), In Vitro and In Vivo Evidence for the Importance in Drug Therapy".

Sata et al, "Functional Analysis of Organic Cation Transporter 3 Expressed in Human Placenta".

COMPOUND, ORGANIC CATION TRANSPORTER 3 DETECTION AGENT, AND ORGANIC CATION TRANSPORTER 3 ACTIVITY INHIBITOR

TECHNICAL FIELD

This invention relates to a novel compound, an organic cation transporter 3 detection agent, and organic cation transporter 3 activity inhibitor.

BACKGROUND ART

Various kinds of medicine are used in medication. Some of them turn to be positive ions (cations) in vivo condition. Nowadays, the study on the transporter (transiport protain) that exist in cell membrane and contribute to transitivity into tissue, absorption, renal excretion, and biliary excretion is rapidly in progress. Among the transporters, an organic cation transporter (OCT) is important to transport cationic medicine.

Recent research has make it clear that OCT3 exist in the kidney, small intestine, lung, heart, and brain as well as placenta.

Nucleoside analogues, quinolines, tricyclic compound is reported as OCT3 inhibitor, but these are difficult to use as medicine because of the problem such as side effect. Guanidine derivative is reported as OCT3 inhibitor (nonpatent literature 1). However, IC50 of famotidine and cimetidine (Histamine H2-receptor antagonist) is 20 μM and 240 μM respectively and IC50 of Ramosetron and granisetron (setron compound) are both less than 100 μM.

Guanidine derivative and its production method is disclosed, for example, in the following literature: JP H2-288860, JP H3-157308, JP H3-291267, JP H5-9173, JP H9-67342, JP H9-67342, JP H9-95477, JP H9-278767, JP H10-120666, JP H10-158233, JP H10-237073, JP 2004-285073, JP 2005-29479, JP 2007-504176, JP 2007-523113, JP 2008-507571, JP 2009-530352, JP 2011-513477, JP 2000-281665, WO 9842690, and EP-A0869120. As disclosed in these literature, Guanidine is already known as active components for the insecticide, cosmetics, medicine, and drug carrier, etc.

On the other hand, WO 2005-084707 (Patent Literature21) discloses the remedy of mental disorder containing an suppressant of organic cation transporter OCT3 gene expression as an active ingredient. US 2007-0136828 (Patent Literature 22) discloses the remedy of depression by inhibiting OCT3 function, containing alkylamine-catechol derivative, quinoline derivative, and bis-quinoline derivative as active ingredients.
WO 2001-93863 pamphlet (Patent Literature 24) discloses the treatent of depression and depressive symptom consisting famotidine as an active ingredient. U.S. Pat. No. 6,403,645 (Patent Literature 25) discloses the remedy of depression consisting transporter Uptake2 (OCT and PMAT).

According to these literature, the treatment of depression and depressive symptom by inhibiting an organic cation transporter OCT3 is established.

CITATION LIST

Patent Literatures

Patent Literature1: JP H2-288860
Patent Literature2: JP H3-157308
Patent Literature3: JP H3-291267
Patent Literature4: JP H5-9173
Patent Literature5: JP H9-67342
Patent Literature6: JP H9-95477
Patent Literature7: JP H9-278767
Patent Literature8: JP H10-120666
Patent Literature9: JP H10-158233
Patent Literature10: JP H10-237073
Patent Literature11: JP 2000-281665
Patent Literature12: JP 2004-285073
Patent Literature13: JP 2005-29479
Patent Literature14: JP 2007-504176
Patent Literature15: JP 2007-523113
Patent Literature16: JP 2008-507571
Patent Literature17: JP 2009-530352
Patent Literature18: JP 2011-513477
Patent Literature19: WO 9842690
Patent Literature20: EP-A0869120
Patent Literature21: WO 2005-084707
Patent Literature22: US 2007-0136828
Patent Literature23: WO 2009-134877
Patent Literature24: WO 2001-93863
Patent Literature25: U.S. Pat. No. 6,403,645

Non-Patent Literature

Non-Patent Literature1: Nies, 2011, Handb Exp Pharmacol., v 201, p 105-167
Non-Patent Literature2: Sata, 2005, J Pharmacol Exp Ther., v 315, p 888-895

As mentioned above, guanidine derivatives are known. However, further novel compounds are demanded.

Thus, an object of the present invention is to provide a novel compound.

In addition, organic cation transporters (OCT) are known to be involved in various diseases, and compounds that bind to OCT3 and compounds that inhibit the activity of OCT3 have been demanded.

Another object of the present invention is to provide an OCT3 detector or activity inhibitor using a guanidine compound.

Solution to Problem

The present invention is basically based on the production of a novel compound. The present invention is also based on the finding that the novel compound inhibits OCT3 activity, for example.

A first aspect of the present invention relates to a compound represented by the following formula (A), a pharmaceutically acceptable salt thereof, or a pharmaceutically acceptable solvate thereof.

$$R^1\text{-}R^2\text{-}R^3\text{-}R^4 \quad (A)$$

(In formula (A), $R^1$ represents a hydrogen atom, a halogen atom, an amino group, a nitro group, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, a group represented by $R^{11}(R^{12})N-$, or a group represented by $R^{13}R^{14}N(R^{15}R^{16}N)C=N-$.

$R^{11}$, $R^{12}$, $R^{13}$, $R^{14}$, $R^{15}$, and $R^{16}$ may be the same or different and represent a hydrogen atom, a halogen atom, a nitro group, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, or an imidazolidine wherein adjacent $R^{13}$ and $R^{15}$, a nitrogen atom, and a carbon atom are joined together to form a ring.

—R² — represents a group represented by one of the following —R²¹— to —R²⁸—.

[Chemical Formula 1]

R²¹:
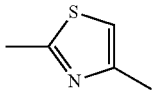

R²²:
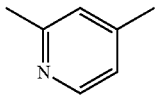

R²³:
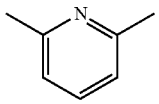

R²⁴:
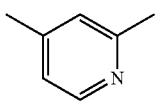

R²⁵:
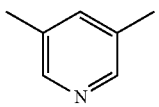

R²⁶:
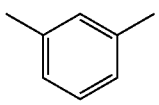

R²⁷:
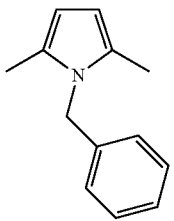

R²⁸:
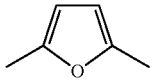

—R³— represents a group represented by —R³¹—, —R³²-R³³—, —R³⁴-R³⁵—, or —R³⁶-R³⁷-R³⁸—.

Further, R³¹ represents a $C_{1-5}$ alkyl group,

R³² represents an oxygen atom (—O—), a sulfur atom (—S—), or —NH—,

R³³ represents a $C_{1-5}$ alkyl group,

R³⁴ represents a $C_{1-5}$ alkyl group,

R³⁵ represents an oxygen atom (—O—), a sulfur atom (—S—), or —NH—,

R³⁶ represents a $C_{1-5}$ alkyl group,

R³⁷ represents an oxygen atom (—O—), a sulfur atom (—S—), or —NH—, and

R³⁸ represents a $C_{1-5}$ alkyl group.

—R⁴ represents
a hydrogen atom,
a halogen atom,
a cyano group,
a $C_{1-3}$ alkoxy group,
a group represented by —N₃,
a group represented by —R⁴¹-R⁴²,
a group represented by —C(NH₂)=NR⁴³,
a group represented by —NHC(NH(R⁴⁶))=R⁴⁴R⁴⁵,
a group represented by —C(=O)NHR⁴⁷,
a group represented by —NHR⁴⁸, or
a group represented by —C(OCH₃)=R⁴⁹.

—R⁴¹— represents a group represented by one of the following —R⁴¹¹— to —R⁴¹³—.

[Chemical Formula 2]

R⁴¹¹
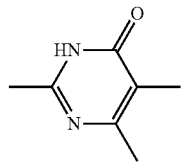

R⁴¹²
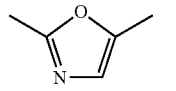

R⁴¹³

R⁴² represents a hydrogen atom, a halogen atom, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, or a $C_{7-10}$ aralkyl group.

Further, R⁴³ represents a hydrogen atom or —SO₂-R⁴³¹.

R⁴³¹ represents an amino group, a $C_{1-3}$ halogenoalkyl group, or a $C_{6-10}$ aryl group.

R⁴⁴ represents a carbon atom or a nitrogen atom.

R⁴⁵ represents a hydrogen atom, a cyano group, or a nitro group.

R⁴⁶ represents a hydrogen atom or a $C_{1-5}$ alkyl group.

R⁴⁷ represents a $C_{1-5}$ alkyl group or —CO—R⁴⁷¹.

R⁴⁷¹ represents a $C_{1-6}$ alkyl group or a $C_{6-10}$ aryl group.

R⁴⁸ represents a hydrogen atom, a $C_{1-5}$ alkyl group, or —CO—CH₂—O—R⁴⁸¹.

R⁴⁵¹ represents a hydrogen atom or —CO—CH₃.

R⁴⁹ represents an oxygen atom or =NH.

However, the following compounds are excluded: compounds wherein

R¹ is formula R¹¹ (H)N(H₂N)C=N—, wherein
R¹¹ is a hydrogen atom or a $C_{1-5}$ alkyl group,
R² is R²¹,
R³ is
—CH₂—S—CH₂—CH₂—,
—CH₂—O—CH₂—CH₂—,
—O—CH₂—CH₂—CH₂—,
—S—CH₂—CH₂—CH₂—,
—CH₂—O—CH₂, or
—CH₂—S—CH₂, and
—R⁴ is
R⁴¹-R⁴², wherein R⁴¹-R⁴² is formula R⁵,
R⁴³, wherein R⁴³ is a hydrogen atom, —SO₂—CF₃, or —SO₂—NH₂, or
R⁴⁷, wherein R⁴⁷ is a methyl group; and compounds wherein
$R^1$ is formula $H_2N(H_2N)C=N—$,
$R^2$ is $R^{21}$,
$R^3$ is
—$CH_2$—S—$CH_2$—$CH_2$— or
—$CH_2$—$CH_2$—$CH_2$—$CH_2$—, and
$R^4$ is
—$R^{48}$, wherein $R^{48}$ is —CO—$CH_2$—O—$R^{481}$, wherein $R^{481}$ is a hydrogen atom.
Formula $R^5$ is

[Chemical Formula 3]

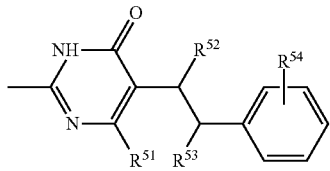

In formula $R^5$, $R^{51}$, $R^{52}$, and $R^{53}$ may be the same or different and represent a hydrogen atom, a methyl group, an ethyl group, or a halogen atom. $R^{54}$ represents a hydrogen atom or a substituent on the phenyl group selected from a methyl group, an ethyl group, a methoxy group, and a halogen atom.

In a preferred mode of the first aspect of the present invention,
$R^1$ represents a group represented by $R^{13}R^{14}N(R^{15}R^{16}N)C=N—$,
—$R^2$— represents a group represented by one of —$R^{21}$— to —$R^{23}$—,
—$R^3$— represents a group represented by —$R^{31}$— or —$R^{36}$-$R^{37}$-$R^{38}$—, and
—$R^4$ represents
a group represented by —$R^{41}$-$R^{42}$,
a group represented by —$C(NH_2)=NR^{43}$,
a group represented by —$NHC(NH(R^{46}))=R^{44}R^{45}$, or
a group represented by —$NHR^{48}$.

In a preferred mode of the first aspect of the present invention,
$R^1$ represents a group represented by $(H_2N)_2C=N—$,
—$R^2$— represents a group represented by one of —$R^{21}$— to —$R^{23}$—,
—$R^3$— represents
a group represented by —$R^{31}$— or —$R^{36}$-$R^{37}$-$R^{38}$—, wherein
—$R^{31}$— represents a butylene group,
—$R^{36}$— represents a methylene group,
—$R^{37}$— represents —O— or —S—, and
—$R^{38}$— represents an ethylene group, and
—$R^4$ represents
a group represented by —$R^{41}$-$R^{42}$,
a group represented by —$C(NH_2)=NR^{43}$,
a group represented by —$NHC(NH(R^{46}))=R^{44}R^{45}$, or
a group represented by —$NHR^{48}$, wherein
—$R^{41}$— represents a group represented by —$R^{411}$—,
—$R^{42}$— represents a $C_{7-10}$ aralkyl group,
$R^{43}$ represents —$SO_2$-$R^{431}$, wherein
$R^{431}$ represents an amino group or a $C_{1-3}$ halogenoalkyl group,
$R^{44}$ represents a nitrogen atom (N),
$R^{45}$ represents a cyano group (CN), and
$R^{46}$ represents a hydrogen atom (H).

In a preferred mode of the first aspect of the present invention,
—$R^2$— represents a group represented by —$R^{21}$—,
—$R^3$— represents a butylene group, and
—$R^4$ represents
a group represented by —$R^{41}$-$R^{42}$,
a group represented by —$C(NH_2)=NR^{43}$,
a group represented by —$NHC(NH(R^{46}))=R^{44}R^{45}$, or
a group represented by —$NHR^{48}$, wherein
—$R^{41}$— represents a group represented by —$R^{411}$—,
—$R^{42}$— represents a $C_{7-10}$ aralkyl group,
$R^{43}$ represents —$SO_2$-$R^{431}$, wherein
$R^{431}$ represents an amino group or a trifluoromethyl group,
$R^{44}$ represents a nitrogen atom,
$R^{45}$ represents a cyano group,
$R^{46}$ represents a hydrogen atom, and
$R^{48}$ represents —CO—$CH_2$—O—$R^{481}$, wherein
$R^{481}$ represents a hydrogen atom.

In a preferred mode of the first aspect of the present invention,
—$R^2$— represents a group represented by —$R^{21}$—,
—$R^3$— represents a group represented by —$R^{36}$-$R^{37}$-$R^{38}$—, wherein
—$R^{31}$— represents a butylene group,
—$R^{36}$— represents a methylene group,
—$R^{37}$— represents —O—, and
—$R^{38}$— represents an ethylene group, and
—$R^4$ represents
a group represented by —$R^{41}$-$R^{42}$,
a group represented by —$C(NH_2)=NR^{43}$,
a group represented by —$NHC(NH(R^{46}))=R^{44}R^{45}$, or
a group represented by —$NHR^{48}$, wherein
—$R^{41}$— represents a group represented by —$R^{411}$—,
—$R^{42}$— represents a $C_{7-10}$ aralkyl group,
$R^{43}$ represents —$SO_2$-$R^{431}$, wherein
$R^{431}$ represents an amino group or a trifluoromethyl group,
$R^{44}$ represents a nitrogen atom,
$R^{45}$ represents a cyano group,
$R^{46}$ represents a hydrogen atom, and
$R^{48}$ represents —CO—$CH_2$—O—$R^{481}$, wherein
$R^{481}$ represents a hydrogen atom.

In a preferred mode of the first aspect of the present invention,
—$R^2$— represents a group represented by —$R^{22}$—,
—$R^3$— represents
a group represented by —$R^{36}$-$R^{37}$-$R^{38}$—, wherein
—$R^{36}$— represents a methylene group,
—$R^{37}$— represents —O— or —S—, and
—$R^{38}$— represents an ethylene group, and
—$R^4$ represents
a group represented by —$R^{41}$-$R^{42}$,
a group represented by —$C(NH_2)=NR^{43}$,
a group represented by —$NHC(NH(R^{46}))=R^{44}R^{45}$, or
a group represented by —$NHR^{48}$, wherein
—$R^{41}$— represents a group represented by —$R^{411}$—,
—$R^{42}$— represents a $C_{7-10}$ aralkyl group,
$R^{43}$ represents —$SO_2$-$R^{431}$, wherein
$R^{431}$ represents an amino group or a trifluoromethyl group,
$R^{44}$ represents a nitrogen atom,
$R^{45}$ represents a cyano group,
$R^{46}$ represents a hydrogen atom, and
$R^{48}$ represents —CO—$CH_2$—O—$R^{481}$, wherein
$R^{481}$ represents a hydrogen atom.

In a preferred mode of the first aspect of the present invention,

—$R^2$— represents a group represented by —$R^{23}$—,

—$R^3$— represents a group represented by —$R^{36}$-$R^{37}$-$R^{38}$—, wherein

—$R^{36}$— represents a methylene group,

—$R^{37}$— represents —O— or —S—, and

—$R^{38}$— represents an ethylene group, and

—$R^4$ represents a group represented by —$R^{41}$-$R^{42}$, a group represented by —C(NH$_2$)=NR$^{43}$, a group represented by —NHC(NH(R$^{46}$))=R$^{44}$R$^{45}$, or a group represented by —NHR$^{48}$, wherein —$R^{41}$— represents a group represented by —$R^{411}$—, —$R^{42}$— represents a $C_{7-10}$ aralkyl group, $R^{43}$ represents —SO$_2$-$R^{431}$, wherein $R^{431}$ represents an amino group or a trifluoromethyl group, $R^{44}$ represents a nitrogen atom, $R^{45}$ represents a cyano group, $R^{46}$ represents a hydrogen atom, and $R^{48}$ represents —CO—CH$_2$—O—$R^{481}$, wherein $R^{481}$ represents a hydrogen atom.

A preferred mode of use of the present invention relates to an organic cation transporter 3 detector containing any of the compounds mentioned above, a pharmaceutically acceptable salt thereof, or a pharmaceutically acceptable solvate thereof as an active ingredient.

A preferred mode of use of the present invention relates to an organic cation transporter 3 activity inhibitor containing any of the compounds mentioned above, a pharmaceutically acceptable salt thereof, or a pharmaceutically acceptable solvate thereof as an active ingredient. This inhibitor serves as a therapeutic agent for depression and depression-like symptoms and is effective as a therapeutic agent for depression and depression-like symptoms, the depression and depression-like symptoms including physical depression, unipolar depression, psychogenic functional diseases, atypical depression, dysthymia, bipolar affective disorders, seasonal depression, and prolonged mood disorders.

A preferred mode of use of the present invention relates to a therapeutic agent for depression and depression-like symptoms, containing any of the compounds mentioned above, a pharmaceutically acceptable salt thereof, or a pharmaceutically acceptable solvate thereof as an active ingredient.

Advantageous Effects of Invention

According to the present invention, a novel compound can be provided.

In addition, according to the present invention, an OCT3 detector and an OCT3 activity inhibitor using the novel compound can be provided.

DESCRIPTION OF EMBODIMENTS

Hereinafter, the compound of the invention will be described.

A first aspect of the present invention relates to a compound represented by the following formula (A), a pharmaceutically acceptable salt thereof, or a pharmaceutically acceptable solvate thereof.

$R^1$-$R^2$-$R^3$-$R^4$ (A)

In formula (A), $R^1$ represents a hydrogen atom, a halogen atom, an amino group, a nitro group, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, a group represented by $R^{11}(R^{12})N$—, or a group represented by $R^{13}R^{14}N(R^{15}R^{16}N)C$=N—.

$R^{11}$, $R^{12}$, $R^{13}$, $R^{14}$, $R^{15}$, and $R^{16}$ may be the same or different and represent a hydrogen atom, a halogen atom, a nitro group, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, or an imidazolidine wherein adjacent $R^{13}$ and $R^{15}$, a nitrogen atom, and a carbon atom are joined together to form a ring.

—$R^2$— represents a group represented by one of the following —$R^{21}$— to —$R^{28}$—.

[Chemical Formula 4]

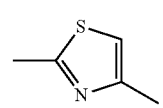
$R^{21}$

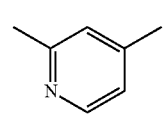
$R^{22}$

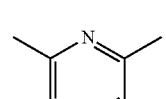
$R^{23}$

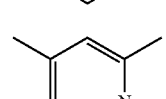
$R^{24}$

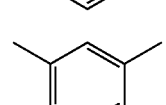
$R^{25}$

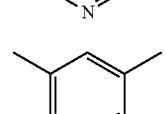
$R^{26}$

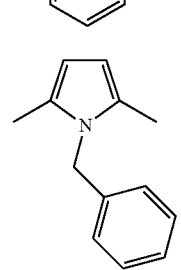
$R^{27}$

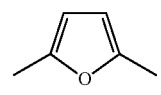
$R^{28}$

—$R^3$— represents a group represented by —$R^{31}$—, —$R^{32}$-$R^{33}$—, —$R^{34}$-$R^{35}$—, or —$R^{36}$-$R^{37}$-$R^{38}$—. Further, $R^{31}$ represents a $C_{1-5}$ alkyl group.

$R^{32}$ represents an oxygen atom (—O—), a sulfur atom (—S—), or —NH—.

$R^{33}$ represents a $C_{1-5}$ alkyl group.

$R^{34}$ represents a $C_{1-5}$ alkyl group.

$R^{35}$ represents an oxygen atom (—O—), a sulfur atom (—S—), or —NH—.

$R^{36}$ represents a $C_{1-5}$ alkyl group.

$R^{37}$ represents an oxygen atom (—O—), a sulfur atom (—S—), or —NH—.

$R^{38}$ represents a $C_{1-5}$ alkyl group.

—$R^4$ represents a hydrogen atom, a halogen atom, a cyano group, a $C_{1-3}$ alkoxy group, a group represented by —$N_3$, a group represented by —$R^{41}$-$R^{42}$, a group represented by —$C(NH_2)$=$NR^{43}$, a group represented by —$NHC(NH(R^{46}))$=$R^{44}R^{45}$, a group represented by —$C(=O)NHR^{47}$, a group represented by —$NHR^{48}$, or a group represented by —$C(OCH_3)$=$R^{48}$.

—$R^{41}$— represents a group represented by one of the following —$R^{411}$— to —$R^{413}$—.

[Chemical Formula 5]

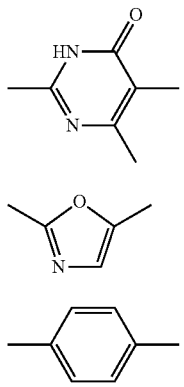

$R^{42}$ represents a hydrogen atom, a halogen atom, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, or a $C_{7-10}$ aralkyl group.

Further, $R^{43}$ represents a hydrogen atom or —$SO_2$-$R^{431}$.

$R^{431}$ represents an amino group, a $C_{1-3}$ halogenoalkyl group, or a $C_{6-10}$ aryl group.

$R^{44}$ represents a carbon atom or a nitrogen atom.

$R^{45}$ represents a hydrogen atom, a cyano group, or a nitro group.

$R^{46}$ represents a hydrogen atom or a $C_{1-5}$ alkyl group.

$R^{47}$ represents a $C_{1-5}$ alkyl group or —CO—$R^{471}$.

$R^{471}$ represents a $C_{1-5}$ alkyl group or a $C_{6-10}$ aryl group.

$R^{48}$ represents a hydrogen atom, a $C_{1-5}$ alkyl group, or —CO—$CH_2$—O—$R^{481}$.

$R^{481}$ represents a hydrogen atom or —CO—$CH_3$.

$R^{49}$ represents an oxygen atom or =NH.

However, the following compounds are excluded. Compounds wherein $R^1$ is formula $R^{11}(H)N(H_2N)C$=N—; $R^{11}$ is a hydrogen atom or a $C_{1-5}$ alkyl group; $R^2$ is $R^{21}$; $R^3$ is —$CH_2$—S—$CH_2$—$CH_2$—, —$CH_2$—O—$CH_2$—$CH_2$—, —O—$CH_2$—$CH_2$—$CH_2$—, —S—$CH_2$—$CH_2$—$CH_2$—, —$CH_2$—O—$CH_2$—, or —$CH_2$—S—$CH_2$—; and —$R^4$ is $R^{41}$-$R^{42}$, wherein $R^{41}$-$R^{42}$ is formula $R^5$, $R^{43}$, wherein $R^{43}$ is a hydrogen atom, —$SO_2$—$CF_3$, or —$SO_2$—$NH_2$, or $R^{47}$, wherein $R^{47}$ is a methyl group.

Compounds wherein $R^1$ is formula $H_2N(H_2N)$ C=N—;

$R^2$ is $R^{21}$;

$R^3$ is —$CH_2$—S—$CH_2$—$CH_2$— or —$CH_2$—$CH_2$—$CH_2$—$CH_2$—; and $R^4$ is —$R^{48}$, wherein $R^{48}$ is —CO—$CH_2$—O—$R^{481}$, wherein $R^{481}$ is a hydrogen atom.

Formula $R^5$ is

[Chemical Formula 6]

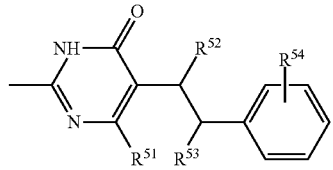

Further, in formula $R^5$, $R^{51}$, $R^{52}$, and $R^{53}$ may be the same or different and represent a hydrogen atom, a methyl group, an ethyl group, or a halogen atom. $R^{54}$ represents a hydrogen atom or a substituent on the phenyl group selected from a methyl group, an ethyl group, a methoxy group, and a halogen atom.

A preferred mode of the first aspect of the present invention is as follows.

$R^1$ represents a group represented by $R^{13}R^{14}N(R^{15}R^{16}N)C$=N—.

—$R^2$— represents a group represented by one of —$R^{21}$— to —$R^{23}$—.

—$R^3$— represents a group represented by —$R^{31}$— or —$R^{36}$-$R^{37}$-$R^{38}$—.

—$R^4$ represents a group represented by —$R^{41}$-$R^{42}$, a group represented by —$C(NH_2)$=$NR^{43}$, a group represented by —$NHC(NH(R^{46}))$=$R^{44}R^{45}$, or a group represented by —$NHR^{48}$.

A preferred mode of the first aspect of the present invention is as follows.

$R^1$ represents a group represented by $(H_2N)_2C$=N—.

—$R^2$— represents a group represented by one of —$R^{21}$— to —$R^{23}$—.

—$R^3$— represents a group represented by —$R^{31}$— or —$R^{36}$-$R^{37}$-$R^{38}$—.

—$R^{31}$— represents a butylene group.

—$R^{36}$— represents a methylene group.

—$R^{37}$— represents —O— or —S—.

—$R^{38}$— represents an ethylene group.

—$R^4$ represents a group represented by —$R^{41}$-$R^{42}$, a group represented by —$C(NH_2)$=$NR^{43}$, a group represented by —$NHC(NH(R^{46}))$=$R^{44}R^{45}$, or a group represented by —$NHR^{48}$.

—$R^{41}$— represents a group represented by —$R^{411}$—.

—$R^{42}$— represents a $C_{7-10}$ aralkyl group.

$R^{43}$ represents —$SO_2$-$R^{431}$.

$R^{431}$ represents an amino group or a $C_{1-3}$ halogenoalkyl group.

$R^{44}$ represents a nitrogen atom (N).

$R^{45}$ represents a cyano group (CN).

$R^{46}$ represents a hydrogen atom (H).

In a preferred mode of the first aspect of the present invention,

—$R^2$— represents a group represented by —$R^{21}$—.

—$R^3$— represents a butylene group.

—$R^4$ represents a group represented by —$R^{41}$-$R^{42}$, a group represented by —$C(NH_2)$=$NR^{43}$, a group represented by —NHC(NH($R^{46}$))=$R^{44}R^{45}$, or
a group represented by —NH$R^{48}$.
—$R^{41}$— represents a group represented by —$R^{411}$—.
—$R^{42}$— represents a $C_{7-10}$ aralkyl group.
$R^{43}$ represents —$SO_2$-$R^{431}$.
$R^{431}$ represents an amino group or a trifluoromethyl group.
$R^{44}$ represents a nitrogen atom.
$R^{45}$ represents a cyano group.
$R^{46}$ represents a hydrogen atom.
$R^{48}$ represents —CO—$CH_2$—O—$R^{481}$.
$R^{481}$ represents a hydrogen atom.

A preferred mode of the first aspect of the present invention relates to the following.
—$R^2$— represents a group represented by —$R^{21}$—.
—$R^3$— represents a group represented by —$R^{36}$-$R^{37}$-$R^{38}$—.
—$R^{31}$— represents a butylene group.
—$R^{36}$— represents a methylene group.
—$R^{37}$— represents —O—.
—$R^{38}$— represents an ethylene group.
—$R^4$ represents
a group represented by —$R^{41}$-$R^{42}$,
a group represented by —C($NH_2$)=$NR^{43}$,
a group represented by —NHC(NH($R^{46}$))=$R^{44}R^{45}$, or
a group represented by —NH$R^{48}$.
—$R^{41}$— represents a group represented by —$R^{411}$—.
—$R^{42}$— represents a $C_{7-10}$ aralkyl group.
$R^{43}$ represents —$SO_2$-$R^{431}$.
$R^{431}$ represents an amino group or a trifluoromethyl group.
$R^{44}$ represents a nitrogen atom.
$R^{45}$ represents a cyano group.
$R^{46}$ represents a hydrogen atom.
$R^{48}$ represents —CO—$CH_2$—O—$R^{481}$.
$R^{481}$ represents a hydrogen atom.

A preferred mode of the first aspect of the present invention relates to the following.
—$R^2$— represents a group represented by —$R^{22}$—.
—$R^3$— represents
a group represented by —$R^{36}$-$R^{37}$-$R^{38}$—.
—$R^{36}$— represents a methylene group.
—$R^{37}$— represents —O— or —S—.
—$R^{38}$— represents an ethylene group.
—$R^4$ represents
a group represented by —$R^{41}$-$R^{42}$,
a group represented by —C($NH_2$)=$NR^{43}$,
a group represented by —NHC(NH($R^{46}$))=$R^{44}R^{45}$, or
a group represented by —NH$R^{48}$.
—$R^{41}$— represents a group represented by —$R^{411}$—.
—$R^{42}$— represents a $C_{7-10}$ aralkyl group.
$R^{43}$ represents —$SO_2$-$R^{431}$.
$R^{431}$ represents an amino group or a trifluoromethyl group.
$R^{44}$ represents a nitrogen atom.
$R^{45}$ represents a cyano group.
$R^{46}$ represents a hydrogen atom.
$R^{48}$ represents —CO—$CH_2$—O—$R^{481}$.
$R^{481}$ represents a hydrogen atom.

A preferred mode of the first aspect of the present invention relates to the following.
—$R^2$— represents a group represented by —$R^{23}$—.
—$R^3$— represents
a group represented by —$R^{36}$-$R^{37}$-$R^{38}$—.
—$R^{36}$— represents a methylene group.
—$R^{37}$— represents —O— or —S—.
—$R^{38}$— represents an ethylene group.
—$R^4$ represents
a group represented by —$R^{41}$-$R^{42}$,
a group represented by —C($NH_2$)=$NR^{43}$,
a group represented by —NHC(NH($R^{46}$))=$R^{44}R^{45}$, or
a group represented by —NH$R^{48}$.
—$R^{41}$— represents a group represented by —$R^{411}$—.
—$R^{42}$— represents a $C_{7-10}$ aralkyl group.
$R^{43}$ represents —$SO_2$-$R^{431}$.
$R^{431}$ represents an amino group or a trifluoromethyl group.
$R^{44}$ represents a nitrogen atom.
$R^{45}$ represents a cyano group.
$R^{46}$ represents a hydrogen atom.
$R^{48}$ represents —CO—$CH_2$—O—$R^{481}$.
$R^{481}$ represents a hydrogen atom.

A preferred mode of use of the present invention relates to an organic cation transporter 3 detector containing any of the compounds mentioned above, a pharmaceutically acceptable salt thereof, or a pharmaceutically acceptable solvate thereof as an active ingredient.

A preferred mode of use of the present invention relates to an organic cation transporter 3 activity inhibitor containing any of the compounds mentioned above, a pharmaceutically acceptable salt thereof, or a pharmaceutically acceptable solvate thereof as an active ingredient. This inhibitor serves as a therapeutic agent for depression and depression-like symptoms and is effective as a therapeutic agent for depression and depression-like symptoms, the depression and depression-like symptoms including physical depression, unipolar depression, psychogenic functional diseases, atypical depression, dysthymia, bipolar affective disorders, seasonal depression, and prolonged mood disorders.

An OCT3 activity inhibitor containing the compound of the invention and the like is effective in the treatment of diseases that involve OCT3 (depression and depression-like symptoms). As described in the Background Art and will be further described below, it has been demonstrate that depression and depression-like symptoms can be treated by inhibiting an organic cation transporter OCT3. For example, an earlier literature (Kitaichi. et al, Neurosci Lett., 2005 July, 1-8; 382(1-2): 195-200) reports that when OCT3 gene expression in mice is suppressed by antisense or knockout technologies, antidepressant action is observed in a forced swimming test. Meanwhile, the OCT3 inhibitor of the invention inhibits the function of OCT3 protein and thus is expected to have the same action as the suppression of OCT3 gene expression.

As demonstrated in the Examples, the compound of the prevent invention, a pharmaceutically acceptable salt thereof, or a pharmaceutically acceptable solvate thereof has OCT3 inhibition activity. Therefore, the present invention also provides a therapeutic agent for depression and depression-like symptoms, containing the above OCT3 inhibitor as an active ingredient. The depression and depression-like symptoms include physical depression, unipolar depression, psychogenic functional diseases, atypical depression, dysthymia, bipolar affective disorders, seasonal depression, and prolonged mood disorders.

A preferred mode of use of the present invention relates to a therapeutic agent for depression and depression-like symptoms, containing any of the compounds mentioned above, a pharmaceutically acceptable salt thereof, or a pharmaceutically acceptable solvate thereof as an active ingredient.

A preferred compound of the present invention is a compound represented by the following formula (I) (represented by $(NH_2)_2C=N-R^2-CH_2-R^{37}-C_2H_4-R^4$), a pharmaceutically acceptable salt thereof, or a pharmaceutically acceptable solvate thereof.

[Chemical Formula 7]

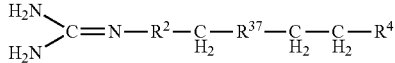
(I)

In formula (I), $R^2$ represents a group represented by formula (II), formula (III), or formula (IV). Incidentally, in formula (II) to formula (IV), the point of attachment to the nitrogen atom (N) adjacent to $R^2$ is indicated with the symbol (*). $R^2$ may be an aromatic heterocyclic group or an alicyclic hydrocarbon group.

[Chemical Formula 8]

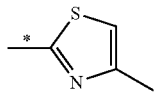
(II)

[Chemical Formula 9]

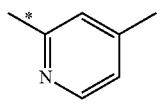
(III)

[Chemical Formula 10]

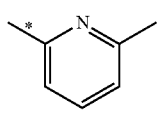
(IV)

$R^{37}$ represents a methylene group (—$CH_2$—), an oxygen atom (—O—), or a sulfur atom (—S—). $R^4$ represents a group represented by one of formula (V) to formula (IX).

[Chemical Formula 11]

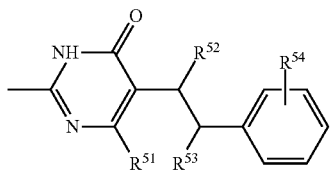
(V)

In formula (V), $R^{51}$, $R^{52}$, and $R^{53}$ may be the same or different and represent a hydrogen atom, a methyl group, an ethyl group, or a halogen atom. $R^{54}$ is a hydrogen atom or represents a group selected from a methyl group, an ethyl group, a methoxy group, and a halogen atom. $R^{54}$ is a group that substitutes a hydrogen atom in the phenyl group in formula (V), and $R^{54}$ may be in the ortho, meta, or para position. Examples of halogen atoms include a fluorine atom, a chlorine atom, a bromine atom, and an iodine atom. In a preferred example of formula (V), $R^{51}$ represents a methyl group, and $R^{52}$, $R^{53}$, and $R^{54}$ each represent a hydrogen atom.

[Chemical Formula 12]

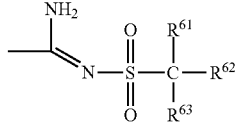
(VI)

In formula (VI), $R^{61}$, $R^{62}$, and $R^{63}$ may be the same or different and represent a hydrogen atom, a methyl group, an ethyl group, or a halogen atom. In a preferred example of formula (VI), $R^{61}$, $R^{62}$, and $R^{63}$ each represent a fluorine atom.

[Chemical Formula 13]

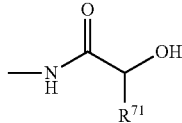
(VII)

In formula (VII), $R^{71}$ represents a hydrogen atom, a methyl group, or an ethyl group. A preferred example of $R^{71}$ is a hydrogen atom.

[Chemical Formula 14]

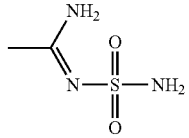
(VIII)

[Chemical Formula 15]

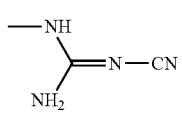
(IX)

Preferred are those excluding compounds wherein, in formula (I), $R^2$ represents a group represented by formula (II), $R^{37}$ represents a sulfur atom (—S—), and $R^4$ represents a group represented by one of formula (V), formula (VI), formula (VII), formula (VIII), and formula (IX); in formula (V), $R^{51}$ represents a methyl group, and $R^{52}$, $R^{53}$, and $R^{54}$ each represent a hydrogen atom; in formula (VI), $R^{61}$, $R^{62}$, and $R^{63}$ each represent a fluorine atom; and in formula (VII), $R^{71}$ represents a hydrogen atom, as well as pharmaceutically acceptable salts thereof and pharmaceutically acceptable solvates thereof.

A preferred mode of a compound represented by formula (I) relates to a compound wherein $R^2$ represents a group represented by formula (II), a pharmaceutically acceptable salt thereof, or a pharmaceutically acceptable solvate thereof. Further, in this preferred mode, $R^{37}$ represents a methylene group (—$CH_2$—). In the case where $R^4$ represents a group represented by formula (V), $R^{51}$ represents a methyl group, and $R^{52}$, $R^{53}$, and $R^{54}$ each represent a hydrogen atom. In the case where $R^3$ represents a group represented by formula (VI), $R^{61}$, $R^{62}$, and $R^{63}$ each represent a fluorine atom. Further, in the case where $R^3$ represents a group represented by formula (VII), $R^{71}$ represents a hydrogen atom.

A preferred mode of a compound represented by formula (I) is a compound wherein $R^2$ represents a group represented by formula (II), $R^2$ represents an oxygen atom (—O—), $R^{51}$ represents a methyl group, $R^{52}$, $R^{53}$, and $R^{54}$ each represent a hydrogen atom, $R^{61}$, $R^{62}$, and $R^{63}$ each represent a fluorine atom, and $R^{71}$ represents a hydrogen atom, a pharmaceutically acceptable salt thereof, or a pharmaceutically acceptable solvate thereof.

A preferred mode of a compound represented by formula (I) relates to a compound wherein $R^2$ represents a group represented by formula (III), a pharmaceutically acceptable salt thereof, or a pharmaceutically acceptable solvate thereof. Further, in this mode, $R^{37}$ represents a sulfur atom (—S—). $R^4$ represents a group represented by one of formula (V) to formula (IX). $R^{51}$ represents a methyl group. $R^{52}$, $R^{53}$, and $R^{54}$ each represent a hydrogen atom. $R^{61}$, $R^{62}$, and $R^{63}$ each represent a fluorine atom. Further, $R^{71}$ represents a hydrogen atom.

In a preferred mode of a compound represented by formula (I), $R^2$ represents a group represented by formula (III), $R^{37}$ represents an oxygen atom (—O—), $R^{51}$ represents a methyl group, $R^{52}$, $R^{53}$, and $R^{54}$ each represent a hydrogen atom, $R^{61}$, $R^{62}$, and $R^{63}$ each represent a fluorine atom, and $R^{71}$ represents a hydrogen atom.

A preferred mode of a compound represented by formula (I) relates to a compound wherein $R^2$ represents a group represented by formula (III), a pharmaceutically acceptable salt thereof, or a pharmaceutically acceptable solvate thereof. Further, in this mode, $R^2$ represents a group represented by formula (III). $R^{37}$ represents a sulfur atom (—S—). $R^4$ represents a group represented by formula (V), formula (VI), or formula (VIII). $R^{51}$ represents a methyl group. $R^{52}$, $R^{53}$, and $R^{54}$ each represent a hydrogen atom. $R^{61}$, $R^{62}$, and $R^{63}$ each represent a fluorine atom. Further, $R^{71}$ represents a hydrogen atom.

A preferred mode of a compound represented by formula (I) relates to a compound wherein $R^2$ represents a group represented by formula (IV), a pharmaceutically acceptable salt thereof, or a pharmaceutically acceptable solvate thereof. $R^{37}$ represents a sulfur atom (—S—). $R^{51}$ represents a methyl group. $R^{52}$, $R^{53}$, and $R^{54}$ each represent a hydrogen atom. $R^{61}$, $R^{62}$, and $R^{63}$ each represent a fluorine atom. $R^{71}$ represents a hydrogen atom.

A preferred mode of a compound represented by formula (I) relates to a compound wherein $R^2$ represents a group represented by formula (IV), a pharmaceutically acceptable salt thereof, or a pharmaceutically acceptable solvate thereof. $R^{37}$ represents a sulfur atom (—S—). $R^4$ represents a group represented by formula (V), formula (VI), or formula (VIII). $R^{51}$ represents a methyl group. $R^{52}$, $R^{53}$, and $R^{54}$ each represent a hydrogen atom. $R^{61}$, $R^{62}$, and $R^{63}$ each represent a fluorine atom. $R^{71}$ represents a hydrogen atom.

In a preferred mode of a compound represented by formula (I), $R^2$ represents a group represented by formula (IV), $R^{37}$ represents an oxygen atom (—O—), $R^{51}$ represents a methyl group, $R^{52}$, $R^{53}$, and $R^{54}$ each represent a hydrogen atom, $R^{61}$, $R^{62}$, and $R^{63}$ each represent a fluorine atom, and $R^{71}$ represents a hydrogen atom.

As used herein, "$C_m$-$C_n$" means that the number of carbon atoms is m to n.

"Aryl group" is a monovalent group resulting from the release of one of the hydrogen atoms attached to the ring of an aromatic hydrocarbon. Examples of $C_6$-$C_{10}$ aryl groups include a phenyl group, an indenyl group, a 1-naphthyl group, and a 2-naphthyl group.

"Aromatic heterocyclic group" is an aromatic heterocyclic group having one to three heteroatoms selected from the group consisting of an oxygen atom, a nitrogen atom, and a sulfur atom in the ring. Examples of 5- to 7-membered aromatic heterocyclic groups include 5-membered aromatic heterocyclic groups such as furyl, thienyl, pyrrolyl, pyrazolyl, imidazolyl, oxazolyl, isoxazolyl, triazolyl, isothiazolyl, 1,2,3-oxadiazolyl, triazolyl, and thiadiazolyl; 6-membered aromatic heterocyclic groups such as pyranyl, pyridyl, pyridazinyl, pyrimidinyl, and pyrazinyl; and 7-membered aromatic heterocyclic groups such as azepinyl.

"Alkylene group" is a divalent group resulting from the loss of two hydrogen atoms from a linear or branched aliphatic hydrocarbon. Examples of $C_1$-$C_{10}$ alkylene groups include a methylene group, a methylmethylene group, an ethylene group, a propylene group, a trimethylene group, a 1-methylethylene group, a tetramethylene group, a 1-methyltrimethylene group, a 2-methyltrimethylene group, a 3-methyltrimethylene group, a 1-methylpropylene group, a 1,1-dimethylethylene group, a pentamethylene group, a 1-methyltetramethylene group, a 2-methyltetramethylene group, a 3-methyltetramethylene group, a 4-methyltetramethylene group, a 1,1-dimethyltrimethylene group, a 2,2-dimethyltrimethylene group, a 3,3-dimethyltrimethylene group, a hexamethylene group, a 1-methylpentamethylene group, a 2-methylpentamethylene group, a 3-methylpentamethylene group, a 4-methylpentamethylene group, a 5-methylpentamethylene group, a 1,1-dimethyltetramethylene group, a 2,2-dimethyltetramethylene group, a 3,3-dimethyltetramethylene group, a 4,4-dimethyltetramethylene group, a heptamethylene group, a 1-methylhexamethylene group, a 2-methylhexamethylene group, a 5-methylhexamethylene group, a 3-ethylpentamethylene group, an octamethylene group, a 2-methylheptamethylene group, a 5-methylheptamethylene group, a 2-ethylhexamethylene group, a 2-ethyl-3-methylpentamethylene group, and a 3-ethyl-2-methylpentamethylene group. As alkylene groups, $C_1$-$C_4$ alkylene groups are preferable, and $C_1$-$C_2$ alkylene groups are more preferable.

"Alkenylene group" is a divalent group resulting from the loss of two hydrogen atoms from a linear or branched aliphatic hydrocarbon containing a double bond. Examples of $C_2$-$C_{10}$ alkenylene groups include an ethenylene group, a 1-propenylene group, a 2-propenylene group, a 2-methyl-1-propenylene group, a 1-butenylene group, a 2-butenylene group, a 3-butenylene group, a 3-methyl-2-butenylene group, a 1-pentenylene group, a 2-pentenylene group, a 3-pentenylene group, a 4-pentenylene group, and a 1-hexenylene group.

"Alkynylene group" is a divalent group resulting from the loss of two hydrogen atoms from a linear or branched aliphatic hydrocarbon containing a triple bond. Examples of $C_2$-$C_{10}$ alkynylene groups include an ethynylene group, a 1-propynylene group, a 2-propynylene group, a 2-methyl-1-propynylene group, a 1-butynylene group, a 2-butynylene group, a 3-butynylene group, a 3-methyl-2-butynylene group, a 1-pentynylene group, a 2-pentynylene group, a 3-pentynylene group, a 4-pentynylene group, and a 1-hexynylene group.

"Alicyclic hydrocarbon group" means a saturated or unsaturated alicyclic hydrocarbon group. Examples of $C_3$-$C_7$ alicyclic hydrocarbon groups include cycloalkyl groups such as a cyclopropyl group, a cyclobutyl group, a cyclopentyl group, a cyclohexyl group, and a cyclopentyl group; and cycloalkenyl groups such as a 2-cyclopenten-1-yl group, a 2-cyclohexen-1-yl group, and a 3-cyclohexen-1-yl group.

"Arylene group" is a divalent group resulting from the release of two of the hydrogen atoms attached to the ring of an aromatic hydrocarbon. Examples of rings forming a $C_6$-$C_{10}$ arylene group include a benzene ring and a naphthalene ring.

"Alkyl group" is a monovalent group resulting from the loss of one hydrogen atom from a linear or branched aliphatic hydrocarbon. Examples of $C_1$-$C_6$ alkyl groups include a methyl group, an ethyl group, a propyl group, an isopropyl group, a butyl group, an isobutyl group, a sec-butyl group, a tert-butyl group, a pentyl group, an isopentyl group, a neopentyl group, a hexyl group, and an isohexyl group. Examples of $C_1$-$C_4$ alkyl groups include a methyl group, an ethyl group, a propyl group, an isopropyl group, a butyl group, an isobutyl group, a sec-butyl group, and a tert-butyl group.

"Alkenyl group" is a monovalent group resulting from the loss of one hydrogen atom from a linear or branched aliphatic hydrocarbon containing a double bond. Examples of $C_2$-$C_6$ alkenyl groups include an ethenyl group, a 1-propenyl group, a 2-propenyl group, a 2-methyl-1-propenyl group, a 1-butenyl group, a 2-butenyl group, a 3-butenyl group, a 3-methyl-2-butenyl group, a 1-pentenyl group, a 2-pentenyl group, a 3-pentenyl group, a 4-pentenyl group, and a 1-hexenyl group. Examples of $C_2$-$C_4$ alkenyl groups include an ethenyl group, a 1-propenyl group, a 2-propenyl group, a 2-methyl-1-propenyl group, a 1-butenyl group, a 2-butenyl group, and a 3-butenyl group.

"Alkynyl group" is a monovalent group resulting from the loss of one hydrogen atom from a linear or branched aliphatic hydrocarbon containing a triple bond. Examples of $C_2$-$C_6$ alkynyl groups include an ethynyl group, a 1-propynyl group, a 2-propynyl group, a 2-methyl-1-propynyl group, a 1-butynyl group, a 2-butynyl group, a 3-butynyl group, a 3-methyl-2-butynyl group, a 1-pentynyl group, a 2-pentynyl group, a 3-pentynyl group, a 4-pentynyl group, and a 1-hexynyl group. Examples of $C_2$-$C_4$ alkynyl groups include an ethenyl group, a 1-propenyl group, a 2-propenyl group, a 2-methyl-1-propenyl group, a 1-butenyl group, a 2-butenyl group, and a 3-butenyl group.

"Alkoxy group" is a monovalent group resulting from the loss of a hydrogen atom from the hydroxyl group of a linear or branched alcohol. Examples of $C_1$-$C_6$ alkoxy groups include a methoxy group, an ethoxy group, a propoxy group, an isopropoxy group, a butoxy group, an isobutoxy group, a sec-butoxy group, a tert-butoxy group, a pentoxy group, an isopentoxy group, a 2-methylbutoxy group, a neopentoxy group, a 1-ethylpropoxy group, a hexyloxy group, a 4-methylpentoxy group, a 3-methylpentoxy group, a 2-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, and a 2-ethylbutoxy group. Examples of $C_1$-$C_4$ alkoxy groups include a methoxy group, an ethoxy group, a propoxy group, an isopropoxy group, a butoxy group, an isobutoxy group, a sec-butoxy group, and a tert-butoxy group.

"Alkylthio group" is a group in which oxygen of an alkoxy group is substituted with sulfur. Examples of $C_1$-$C_6$ alkylthio groups include a methylthio group, an ethylthio group, a propylthio group, an isopropylthio group, a butylthio group, an isobutylthio group, a sec-butylthio group, a tert-butylthio group, a pentylthio group, an isopentylthio group, a 2-methylbutylthio group, a neopentylthio group, a 1-ethylpropoxy group, a hexyloxy group, a 4-methylpentylthio group, a 3-methylpentylthio group, a 2-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group, and a 2-ethylbutylthio group. Examples of $C_1$-$C_4$ alkylthio groups include a methylthio group, an ethylthio group, a propylthio group, an isopropylthio group, a butylthio group, an isobutylthio group, a sec-butylthio group, and a tert-butylthio group.

"Alkylsulfonyl group" is a monovalent group in which one of the hydrogen atoms of an alkyl group is substituted with a sulfonyl group. Examples of $C_1$-$C_4$ alkylsulfonyl groups include a methylsulfonyl group, an ethylsulfonyl group, a propylsulfonyl group, an isopropylsulfonyl group, a butylsulfonyl group, an isobutylsulfonyl group, a sec-butylsulfonyl group, and a tert-butylsulfonyl group.

"Arylsulfonyl group" is a monovalent group in which one of the hydrogen atoms of an aryl group is substituted with a sulfonyl group. Examples of $C_6$-$C_{12}$ arylsulfonyls include a phenylsulfonyl group, an indenylsulfonyl group, a 1-naphthylsulfonyl group, and a 2-naphthylsulfonyl group.

Examples of halogens include fluorine, chlorine, bromide, and iodine.

"Halogenoalkyl group" is a monovalent group in which at least one of the hydrogen atoms of an alkyl group is substituted with a halogen atom. Examples of $C_1$-$C_6$ halogenoalkyl groups include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, a 2-iodoethyl group, a 3-chloropropyl group, a 4-fluorobutyl group, a 6-iodohexyl group, and a 2,2-dibromoethyl group.

"Aralkyl group" is a monovalent group in which one of the hydrogen atoms of an alkyl group is substituted with an aryl group. Examples of $C_7$-$C_{16}$ aralkyl groups include a benzyl group, a naphthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 5-phenylpentyl group, a 5-naphthylpentyl group, a 6-phenylhexyl group, and a 6-naphthylhexyl group.

A pharmaceutically acceptable salt thereof means a salt of a compound represented by formula (A). Examples of pharmaceutically acceptable salts include salts of inorganic bases, ammonia, organic bases, inorganic acids, organic acids, basic amino acids, halogen ions, and the like, and inner salts. Examples of inorganic bases include alkali metals (Na, K, etc.) and alkaline earth metals (Ca, Mg, etc.). Examples of organic bases include trimethylamine, triethylamine, corrin, procaine, and ethanolamine. Examples of inorganic acids include hydrochloric acid, hydrobromic acid, sulfuric acid, nitric acid, and phosphoric acid. Examples of organic acids include p-toluenesulfonic acid, methanesulfonic acid, formic acid, trifluoroacetic acid, and maleic acid. Examples of basic amino acids include lysine, arginine, ornithine, and histidine.

A pharmaceutically acceptable solvate thereof means a solvate of a compound represented by formula (A). An example of a solvate is a hydrate. The compound of the prevent invention may absorb atmospheric moisture during storage and turn into a hydrate. The present invention encompasses such a hydrate.

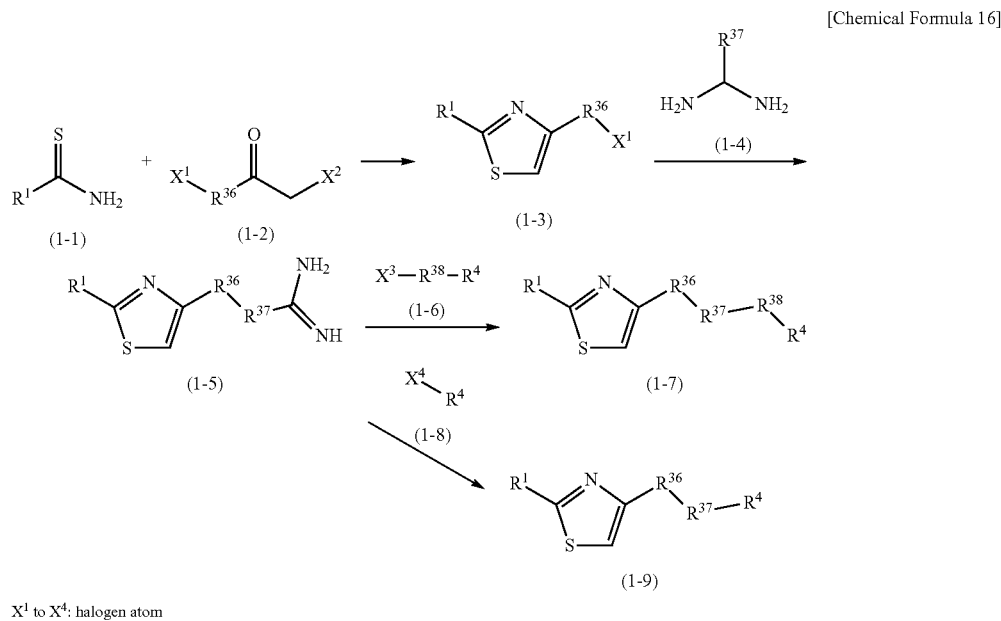

[Chemical Formula 16]

$X^1$ to $X^4$: halogen atom

Next, examples of methods for producing the compound of the prevent invention will be described. The present invention relates to a guanidine derivative, for example. Therefore, in the following schemes, a person skilled in the art can suitably modify the compounds and reaction conditions used for the reactions with reference to known art and also, for example, the production methods disclosed in the references cited herein.

1. Synthesis of the Following $R^1$-$R^2$-$R^3$-$R^4$ (Scheme 1) $R^1$
    $R^1$ represents
        a hydrogen atom, a halogen atom,
        an amino group, a nitro group, a $C_{1-5}$ alkyl group, a $C_{1-3}$ alkoxy group, a $C_{1-3}$ alkylthio group,
        a $C_{1-3}$ halogenoalkyl group, a $C_{6-10}$ aryl group,
        a group represented by $R^{11}(R^{12})N-$, or
        a group represented by $R^{13}R^{14}N(R^{15}R^{16}N)C=N-$.
    $R^{11}$, $R^{12}$, $R^{13}$, $R^{14}$, $R^{15}$, and $R^{16}$ may be the same or different and represent
        a hydrogen atom,
        a halogen atom,
        a nitro group,
        a $C_{1-6}$ alkyl group,
        a $C_{1-3}$ alkoxy group,
        a $C_{1-3}$ alkylthio group,
        a $C_{1-3}$ halogenoalkyl group, or
        a $C_{6-10}$ aryl group.
    $R^2$
        $R^2$ represents a thiazole ring.
    $R^3$
        $R^3$ represents a group represented by $-R^{36}$-$R^{37}$-$R^{38}-$.
        $R^{36}$ represents a $C_{1-5}$ alkyl group,
        $R^{37}$ represents an oxygen atom ($=O$), a sulfur atom ($=S$), or a group represented by $=NH$, and
        $R^{38}$ represents a $C_{1-5}$ alkyl group.

$R^4$
    $R^4$ represents a hydrogen atom, a halogen atom, a cyano group, a $C_{1-3}$ alkoxy group, or a group represented by $-N_3$.

The above "halogen atom" means a halogen atom. The same applies hereinafter.

(1-1)+(1-2)→(1-3) (Condensation reaction)    (i)

A compound represented by formula (1-1) can be obtained using a conventional method or the technique shown in huaxue yanjiu yu yingyong, 2006, 18 (2), 186-188. A compound represented by formula (1-2) can be obtained, for example, using a conventional method or the technique shown in JP 2002-53566 A.

(i) Reaction Solvent

Examples of reaction solvents used in step (i) of Scheme 1 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 1 include acetone, ethanol, and mixed solvents thereof.

(ii) Catalyst

Step (i) of Scheme 1 may be performed in the presence of a catalyst or in the absence of a catalyst. Examples of catalysts used in step (i) of Scheme 1 include $MgSO_4$, which is a dehydrator.

(iii) Reaction Temperature

The reaction temperature in step (i) of Scheme 1 may be adjusted according to the raw material compounds, solvent, and the like, and is preferably 10 to 100° C.

(iv) Reaction Time

The reaction time in step (i) of Scheme 1 may be adjusted according to the raw material compounds, solvent, and the like, and is preferably 2 to 24 hours.

(v) Operation

In step (i) of Scheme 1, it is preferable that the raw material compounds (1-1 and 1-2) and a catalyst are dissolved in a reaction solvent, and then stirred or refluxed at a reaction temperature. Stirring can be performed with a known stirring device, and refluxing can be performed with a known refluxing device.

(1-3)+(1-4)→(1-5) (E1 reaction)  (ii)

A compound represented by formula (1-4) can be obtained by purchasing a commercially available product. Alternatively, it may also be produced in the same manner as known from references known to those skilled in the art.

(i) Reaction Solvent

Examples of reaction solvents used in step (ii) of Scheme 1 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.

Preferred examples of reaction solvents used in step (ii) of Scheme 1 include ethanol and mixed solvents thereof.

(ii) Catalyst

Step (ii) of Scheme 1 may be performed in the presence of a catalyst or in the absence of a catalyst.

(iii) Reaction Temperature

The reaction temperature in step (ii) of Scheme 1 may be adjusted according to the raw material compounds, solvent, and the like, and is preferably 10 to 120° C.

(iv) Reaction Time

The reaction time in step (ii) of Scheme 1 may be adjusted according to the raw material compounds, solvent, and the like, and is preferably 0.25 hours to 12 hours.

(v) Operation

In step (ii) of Scheme 1, it is preferable that the raw material compounds (1-3) and (1-4) and a catalyst are dissolved in a reaction solvent, and then stirred or refluxed at a reaction temperature. Stirring can be performed with a known stirring device, and refluxing can be performed with a known refluxing device.

(1-5)+(1-6)→(1-7) or (1-5)+(1-8)→(1-9)  (iii)

A compound represented by formula (1-6) and a compound represented by formula (1-8) can each be obtained by purchasing a commercially available product. Alternatively, they may also be produced in the same manner as known from references known to those skilled in the art.

(i) Reaction Solvent

Examples of reaction solvents used in step (iii) of Scheme 1 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.

Preferred examples of reaction solvents used in step (iii) of Scheme 1 include alcohol solvents such as methanol and ethanol, halogen solvents such as dichloromethane and chloroform, polar solvents such as dimethylformamide and acetonitrile, ether solvents such as tetrahydrofuran, water, and mixed solvents thereof.

(ii) Catalyst

Step (iii) of Scheme 1 may be performed in the presence of a catalyst or in the absence of a catalyst. Examples of catalysts used in step (iii) of Scheme 1 include sodium hydroxide and triethylamine.

(iii) Reaction Temperature

The reaction temperature in step (iii) of Scheme 1 may be adjusted according to the raw material compounds, solvent, and the like, and is preferably −50 to 50° C.

(iv) Reaction Time

The reaction time in step (iii) of Scheme 1 may be adjusted according to the raw material compounds, solvent, and the like, and is preferably 0.5 hours to 12 hours.

(v) Operation

In step (iii) of Scheme 1, it is preferable that the raw material compounds (1-5 and 1-6 or 1-8) and a catalyst are dissolved in a reaction solvent and stirred at a reaction temperature. Stirring can be performed with a known stirring device.

2. Synthesis of the Following $R^1$-$R^2$-$R^3$-$R^4$ (Scheme 2)

$R^1$—

$R^1$ is the same as in Scheme 1.

$R^2$ $R^2$ is a benzene ring, a furan ring, or a pyridine ring.

$R^3$ $R^3$ represents a group represented by —$R^{36}$-$R^{37}$-$R^{38}$—, wherein $R^{36}$ represents a $C_{1-5}$ alkyl group, $R^{37}$ represents an oxygen atom (=O), a sulfur atom (=S), or a group represented by =NH, and $R^{38}$ represents a $C_{1-5}$ alkyl group.

$R^4$ $R^4$ represents a hydrogen atom, a halogen atom, a cyano group, a $C_{1-3}$ alkoxy group, or a group represented by —$N_3$.

[Chemical Formula 17]

$X^1$ to $X^3$: halogen atom (2-2)→(2-3) (Reduction reaction)  (i)

A compound represented by formula (2-2) can be obtained by adding an $R^1$ group to a compound represented by formula (2-1) by a method known from references known to those skilled in the art. A compound represented by formula (2-1) can be obtained by purchasing a commercially available product. Alternatively, it may also be produced in the same manner as known from references known to those skilled in the art.

(i) Reaction Solvent

Examples of reaction solvents used in step (i) of Scheme 2 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 2 include methanol.

(ii) Catalyst

Step (i) of Scheme 2 may be performed in the presence of a catalyst or in the absence of a catalyst. Examples of catalysts used in step (i) of Scheme 2 include sodium borohydride, sodium triacetoxy borohydride, and the like.

(iii) Reaction Temperature

The reaction temperature in step (i) of Scheme 2 may be adjusted according to the raw material compound, solvent, and the like, and is preferably 10 to 100° C.

(iv) Reaction Time

The reaction time in step (i) of Scheme 2 may be adjusted according to the raw material compound, solvent, and the like, and is preferably 0.5 hours to 12 hours.

(v) Operation

In step (i) of Scheme 2, it is preferable that the raw material compound (2-2) and a catalyst are dissolved in a reaction solvent and stirred at a reaction temperature. Stirring can be performed with a known stirring device.

Incidentally, also in the case where R2 is a pyrrole ring, the compound can be synthesized in the same manner as this scheme.

(2-3)→(2-4) (Halogenation of alcohol) (ii)

(i) Reaction Solvent

Step (ii) of Scheme 2 may be performed in the presence of a reaction solvent. Examples of reaction solvents used in step (ii) of Scheme 2 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.

(ii) Catalyst

Step (ii) of Scheme 2 may be performed in the presence of a catalyst or in the absence of a catalyst. Examples of catalysts used in step (ii) of Scheme 2 include, but are not limited to, triethylamine, pyridine, and the like.

(iii) Reaction Temperature

The reaction temperature in step (ii) of Scheme 2 may be adjusted according to the raw material compound, solvent, and the like, and is preferably −20 to 100° C.

(iv) Reaction Time

The reaction time in step (ii) of Scheme 2 may be adjusted according to the raw material compound, solvent, and the like, and is preferably 0.25 hours to 12 hours.

(v) Operation

In step (ii) of Scheme 2, it is preferable that the raw material compound (2-3), a halogenating agent, and a catalyst are dissolved in a reaction solvent, and then stirred or refluxed at a reaction temperature. Preferred examples of halogenating agents include, but are not limited to, $SOCl_2$. Stirring can be performed with a known stirring device, and refluxing can be performed with a known refluxing device.

(2-4)+(1-4)→(2-5) (E1 reaction) (iv)

The reaction catalyst and the like in this step are the same as in Scheme 1 (ii).

(2-5)+(1-6)→(2-6) or (2-5)+(1-8)→(2-7) (v)

The reaction catalyst and the like in this step are the same as in Scheme 1 (iii).

3. Synthesis of the Following $R^1$-$R^2$-$R^3$-$R^4$ (Scheme 3)

$R^1$ $R^1$ is the same as in Scheme 1.

$R^2$ $R^2$ represents a 1-phenyl-1H-pyrrole ring.

$R^3$ $R^3$ represents a group represented by —$R^{36}$-$R^{37}$-$R^{38}$—, wherein $R^{36}$ represents a $C_{1-5}$ alkyl group, $R^{37}$ represents an oxygen atom (=O), a sulfur atom (=S), or a group represented by =NH, and $R^{38}$ represents a $C_{1-5}$ alkyl group.

$R^4$ $R^4$ represents a hydrogen atom, a halogen atom, a cyano group, a $C_{1-3}$ alkoxy group, or a group represented by —$N_3$.

[Chemical Formula 18]

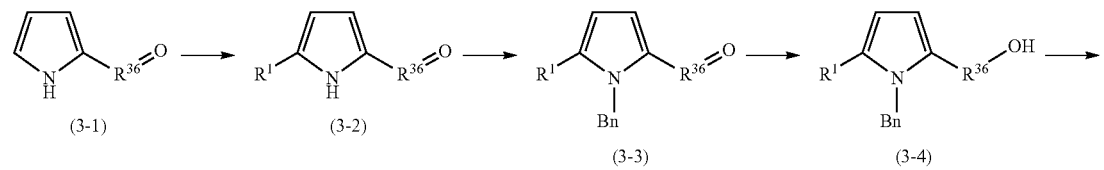

(3-1)　　　(3-2)　　　(3-3)　　　(3-4)

-continued

[Chemical structures: (3-5), (3-6), (3-7), (1-6), (3-8), (1-8), (3-9)]

$X^1$ to $X^3$: halogen atom (3-1)→(3-2) (Addition of $R^1$ group)     (i)

A compound represented by formula (3-2) can be obtained by adding an $R^1$ group to a compound represented by formula (3-1) by a method known from references known to those skilled in the art. A compound represented by formula (3-1) can be obtained by purchasing a commercially available product. Alternatively, it may also be produced in the same manner as known from references known to those skilled in the art.

(3-2)→(3-3) (Phenylation of pyrrole ring)     (ii)

(i) Reaction Solvent

Examples of reaction solvents used in step (ii) of Scheme 3 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.

Preferred examples of reaction solvents used in step (ii) of Scheme 3 include ethanol, dimethylformamide, or mixed solvents thereof.

(ii) Catalyst

Step (ii) of Scheme 3 may be performed in the presence of a catalyst or in the absence of a catalyst.

(iii) Reaction Temperature

The reaction temperature in step (ii) of Scheme 3 may be adjusted according to the raw material compound, solvent, and the like, and is preferably 10° C. to 150° C.

(iv) Reaction Time

The reaction time in step (ii) of Scheme 3 may be adjusted according to the raw material compound, solvent, and the like, and is preferably 12 hours to 36 hours.

(v) Operation

In step (ii) of Scheme 3, it is preferable that a sodium salt of the raw material compound (3-2) is prepared, then dissolved in a reaction solvent together with benzyl chloride and a catalyst, and heated at a reaction temperature. Heating can be performed with a known heating device.

(3-3)→(3-4) (Reduction reaction)     (iii)

The reaction catalyst and the like in this scheme are the same as in Scheme 2 (i).

(3-4)→(3-5) (Halogenation of alcohol)     (iv)

The reaction catalyst and the like about this step are the same as in Scheme 2 (ii).

(3-5)+(3-6)→(3-7) (E1 reaction)     (v)

The reaction catalyst and the like about this step are the same as in Scheme 1 (ii).

(3-7)+(1-6)→(3-8) or (3-7)+(1-8)→(3-9)

The reaction catalyst and the like about this step are the same as in Scheme 1 (iii).

4. Synthesis of the Following $R^1$-$R^2$-$R^3$-$R^4$ (Scheme 4)

$R^1$ $R^1$ is the same as in Scheme 1.

$R^2$ $R^2$ represents a thiazole ring, a benzene ring, a furan ring, a pyridine ring, or a 1-phenyl-1H-pyrrole ring.

$R^3$ $R^3$ represents a group represented by —$R^{31}$—, wherein $R^{31}$ represents a $C_{1-5}$ alkyl group.

$R^4$ $R^4$ represents a hydrogen atom, a halogen atom, a cyano group, a $C_{1-3}$ alkoxy group, or a group represented by —$N_3$.

[Chemical Formula 19]

[Chemical structures: (2-4), (4-1), (4-2), (4-3), (1-8), (4-4)]

$X^1$ and $X^2$: halogen atom (2-4)→(4-1) (Synthesis of azide)     (i)

(i) Reaction Solvent

Examples of reaction solvents used in step (i) of Scheme 4 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 4 include dimethylformamide, dimethylsulfoxide, and mixed solvents thereof.

(ii) Catalyst

Examples of catalysts used in step (i) of Scheme 4 include $NaN_3$ (sodium azide).

(iii) Reaction Temperature

The reaction temperature in step (i) of Scheme 4 may be adjusted according to the raw material compound, solvent, and the like, and is preferably −20 to 100° C.

(iv) Reaction Time

The reaction time in step (i) of Scheme 4 may be adjusted according to the raw material compound, solvent, and the like, and is preferably 3 hours to 24 hours.

(v) Operation

In step (i) of Scheme 4, it is preferable that the raw material compound (2-4) and a catalyst are dissolved in a reaction solvent and stirred at a reaction temperature. Stirring can be performed with a known stirring device.

(4-1)→(4-2) (Staudinger reduction)  (ii)

(i) Reaction Solvent

Examples of reaction solvents used in step (ii) of Scheme 4 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.

Preferred examples of reaction solvents used in step (ii) of Scheme 4 include tetrahydrofuran, water, ether, and mixed solvents thereof.

(ii) Catalyst

Examples of catalysts used in step (ii) of Scheme 4 include triphenylphosphine, which is a trivalent phosphate compound.

(iii) Reaction Temperature

The reaction temperature in step (ii) of Scheme 4 may be adjusted according to the raw material compound, solvent, and the like, and is preferably 10 to 100° C.

(iv) Reaction Time

The reaction time in step (ii) of Scheme 4 may be adjusted according to the raw material compound, solvent, and the like, and is preferably 1 hour to 24 hours.

(v) Operation

In step (ii) of Scheme 4, it is preferable that the raw material compound (4-1) and a catalyst are dissolved in a reaction solvent and stirred at a reaction temperature. Stirring can be performed with a known stirring device.

(4-2)→(4-3)  (iii)

(i) Reaction Solvent

Examples of reaction solvents used in step (iii) of Scheme 4 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 4 include methanol and mixed solvents thereof.

(ii) Catalyst

Step (iii) of Scheme 4 may be performed in the presence of a catalyst or in the absence of a catalyst.

(iii) Reaction Temperature

The reaction temperature in step (iii) of Scheme 4 may be adjusted according to the raw material compound, solvent, and the like, and is preferably 10 to 100° C.

(iv) Reaction Time

The reaction time in step (iii) of Scheme 4 may be adjusted according to the raw material compound, solvent, and the like, and is preferably 0.5 hours to 12 hours.

(v) Operation

In step (iii) of Scheme 4, it is preferable that the raw material compound (4-2), a guanidine compound (e.g., 1,3-bis(tert-butoxycarbonyl-2-(trifluoromethanesulfonyl)guanidine), and a catalyst are dissolved in a reaction solvent and stirred at a reaction temperature. Stirring can be performed with a known stirring device.

(iv) (4-3)+(1-8)→(4-4)

The reaction catalyst and the like in this step are the same as in Scheme 1 (iii).

5. Synthesis of the Following $R^1$-$R^2$-$R^3$-$R^4$ (Scheme 5)

$R^1$ $R^1$ is the same as in Scheme 1.

$R^2$ $R^2$ is the same as in Scheme 4.

$R^3$ $R^3$ represents a group represented by —$R^{32}$-$R^{33}$—, wherein $R^{32}$ represents an oxygen atom (=O), a sulfur atom (=S), or a group represented by =NH, and $R^{33}$ represents a $C_{1-5}$ alkyl group.

$R^4$ $R^4$ represents a hydrogen atom, a halogen atom, a cyano group, a $C_{1-3}$ alkoxy group, or a group represented by —$N_3$.

[Chemical Formula 20]

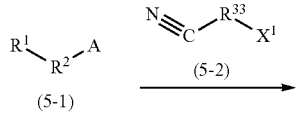

A: OH, SH, OR $NH_2$

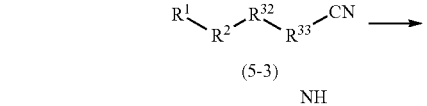

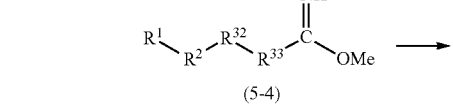

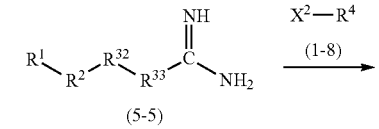

$X^1$ and $X^2$: halogen atom (5-1)+(5-2)→(5-3)  (i)

A compound represented by formula (5-1) and a compound represented by formula (5-2) can each be obtained by purchasing a commercially available product. Alternatively, they may also be produced in the same manner as known from references known to those skilled in the art. For example, the technique shown in Synthesis; English; 9; 1984; 765-766, can be used.

(i) Reaction Solvent

Examples of reaction solvents used in step (i) of Scheme 5 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 5 include dimethylformamide and mixed solvents thereof.

(ii) Catalyst

Step (i) of Scheme 5 may be performed in the presence of a catalyst or in the absence of a catalyst. Preferred examples of catalysts used in step (i) of Scheme 5 include $AgCO_3$.

(iii) Reaction Temperature

The reaction temperature in step (i) of Scheme 5 may be adjusted according to the raw material compounds, solvent, and the like, and is preferably 100 to 200° C.

(iv) Reaction Time

The reaction time in step (i) of Scheme 5 may be adjusted according to the raw material compounds, solvent, and the like, and is preferably 1 hour to 10 hours.

(v) Operation

In step (i) of Scheme 5, it is preferable that the raw material compounds (5-1) and (5-2) and a catalyst are dissolved in a reaction solvent and stirred at a reaction temperature. Stirring can be performed with a known stirring device.

(5-3)→(5-4) (Synthesis of imidate) (ii)

(i) Reaction Solvent

Examples of reaction solvents used in step (ii) of Scheme 5 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (ii) of Scheme 5 include methanol, dichloromethane, chloroform, and mixed solvents thereof.

(ii) Catalyst

Step (ii) of Scheme 5 may be performed in the presence of a catalyst or in the absence of a catalyst.

(iii) Reaction Temperature

The reaction temperature in step (ii) of Scheme 5 may be adjusted according to the raw material compound, solvent, and the like, and is preferably −50° C. to 10° C.

(iv) Reaction Time

The reaction time in step (ii) of Scheme 5 may be adjusted according to the raw material compound, solvent, and the like, and is preferably as follows.

(v) Operation

In step (ii) of Scheme 5, it is preferable that the raw material compound (5-3) and a catalyst are dissolved in a reaction solvent and bubbled with hydrogen chloride gas at a reaction temperature for 1 to 10 hours. Bubbling can be performed with a known bubbling device. It is preferable that the mixture is then allowed to stand for 5 to 24 hours.

(5-4)→(5-5) (Methoxy group→amino group substitution) (iii)

(i) Reaction Solvent

Examples of reaction solvents used in step (iii) of Scheme 5 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 5 include methanol and mixed solvents thereof.

(ii) Catalyst

Step (iii) of Scheme 5 may be performed in the presence of a catalyst or in the absence of a catalyst. Examples of catalysts used in step (iii) of Scheme 5 include $NH_4Cl$.

(iii) Reaction Temperature

The reaction temperature in step (iii) of Scheme 5 may be adjusted according to the raw material compound, solvent, and the like, and is preferably 10° C. to 100° C.

(iv) Reaction Time

The reaction time in step (iii) of Scheme 5 may be adjusted according to the raw material compound, solvent, and the like, and is preferably 0.5 to 24 hours.

(v) Operation

In step (iii) of Scheme 5, it is preferable that the raw material compound (5-4) and a catalyst are dissolved in a reaction solvent and stirred at a reaction temperature. Stirring can be performed with a known stirring device.

(5-5)+(1-8)→(5-6) (iv)

The reaction catalyst and the like in this scheme are the same as in Scheme 1 (iii).

6. Synthesis of the Following $R^1$-$R^2$-$R^3$-$R^4$ (Scheme 6)

$R^1$ $R^1$ is the same as in Scheme 1.

$R^2$ $R^2$ represents a thiazole ring.

$R^3$

—$R^3$— represents a group represented by —$R^{31}$—, —$R^{32}$-$R^{33}$—, —$R^{34}$-$R^{35}$—, or —$R^{36}$-$R^{37}$-$R^{38}$—, wherein $R^{31}$ represents a $C_{1-5}$ alkyl group, $R^{32}$ represents an oxygen atom (=O), a sulfur atom (=S), or a group represented by =NH, $R^{33}$ represents a $C_{1-5}$ alkyl group, $R^{34}$ represents a $C_{1-5}$ alkyl group, $R^{35}$ represents an oxygen atom (=O), a sulfur atom (=S), or a group represented by =NH, $R^{36}$ represents a $C_{1-5}$ alkyl group, $R^{37}$ represents an oxygen atom (=O), a sulfur atom (=S), or a group represented by =NH, and $R^{38}$ represents a $C_{1-5}$ alkyl group.

$R^4$ $R^4$ represents a group represented by —$R^{41}$-$R^{42}$, wherein $R^{41}$ represents a benzene ring, and $R^{42}$ represents a hydrogen atom, a halogen atom, a $C_{1-6}$ alkyl group, a $C_{1-3}$ alkoxy group, a $C_{1-3}$ alkylthio group, a $C_{1-3}$ halogenoalkyl group, a $C_{6-10}$ aryl group, or a $C_{7-10}$ aralkyl group.

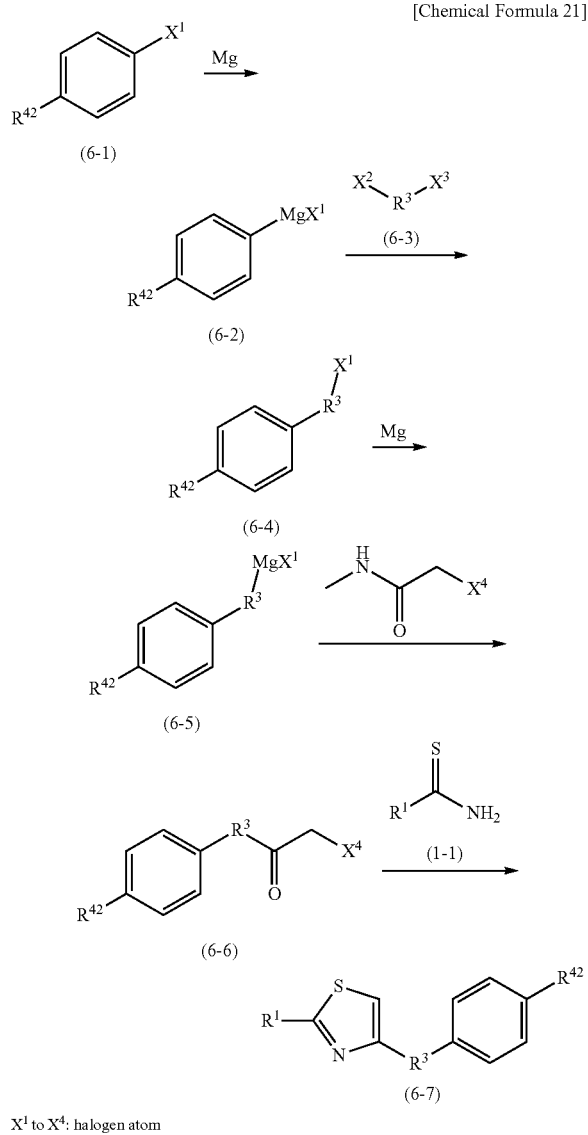

[Chemical Formula 21]

$X^1$ to $X^4$: halogen atom (6-1)→(6-2) (Addition of magnesium)  (i)

A compound represented by formula (6-1) can be obtained by purchasing a commercially available product. Alternatively, it may also be produced in the same manner as known from references known to those skilled in the art.
(i) Reaction Solvent
Examples of reaction solvents used in step (i) of Scheme 6 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof.
Preferred examples of reaction solvents used in step (i) of Scheme 6 include tetrahydrofuran and mixed solvents thereof.
(ii) Catalyst
Examples of catalysts used in step (i) of Scheme 6 include magnesium.

(iii) Reaction Temperature
The reaction temperature in step (i) of Scheme 6 may be adjusted according to the raw material compound, solvent, and the like, and is preferably 10 to 100° C.
(iv) Reaction Time
The reaction time in step (i) of Scheme 6 may be adjusted according to the raw material compound, solvent, and the like, and is preferably 1 hour to 12 hours.
(v) Operation
In step (i) of Scheme 6, it is preferable that the raw material compound (6-1) and a catalyst are slowly added to a reaction solvent, dissolved, and stirred at a reaction temperature. Stirring can be performed with a known stirring device.

(6-2)+(6-3)→(6-4) (Addition of $R^3$ group)  (ii)

A compound represented by formula (6-3) can be obtained by purchasing a commercially available product. Alternatively, it may also be produced in the same manner as known from references known to those skilled in the art.
(i) Reaction Solvent
Examples of reaction solvents used in step (ii) of Scheme 6 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (ii) of Scheme 6 include tetrahydrofuran and mixed solvents thereof.
(ii) Catalyst
Step (ii) of Scheme 6 may be performed in the presence of a catalyst or in the absence of a catalyst. Examples of catalysts used in step (iv) of Scheme 6 include CuBr and LiBr.
(iii) Reaction Temperature
The reaction temperature in step (ii) of Scheme 6 may be adjusted according to the raw material compounds, solvent, and the like, and is preferably 10 to 100° C.
(iv) Reaction Time
The reaction time in step (ii) of Scheme 6 may be adjusted according to the raw material compounds, solvent, and the like, and is preferably 1 hour to 12 hours.
(v) Operation
In step (ii) of Scheme 6, it is preferable that the raw material compounds (6-2 and 6-3) and a catalyst are dissolved in a reaction solvent and stirred at a reaction temperature. Stirring can be performed with a known stirring device.

(6-4)→(6-5) (Release of Mg)  (iii)

(i) Reaction Solvent
Examples of reaction solvents used in step (iii) of Scheme 6 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 6 include tetrahydrofuran and mixed solvents thereof.
(ii) Catalyst
Examples of catalysts used in step (iii) of Scheme 6 include magnesium.

(iii) Reaction Temperature

The reaction temperature in step (iii) of Scheme 6 may be adjusted according to the raw material compound, solvent, and the like, and is preferably 10 to 100° C.

(iv) Reaction Time

The reaction time in step (iii) of Scheme 6 may be adjusted according to the raw material compound, solvent, and the like, and is preferably 1 hour to 12 hours.

(v) Operation

In step (iii) of Scheme 6, it is preferable that the raw material compound (6-4) and a catalyst are slowly added to a reaction solvent, dissolved, and stirred at a reaction temperature. Stirring can be performed with a known stirring device.

$$(6\text{-}5) \rightarrow (6\text{-}6) \quad \text{(iv)}$$

The reaction catalyst and the like in this scheme are the same as in Scheme 1 (iii).

A compound represented by formula (6-5) is allowed to react with 2-chloro-N-methylacetamide, and thus, a compound represented by formula (6-6) can be obtained.

$$(6\text{-}6)+(1\text{-}1) \rightarrow (6\text{-}7) \quad \text{(v)}$$

The reaction catalyst and the like in this scheme are the same as in Scheme 1 (i).

6a. Synthesis of the Following $R^1$-$R^2$-$R^3$-$R^4$ (Scheme 6-1)

$R^1$ $R^1$ is the same as in Scheme 1.

$R^2$ $R^2$ represents a benzene ring, a furan ring, a pyridine ring, or a 1-phenyl-1H-pyrrole ring.

$R^3$ $R^3$ is the same as in Scheme 6.

$R^4$ $R^4$ is the same as in Scheme 6.

[Chemical Formula 22]

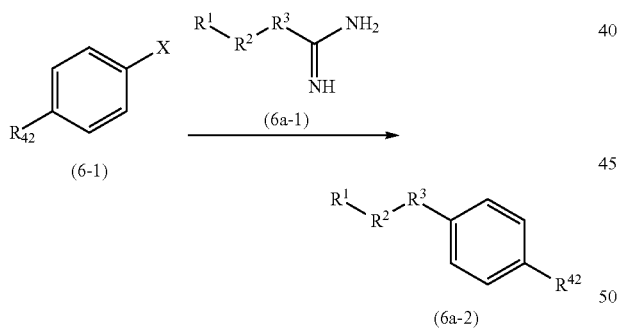

X: halogen atom $$(6\text{-}1)+(6a\text{-}1) \rightarrow (6a\text{-}2) \quad \text{(i)}$$

As a compound represented by formula (6-1), as described above, a commercially available product can be suitably used. A compound represented by formula (6a-1) can be produced in the same manner as known from references known to those skilled in the art. The reaction catalyst are the like are the same as in Scheme 1 (iii).

7. Synthesis of the Following $R^1$-$R^2$-$R^3$-$R^4$ (Scheme 7)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —$R^{41}$-$R^{42}$, wherein $R^{41}$ represents an oxazole ring, and $R^{42}$ represents a hydrogen atom, a halogen atom, a $C_{1\text{-}6}$ alkyl group, a $C_{1\text{-}3}$ alkoxy group, a $C_{1\text{-}3}$ alkylthio group, a $C_{1\text{-}3}$ halogenoalkyl group, a $C_{6\text{-}10}$ aryl group, or a $C_{7\text{-}10}$ aralkyl group.

[Chemical Formula 23]

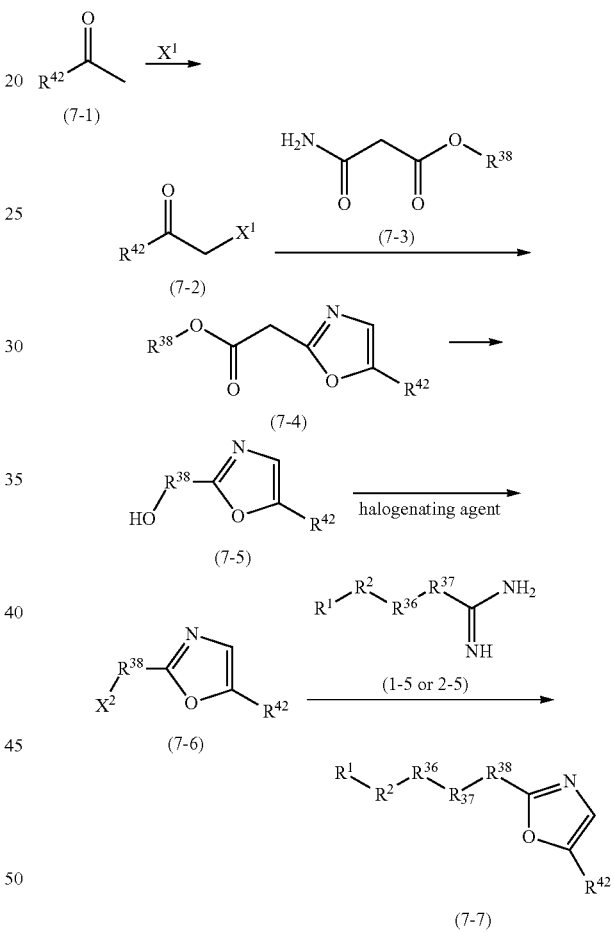

$X^1$ and $X^2$: halogen atom $$(7\text{-}1) \rightarrow (7\text{-}2) \quad \text{(i)}$$

A compound represented by formula (7-1) can be obtained by purchasing a commercially available product. Alternatively, it may also be produced in the same manner as known from references known to those skilled in the art.

(i) Reaction Solvent

Examples of reaction solvents used in step (i) of Scheme 7 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 7 include methanol and mixed solvents thereof.
(ii) Catalyst
Examples of catalysts used in step (i) of Scheme 7 include elemental halogen.
(iii) Reaction Temperature
The reaction temperature in step (i) of Scheme 7 may be adjusted according to the raw material compound, solvent, and the like, and is preferably 10 to 100° C.
(iv) Reaction Time
The reaction time in step (i) of Scheme 7 may be adjusted according to the raw material compound, solvent, and the like, and is preferably 0.5 hours to 12 hours.
(v) Operation
In step (i) of Scheme 7, it is preferable that the raw material compound (7-1) and a catalyst are dissolved in a reaction solvent and stirred at a reaction temperature. Stirring can be performed with a known stirring device.

(7-2)+(7-3)→(7-4)  (ii)

A compound represented by formula (7-3) can be obtained by purchasing a commercially available product. Alternatively, it may also be produced in the same manner as known from references known to those skilled in the art.
(i) Reaction Solvent
Examples of reaction solvents used in step (ii) of Scheme 7 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (ii) of Scheme 7 include ethanol and mixed solvents thereof.
(ii) Catalyst
Step (ii) of Scheme 7 may be performed in the presence of a catalyst or in the absence of a catalyst.
(iii) Reaction Temperature
The reaction temperature in step (ii) of Scheme 7 may be adjusted according to the raw material compounds, solvent, and the like.
(iv) Reaction Time
The reaction time in step (ii) of Scheme 7 may be adjusted according to the raw material compounds, solvent, and the like, and is preferably 24 hours to 72 hours.
(v) Operation
In step (ii) of Scheme 7, it is preferable that the raw material compounds (7-2 and 7-3) and a catalyst are dissolved in a reaction solvent and refluxed at a reaction temperature. Refluxing can be performed with a known refluxing device.

(7-4)→(7-5) (Reduction)  (iii)

The reaction catalyst and the like in this step are the same as in Scheme 2 (i).

(7-5)→(7-6) (Halogenation of alcohol)  (iv)

The reaction catalyst and the like are the same as in Scheme 2 (ii).

(7-6)+(1-5) or (2-5)→(7-7)  (v)

The reaction catalyst and the like are the same as in Scheme 1 (iii).

8. Synthesis of the Following $R^1$-$R^2$-$R^3$-$R^4$ (Scheme 8)
$R^1$
$\quad R^1$ is the same as in Scheme 1.
$R^2$
$\quad R^2$ is the same as in Scheme 4.
$R^3$
$\quad R^3$ is the same as in Scheme 6.
$R^4$
$\quad R^4$ is a group represented by —$R^{41}$-$R^{42}$, wherein
$\quad R^{41}$ represents a tetrahydropyridine ring, and
$\quad R^{42}$ represents
$\quad$ a hydrogen atom,
$\quad$ a halogen atom,
$\quad$ a $C_{1-5}$ alkyl group,
$\quad$ a $C_{1-3}$ alkoxy group,
$\quad$ a $C_{1-3}$ alkylthio group,
$\quad$ a $C_{1-3}$ halogenoalkyl group,
$\quad$ a $C_{6-10}$ aryl group, or
$\quad$ a $C_{7-10}$ aralkyl group.

[Chemical Formula 24]

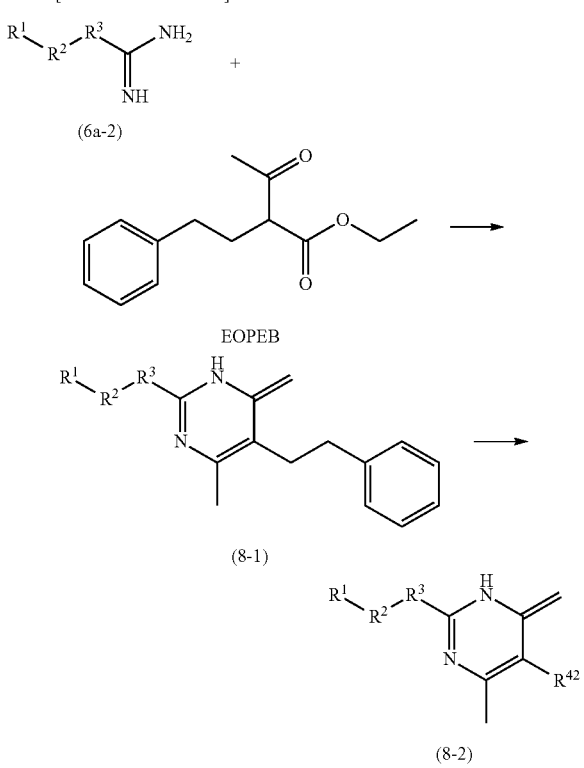

(6a-2)→(8-1)  (i)

(i) Reaction Solvent
Examples of reaction solvents used in step (i) of Scheme 8 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 8 include methanol and mixed solvents thereof.

(ii) Catalyst

Examples of catalysts used in step (i) of Scheme 8 include NaOH and $CH_3ONa$.

(iii) Reaction Temperature

The reaction temperature in step (i) of Scheme 8 may be adjusted according to the raw material compound, solvent, and the like, and is preferably 10° C. to 100° C.

(iv) Reaction Time

The reaction time in step (i) of Scheme 8 may be adjusted according to the raw material compound, solvent, and the like, and is preferably 2 hours to 24 hours.

(v) Operation

In step (i) of Scheme 8, it is preferable that the raw material compound (6a-2), ethyl 3-oxo-2-(2-phenylethyl) butanoate (EOPEB; commercially available product), and a catalyst are dissolved in a reaction solvent and stirred at a reaction temperature. Stirring can be performed with a known stirring device.

$$(8\text{-}1) \rightarrow (8\text{-}2) \quad \text{(ii)}$$

The $C_6H_5CH_2CH_2$— group of a compound represented by formula (8-1) can be substituted with an $R^{42}$ group by a method known from references known to those skilled in the art.

9. Synthesis of $R^1$-$R^2$-$R^3$-$R^4$ (Scheme 9)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —C($NH_2$)=$NR^{43}$, wherein $R^{43}$ represents a hydrogen atom or —$SO_2$-$R^{431}$, wherein $R^{431}$ represents an amino group, a $C_{1-3}$ halogenoalkyl group, or a $C_{6-10}$ aryl group.

[Chemical Formula 25]

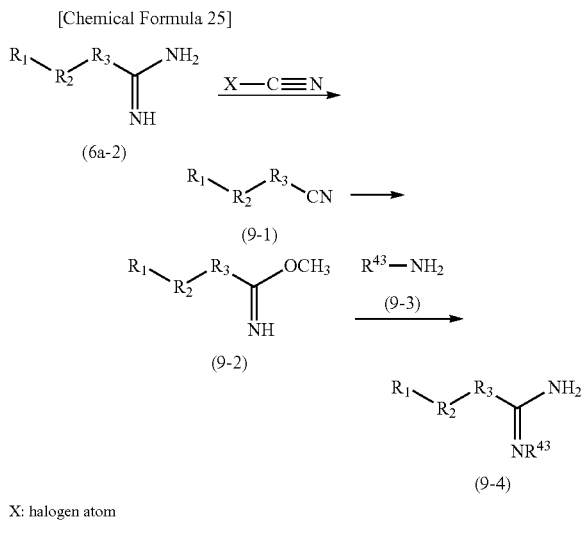

X: halogen atom $$(6a\text{-}2) \rightarrow (9\text{-}1) \quad \text{(i)}$$

The reaction catalyst and the like in this step are the same as in Scheme 1 (iii).

A compound represented by formula (6a-2) is allowed to react with X—CN (X: halogen atom), and thus, a compound represented by formula (9-1) can be obtained.

$$(9\text{-}1) \rightarrow (9\text{-}2) \quad \text{(ii)}$$

The reaction catalyst and the like in this step are the same as in Scheme 5 (ii).

$$(9\text{-}2) + (9\text{-}3) \rightarrow (9\text{-}4) \quad \text{(iii)}$$

A compound represented by formula (9-3) can be obtained by purchasing a commercially available product. Alternatively, it may also be produced in the same manner as known from references known to those skilled in the art.

(i) Reaction Solvent

Examples of reaction solvents used in step (iii) of Scheme 9 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 9 include methanol and mixed solvents thereof.

(ii) Catalyst

Step (iii) of Scheme 9 may be performed in the presence of a catalyst or in the absence of a catalyst. Examples of catalysts used in step (i) of Scheme 1 include $NH_4Cl$.

(iii) Reaction Temperature

The reaction temperature in step (iii) of Scheme 9 may be adjusted according to the raw material compounds, solvent, and the like, and is preferably 10 to 100° C.

(iv) Reaction Time

The reaction time in step (iii) of Scheme 9 may be adjusted according to the raw material compounds, solvent, and the like, and is preferably 0.5 hours to 24 hours.

(v) Operation

In step (iii) of Scheme 9, it is preferable that the raw material compounds (9-2 and 9-3) and a catalyst are dissolved in a reaction solvent and stirred at a reaction temperature. Stirring can be performed with a known stirring device.

10. Synthesis of the Following $R^1$-$R^2$-$R^3$-$R^4$ (Scheme 10)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —NHC(NH($R^{46}$))=$R^{44}R^{45}$, wherein $R^{44}$ represents a carbon atom or a nitrogen atom, $R^{45}$ represents a hydrogen atom, a cyano group, or a $C_{1-5}$ nitro group, and $R^{46}$ represents a hydrogen atom or a $C_{1-5}$ alkyl group.

{Chemical Formula 26}

-continued

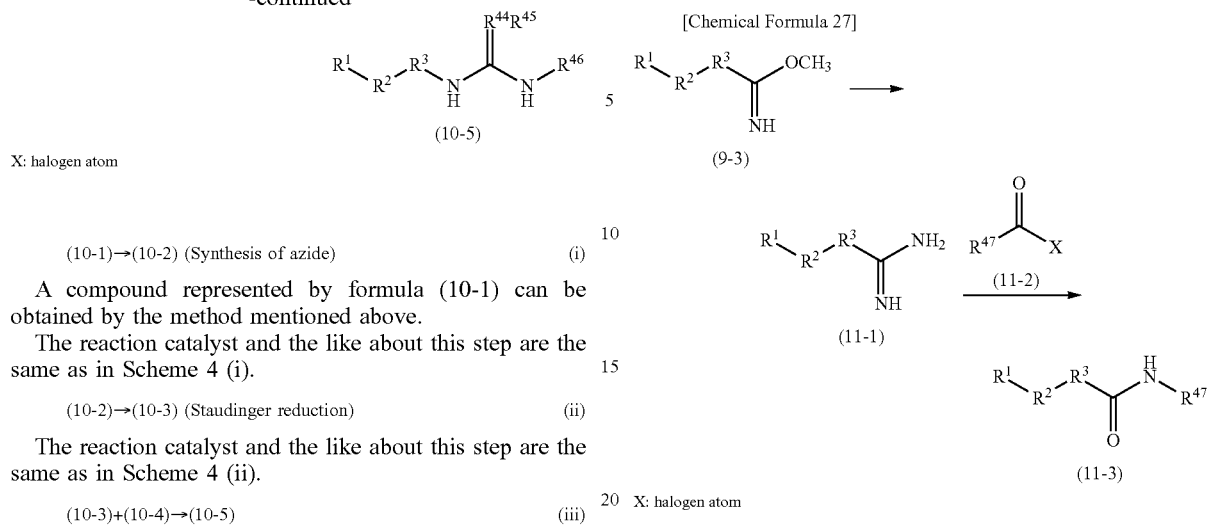

(10-5)

X: halogen atom (10-1)→(10-2) (Synthesis of azide)  (i)

A compound represented by formula (10-1) can be obtained by the method mentioned above.

The reaction catalyst and the like about this step are the same as in Scheme 4 (i).

(10-2)→(10-3) (Staudinger reduction)  (ii)

The reaction catalyst and the like about this step are the same as in Scheme 4 (ii).

(10-3)+(10-4)→(10-5)  (iii)

A compound represented by formula (10-4) can be obtained by purchasing a commercially available product. Alternatively, it may also be produced in the same manner as known from references known to those skilled in the art.
(i) Reaction Solvent Examples of reaction solvents used in step (iii) of Scheme 10 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 10 include methanol and mixed solvents thereof.
(ii) Catalyst Step (iii) of Scheme 10 may be performed in the presence of a catalyst or in the absence of a catalyst. Examples of catalysts used in step (iii) of Scheme 10 include $Et_3N$.
(iii) Reaction Temperature The reaction temperature in step (iii) of Scheme 10 may be adjusted according to the raw material compounds, solvent, and the like, and is preferably 10 to 100° C.
(iv) Reaction Time The reaction time in step (iii) of Scheme 10 may be adjusted according to the raw material compounds, solvent, and the like, and is preferably 2 hours to 24 hours.
(v) Operation In step (iii) of Scheme 10, it is preferable that the raw material compounds (10-3) and (10-4) and a catalyst are dissolved in a reaction solvent, and then stirred or refluxed at a reaction temperature. Stirring can be performed with a known stirring device, and refluxing can be performed with a known refluxing device.

11. Synthesis of the Following $R^1$-$R^2$-$R^3$-$R^4$ (Scheme 11)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —C(=O)NHR$^{47}$, wherein $R^{47}$ represents a $C_{1-5}$ alkyl group or —CO—R$^{471}$, wherein $R^{471}$ represents a $C_{1-5}$ alkyl group or a $C_{6-10}$ aryl group.

[Chemical Formula 27]

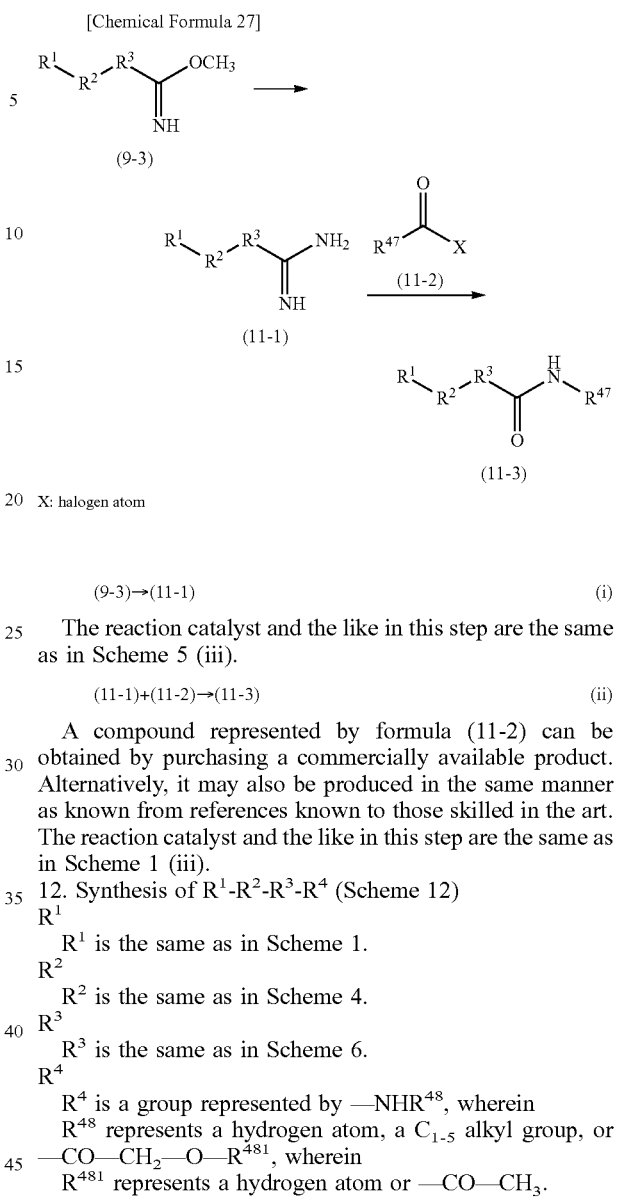

X: halogen atom (9-3)→(11-1)  (i)

The reaction catalyst and the like in this step are the same as in Scheme 5 (iii).

(11-1)+(11-2)→(11-3)  (ii)

A compound represented by formula (11-2) can be obtained by purchasing a commercially available product. Alternatively, it may also be produced in the same manner as known from references known to those skilled in the art. The reaction catalyst and the like in this step are the same as in Scheme 1 (iii).

12. Synthesis of $R^1$-$R^2$-$R^3$-$R^4$ (Scheme 12)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —NHR$^{48}$, wherein $R^{48}$ represents a hydrogen atom, a $C_{1-5}$ alkyl group, or —CO—CH$_2$—O—R$^{481}$, wherein $R^{481}$ represents a hydrogen atom or —CO—CH$_3$.

[Chemical Formula 28]

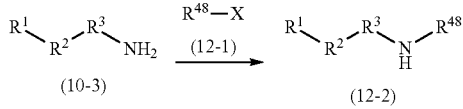

X: halogen atom (10-3)+(12-1)→(12-2) (Synthesis of amide compound)  (i)

A compound represented by formula (12-1) can be produced by the method mentioned above.
(i) Reaction Solvent Examples of reaction solvents used in step (i) of Scheme 12 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 12 include tetrahydrofuran, methanol, and mixed solvents thereof.

(ii) Catalyst

Step (i) of Scheme 12 may be performed in the presence of a catalyst or in the absence of a catalyst. Examples of catalysts used in step (i) of Scheme 12 include Et3N and pyridine.

(iii) Reaction Temperature

The reaction temperature in step (i) of Scheme 12 may be adjusted according to the raw material compounds, solvent, and the like, and is preferably −20 to 100° C.

(iv) Reaction Time

The reaction time in step (i) of Scheme 12 may be adjusted according to the raw material compounds, solvent, and the like, and is preferably 1 hour to 72 hours.

(v) Operation

In step (i) of Scheme 12, it is preferable that the raw material compounds (10-3) and (12-1) and a catalyst are dissolved in a reaction solvent and stirred at a reaction temperature. Stirring can be performed with a known stirring device.

13. Synthesis of the Following $R^1$-$R^2$-$R^3$-$R^4$ (Scheme 13)

$R^1$ $R^1$ is the same as in Scheme 1.

$R^2$ $R^2$ is the same as in Scheme 4.

$R^3$ $R^3$ is the same as in Scheme 6.

$R^4$ $R^4$ is a group represented by —N═C(NH$_2$)—NHR$^{50}$, wherein $R^{50}$ represents a hydrogen atom or —SO$_2$—R$^{501}$, wherein $R^{501}$ represents an amino group, a $C_{1-3}$ halogenoalkyl group, or a $C_{6-10}$ aryl group.

[Chemical Formula 29]

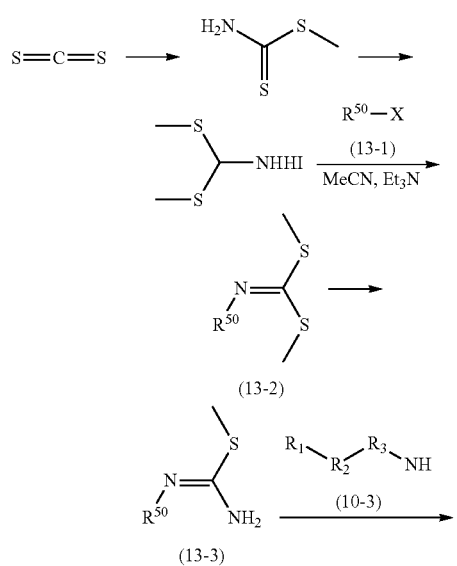

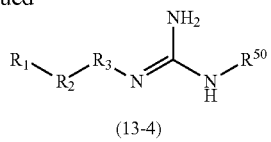

X: halogen atom

S,S-dimethyliminodithiocarbonate hydroiodide+(13-1)→(13-2)                (i)

S,S-dimethyliminodithiocarbonate hydroiodide can be obtained using a conventional method or the technique shown in Synthesis, 1985, 948-949, for example.

A compound represented by formula (13-1) can be obtained using a conventional method or the technique shown in Chemische Berichte (1958), 91, 1339-41, for example.

(i) Reaction Solvent

Examples of reaction solvents used in step (i) of Scheme 13 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 13 include acetonitrile, dichloromethane, and mixed solvents thereof.

(ii) Catalyst

Step (i) of Scheme 13 may be performed in the presence of a catalyst or in the absence of a catalyst. Examples of catalysts used in step (i) of Scheme 13 include triethylamine.

(iii) Reaction Temperature

The reaction temperature in step (i) of Scheme 13 may be adjusted according to the raw material compounds, solvent, and the like, and is preferably −100° C. to 100° C.

(iv) Reaction Time

The reaction time in step (i) of Scheme 13 may be adjusted according to the raw material compounds, solvent, and the like, and is preferably 2 hours to 24 hours.

(v) Operation

In step (i) of Scheme 13, it is preferable that the raw material compounds (13-1 and S,S-dimethyliminodithiocarbonate hydroiodide) and a catalyst are dissolved in a reaction solvent and stirred at a reaction temperature. Stirring can be performed with a known stirring device.

(13-2)→(13-3) (Methylthio Group→Amino Group substitution)                (ii)

(i) Reaction Solvent

Examples of reaction solvents used in step (ii) of Scheme 13 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (ii) of Scheme 13 include toluene and mixed solvents thereof.

(ii) Catalyst

Step (ii) of Scheme 13 may be performed in the presence of a catalyst or in the absence of a catalyst. Examples of catalysts used in step (ii) of Scheme 13 include ammonia.

(iii) Reaction Temperature

The reaction temperature in step (ii) of Scheme 13 may be adjusted according to the raw material compound, solvent, and the like, and is preferably 10° C. to 100° C.

(iv) Reaction Time

The reaction time in step (ii) of Scheme 13 may be adjusted according to the raw material compound, solvent, and the like, and is preferably 5 minutes to 10 hours.

(v) Operation

In step (ii) of Scheme 13, it is preferable that the raw material compound (13-2) and a catalyst are dissolved in a reaction solvent at a reaction temperature.

(13-3)+(10-3)→(13-4)  (iii)

(i) Reaction Solvent

Examples of reaction solvents used in step (iii) of Scheme 13 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (iii) of Scheme 13 include methanol and mixed solvents thereof.

(ii) Catalyst

Step (iii) of Scheme 13 may be performed in the presence of a catalyst or in the absence of a catalyst.

(iii) Reaction Temperature

The reaction temperature in step (iii) of Scheme 13 may be adjusted according to the raw material compounds, solvent, and the like, and is preferably 10 to 100° C.

(iv) Reaction Time

The reaction time in step (iii) of Scheme 13 may be adjusted according to the raw material compounds, solvent, and the like, and is preferably 2 hours to 24 hours.

(v) Operation

In step (iii) of Scheme 13, it is preferable that the raw material compounds (13-3 and 10-3) and a catalyst are dissolved in a reaction solvent and heated at a reaction temperature. Heating can be performed with a known heating device.

14. Synthesis of the Following $R^1$-$R^2$-$R^3$-$R^4$ (Scheme 14)

$R^1$ $R^1$ represents a group represented by $R^{13}R^{14}N(R^{15}R^{16}N)C=N-$.

$R^{11}$, $R^{12}$, $R^{13}$, $R^{14}$, $R^{15}$, and $R^{16}$ may be the same or different and represent a hydrogen atom, a halogen atom, a nitro group, a $C_{1-5}$ alkyl group, a $C_{1-3}$ alkoxy group, a $C_{1-3}$ alkylthio group, a $C_{1-3}$ halogenoalkyl group, a $C_{6-10}$ aryl group, or an imidazolidine wherein adjacent $R^{13}$ and $R^{15}$, a nitrogen atom, and a carbon atom are joined together to form a ring.

$R^2$ $R^2$ is the same as in Scheme 4.

$R^3$ $R^3$ is the same as in Scheme 6.

$R^4$ $R^4$ represents a hydrogen atom, a halogen atom, a cyano group, a $C_{1-3}$ alkoxy group, a group represented by $-N_3$, a group represented by $-R^{41}$-$R^{42}$, a group represented by $-C(NH_2)=NR^{43}$, a group represented by $-NHC(NH(R^{46}))=R^{44}R^{45}$, a group represented by $-C(=O)NHR^{47}$, a group represented by $-NHR^{48}$, a group represented by $-C(OCH_3)=R^{49}$, or a group represented by $-N=C(NH_2)-NHR^{50}$.

$R^{41}$ represents ($R^{41}$ of V, V', V" of the table), $R^{42}$ represents a hydrogen atom, a halogen atom, a $C_{1-6}$ alkyl group, a $C_{1-3}$ alkoxy group, a $C_{1-3}$ alkylthio group, a $C_{1-3}$ halogenoalkyl group, a $C_{6-10}$ aryl group, or a $C_{7-10}$ aralkyl group, $R^{43}$ represents a hydrogen atom or $-SO_2$-$R^{431}$, wherein $R^{431}$ represents an amino group, a $C_{1-3}$ halogenoalkyl group, or a $C_{6-40}$ aryl group, $R^{44}$ represents a carbon atom or a nitrogen atom, $R^{45}$ represents a hydrogen atom, a cyano group, or a $C_{1-5}$ nitro group, $R^{46}$ represents a hydrogen atom or a $C_{1-5}$ alkyl group, $R^{47}$ represents a $C_{1-5}$ alkyl group or $-CO-R^{471}$, wherein $R^{471}$ represents a $C_{1-5}$ alkyl group or a $C_{6-10}$ aryl group, $R^{48}$ represents a hydrogen atom, a $C_{1-5}$ alkyl group, or $-CO-CH_2-O-R^{481}$, wherein $R^{481}$ represents a hydrogen atom or $-CO-CH_3$, $R^{49}$ represents an oxygen atom or a group represented by $=NH$, and $R^{50}$ represents a hydrogen atom or $-SO_2$-$R^{501}$, wherein $R^{501}$ represents an amino group, a $C_{1-3}$ halogenoalkyl group, or a $C_{6-10}$ aryl group.

[Chemical Formula 30]

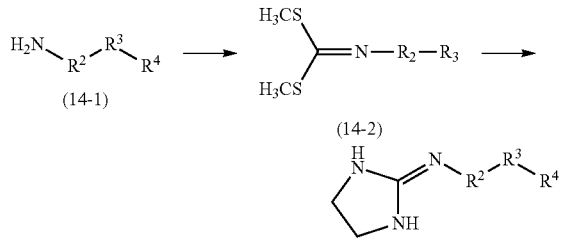

(14-1)→(14-2)  (i)

A compound represented by formula (14-1) can be produced by the method mentioned above.

(i) Reaction Solvent

Examples of reaction solvents used in step (i) of Scheme 14 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (i) of Scheme 14 include dimethylformamide.

(ii) Catalyst

Step (i) of Scheme 14 may be performed in the presence of a catalyst or in the absence of a catalyst. Examples of catalysts used in step (i) of Scheme 14 include NaOH, $CS_2$, and $CH_3I$.

(iii) Reaction Temperature

The reaction temperature in step (i) of Scheme 14 may be adjusted according to the raw material compound, solvent, and the like, and is preferably −50 to 50° C.

(iv) Reaction Time

The reaction time in step (i) of Scheme 14 may be adjusted according to the raw material compound, solvent, and the like, and is preferably 1 hour to 24 hours.

(v) Operation

In step (i) of Scheme 14, it is preferable that the raw material compound (14-1) and a catalyst are dissolved in a reaction solvent and stirred at a reaction temperature. Stirring can be performed with a known stirring device.

(14-2)→(14-3)  (ii)

(i) Reaction Solvent

Examples of reaction solvents used in step (ii) of Scheme 14 include ether solvents such as dioxane and tetrahydrofuran; alcohol solvents such as methanol and ethanol; polar solvents such as dimethylformamide, dimethylsulfoxide, acetonitrile, and acetone; halogen solvents such as dichloromethane and chloroform; hydrocarbon solvents such as benzene and toluene; ester solvents such as ethyl acetate and butyl acetate; water; and mixed solvents thereof. Preferred examples of reaction solvents used in step (ii) of Scheme 14 include dimethylformamide.

(ii) Catalyst

Step (ii) of Scheme 14 may be performed in the presence of a catalyst or in the absence of a catalyst. Examples of catalysts used in step (i) of Scheme 1 include ethylenediamine.

(iii) Reaction Temperature

The reaction temperature in step (ii) of Scheme 14 may be adjusted according to the raw material compound, solvent, and the like, and is preferably 50° C. to 150° C.

(iv) Reaction Time

The reaction time in step (ii) of Scheme 14 may be adjusted according to the raw material compound, solvent, and the like, and is preferably 2 hours to 24 hours.

(v) Operation

In step (ii) of Scheme 14, it is preferable that the raw material compound (14-2) and a catalyst are dissolved in a reaction solvent and stirred at a reaction temperature. Stirring can be performed with a known stirring device.

Scheme 15

Scheme 15 is a reaction scheme to obtain a compound of formula (A-3) (guanidine compound) from a compound of formula (A-1).

[Chemical Formula 31]

(A-1)

↓

(A-2)

↓

(A-3)

In the above formula, $R^2$ represents a group represented by formula (II), formula (III), or formula (IV). These are equivalent to $R^{21}$, $R^{22}$, and $R^{23}$, respectively. Incidentally, in formula (II) to formula (IV), the point of attachment to the nitrogen atom (N) adjacent to $R^1$ is indicated with the symbol (*).

[Chemical Formula 32]

(II)

[Chemical Formula 33]

(III)

[Chemical Formula 34]

(IV)

Further, $R^{37}$ represents a methylene group (—$CH_2$—), an oxygen atom (—O—), or a sulfur atom (—S—). When $R^{37}$ is a methylene group (—$CH_2$—), an oxygen atom (—O—), and a sulfur atom (—S—), the compounds of formula (A-1) are 5-chloro-pentanoyl chloride, (2-chloro-ethoxy)-acetyl chloride, and (2-chloro-ethylsulfanyl)-acetyl chloride, respectively. These compounds are commercially available.

[Chemical Formula 35]

From a compound of formula (A-1), a compound of formula (A-2) can be obtained as follows. The following synthesis method may be performed with reference to the methods disclosed in, for example, the specification of U.S. Pat. No. 4,362,736 and J. Med. Chem., 2004, 47, 2935. That is, compounds represented by formula (A-1) are commercially available and thus each obtained. While stirring an ether solution of diazomethane prepared with potassium hydroxide, chloroform, and hydrazine with ice-cooling, a compound represented by formula (A-1) is added dropwise and then allowed to stand. Subsequently, hydrogen chloride gas is passed through the solution, and sodium hydroxide is added to separate the ether layer. The ether layer is washed with water, dried over magnesium sulfate, and distilled off. The residue is distilled at reduced pressure, and thus, a compound represented by formula (A-2) can be obtained.

From a compound of formula (A-2), a compound of formula (A-3) can be obtained as follows. The following synthesis method may be performed with reference to the methods disclosed in, for example, Macromol. Rapid Commun., 2006, 27, 1739, J. Org. Chem., 1982, 47, 4327, J. Org. Chem., 1998, 63, 2796, and Tetrahedron Letters, 1997, 38, 1065. A mixed solution of a compound of formula (A-2) and guanylthiourea using acetone as a solvent is stirred and refluxed. After confirming the disappearance of the starting material by thin-layer chromatography (TLC), the solvent is removed at reduced pressure, and the residue is purified by chromatography (dichloromethane/methanol, 50/1). In this manner, a compound of formula (A-3) can be obtained.

Here, by using a compound having a group represented by formula (III) or formula (IV) in place of guanylthiourea, a compound of formula (A-3) wherein $R^2$ is represented by formula (III) or formula (IV) can be obtained.

Scheme 16

Scheme 16 is a reaction scheme to obtain a compound of formula (A-6) from a compound of formula (A-3).

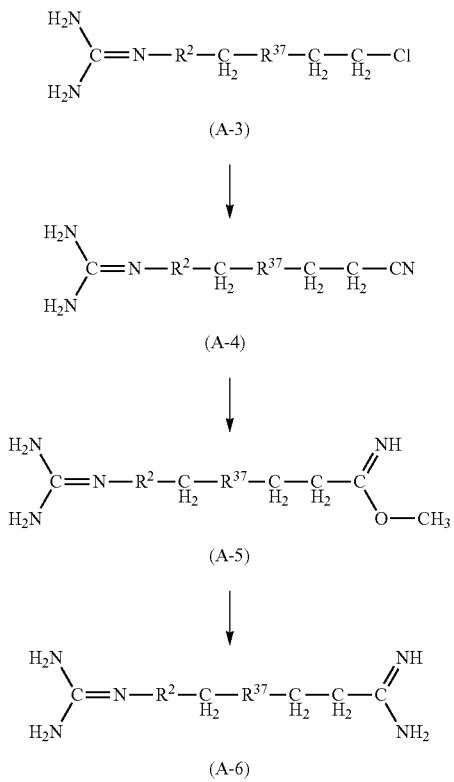

From a compound of formula (A-3), a compound of formula (A-4) can be obtained as follows. The following synthesis method may be performed with reference to the methods disclosed in, for example, the specification of U.S. Pat. No. 4,362,736 and J. Med. Chem., 2004, 47, 2935. A compound of formula (A-3) and sodium cyanide are added to dimethylsulfoxide, and the solution is heated at 75° C. overnight. Subsequently, the reaction liquid is removed at reduced pressure, and the residue is purified using chromatography (dichloromethane/methanol, 50/1). In this manner, a compound of formula (A-4) can be obtained.

From a compound of formula (A-4), a compound of formula (A-5) can be obtained as follows. The following synthesis method may be performed with reference to the method disclosed in J. Med. Chem. 1983, 26, 140. A solution of a compound of formula (A-4) using anhydrous methanol and chloroform as solvents is cooled to 0° C., and, while maintaining the same temperature, dry hydrogen chloride gas is continuously bubbled into the mixture for 3 hours. Subsequently, the mixture is maintained at 0 to 4° C. for 20 hours and then concentrated at reduced pressure to give a crystalline solid of imide hydrochloride. The reaction mixture is added to ice-cooled water containing an excess of potassium carbonate to give free imidic acid. The mixed solution is filtered, and the residue is washed with ethanol, and thus, a compound of formula (A-5) can be obtained.

From a compound of formula (A-5), a compound of formula (A-6) can be obtained as follows. The following synthesis method may be performed with reference to the method disclosed in J. Med. Chem. 1983, 26, 140. Ammonium chloride is added to a solution of a compound of formula (A-5) using methanol as a solvent. The reaction mixture is stirred at room temperature for 12 hours. After confirming the disappearance of the starting material by thin-layer chromatography (TLC), the solvent is removed at reduced pressure, and the residue is purified by chromatography (dichloromethane/methanol/ammonia monohydrate, 200/20/1), and thus, a compound of formula (A-6) can be obtained.

Scheme 17 (Scheme to Obtain a Compound Wherein $R^4$ is Represented by Formula (V))

Scheme 17 is a reaction scheme to obtain a compound of formula (A-7) from a compound of formula (A-6).

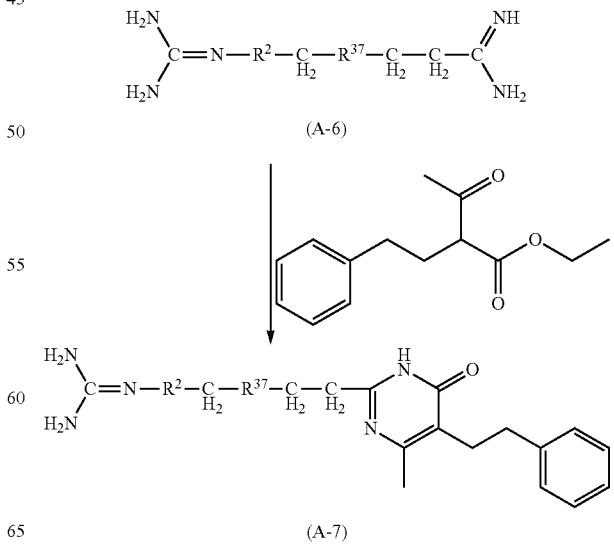

From a compound of formula (A-6), a compound of formula (A-7) can be obtained as follows. The following synthesis method may be performed with reference to the methods disclosed in, for example, J. Am. Chem. Soc., 1949, 71, 616, and the specification of U.S. Pat. No. 4,362,736. A compound of formula (A-6) and sodium ethoxide are added to anhydrous methanol at room temperature. Subsequently, commercially available ethyl 3-oxo-2-(2-phenylethyl)butanoate (EOPEB) is added to the solution and stirred at room temperature for 12 hours. After confirming the disappearance of the starting material by thin-layer chromatography (TLC), the solvent is removed at reduced pressure, and the residue is purified by chromatography (dichloromethane/methanol, 50/1), and thus, a compound of formula (A-7) can be obtained.

By using compounds wherein the phenyl group of 3-oxo-2-(2-oxo-2-phenyl-ethyl)-butyric acid ethyl ester or hydrogen atoms at other positions are substituted with other groups, compounds wherein $R^4$ is represented by formula (V) (i.e., $R^5$), wherein $R^{51}$ to $R^{54}$ are various substituents, can be synthesized.

Scheme 18 (Scheme to Obtain a Compound Wherein $R^4$ is Represented by Formula (VI))

Scheme 18 is a scheme to obtain a compound wherein $R^4$ is represented by formula (VI).

[Chemical Formula 38]

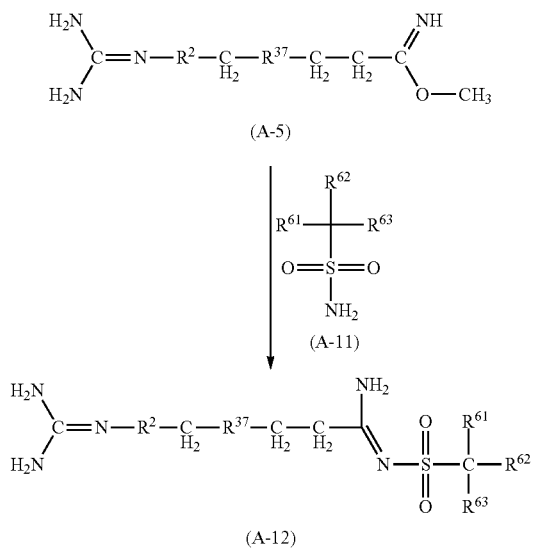

A compound wherein $R^4$ is represented by formula VI can be obtained as follows. The following synthesis method may be performed with reference to the methods disclosed in the specification of U.S. Pat. No. 4,362,736 and J. Med. Chem., 2004, 47, 2935. An anhydrous methanol/chloroform solution of a compound of formula (A-4) is cooled to 0° C., and then dry hydrogen chloride gas is bubbled into the mixture at the same temperature for 3 hours. Subsequently, the mixed solution is maintained at 0 to 4° C. for 20 hours and then concentrated at reduced pressure to give a crystalline solid of imide hydrochloride. The reaction mixture is added to ice-cooled water containing an excess of potassium carbonate to give free imidic acid. The mixed solution is filtered, and the residue is washed with ethanol to give a compound of formula (A-5). The compound of formula (A-5) is dissolved in methanol, and trifluoromethanesulfonamide is added to the solution. The reaction mixture is stirred at room temperature for 12 hours. After confirming the disappearance of the starting material by thin-layer chromatography (TLC), the solvent is removed at reduced pressure, and the residue is purified by chromatography (dichloromethane/methanol, 30/1), and thus, a compound of formula (A-12), wherein $R^4$ is represented by formula VI, can be obtained.

As described above, a compound represented by formula (A-12) can be obtained by allowing a sulfonamide compound represented by formula (A-11) to act on a compound represented by Scheme 16 (A-5).

$R^{61}$, $R^{62}$, and $R^{63}$ may be the same or different and represent a hydrogen atom, a methyl group, an ethyl group, or a halogen atom. Preferred examples of $R^{61}$, $R^{62}$, and $R^{63}$ include halogen atoms, more preferably a fluorine atom.

Scheme 19 (Scheme to Obtain a Compound Wherein $R^3$ is Represented by Formula (VIII))

Scheme 19 is a scheme to obtain a compound wherein $R^3$ is represented by formula (VIII).

[Chemical Formula 39]

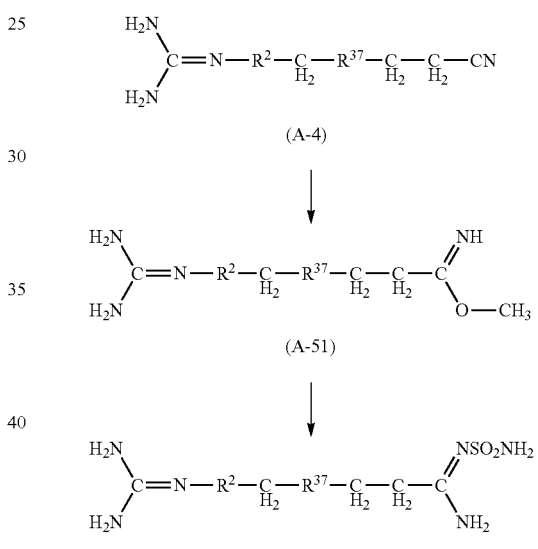

An anhydrous methanol/chloroform (10 ml/20 ml) solution of the compound represented by formula (A-4) described above is cooled to 0° C., and then hydrogen chloride gas is bubbled into the mixture at the same temperature. The mixed solution is maintained at 0 to 4° C. for 20 hours, for example. The solution is concentrated at reduced pressure, and thus, a crystalline solid of imide hydrochloride can be obtained. The solution is added to ice-cooled water containing an excess of potassium carbonate, and thus, free imidic acid can be obtained. The solution is filtered, and the residue is washed with ethanol, and thus, a compound represented by formula (A-51) can be obtained. The compound represented by formula (A-51) is dissolved in methanol, and diamide sulfate is added to the solution. The reaction mixture is stirred at room temperature. After confirming the disappearance of the starting material by thin-layer chromatography (TLC), the solvent is removed at reduced pressure, and the residue is purified by chromatography. In this manner, a compound represented by formula (A-52) can be obtained.

Scheme 20 (Scheme to Obtain a Compound Wherein $R^4$ is Represented by Formula (IX))

Scheme 20 is a scheme to obtain a compound wherein $R^4$ is represented by formula (IX).

[Chemical Formula 40]

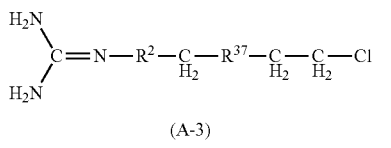

(A-3)

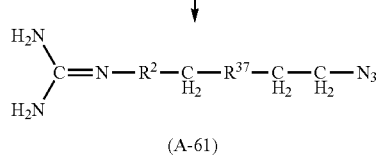

(A-61)

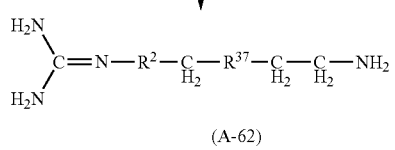

(A-62)

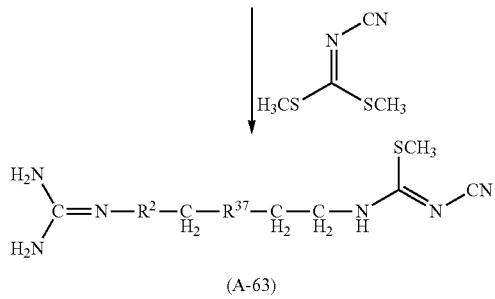

(A-63)

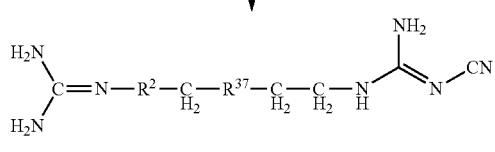

(A-64)

The following process can be performed with reference to the following literatures.

a) U.S. Pat. No. 4,362,736 A; b) J. Med. Chem., 2004, 47, 2935, Macromol. Rapid Commun., 2006, 27, 1739; c) J. Org. Chem., 1982, 47, 4327; J. Org. Chem., 1998, 63, 2796; d) Tetrahedron Letters, 1997, 38, 1065., J. Med. Chem., 1983, 26, 140; e) J. Am. Chem. Soc, 1959, 81, 2220; f) J. Am. Chem. Soc, 1959, 81, 4635., Macromol. Rapid Commun., 2006, 27, 1739; g) J. Org. Chem., 1982, 47, 4327.

The compound represented by formula (A-3) obtained above, dimethylsulfoxide, and sodium azide are mixed and then heated to 75° C. with stirring. After confirming the disappearance of the starting material by thin-layer chromatography (TLC), the solvent is removed at reduced pressure, and the residue is purified by chromatography, and thus, a compound represented by formula (A-61) can be obtained.

Triphenylphosphine is added to a tetrahydrofuran/aqueous solution of the compound represented by formula (A-61). The reaction solution is stirred at room temperature. After confirming the disappearance of the starting material by thin-layer chromatography (TLC), the solvent is removed at reduced pressure, and then ethanol is added to the residue to cause crystallization, and thus, a compound represented by formula (A-62) can be obtained.

A liquid mixture of anhydrous methanol, the compound represented by formula (A-62), 3,3-bis(methylthio)acrylonitrile, and triethylamine is stirred at room temperature in a nitrogen atmosphere for 12 hours. After confirming the disappearance of the starting material by thin-layer chromatography (TLC), the solvent is removed at reduced pressure. The collected residue is washed with diethyl ether and dried, and thus, a compound represented by formula (A-63) can be obtained. Aqueous ammonia is added to a methanol solution of the compound represented by (A-63) and refluxed all night. After confirming the disappearance of the starting material by thin-layer chromatography (TLC), the solvent is removed at reduced pressure, and then the residue is purified by chromatography, and thus, a compound represented by formula (A-64) can be obtained.

Scheme 21 (Scheme to Obtain a Compound Wherein $R^4$ is Represented by Formula (VII))

Scheme 21 is a scheme to obtain a compound wherein $R^4$ is represented by formula (VII).

[Chemical Formula 41]

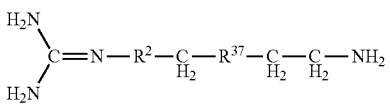

(A-62)

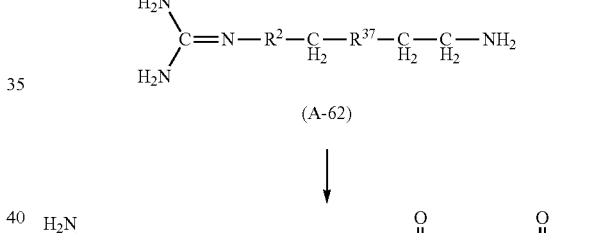

(A-71)

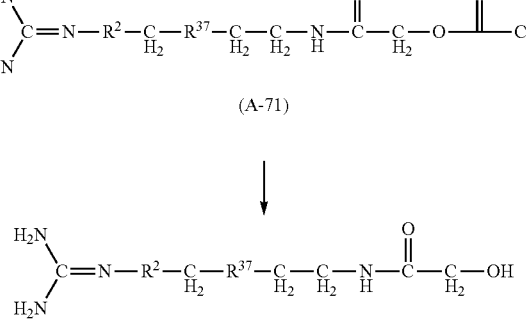

(A-72)

This scheme can be performed with reference to the following literatures.

a) J. Med. Chem., 1983, 26, 140; b) J. Am. Chem. Soc, 1959, 81, 2220; c) J. Am. Chem. Soc, 1959, 81, 4635; d) Macromol. Rapid Commun., 2006, 27, 1739; J. Org. Chem., 1982, 47, 4327.

A liquid mixture of 10 ml of anhydrous methanol, a compound represented by formula (A-62), 3,3-bis(methylthio)acrylonitrile, and triethylamine is stirred at room temperature in a nitrogen atmosphere. After confirming the disappearance of the starting material by thin-layer chromatography (TLC), the solvent is removed at reduced pressure.

The collected residue is washed with diethyl ether and dried, and thus, a compound represented by formula (A-71) can be obtained. Aqueous ammonia is added to a methanol solution of the compound represented by (A-71) and refluxed all night. After confirming the disappearance of the starting material by thin-layer chromatography (TLC), the solvent is removed at reduced pressure, and then the residue is purified by chromatography, and thus, a compound represented by formula (A-72) can be obtained.

In particular, compounds wherein formula $R^2$ is represented by formula (III) can also be produced, in addition to the above scheme, by suitably modifying the methods disclosed in Steps 9 to 11 in the Examples. In addition, compounds wherein $R^3$ is formula (VI), (VII), or (IX) can also be produced with reference to the above Scheme 18, for example. Also in the case where $R^2$ is not a sulfur atom (—S—) but a methylene group (—$CH_2$—) or an oxygen atom (—O—), such compounds can be produced with reference thereto.

In particular, compounds wherein formula $R^2$ is represented by $R^{23}$ can also be produced, in addition to the above scheme, by suitably modifying the methods disclosed in the Examples. In addition, compounds wherein $R^3$ is formula (VI), (VII), or (IX) can also be produced with reference to the above Scheme 18, for example. Also in the case where $R^{37}$ is not a sulfur atom (—S—) but a methylene group (—$CH_2$—) or an oxygen atom (—O—), such compounds can be produced with reference thereto.

Scheme to Obtain Salt

A pharmaceutically acceptable salt of the compound of the prevent invention is also generated in the course of compound production. By purifying the salt thus generated, a pharmaceutically acceptable salt of the compound can be produced. In addition, by adding an alkali, for example, a hydroxyl group contained in the compound can be easily substituted with an alkali salt. Like this, after the production of the compound of the prevent invention, the compound is allowed to act with an acid or an alkali, and thus, a pharmaceutically acceptable salt of the compound of the prevent invention can be generated.

Scheme to Obtain Hydrate

When the compound of the prevent invention is allowed to stand, it forms a hydrate. Therefore, for example, after the production of the compound of the prevent invention, the compound is allowed to stand in the presence of moisture, and thus, a hydrate can be obtained.

OCT3 Detection Agent Containing the Compound of the Present Invention

Aqueous solution of an agent containing the compound of the present invention is dropped on biological tissue, cultivation cell, artificial membrane and the like, to confirm abundance of OCT3 protein. Then, since the compound 6 of the present invention binds to OCT3 protein, concentration of the compound of the present invention in the aqueous solution is decreased. Namely, when the concentration of the compound of the present invention in the aqueous solution is measured, if the concentration is decreased, then existence of OCT3 protein is proved. Antibody for OCT3 protein is commercially available and is usable as a detection agent. However, since the agent, which is high molecular weight protein, is weak to heat, the agent is required to be preserved at low temperature. Further, since the agent is high molecular weight protein, the agent is difficult to be preserved for a long time and production cost is high. On the other hand, the compound of the present invention and the like is heat-resistant, can be preserved at normal temperature for a long time, and can be produced by chemical synthesis relatively at low cost.

OCT3 activity inhibitor containing the compound of the present invention can be produced in a similar manner to that disclosed in Re-publication of PCT International Publication No. 2005/084707. An example of OCT3 activity is a transport activity of: monoamine neurotransmitter such as dopamine, serotonin, noradrenaline, histamine, and acetylcholine; dopamine neurotoxin MPP+; stimulant drug and the like. These activities can be measured in accordance with a method disclosed in Br J. Pharmacol. 2002; 136(6): 829-836.

According to a literature Kitaichi et al., Neuroscience Letters, 2005, 382: 195-200, antidepressant activity of OCT3 antisense having OCT3 inhibitory activity is confirmed from shortening of akinesis times of mice in forced swimming test. Another literature Sata et al., J Pharmacol Exp Ther. 2005, 315(2): 888-895 reports that famotidine has strong OCT3 activity inhibition action. Further, according to WO 01/93863, antidepressant activity is confirmed by various diagnostic methods in clinical trials using famotidine. From the above results, OCT3 activity inhibitor containing the compound of the present invention and the like is effective for treatment of depression and depression-like symptoms (including physical depression, unipolarity depression, psychogenic functional disease, non-fixed form depression, dysthymia, bipolar affective disorder, seasonal depression, and continuous mood disorder).

As verified by examples, the compound of the present invention, pharmaceutically acceptable salts thereof, or pharmaceutically acceptable solvates thereof has OCT3 inhibitory activity. Thus, the present invention provides a treatment agent for depression and depression-like symptoms containing the above described OCT3 inhibitor as an active ingredient. Physical depression, unipolarity depression, psychogenic functional disease, non-fixed form depression, dysthymia, bipolar affective disorder, seasonal depression, and continuous mood disorder are included in depression and depression-like symptoms.

The compound of the present invention can be administered orally or parenterally, and can be formulated in a form suitable for the administration type. In a case of using the compound of the present invention clinically, pharmaceutically acceptable carriers can be added to the compound of the present invention for various formulations depending on the administration type, and then the compound of the present invention can be administered. Various additives conventionally known in the field of pharmaceutical preparation can be used as the carrier. Gelatin, lactose, white soft sugar, titanium oxide, starch, crystalline cellulose, hydroxypropyl methylcellulose, carboxymethyl cellulose, corn starch, microcrystalline wax, white petrolatum, magnesium alumino metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light anhydrous silicic acid, talc, vegetable oil, benzyl alcohol, gum arabic, propylene glycol, polyalkylene glycol, cyclodextrin, hydroxypropyl cyclodextrin and the like are exemplary additives.

Solid preparation such as tablet, capsule, granule, powder, or suppository, or liquid preparation such as syrup, elixir, or injection are exemplary dosage forms of the formulated mixture of the compound of the present invention and the above carriers. These preparations can be prepared in accordance with conventionally known method in the field of pharmaceutical preparation. Note that the liquid preparation may be dissolved or suspended in water or another suitable solvent when the liquid preparation is used. In particular, the injection may be dissolved or suspended in saline or glucose solution as necessary, and buffer or preservative may further be added.

The compound of the present invention can be contained in these preparations, by weight, 1.0 to 100%, preferably 1.0 to 60% to the entire pharmaceutical composition, and the pharmaceutically acceptable carrier can be contained in these preparations, by weight, 0 to 99.0%, preferably 40 to 99.0%.

In a case of using the compound of the present invention as a preventive agent or a treatment agent for the above described diseases or illness, a dose and the number of administrations thereof differ depending on sex, age, and weight of a patient, degree of symptoms, type and range of therapeutic effect to be obtained and the like. In general, in a case of oral administration, 0.001 to 10 mg, preferably 0.01 to 2 mg of the preventive agent or the treatment agent is administered per 1 kg of body weight of adult per day, at one time or divided into several times. Further, preventive administration is possible depending on the symptom.

Specific explanations of present invention are made below by using examples. The examples of the present invention, however, can be appropriately modified within a range obvious for those skilled in the art, and are not limited thereto. In the following examples, names such as SR2068 and formulae such as formula (A-1) are used only for identifying compounds, and are neither general names nor general formulae.

Example 1

Step 1. Synthesis of 2-[4-(4-chlorobutyl)thiazole-2-yl]guanidine from 5-chlorovaleric acid chloride

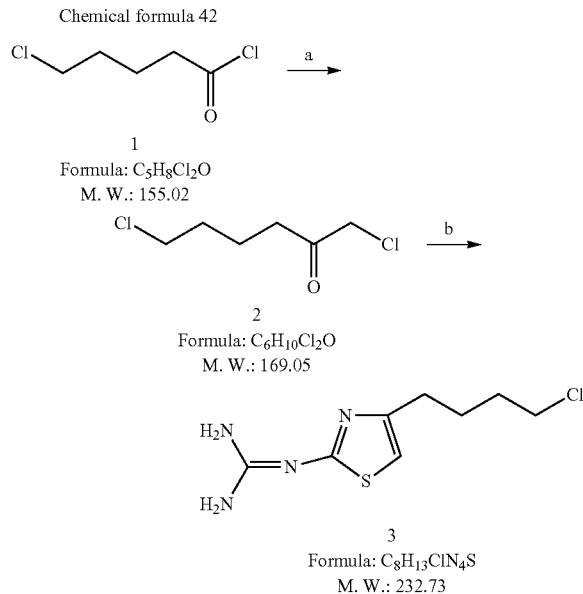

Material
Commercially available 5-chlorovaleric acid chloride
  Reagent and Condition
  a) Cyanamide, Ether, 0° C.
  b) Guanylthiourea, Aceton, 70° C.

Experimental Procedure

Synthesis of 1,6-dichlorohexane-2-one (Compound 2)[1]

200 ml of ether solution of diazomethane adjusted by potassium hydroxide (80 g, 1.43 mol), chloroform (48 g, 0.41 mol), and hydrazine (11.76 g, 85%, 0.2 mol) was dropped into 30 ml of ether solution of 5-chlorovaleric acid chloride (6 g, 39 mmol) at 0° C. while being stirred, and the solution was left for 2 hours at the same temperature.

Hydrogen chloride gas was passed through the solution for 0.5 hours. 100 ml of 1 mol/L sodium hydroxide was added to separate an ether layer. Ether was washed by water twice, dried by magnesium sulfate, and distilled to be removed. The residue was distilled under reduced pressure to obtain 1,6-dichlorohexane-2-one (4.8 g, 73.3%).

Synthesis of 2-[4-(4-chlorobutyl)thiazole-2-yl]guanidine (Compound 3)[1]

Liquid mixture prepared by mixing 1,6-dichlorohexane-2-one (4.7 g, 28 mmol) and guanylthiourea (3.3 g, 28 mmol) in 80 ml of aceton as a solvent was stirred and refluxed at 75° C. overnight. Disappearance of starting material was confirmed by thin layer chromatography (TLC), the solvent was removed under reduced pressure, and the residue was refined by chromatography (dichloromethane/methanol, 50/1) to obtain 2-[4-(4-chlorobutyl)thiazole-2-yl]guanidine (3.77 g, 58%) (Compound 3).

$^1$H-NMR (d$^6$-DMSO, 300 MHz): δ1.71 (br, 2H); 1.92 (br, 2H); 2.53 (br, 2H); 3.34 (br, 2H, NH); 3.66 (br, 2H); 6.35 (S, 1H); 6.94 (br, 2H, NH).

M.W.: 232, ESI-MS: 233 (M+H).

REFERENCE 1. i) U.S. Pat. No. 4,362,736A; ii) J. Med. Chem. 2004, 47, 2935

Step 2. Synthesis of SR-2068 from 2-[4-(4-chlorobutyl)thiazole-2-yl]guanidine

Chemical formula 43

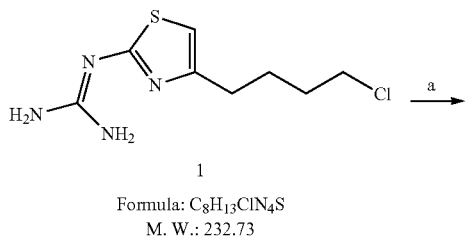

1
Formula: C$_8$H$_{13}$ClN$_4$S
M. W.: 232.73

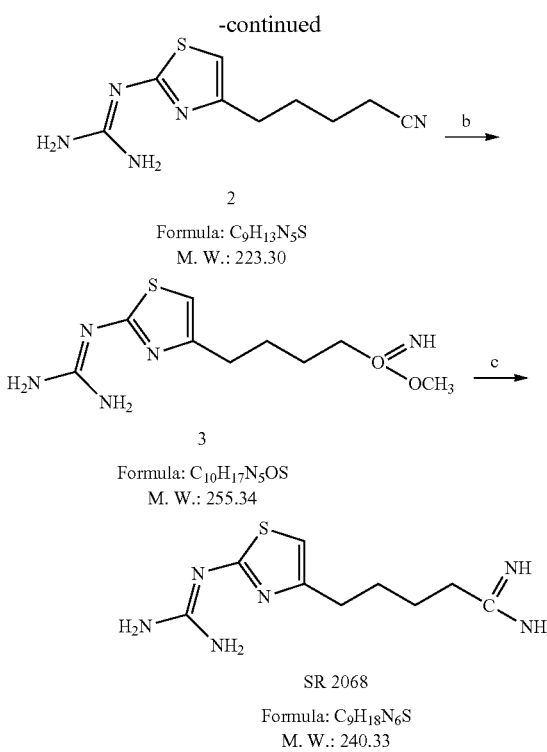

2

Formula: C₉H₁₃N₅S
M. W.: 223.30

3

Formula: C₁₀H₁₇N₅OS
M. W.: 255.34

SR 2068

Formula: C₉H₁₈N₆S
M. W.: 240.33

Material

2-[4-(4-chlorobutyl)thiazole-2-yl]guanidine (Final product of step 1 (Compound 3 of step 1))

Reagent and Condition
a) Sodium azide, Dimethyl sulfoxide, 75° C.
b) Anhydrous hydrochloric acid, Methanol/Chloroform
c) Ammonium chloride, Anhydrous methanol Experimental Procedure Synthesis of 2-[4-(4-cyanobutyl)thiazole-2-yl]guanidine (Compound 2)[1]

2-[4-(4-chlorobutyl)thiazole-2-yl]guanidine (Compound 1) (4.64 g, 20 mmol) and sodium cyanide (1.18 g, 24 mmol) were added to 30 ml of dimethyl sulfoxide, and the solution was heated at 75° C. overnight. Then, the reaction liquid was removed under reduced pressure, and the residue was refined by chromatography (dichloromethane/methanol, 50/1) to obtain 2-[4-(4-cyanobutyl)thiazole-2-yl]guanidine (4.05 g, 91%) (Compound 2).

$^1$H-NMR (d$^6$-DMSO, 300 MHz): δ1.73 (br, 4H); 2.56 (br, 2H); 3.35 (br, 3H, NH); 3.71 (d, 2H); 6.38 (s, 1H); 6.92 (br, 1H, NH).
M.W.: 223, ESI-MS: 224 (M+H).

Synthesis of 5-[2-(diaminomethyleneamino)thiazole-4-yl]pentaimideamide (SR-2068)[2]

Solution prepared by dissolving 2-[4-(4-cyanobutyl)thiazole-2-yl]guanidine (Compound 2) (0.45 g, 2 mmol) in methanol anhydride and chloroform (10 ml/20 ml) as a solvent was cooled to 0° C., and dry hydrogen chloride gas was blown into the solution continuously for 3 hours while maintaining the temperature at the same temperature. After that, the mixture was kept at 0° C. to 4° C. for 20 hours, and then concentrated under reduced pressure to obtain crystalline solid of imidehydrochloride. Reaction mixture thereof was added to ice chilled water containing excessive potassium carbonate to obtain released imide acid. The mixed solution was filtered, and the residue was washed by ethanol to obtain the compound 3. The compound 3 was dissolved in 5 ml of methanol, and ammonium chloride (0.16 g, 3 mmol) was added to the solution. Reaction mixture was stirred at room temperature for 12 hours, and disappearance of starting material was confirmed by thin layer chromatography (TLC). After that, the solvent was removed under reduced pressure, and the residue was refined by chromatography (dichloromethane/methanol/ammonia monohydrate, 200/20/1) to obtain compound SR-2068 (0.35 g, 73%).

$^1$H-NMR (d$^6$-DMSO, 400 MHz): δ1.58 (br, 4H); 2.05 (br, 2H); 3.13 (br, 2H); 3.29 (br, 7H, NH); 6.25 (s, 1H).
M.W.: 240, ESI-MS: 241 (M+H).

REFERENCES 1. i) U.S. Pat. No. 4,362,736A; ii) J. Med. Chem. 2004, 47, 2935
2. J. Med. Chem. 1983, 26, 140.

Step 3. Synthesis of SR-2076 from SR-2068

Chemical formula 44

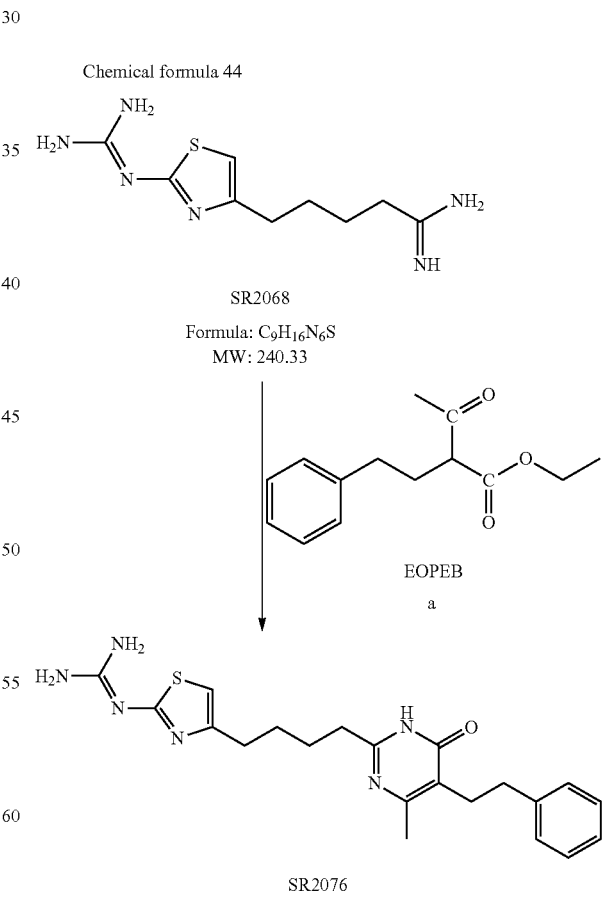

SR2068

Formula: C₉H₁₆N₆S
MW: 240.33

EOPEB

SR2076

Formula: C₂₁H₂₆N₆OS
MW: 410.54

Material

Ethyl3-oxo-2(2-phenylethyl)butanoate (EOPEB): commercial product

SR-2068: 5-[2-(diaminomethyleneamino)thiazole-4-yl]pentaimideamide: Final product of step 2

Reagent and Condition
a) Sodium ethoxide, methanol anhydride

Experimental Procedure

Synthesis of SR-2076[1]

5-[2-(diaminomethyleneamino)thiazole-4-yl]pentaimideamide (SR-2068) (0.48 g, 2 mmol) and sodium ethoxide (0.34 g, 5 mmol) were added to 20 ml of methanol anhydride at room temperature. Then, ethyl3-oxo-2-(2-phenylethyl) butanoate (EOPEB) (0.496 g, 2 mmol) was added to the mixed solution and continuously stirred at room temperature for 12 hours. After disappearance of starting material was confirmed by thin layer chromatography (TLC), the solvent was removed under reduced pressure, and the residue was refined by chromatography (dichloromethane/methanol, 50/1) to obtain product compound SR-2076 (0.43 g, 52%).

$^1$H-NMR (CD$_3$-OD, 300 MHz): δ1.725 (br, 4H); 1.975 (S, 3H); 2.60 (br, 4H); 2.762 (br, 4H); 6.307 (S, 1H); 7.149 to 7,193 (m, 5H).

M.W.: 410, ESI-MS: 411 (M+H).

REFERENCE 1. i) J. Am. Chem. Soc. 1949, 71; 616; ii) U.S. Pat. No. 4,362,736A

Example 2

Step 4. Synthesis of SR-2065 from 2-(4-(4-cyanobutyl)thiazol-2-yl)guanidine

Chemical formula 45

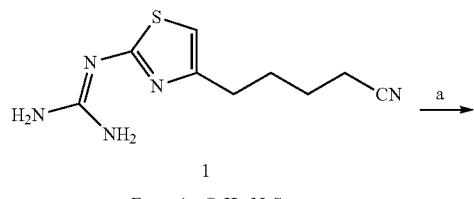

1

Formula: C$_9$H$_{13}$N$_5$S
M. W.: 223.30

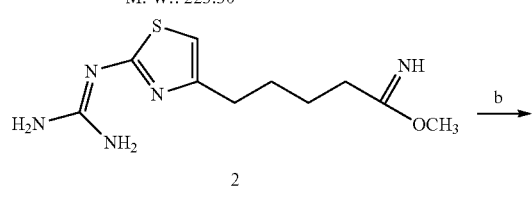

2

Formula: C$_{10}$H$_{17}$N$_5$OS
M. W.: 255.34

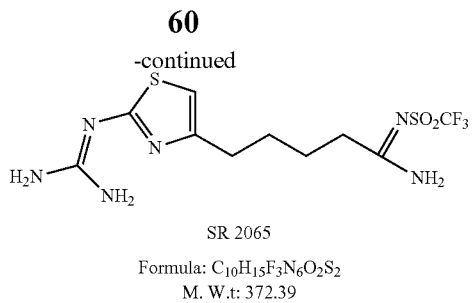

SR 2065

Formula: C$_{10}$H$_{15}$F$_3$N$_6$O$_2$S$_2$
M. W.t: 372.39

Reagent and Condition
b) dry HCl, MeOH/CHCl$_3$;
b) CF$_3$SO$_2$NH$_2$, dry MeOH.

Material 2-(4-(4-cyanobutyl)thiazol-2-yl)guanidine

Experimental Procedure

Synthesis of SR-2065[1]

A solution of 2-(4-(4-cyanobutyl)thiazol-2-yl)guanidine 1[2] (0.45 g, 2 mmol) in anhydrous methanol/chloroform (10 ml/20 ml) was cooled to 0° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give compound 2. This intermediate was dissolved in the 5 mL methanol and trifluoromethane sulfonamide (0.447 g, 3 mmol) was added to the solution. The reaction mixture was stirred at the room temperature for 12 h, when TLC showed no starting material remained, the solvent was removed under reduced pressure and the residue was purified by chromatography (DCM/MeOH, 30/1) to give compound SR 2065 (0.27 g, 36%).

$^1$H-NMR (CD$_3$OD, 300 MHz): δ1.64 (br, 4H); 2.38 (br, 2H); 2.61 (br, 2H); 4.83 (br, 6H, NH); 6.70 (s, 1H). M.W.: 372; ESI-MS: 373 (M+H).

REFERENCES 1. i) U.S. Pat. No. 4,362,736A; ii) J. Med. Chem. 2004, 47, 2935

Example 3

Step 5. Synthesis of SR-2066 from 2-(4-(4-cyanobutyl)thiazol-2-yl)guanidine

Chemical formula 46

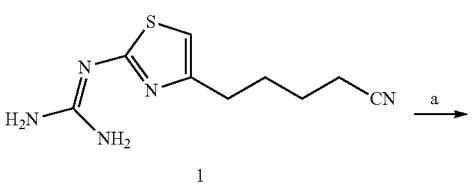

1

Formula: C$_9$H$_{13}$N$_5$S
M. W.: 223.30

-continued

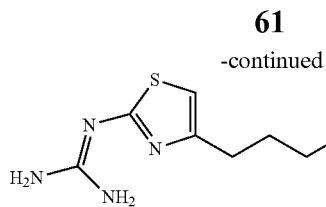

2
Formula: C$_{10}$H$_{17}$N$_5$OS
M. W.: 255.34

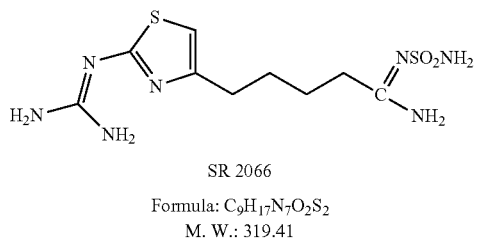

SR 2066
Formula: C$_9$H$_{17}$N$_7$O$_2$S$_2$
M. W.: 319.41

Reagent and Condition
b) Trifluoromethanesulfonamide, dry MeOH

Material 2-(4-(4-cyanobutyl)thiazol-2-yl)guanidine

Experimental Procedure

Synthesis of SR-2066[1]

A solution of 2-(4-(4-cyanobutyl)thiazol-2-yl)guanidine [2] (0.45 g, 2 mmol) in anhydrous methanol/chloroform (10 ml/20 ml) was cooled to 0° C., then dry HCl gas was bubbled for 3 h under this temperature. After that, the mixture was allowed to stand at 0–4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give compound 2. This intermediate was dissolved in the 5 ml methanol and sulfuric diamide (0.288 g, 3 mmol) was added to the solution. The reaction mixture was stirred at ° C. for 12 h, when TLC showed no starting material remained, the solvent was removed under reduced pressure and the residue was purified by chromatography (DCM/MeOH/NH$_3$H$_2$O, 200/20/1) to give compound SR 2066 (0.43 g, 67%).

$^1$H-NMR (CD$_3$OD, 300 MHz): δ1.71 (br, 4H); 2.27 (br, 2H); 2.59 (br, 2H); 4.83 (br, 8H, NH); 6.33 (s, 1H).

M.W.: 319, ESI-MS: 320 (M+H).

REFERENCES 1. i) U.S. Pat. No. 4,362,736A; ii) J. Med. Chem. 2004, 47, 2935

Step 6. Synthesis of 2-(4-(4-aminobutyl)thiazol-2-yl)guanidine from 5-chlorovalerylchloride from 5-Chlorovaleryl chloride Chemical formula 47

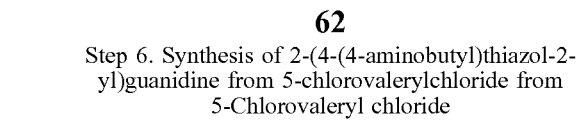

1
Formula: C$_5$H$_8$Cl$_2$O
M. W.: 155.02

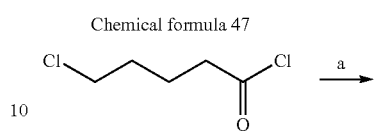

2
Formula: C$_6$H$_{10}$Cl$_2$O
M. W.: 169.05

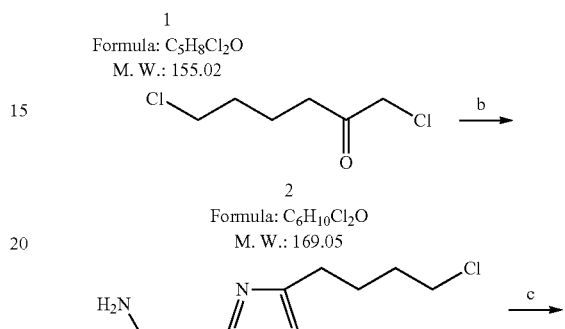

3
Formula: C$_8$H$_{13}$ClN$_4$S
M. W.: 232.73

4
Formula: C$_8$H$_{13}$N$_7$S
M. W.: 239.30

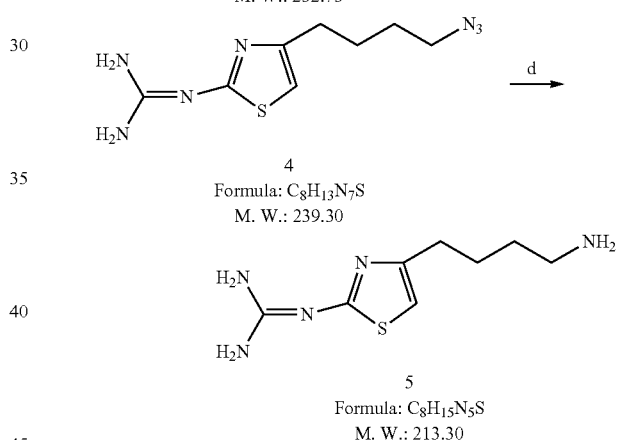

5
Formula: C$_8$H$_{15}$N$_5$S
M. W.: 213.30

Reagent and Condition
a) CH$_2$N$_2$, ether, 0° C.
b) guanylthiourea, acrtone, 70° C.
c) NaN$_3$, DMSO, 70° C.
d) PPh$_3$, THF/H$_2$O Experimental Procedure Synthesis of 1,6-dichlorohexan-2-one (Compound 2)[1]

To 200 ml of ether solution of diazomethane prepared from KOH (80 g, 1.43 mol), chloroform (48 g, 0.41 mol) and NH2NH2.H2O (11.76 g, 85%, 0.2 mol) was added under stirring 30 ml of ether solution of 5-chlorovalerylchloride (6 g, 39 mmol) dropwise at 0° C., and the solution was allowed to stand the same temperature for 2 h. Hydrogen chloride gas was passed through the reaction solution for 0.5 h. To the solution was added 100 ml of 1M NaOH and the ether layer was separated. The ether was washed twice with water, dried with magnesium sulfate and removed by distillation. The residue was distilled under reduced pressure to provide 1,6-dichlorohexan-2-one 2 (4.8 g, 73.3%) (Compound 2).

Synthesis of 2-(4-(4-chlorobutyl)thiazol-2-yl)guanidine (Compound 3)[1]

The suspension of 1,6-dichlorohexan-2-one (4.7 g, 28 mmol) and guanylthiourea (3.3 g, 28 mmol) in 80 ml acetone was stirred and refluxed at 75° C. over night. When TLC showed no starting material remained, the solvent was removed under reduced pressure and the residue was purified by chromatography (DCM/Methanol, 50/1) to give compound 3 (3.77 g, 58%).

$^1$H-NMR (d$^6$-DMSO, 300 MHz): δ1.71 (br, 2H); 1.92 (br, 2H); 2.53 (br, 2H); 3.34 (br, 2H, NH); 3.66 (br, 2H); 6.35 (s, 1H); 6.94 (br, 2H, NH). M.W.: 232, ESI-MS: 233 (M+H).

Synthesis of 2-(4-(4-azidobutyl)thiazol-2-yl)guanidine (Compound 4)[2]

To 30 ml of dimethylsulfoxide was added 2-(4-(4-chlorobutyl)thiazol-2-yl)guanidine 3 (1.16 g, 5 mmol) and sodium azide (0.36 g, 5.5 mmol), and the mixture was stirred and heated at 75° C. over night. When TLC showed no starting material remained, the reaction solution was removed under reduced pressure and the residue was purified by chromatography (DCM/Methol, 50/1) to give 2-(4-(4-azidobutyl)thiazol-2-yl)guanidine (1.17 g, 98%) (Compound 4)

$^1$H NMR (d$^6$-DMSO, 300 MHz): δ1.76 (br, 4H); 2.54 (br, 2H); 3.34 (br, 2H, NH); 3.71 (br, 2H); 6.38 (s, 1H); 7.05 (br, 2H, NH)

Synthesis of 2-(4-(4-aminobutyl)thiazol-2-yl)guanidine (Compound 5)[2]

To the solution of 2-(4-(4-azido butyl)thiazol-2-yl)guanidine (Compound 4) (0.96 g, 4 mmol) in the 30 ml THF/H$_2$O solution (v/v, 2/1), the triphenylphosphine (1.25 g, 4.8 mmol) was added. The reaction mixture was stirred at room temperature for 4 h, when TLC showed no starting material remained, the solvent was removed under reduced pressure and the residue was crystallized from ethanol to give 2-(4-(4-aminobutyl)thiazol-2-yl)guanidine (0.77 g, 90%) (5). M.W.: 213; ESI-MS: 214 (M+H).

REFERENCES 1. i) U.S. Pat. No. 4,362,736A; ii) J. Med. Chem. 2004, 47, 2935
2. i) Macromol. Rapid Commun. 2006, 27, 1739; ii) J. Org. Chem. 1982, 47, 4327; iii) J. Org. Chem. 1998, 63, 2796; iv) Tetrahedron Letters, 1997, 38, 1065.

Example 4

Step 7. Synthesis of SR-2069 from 2-(4-(4-aminobutyl)thiazol-2-yl)guanidine

Chemical formula 48

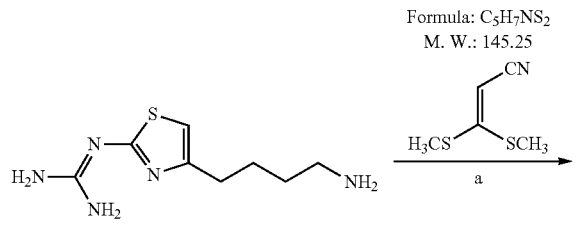

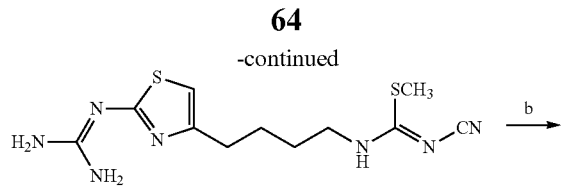

2
Formula: C$_{11}$H$_{17}$N$_7$S$_2$
M. W.: 311.43

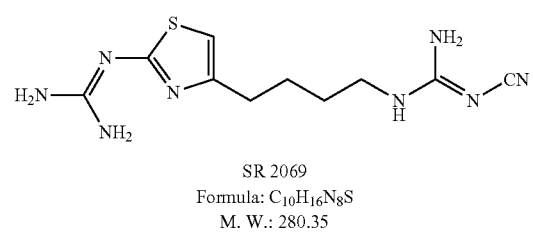

SR 2069
Formula: C$_{10}$H$_{16}$N$_8$S
M. W.: 280.35

Reagent and Condition a) 3,3-bis(methylthio)acrylonitrile, Et3N, MeOH;
b) NH3.H2O, MeOH, 70° C.

Material 2-(4-(4-aminobutyl)thiazol-2-yl)guanidine

Experimental Procedure

Synthesis of SR-2069[1]

A mixture of 2-(4-(4-aminobutyl)thiazol-2-yl)guanidine 1[2] (0.426 g, 2 mmol), 3,3-bis(methylthio)acrylonitrile (0.29 g, 2 mmol) and triethylamine (0.404 g, 4 mmol) in 10 ml dry methanol was stirred at room temperature under nitrogen atmosphere for 12 h, when TLC showed no starting material remained, the solvent was removed under reduced pressure. The residue was collected, washed with diethyl ether and dried to give intermediate 2. To the solution of intermediate 2 in 5 ml methanol, 20 ml aqueous ammonia (28%) was added to the solution. The reaction mixture was refluxed overnight, when TLC showed no starting material remained, the solvent was removed under reduced pressure and the residue was purified by chromatography (DCM/MeOH, 15/1) to give compound SR 2069 (0.33 g, 59%).

$^1$H-NMR (d$^6$-DMSO, 400 MHz): δ1.42 (m, 2H); 1.52 (m, 2H); 2.43 (t, 2H); 3.02 (t, 2H); 3.38 (br, 4H); 6.34 (s, 1H); 7.02 (b, 2H).

M.W.: 280; ESI-MS: 281 (M+H).

REFERENCES 1. i) J. Med. Chem. 1983, 26, 140; ii) J. Am. Chem. Soc 1959, 81, 2220; iii) J. Am. Chem. Soc 1959, 81, 4635.
2. i) Macromol. Rapid Commun. 2006, 27, 1739; ii) J. Org. Chem. 1982, 47, 4327.

Example 5

Step 8. Synthesis of SR-2073 from 2-(4-(4-aminobutyl)thiazol-2-yl)guanidine

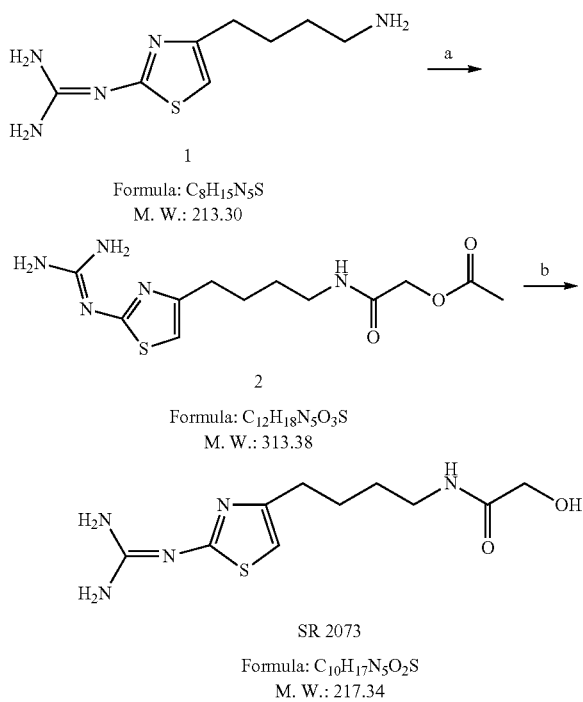

Chemical formula 49

1
Formula: C$_8$H$_{15}$N$_5$S
M. W.: 213.30

2
Formula: C$_{12}$H$_{18}$N$_5$O$_3$S
M. W.: 313.38

SR 2073
Formula: C$_{10}$H$_{17}$N$_5$O$_2$S
M. W.: 217.34

Reagent and Condition
a) 2-chloro-2-oxoethyl acetate, Et3N, DMF, 0° C.;
b) 1M NaOH aq.

Material 2-(4-(4-aminobutyl)thiazol-2-yl)guanidine

Experimental Procedure

SR2073[1]

To a mixture of 2-(4-(4-aminobutyl)thiazol-2-yl)guanidine 1 [2] (0.213 g, 1 mmol) and dry triethylamine (0.202 g, 2 mmol) in 15 ml dry DMF at 0° C. under nitrogen atmosphere, 2-chloro-2-oxoethyl acetate (0.136 g, 1 mmol) was added dropwise at 0° C. The reaction mixture was stirred for 2 h at the room temperature. When TLC showed no compound 1 remained, 10 ml 1M NaOH was added and the reaction mixture was stirred another 1 h. Then the solvent was removed under reduced pressure and the residue was purified by chromatography (DCM/Methanol, 20/1) to give compound SR 2073 (0.19 g, 70%).

$^1$H-NMR (d$^6$-DMSO, 300 MHz): δ1.46 (br, 2H); 1.57 (br, 2H); 2.03 (s, 2H); 3.16 (br, 3H); 3.36 (br, 3H, NH); 3.77 (s, 2H); 6.39 (s, 1H); 7.12 (br, 1H, NH);

M.W.: 271, ESI-MS: 272 (M+H).

REFERENCES 1. i) Chem. Pharm. Bull. 1992, 40, 2062.
2. i) Macromol. Rapid Commun. 2006, 27, 1739; ii) J. Org. Chem. 1982, 47, 4327; iii) J. Org. Chem. 1998, 63, 2796; iv) Tetrahedron Letters, 1997, 38, 1065.

Example 6

Step 9. Synthesis of SR-2023 from [4-(4-aminobutyl)thiazole-2-yl]guanidine

Chemical formula 50

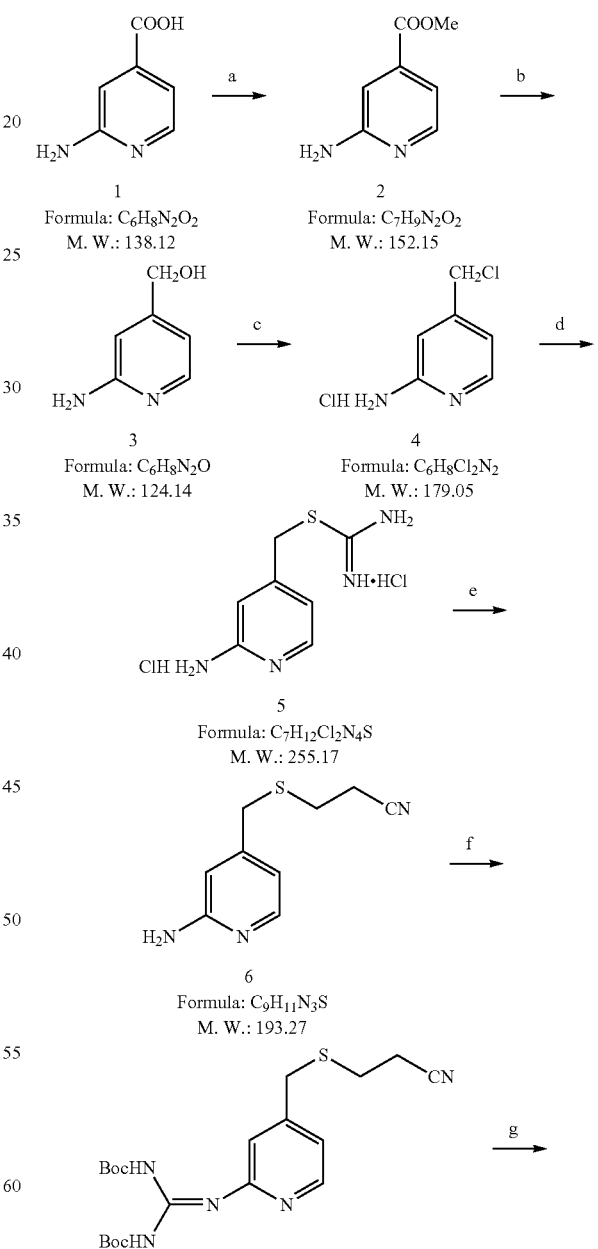

1
Formula: C$_6$H$_8$N$_2$O$_2$
M. W.: 138.12

2
Formula: C$_7$H$_9$N$_2$O$_2$
M. W.: 152.15

3
Formula: C$_6$H$_8$N$_2$O
M. W.: 124.14

4
Formula: C$_6$H$_8$Cl$_2$N$_2$
M. W.: 179.05

5
Formula: C$_7$H$_{12}$Cl$_2$N$_4$S
M. W.: 255.17

6
Formula: C$_9$H$_{11}$N$_3$S
M. W.: 193.27

7
Formula: C$_{20}$H$_{29}$N$_5$O$_4$S
M.W.: 435.54

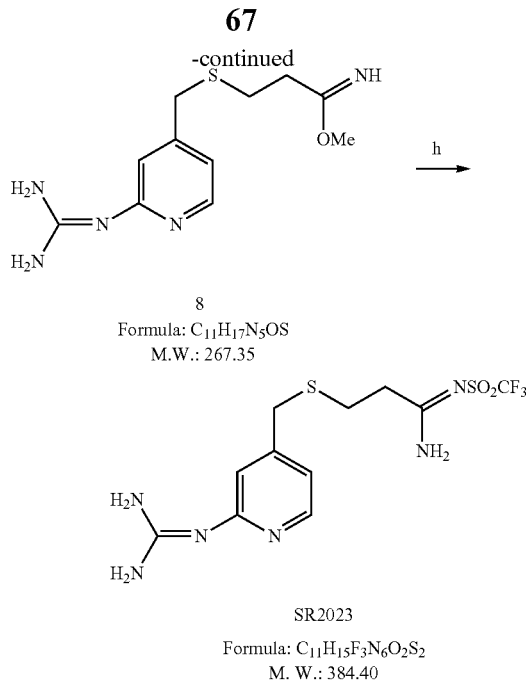

8
Formula: C₁₁H₁₇N₅OS
M.W.: 267.35

SR2023
Formula: C₁₁H₁₅F₃N₆O₂S₂
M. W.: 384.40

Reagent and Condition
a) Thionyl chloride, Methanol, 40° C.
b) Lithium aluminum hydride, Tetrahydrofuran
c) Thionyl chloride
d) Thiourea, Ethanol, 70° C.
e) 3-bromopropionitrile, Sodium hydroxide, 0-5° C.
f) N, N'-2-Boc-S-methylisothiourea, Mercury chloride, N, N-dimethylformamide
g) Dried hydrogen chloride gas, Methanol/Chloroform, room temperature, 12 hours, Methanol
h) Trifluoromethane sulfonamide, Ammonium Chloride, Anhydrous methanol Material 2-aminoisonicotinic acid Experimental Procedure Synthesis of methyl 2-aminoisonicotinate (Compound 2)[1]

Methanol solution (1.8 L) of 2-aminoisonicotinic acid (207 g, 1.5 mol) was added to thionyl chloride (238 g, 2 mol) at 50° C. by dropping. The solution was stirred for 5 more hours at the same temperature. Then, the solvent was removed under reduced pressure, and saturated aqueous solution of sodium carbonate was added to the residue to be basic of pH=9-10. After extracting the mixed solution by using dichloromethane (3×300 ml), organic layer was collected and dried by using anhydrous sodium sulfate. The solvent was concentrated to obtain methyl 2-aminoisonicotinate (189 g, 83%) (Compound 2) of yellow solid.
$^1$H-NMR (d$^6$-DMSO, 300 MHz): δ3.96 (S, 3H); 7.14 (d, 1H); 7.49 (br, 1H); 8.07 (d, 1H); 8.18 (br, 2H, NH).

Synthesis of (2-aminopyridine-4-yl)methanol (Compound 3)[2]

600 ml of anhydrous tetrahydrofuran solution of lithium aluminum hydride (115 g, 3 mol) was added to 200 ml of anhydrous tetrahydrofuran solution of methyl aminoisonicotinate (153 g, 1 mol) for 1 hour at 0° C. by dropping. The solution was stirred for 12 more hours at room temperature. After disappearance of starting material was confirmed by thin layer chromatography (TLC), sodium sulfate decahydrate (590 g, 3.6 mol) was added to the mixed solution. After stirring for 2 more hours at room temperature, the solution was filtered by celite layer and solid content was washed by tetrahydrofuran (3×200 ml). Filtrate was concentrated under reduced pressure, and the residue was refined by chromatography (dichloromethane/methanol, 30/1) to obtain (2-aminopyridine-4-yl)methanol (33.4 g, 27%) (Compound 3).
$^1$H-NMR (d$^6$-DMSO, 300 MHz): δ4.38 (br, 2H); 5.92 (br, 2H, NH); 6.41-6.47 (m, 2H); 7.78 (d, 1H).

Synthesis of 4-(chloromethyl)pyridine-2-amine hydrochloride (Compound 4)[2]

4 ml of pyridine as a catalyst was added to 110 ml of thionyl chloride solution of (2-aminopyridine-4-yl)methanol (31 g, 0.25 mol). The solution was kept at 75° C. and refluxed for 8 hours. Then, excessive thionyl chloride was removed under reduced pressure, and the residue was refined by chromatography (dichloromethane/methanol, 50/1) to obtain 4-(chloromethyl)pyridine-2-amine hydrochloride (33.8 g, 76%) (Compound 4).
M.W.: 179 (hydrochloride); EI-MS: 142 (M$^+$).

Synthesis of (2-aminopyridine-4-yl)methylcarbamimidethioacid hydrochloride (Compound 5)[3]

Compound 4 (26.7 g, 0.15 mol) and 150 ml of ethanol aqueous solution of thiourea (15.2 g, 0.2 mol) were stirred for 3 hours at 80° C. under a nitrogen atmosphere. After cooling at room temperature, the solution was filtered and the residue was washed by ethanol. Compound 7 (28.9 g, 76%) was obtained by crystallization using 95% ethanol.
$^1$H-NMR (d$^6$-DMSO, 300 MHz): δ3.69 (br, 5H, NH); 4.67 (S, 2H); 6.88 (d, 1H); 7.10 (S, 1H); 7.98 (d, 1H); 8.09 (br, 2H, NH).

Synthesis of 3-[(2-aminopyridine-4-yl)methylthio]propionitrile (Compound 6)[3]

Solution prepared by dissolving Compound 5 (2.54 g, 0.1 mol) and 3-bromopropionitrile (14.1 g, 0.1 mol) in ethanol/water (100 ml/100 ml) as a solvent was cooled to 0° C., and aqueous solution of sodium hydroxide (16 g for 80 ml of water) was added by dropping. After stirring for 1 hour at 0° C. and for 3 hours at room temperature, the solution was filtered and the residue was washed by water. 3-[(2-aminopyridine-4-yl)methylthio]propionitrile (15.6 g, 80.8%) (Compound 6) was obtained by crystallization using ethanol.
$^1$H-NMR (d$^6$-DMSO, 300 MHz): δ2.68 (m, 2H); 2.79 (m, 2H); 3.69 (s, 2H); 4.61 (br, 2H, NH); 6.40 (d, 1H); 6.64 (d, 1H); 7.37 (t, 1H). M.W.: 193; ESI-MS: 194 (M+H).

Synthesis of 2-{4-[(2-cyanoethylthio)methyl]pyridine-2-yl}-1,3-N,N'-2-Boc-guanidine (Compound 7)[4]

Mercury chloride(II) (19.2 g, 70 mmol) was added to 150 ml of anhydrous N, N-dimethylformamide solution of 3-((2- aminopyridine-4-yl)methylthio)propionitrile (13.6 g, 70 mmol), N, N'-2-Boc-S-methyleisothiourea (20.3 g, 70 mmol), and triethylamine (35.5 g, 350 mmol) at room temperature, and stirred for 12 hours at the same temperature. After disappearance of starting material was confirmed by thin layer chromatography (TLC), the solvent was removed under reduced pressure. The residue was refined by chromatography (hexane/ethyl acetate, 30/1) to obtain 2-{4-[(2-cyanoethylthio)methyl]pyridine-2-yl}-1,3-N,N'-2-Boc-guanidine (11.9 g, 39%) (Compound 7).

M.W.: 435; ESI-MS: 436 (M+H).

Synthesis of SR2023[5]

Anhydrous methanol/chloroform solution (10 ml/20 ml) of 2-{4-[(2-cyanoethylthio)methyl]pyridine-2-yl}-1,3-N,N'-2-Boc-guanidine (2.18 g, 5 mmol) (Compound 7) was cooled to 0° C., and dry hydrogen chloride gas was blown into the solution continuously for 3 hours while maintaining the temperature at the same temperature. After that, the solution was kept at 0° C. to 4° C. for 20 hours, and then concentrated under reduced pressure to obtain a crystal of imidehydrochloride. Reaction liquid thereof was added to ice chilled water containing saturating amount of potassium carbonate to obtain released imide acid. The solution was filtered, and the residue was washed by ethanol to obtain Compound 8. The Compound 8 was dissolved in 10 ml of methanol, and trifluoromethane sulfonamide (0.745 g, 5 mmol) was added to the solution. Reaction liquid was stirred at room temperature for 12 hours. After disappearance of starting material was confirmed by thin layer chromatography (TLC), the solvent was removed under reduced pressure. The residue was refined by chromatography (dichloromethane/methanol, 30/1) to obtain SR-2023 (0.41 g, 21%).

$^1$H-NMR(CD$_3$OD, 300 MHz): δ2.80-2.87 (m, 4H); 3.71 (S, 2H); 4.83 (br, 6H, NH); 6.93 (br, 1H); 7.10 (t, 1H); 8.17 (t, 1H). M.W.: 384; ESI-MS: 385 (M+H).

REFERENCES

1. Journal of Antibiotics, 1991, 44(10), 1172
2. PCT Int. Appl., 2004101533, 2004
3. i) J. Med. Chem. 2004, 47, 2935; ii) WO 2005009986
4. i) J. Med. Chem. 1987, 30, 1787; ii) J. Org. Chem. 2003, 68, 2290; iii) Bio. Med. Chem. Lett. 2002, 12, 181; iv) Bio. Med. Chem. Lett. 2002, 12, 185; v) Bio. Med. Chem. Lett. 2004, 14, 3227.
5. U.S. Pat. No. 4,362,736a Example 7

Step 10. Synthesis of SR-2219 from 3-((2-aminopyridin-4-yl)methylthio)propanimidamide Chemical formula 51

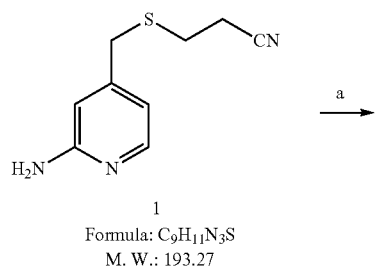

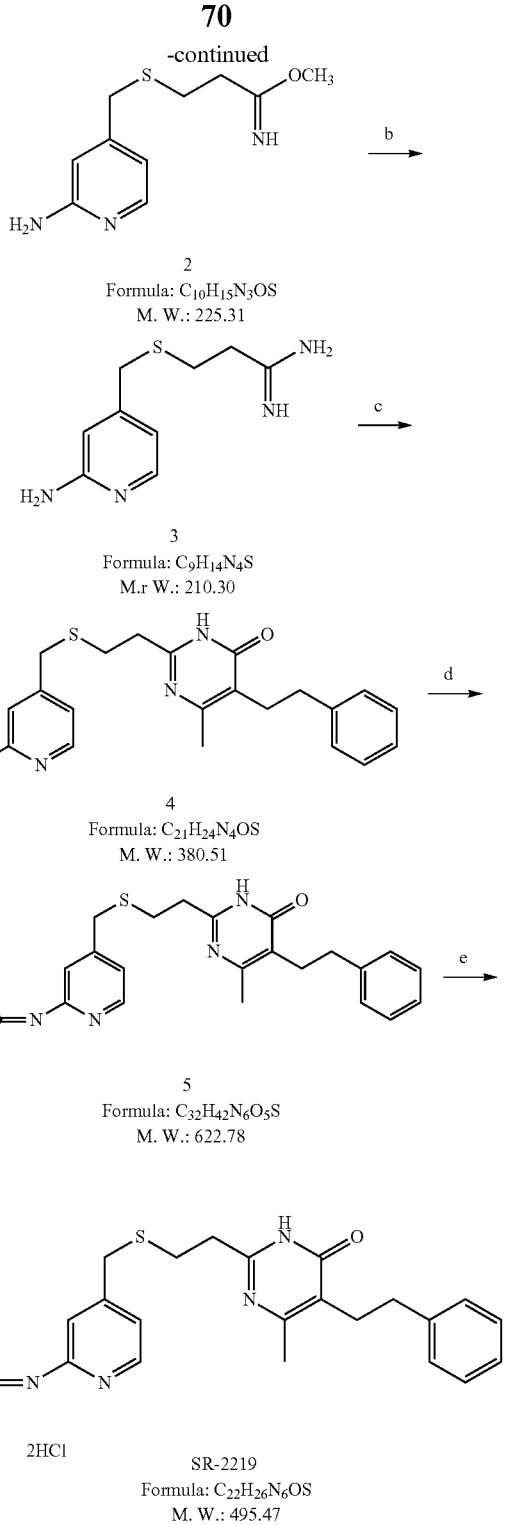

Reagent and Condition a) dry HCl gas, MeOH/CHCl$_3$ rt (room temperature) 12 h;
b) NH$_4$Cl, MeOH;
c) NaOMe, Ethyl 3-oxo-2-(2-phenylethyl)butanoate (EOPEB), MeOH;
d), N,N'-Bis(Boc)-S-methylisothiourea, HgCl$_2$, DMF, rt;
e) dry HCl gas, MeOH/CHCl$_3$.

Material 3-((2-aminopyridin-4-yl)methylthio)propanimidamide

Experimental Procedure

Synthesis of 3-((2-aminopyridin-4-yl)methylthio)propanimidamide hydrochloride (Compound 3)[1]

A solution of compound 1[2] (1.93 g, 10 mmol) in anhydrous methanol/chloroform (20 ml/40 ml) was cooled to 0° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give to give compound 2. This intermediate (compound 2) was dissolved in the 20 ml methanol and ammonium chloride (0.8 g, 15 mmol) was added to the solution. The reaction mixture was stirred at the room temperature for 12 h, when TLC showed no starting material remained, the solvent was removed under reduced pressure and the residue was purified by chromatography (DCM/MeOH/NH$_3$H$_2$O, 200/20/1) to give compound 3 (1.62, 76.8%).

M.W.: 210; ESI-MS: 211 (M+H).

Synthesis of 2-(2-((2-aminopyridin-4-yl)methylthio)ethyl)-6-methyl-5-phenethylpyrimidin-4(3H)-one (Compound 4)[3]

A solution of compound 3 (1.47 g, 7 mmol) and EtONa (1.19 g, 17.5 mmol) were added into in 50 ml anhydrous methanol at room temperature, then the ethyl 3-oxo-2-(2-phenylethyl)butanoate (EOPEB) (1.74 g, 7.4 mmol) was added into mixture and stirred for 12 h under this temperature. When TLC showed no starting material remained, the solvent was removed under reduced pressure. The residue was purified by chromatography (DCM/MeOH, 50/1) to give compound 4 (1.86 g, 70%). MW: 380; ESI-MS: 381 (M+H)

Synthesis of Compound 5[4]

A solution of compound 4 (1.52 g, 4 mmol), N,N'-Bis(Boc)-S-methylisothiourea[4a] (1.16 g, 4 mmol) and Et3N (2.02 g, 20 mmol) were added into in 50 ml anhydrous DMF at room temperature, then the mercury(II) chloride (1.09 g, 4 mmol) was added into mixture and stirred for 12 h under this temperature. When TLC showed no starting material remained, the solvent was removed under reduced pressure. The residue was purified by chromatography (EtOAc/Hexane, 20/1) to give compound 5 (1.25 g, 51%).

M.W.: 622; ESI-MS: 623 (M+H).

Synthesis of SR-2219

A solution of compound 5 (0.94 g, 1.5 mmol) in anhydrous methanol/chloroform (10 ml/10 ml) was cooled to 0° C., then dry HClgas was bubbled for 4 h under this temperature. When TLC showed no starting material remained, the solvent was removed under reduced pressure and the residue was purified by chromatography (DCM/MeOH, 30/1) to give SR 2219 (0.50 g, 67%). $^1$H-NMR (d$^6$-DMSO, 300 MHz): δ2.17 (s, 3H); 2.64 (m, 4H); 2.76 (m, 4H); 3.34 (br, 5H, NH); 3.82 (s, 2H); 7.02 (s, 1H); 7.14~7.29 (m, 6H), 8.24 (d, 1H).

M.W.: 495 (hydrochloride); ESI-MS: 423 (M+H).

REFERENCES

1. U.S. Pat. No. 4,362,736A
2. Detailed synthesis methods as shown in the report of SR 2023
3. J. Am. Chem. Soc. 1949, 71
4. i) J. Med. Chem. 1987, 30, 1787; ii) J. Org. Chem. 2003, 68, 2290; iii) Bio. Med. Chem. Lett. 2002, 12, 181 iv) Bio. Med. Chem. Lett. 2002, 12, 185; v) Bio. Med. Chem. Lett. 2004, 14, 3227; vi) Macromol. Rapid Commun. 2006, 27, 1739

Example 8

Step 11. Synthesis of SR-2229 from (2-aminopyridin-4-yl)methylthio)

Chemical formula 52

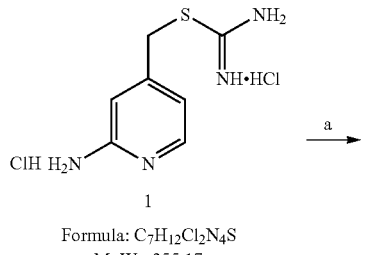

1

Formula: C$_7$H$_{12}$Cl$_2$N$_4$S
M. W.: 255.17

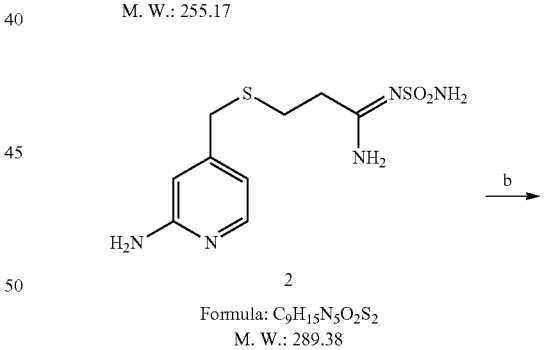

2

Formula: C$_9$H$_{15}$N$_5$O$_2$S$_2$
M. W.: 289.38

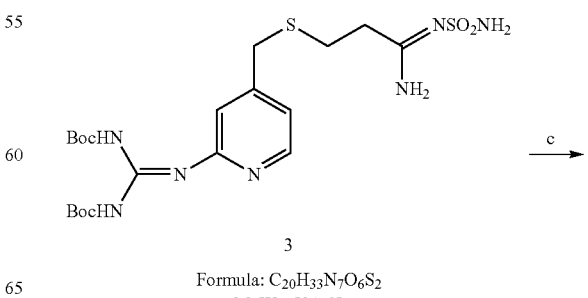

3

Formula: C$_{20}$H$_{33}$N$_7$O$_6$S$_2$
M. W.: 531.65

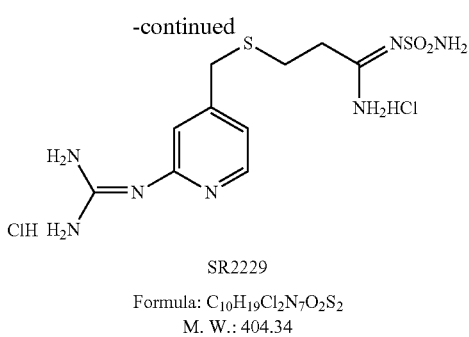

SR2229

Formula: C₁₀H₁₉Cl₂N₇O₂S₂
M. W.: 404.34

Reagent and Condition a) 3-chloro-N'-sulfamoylpropanimidamide, EtOH, NaOH, 0° C.; 12 h; b) N,N'-Bis(Boc)-S-methylisothiourea, HgCl₂, DMF c) dry HCl gas, MeOH/CHCl₃

Material (2-aminopyridin-4-yl)methylthio) (Compound 1)

Experimental Procedure

Synthesis of 3((2-aminopyridin-4-yl)methylthio)-N'-sulfamoylpropanimidamide (2)[1]

A solution of compound 1m (2.54 g, 10 mmol) and 3-chloro-N'-sulfamoylpropanimidamide (1.85 g, 10 mmol) in ethanol/water (100 ml/100 ml) was cooled at 0° C., then aq. NaOH (2 g in 10 ml water) was added dropwise. After stirring 1 h at 0° C. and another 3 h at room temperature the mixture was filtered and the residue was washed with water, crystallization from ethanol gave the crude product, the residue was purified by chromatography (DCM/MeOH, 20/1) to give compound 2 (2.22 g, 76.8%).

¹H-NMR (d⁶-DMSO, 200 MHz): δ2.38 (m, 2H); 2.62 (m, 2H); 3.40 (br, 4H, NH); 3.61 (s, 2H); 5.74 (br, 2H, NH); 6.31 (d, 1H); 6.47 (br, 1H); 7.83 (d, 1H).

M.W.: 289; ESI-MS: 290 (M+H).

Synthesis of Compound 3[3]

A solution of compound 2 (2.02 g, 7 mmol), N,N'-Bis(Boc)-S-methylisothiourea[3a] (2.03 g, 7 mmol) and Et3N (0.71 g, 7 mmol) were added into in 20 ml anhydrous DMF at room temperature, then the mercury(II) chloride (1.92 g, 7 mmol) was added into mixture and stirred for 12 h under this temperature. When TLC showed no starting material remained, the solvent was removed under reduced pressure, the residue was purified by chromatography (DCM/MeOH, 50/1) to give compound 3 (1.56 g, 42%).

M.W.: 531; ESI-MS: 532 (M+H).

Synthesis of SR 2229[4]

A solution of compound 3 (1.06 g, 2 mmol) in anhydrous methanol/chloroform (10 ml/10 ml) was cooled to 0° C., then dry HClgas was bubbled for 4 h under this temperature. When TLC showed no starting material remained, the solvent was removed under reduced pressure and the residue was purified by chromatography (DCM/MeOH, 30/1) to give SR 2229 (0.54 g, 66.8%).

¹H-NMR (CD₃OD, 300 MHz): δ2.86 (m, 4H); 3.87 (s, 2H); 4.93 (br, 10H, NH); 7.12 (m, 1H); 7.22 (m, 1H), 8.28 (m, 1H).

M.W.: 404 (hydrochloride); ESI-MS: 332 (M+H).

REFERENCES 1. i) J. Med. Chem. 2004, 47, 2935; ii) WO 2005009986
2. Detailed synthesis methods as shown in the report of SR 2023
3. i) J. Med. Chem. 1987, 30, 1787; ii) J. Org. Chem. 2003, 68, 2290; iii) Bio. Med. Chem. Lett. 2002, 12, 181 iv) Bio. Med. Chem. Lett. 2002, 12, 185; v) Bio. Med. Chem. Lett. 2004, 14, 3227
4. Macromol. Rapid Commun. 2006, 27, 1739

Example 9

Step 12. Synthesis of SR-2036 from 6-methylpyridin-2-amine

Chemical formula 53

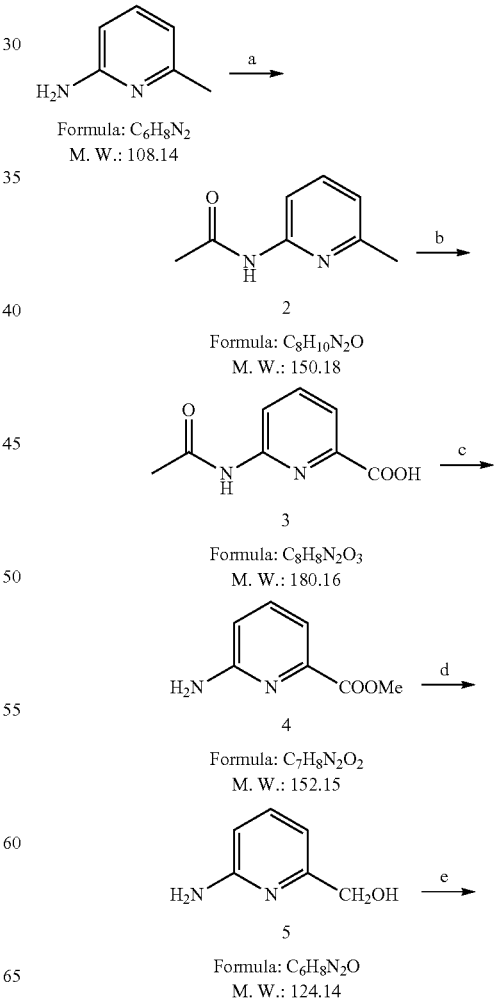

-continued

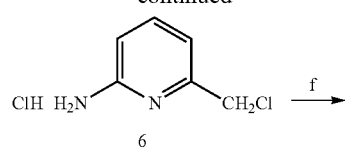

6

Formula: C₆H₈Cl₂N₂
M. W.: 179.05

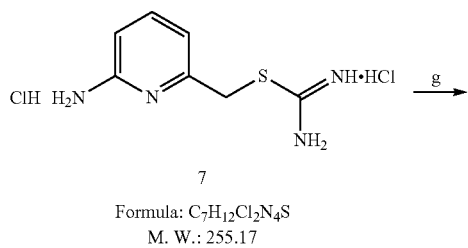

7

Formula: C₇H₁₂Cl₂N₄S
M. W.: 255.17

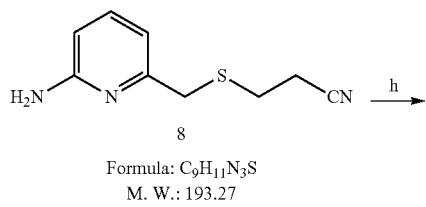

8

Formula: C₉H₁₁N₃S
M. W.: 193.27

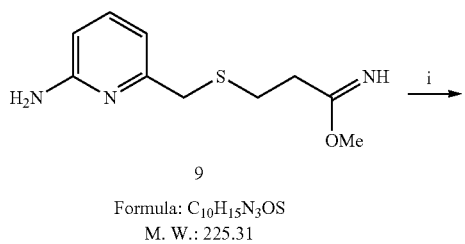

9

Formula: C₁₀H₁₅N₃OS
M. W.: 225.31

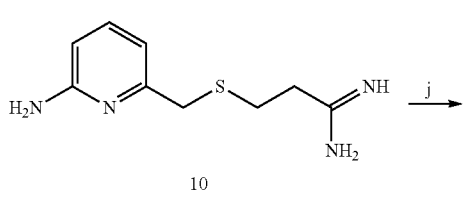

10

Formula: C₉H₁₄N₄S
M. W.: 210.30

Chemical formula 54

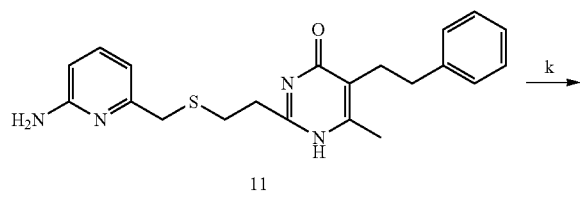

11

Formula: C₂₁H₂₄N₄OS
M. W.: 380.51

-continued

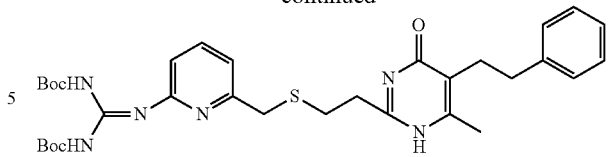

12

Formula: C₃₂H₄₂N₆O₅S
M. W.: 622.78

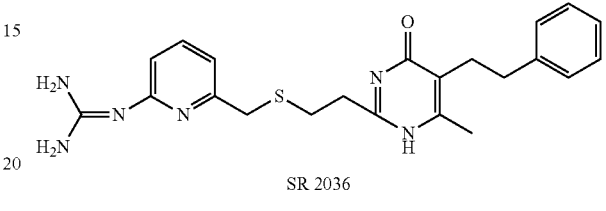

SR 2036

Formula: C₂₂H₂₆N₆OS
M. W.: 422.55

Reagent and Condition
a) Ac₂O, NaHCO₃, rt, 12 h;
b) KMnO₄, 80° C., 4 h;
c) SOCl₂, MeOH, 40° C.;
d) LiAlH₄, THF;
e) SOCl₂;
f) thiourea, EtOH, 70° C.;
g) 3-bromopropanenitrile, NaOH, 0-5° C.;
h) dry HCl gas, MeOH/CHCl₃ rt, 12 h;
i) NH₄Cl, MeOH;
j) NaOMe, Ethyl 3-oxo-2-(2-phenylethyl)butanoate (EOPEB), MeOH;
k) N,N'-Bis(Boc)-S-methylisothiourea, HgCl₂, DMF, rt;
l) dry HCl gas, MeOH/CHCl₃

Material 6-methylpyridin-2-amine

Experimental Procedure

Synthesis of N-(6-methylpyridin-2-yl)acetamide (Compound 2)[1]

Ac₂O (245 g, 2.40 mol) was added dropwise to a solution of 6-methylpyridin-2-amine 1 (216.3 g, 2.00 mol) in dichloromethane (2.3 L) at room temperature. The mixture was stirred for 12 hours at room temperature and then water (1.15 L) was added at 20° C. and stirred for another 10 minutes. The water phase was extracted with dichloromethane (1.15 L) again, then the organic layers were combined and was washed with a saturated solution of sodium hydrogen carbonate (600 mL). Dried with anhydrous sodium sulfate the solvent was concentrated to give yellow solid (285 g, 95%). ¹H-NMR (CDCl₃, 300 MHz): δ2.17 (s, 3H); 2.44 (s, 3H); 6.91 (d, 1H); 7.59 (t, 1H); 8.01 (d, 1H); 8.58 (s, 1H).

Synthesis of 6-acetamidopicolinic acid (Compound 3)[1]

6-acetamidopicolinic acid (3)[1]

To a solution of N-(6-methylpyridin-2-yl)acetamide 2 (285 g, 1.90 mol) in 2.85 L water was added $KMnO_4$ (750.5 g, 4.75 mol) in portions during a period of 3 hr at 80° C. After stirred at 80° C. for another 3 h, the mixture was filtered through a pad of Celite and the Celite cake was washed with hot water (2×300 ml). The filtrate was concentrated under reduced pressure to about 300 ml, and acidified with 6N HCl to pH=3-3.5. The resulting precipitate was collected by filtration, dried to give white solid (171 g, 50%).

$^1$H-NMR (d$^6$-DMSO, 300 MHz): δ0.86 (s, 3H); 5.96 (d, 1H); 6.09 (t, 1H); 6.29 (d, 1H).

Synthesis of Methyl 6-aminopicolinate (Compound 4)[1]

Methyl 6-aminopicolinate(4)[1]

To a solution of 6-acetamidopicolinic acid 3 (171 g, 0.95 mol) in methanol (1.7 L) was added dropwise $SOCl_2$ (170 g, 1.43 mol) at 50° C. After the addition the mixture was stirred for an additional 5 hour while maintaining the temperature at the same temperature. Then the solvent was removed under reduced pressure, the residue was basified with a saturated solution of sodium carbonate to pH=9-10 and extracted with dichloromethane (3×650 ml). The organic layers were combined and dried with anhydrous sodium sulfate and concentrated to give yellow solid Methyl 6-aminopicolinate(115 g, 80%) (Compound 4).

$^1$H-NMR (CDCl$_3$, 300 MHz): δ3.97 (s, 3H); 4.88 (s, 2H); 6.70 (d, 1H); 7.50 (t, 1H); 7.59 (d, 1H).

Synthesis of Methyl (6-methylpyridin-2-yl) methanol (Compound 5)[2]

(6-methylpyridin-2-yl) methanol (5)[2]

To a solution of $LiAlH_4$ (86 g, 2.25 mol) in 500 ml anhydrous THF was added dropwise (over 1 h) the methyl 6-aminopicolinate 4 (114 g, 0.75 mol) in the solution of 200 ml anhydrous THF at 0° C. The reaction mixture was stirred over 12 h under the room temperature until TLC showed no starting material remained. $Na_2SO_4 \cdot 10H_2O$ (442.8 g, 2.7 mol) was added the mixture in portions and the reaction mixture was stirred at room temperature for another 2 h. Then the mixture was filtered through a pad of Celite, and the Celite cake was washed with THF (2×200 mL). The filtrate was concentrated under reduced pressure, the residue was purified by chromatography (DCM/Methol, 30/1) to give (6-methylpyridin-2-yl) compound 5 (29.8 g, 32%).

$^1$H-NMR (d$^6$-DMSO, 300 MHz): δ4.30 (s, 2H); 5.26 (m, 1H, OH); 5.78 (br, 2H, NH); 6.27 (d, 1H); 6.57 (d, 1H); 7.34 (t, 1H).

Synthesis of 6-(chloromethyl)pyridin-2-amine hydrochloride (compound 6)[2]

6-(chloromethyl)pyridin-2-amine hydrochloride(6)[2]

To a solution of (6-methylpyridin-2-yl) methanol 5 (24.8 g, 0.2 mol) in 100 ml $SOCl_2$ was added 3 ml pyridine as catalysis. The reaction mixture was refluxed at 75° C. for 8 h, and the excessive $SOCl_2$ was removed under reduced pressure. The residue was purified by chromatography (DCM/Methol, 50/1) to give compound 6 (28.9 g, 81%).

$^1$H-NMR (d$^6$-DMSO, 300 MHz): δ4.57 (s, 2H); 6.30 (br, 2H, NH); 6.47 (d, 1H); 7.47 (d, 1H); 7.73 (t, 1H); 8.07 (b, 1H, NH).

Synthesis of (6-aminopyridin-2-yl)methyl carbamimidothioate hydrochloride(compound 7)[3]

(6-aminopyridin-2-yl)methyl carbamimidothioate hydrochloride(7)[3]

A solution of 6-(chloromethyl)pyridin-2-amine hydrochloride (compound 6) (26.7 g, 0.15 mol) and thiourea (15.2 g, 0.2 mol) in 150 ml EtOH was stirred at 80° C. under nitrogen atmosphere for 3 h. After cooled at room temperature, the mixture was filtered and the residue washed with EtOH. Crystallization from 95% ethanol gave the compound 7 (31.6 g, 83%).

$^1$H-NMR (d$^6$-DMSO, 300 MHz): δ3.56 (b, 5H, NH); 4.70 (s, 2H); 7.84 (m, 1H); 9.46 (br, 1H); 8.07 (br, 2H, NH); 9.73 (br, 1H).

Synthesis of 3-((6-aminopyridin-2-yl)methylthio)propanenitrile (8)[3]

3-((6-aminopyridin-2-yl)methylthio)propanenitrile (8)[3]

A solution of compound 7 (25.4 g, 0.1 mol) and $BrCH_2CH_2CN$ (14.1 g, 0.1 mol) in ethanol/water (100 ml/100 ml) was cooled at 0° C., then aq. NaOH (16 g in 80 ml water) was added dropwise to this mixture. After stirring 1 h at 0° C. and another 3 h at room temperature the mixture was filtered and the residue was washed with water. Crystallization from ethanol gave the compound 8 (15.6 g, 81%).

$^1$H-NMR (d$^6$-DMSO, 300 MHz): δ2.63 (m, 2H); 2.79 (m, 2H); 3.69 (s, 2H); 4.61 (br, 2H, NH); 6.40 (d, 1H); 6.64 (d, 1H); 7.37 (t, 1H).

Synthesis of 3-((6-aminopyridin-2-yl)methylthio)propanimidamide hydrochloride (compound 10)[4]

3-((6-aminopyridin-2-yl)methylthio)propanimidamide hydrochloride (10)[4]

A solution of compound 8 (1.93 g, 10 mmol) in anhydrous methanol/chloroform (20 ml/40 ml) was cooled to 0° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give to compound 9. This intermediate (compound 9) was dissolved in the 20 mL methanol and ammonium chloride (0.8 g, 15 mmol) was added to the solution. The reaction mixture was stirred at the room temperature for 12 h, when TLC showed no starting material remained, the solvent was removed under reduced pressure and the residue was purified by chromatography (DCM/MeOH/NH$_3$H$_2$O, 200/20/1) to give compound 10 (1.49, 70.6%).

M.W.: 210, ESI-MS: 211 (M+H).

Synthesis of 2-(2-((6-aminopyridin-2-yl)methylthio)ethyl)-6-methyl-5-phenethylpyrimidin-4(1H)-one (compound 11)[5]

2-(2-((6-aminopyridin-2-yl)methylthio)ethyl)-6-methyl-5-phenethylpyrimidin-4(1H)-one (11)[5]

A solution of compound 10 (1.47 g, 7 mmol) and EtONa (1.19 g, 17.5 mmol) were added into in 50 ml anhydrous methanol at room temperature, then the ethyl 3-oxo-2-(2-phenylethyl)butanoate (EOPEB)[8] (1.74 g, 7 mmol) was added into mixture and stirred for 12 h under this temperature. When TLC showed no starting material remained, the solvent was removed under reduced pressure and the residue was purified by chromatography (DCM/MeOH, 50/1) to give compound 11 (1.81 g, 68%).

$^1$H-NMR (d$^6$-DMSO, 300 MHz): δ2.03 (s, 3H); 2.65 (s, 4H); 2.80 (br, 4H); 3.68 (s, 2H); 5.90 (br, 3H, NH); 6.32 (d, 1H); 6.47 (d, 1H); 7.19-7.37 (m, 6H).
M.W.: 380, ESI-MS: 381 (M+H).

Synthesis of compound 12[6]

Compound 12[6]

A solution of compound 11 (1.52 g, 4 mmol), N,N'-Bis(Boc)-S-methylisothiourea (1.16 g, 4 mmol) and Et$_3$N (2.02 g, 20 mmol) were added into 50 ml anhydrous DMF at room temperature, then the mercury(II) chloride (1.09 g, 4 mmol) was added into mixture and stirred for 12 h under this temperature. When TLC showed no starting material remained, the solvent was removed under reduced pressure and the residue was purified by chromatography (EtOAc/Hexane, 20/1) to give compound 12 (1.06 g, 42.6%).

$^1$H-NMR (d$^6$-DMSO, 300 MHz): δ1.44 (br, 18H); 1.99 (s, 3H); 2.57 (m, 4H); 2.77 (m, 4H); 3.80 (s, 2H); 6.57 (br, 3H, NH), 7.16~7.29 (m, 6H), 7.85 (t, 1H); 8.08 (d, 1H).
M.W.: 622, ESI-MS: 623 (M+H).

Synthesis of SR 2036[7]

SR 2036[7]

A solution of compound 12 (0.94 g, 1.5 mmol) in anhydrous methanol/chloroform (10 ml/10 ml) was cooled to 0° C., then dry HCl gas was bubbled for 4 h under this temperature. When TLC showed no starting material remained, the solvent was removed under reduced pressure and the residue was purified by chromatography (DCM/MeOH, 30/1) to give SR 2036 (0.54, 85%).

$^1$H-NMR (CD$_3$OD, 300 MHz): δ1.97 (s, 3H); 2.82 (m, 4H); 2.89 (m, 4H); 3.89 (s, 2H); 4.99 (b, 5H, NH); 6.93 (m, 1H); 7.13-7.24 (m, 6H), 7.81 (m, 1H).
M.W.: 422, ESI-MS: 423 (M+H).

REFERENCES

1. Journal of Antibiotics, 1991, 44(10), 1172
2. PCT Int. Appl., 2004101533, 2004
3. a) J. Med. Chem. 2004, 47, 2935; b) WO 2005009986
4. U.S. Pat. No. 4,362,736A
5. J. Am. Chem. Soc. 1949, 71
6. i) J. Med. Chem. 1987, 30, 1787; ii) J. Org. Chem. 2003, 68, 2290; iii) Bio. Med. Chem. Lett. 2002, 12, 181 iv) Bio. Med. Chem. Lett. 2002, 12, 185; v) Bio. Med. Chem. Lett. 2004, 14, 3227.
7. Macromol. Rapid Commun. 2006, 27, 1739.
8. Obtained from market Example 10

Step 13. Synthesis of SR-2022 from 3-((6-aminopyridin-2-yl)methylthio)propanenitrile

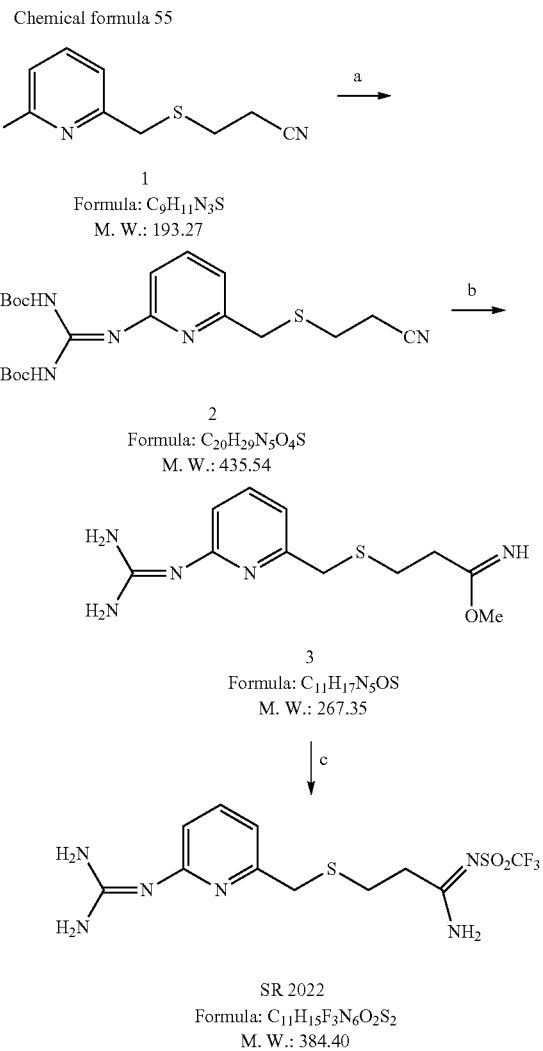

Reagent and Condition:
a) N,N'-Bis(Boc)-S-methylisothiourea, HgCl$_2$, DMF
b) dry HCl gas, MeOH/CHCl$_3$, 12 h;
c) CF$_3$SO$_2$NH$_2$, MeOH Material 3-((6-aminopyridin-2-yl)methylthio)propanenitrile (compound 1)

Experimental Procedure

Synthesis of Compound 2[1]

Compound 2[1]

A solution of 3-((6-aminopyridin-2-yl)methylthio)propanenitrile 1[2] (1.93 g, 10 mmol), N,N'-Bis(Boc)-S-methylisothiourea (2.9 g, 10 mmol) and Et₃N (5.05 g, 50 mmol) were added into 100 ml anhydrous DMF at room temperature, then the mercury(II) chloride (2.73 g, 10 mmol) was added into mixture and stirred for 12 h under this temperature. When TLC showed no starting material remained, the solvent was removed under reduced pressure, the residue was purified by chromatography (EtOAc/Hexane, 30/1) to give compound 2 (2.48 g, 57%). M.W.: 435; ESI-MS: 436 (M+H).

Synthesis of SR 2022[3]

SR 2022[3]

A solution of compound 2 (2.18 g, 5 mmol) in anhydrous methanol/chloroform (10 ml/20 ml) was cooled to 0° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give compound 3. This intermediate was dissolved in the 10 ml methanol and trifluoromethane sulfonamide (0.745 g, 5 mmol) was added to the solution. The reaction mixture was stirred at the room temperature for 12 h. When TLC showed no starting material remained, the solvent was removed under reduced pressure and the residue was purified by chromatography (DCM/MeOH, 30/1) to give compound SR 2022 (0.52 g, 27%).
¹H-NMR (CD₃OD, 300 MHz): δ2.61-2.68 (m, 4H); 3.82 (s, 2H); 4.82 (br, 6H, NH); 6.81 (d, 1H); 7.14 (d, 1H); 7.72 (d, 1H). M.W.: 384; ESI-MS: 385 (M+H).

REFERENCES 1. a) J. Med. Chem. 1987, 30, 1787; b) J. Org. Chem. 2003, 68, 2290; c) Bio. Med. Chem. Lett. 2002, 12, 181 d) Bio. Med. Chem. Lett. 2002, 12, 185; e) Bio. Med. Chem. Lett. 2004, 14, 3227.
2. Detailed synthesis methods as shown in the report of SR 2036
3. a) J. Med. Chem. 2004, 47, 2935; b) U.S. Pat. No. 4,362,736A Example 11

Step 14. Synthesis of SR-2230 from (6-aminopyridine-2-11) Cyanocarbamimidothioic acid methyl ester chloride Chemical formula 56

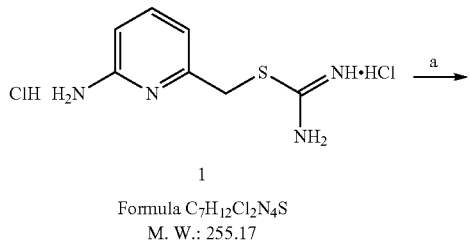

1
Formula C₇H₁₂Cl₂N₄S
M. W.: 255.17

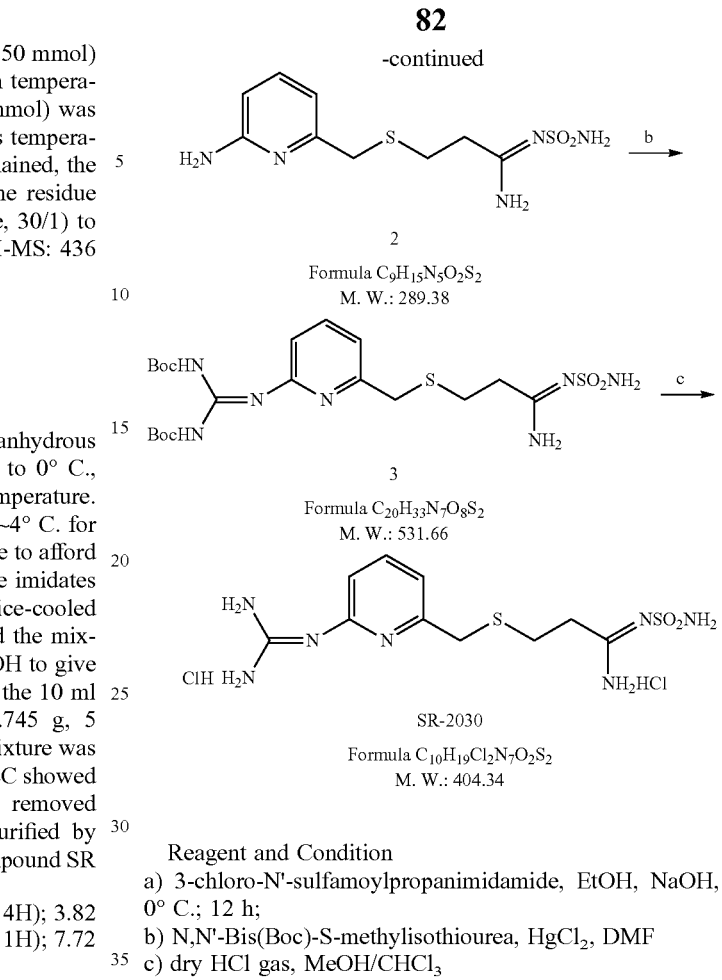

2
Formula C₉H₁₅N₅O₂S₂
M. W.: 289.38

3
Formula C₂₀H₃₃N₇O₈S₂
M. W.: 531.66

SR-2030
Formula C₁₀H₁₉Cl₂N₇O₂S₂
M. W.: 404.34

Reagent and Condition
a) 3-chloro-N'-sulfamoylpropanimidamide, EtOH, NaOH, 0° C.; 12 h;
b) N,N'-Bis(Boc)-S-methylisothiourea, HgCl₂, DMF
c) dry HCl gas, MeOH/CHCl₃

Material 6-aminopyridine-2-11) Cyanocarbamimidothioic acid methyl ester chloride (Compound 1)

Experimental Procedure

Synthesis of 3-((6-aminopyridin-2-yl)methylthio)-N'-sulfamoylpropanimidamide (compound 2)[1]

3-((6-aminopyridin-2-yl)methylthio)-N'-sulfamoyl-propanimidamide (2)[1]

A solution of compound 1[2] (2.54 g, 10 mmol) and 3-chloro-N'-sulfamoylpropanimidamide (1.85 g, 10 mmol) in ethanol/water (100 ml/100 ml) was cooled at 0° C., then aq. NaOH (2 g in 10 ml water) was added dropwise. After stirring 1 h at 0° C. and another 3 h at room temperature the mixture was filtered and the residue was washed with water, crystallization from ethanol gave the crude product, the residue was purified by chromatography (DCM/MeOH, 20/1) to give compound 2 (2.07 g, 71.6%).
¹H-NMR (d⁶-DMSO, 200 MHz): δ2.46 (m, 2H); 2.70 (m, 2H); 3.38 (br, 4H, NH); 3.60 (s, 2H); 5.74 (br, 2H, NH); 6.31 (d, 1H); 6.52 (b, 1H); 7.31 (t, 1H). M.W.: 289; ESI-MS: 290 (M+H).

Synthesis of Compound 3

Compound 3: A solution of 3-((6-aminopyridin-2-yl) methylthio)N'-sulfamoyl propanimida m-ide (2.02 g, 7 mmol), N,N'-Bis(Boc)-S-methylisothiourea (2.03 g, 7 mmol) and Et3N (0.71 g, 7 mmol) were added into 20 ml anhydrous DMF at room temperature, then the mercury(II) chloride (1.92 g, 7 mmol) was added into mixture and stirred for 12 h under this temperature. When TLC showed no starting material remained, the solvent was removed under reduced pressure, the residue was purified by chromatography (DCM/MeOH, 50/1) to give compound 3 (1.56 g, 43%). M.W.: 531; ESI-MS: 532 (M+H).

Synthesis of SR 2230[3]

SR 2230[3] A solution of compound 3 (1.06 g, 2 mmol) in anhydrous methanol/chloroform (10 ml/10 ml) was cooled to 0° C., then dry HClgas was bubbled for 4 h under this temperature. When TLC showed no starting material remained, the solvent was removed under reduced pressure and the residue was purified by chromatography (DCM/MeOH, 30/1) to give SR 2230 (OK-030) (0.58 g, 71.8%). $^1$H-NMR (CD$_3$OD, 300 MHz): δ2.88~2.92 (m, 4H); 3.98 (s, 2H); 4.98 (br, 10H, NH); 6.91 (m, 1H); 7.26 (m, 1H); 7.87 (m, 1H). M.W.: 404 (hydrochloride); ESI-MS: 332 (M+H).

REFERENCES 1. a) J. Med. Chem. 2004, 47, 2935; b) WO 2005009986
2. Detailed synthesis methods as shown in the report of SR 2036
3. a) J. Med. Chem. 1987, 30, 1787; b) J. Org. Chem. 2003, 68, 2290; c) Bio. Med. Chem. Lett. 2002, 12, 181 d) Bio. Med. Chem. Lett. 2002, 12, 185; e) Bio. Med. Chem. Lett. 2004, 14, 3227.
4. Macromol. Rapid Commun. 2006, 27, 1739.

Example 12

In order to measure an activity that inhibits OCT3 from incorporating a substrate (OCT3 inhibition activity) for each compound, histamine incorporation experiments as described below were performed.

Histamine incorporation experiments were performed in accordance with a method disclosed in Br J Pharmacol. 2002; 136(6): 829-836. In the experiments, HEK293 cells were used. The HEK293 cell is a human embryonal renal cell strain expressing human organic cation transporter 3 (hOCT3). The HEK 293 cells were inoculated onto 24-well plates at $1.5 \times 10^5$ cells/well, and were cultivated overnight in a carbon dioxide incubator. Test substances were dissolved in 100% DMSO solution and then dissolved in HBSS-HEPES solution (buffer solution prepared by dissolving 9.7 g Hank's Balanced Salt, 1.4% sodium bicarbonate 25 mL, and 1M HEPES 25 mL in 940 mL ultra pure water, and by adjusting to pH7.4 with 1M sodium hydroxide). After removing culture media for cell culture, pretreatment was performed for 5 minutes with 1 mL HBSS-HEPES solution. Then, the test substance and [3H]histamine (final concentration 100 nM) were added to the cells and reacted for 1 minute at room temperature. After the reaction was completed, the reaction was stopped by ice-cooled HBSS-HEPES solution, extracellular fluid was aspirated by an aspirator, and then the cells were washed twice with HBSS-HEPES. After washing, the cells were dissolved in 0.5M sodium hydroxide solution. The amount of histamine in the cells was found by measuring a radioactivity in a cell lysis solution by a liquid scintillation counter. Protein content in the cells was measured by Lowry method (J Biol Chem. 1951; 193(1): 265-75) by using the cell lysis solution, and translated into histamine incorporation amount per protein content for each experiment. A histamine incorporation rate (%) in the presence of 30 µM of the test substance was calculated by regarding a histamine incorporation amount in a case of no incorporation inhibitor as 100% (control) of histamine incorporation rate. A value (%) obtained by subtracting the histamine incorporation rate from 100(%) was calculated as an OCT3 inhibition rate (%). Further, an OCT3 inhibition activity (IC$_{50}$ value and IC$_{80}$ value) was calculated by a control curve in a range of concentration of the test substance from $10^{-7}$ µM to $10^{-3}$ µM.

The results were shown in table 1. The following relates to those indicating —R$^3$— by —CH$_2$-R$^{37}$—C$_2$H$_4$— in formula (A).

TABLE 1

| Substituent of Formula (A) | | | Compound | Compound Concentration 30 µM | | | |
|---|---|---|---|---|---|---|---|
| R$^2$ | R$^{37}$ | R$^4$ | ID | Histamine Incorporation Rate to Control (%) | OCT3 Inhibition Rate (%) | OCT3 Inhibition Activity IC$_{50}$ (µM) | OCT3 Inhibition Activity IC$_{80}$ (µM) |
| R$^{21}$ | CH$_2$ | Formula V | SR-2076 | 11.8 | 88.2 | 1.9 | 8 |
| R$^{21}$ | CH$_2$ | Formula VI | SR-2065 | 41.5 | 58.5 | 24 | 90 |
| R$^{21}$ | CH$_2$ | Formula VII | SR-2073 | 52.9 | 47.1 | | |
| R$^{21}$ | CH$_2$ | Formula VIII | SR-2066 | 58.1 | 41.9 | | |
| R$^{21}$ | CH$_2$ | Formula IX | SR-2069 | 48.6 | 51.4 | | |
| R$^{21}$ | S | Formula VII | SR-2045 | 35.2 | 64.8 | 12.4 | 56 |
| R$^{22}$ | S | Formula V | SR-2219 | 22.6 | 77.4 | 19 | 49 |
| R$^{22}$ | S | Formula VI | SR-2023 | 15.0 | 85.0 | 6.5 | 28 |
| R$^{22}$ | S | Formula VIII | SR-2229 | 55.8 | 44.2 | | |
| R$^{23}$ | S | Formula V | SR-2036 | 15.4 | 84.6 | 5.9 | 27 |
| R$^{23}$ | S | Formula VI | SR-2022 | 21.0 | 79.0 | 10.5 | 30 |
| R$^{23}$ | S | Formula VIII | SR-2230 | 41.4 | 58.6 | | |

Famotidine is reported as a compound having strong OCT3 inhibition activity (Sata et al., J Pharmacol Exp Ther. 2005, 315(2): 888-95), and results of comparing OCT3 inhibition activities between these compounds and the above described compound having strong activity are as follows. Note that a histamine incorporation rate (%) in the presence of 10 µM of the test substance was calculated by regarding a histamine incorporation amount in a case of no incorporation inhibitor as 100% (control) of histamine incorporation rate. A value (%) obtained by subtracting the histamine incorporation rate from 100(%) was calculated as an OCT3 inhibition rate (%). Further, an OCT3 inhibition activity ($IC_{50}$ value and $IC_{80}$ value) was calculated by a control curve in a range of concentration of the test substance from $10^{-7}$ μM to $10^{-3}$ μM.

TABLE 2

| Compound Name | Compound Concentration 10 μM | | | |
|---|---|---|---|---|
| | Histamine Incorporation Rate to Control (%) | OCT3 Inhibition Rate (%) | OCT3 Inhibition Activity $IC_{50}$ (μM) | OCT3 Inhibition Activity $IC_{80}$ (μM) |
| FAMOTIDINE | 92.4 | 7.6 | 67.6 | 330 |
| SR-2076 | 14.8 | 85.2 | 1.9 | 8 |
| SR-2065 | 72.9 | 27.1 | 24 | 90 |
| SR-2045 | 56.6 | 43.4 | 12.4 | 56 |
| SR-2219 | 51.5 | 48.5 | 19 | 49 |
| SR-2023 | 36.7 | 63.3 | 6.5 | 28 |
| SR-2036 | 33.7 | 66.3 | 5.9 | 27 |
| SR-2022 | 50.0 | 50.0 | 10.5 | 30 |

From table 2, it can be understood that each compound of the present invention has OCT3 inhibition activity.

Example 13

Example Relates to SR2051

Target Compound

Chemical formula 57

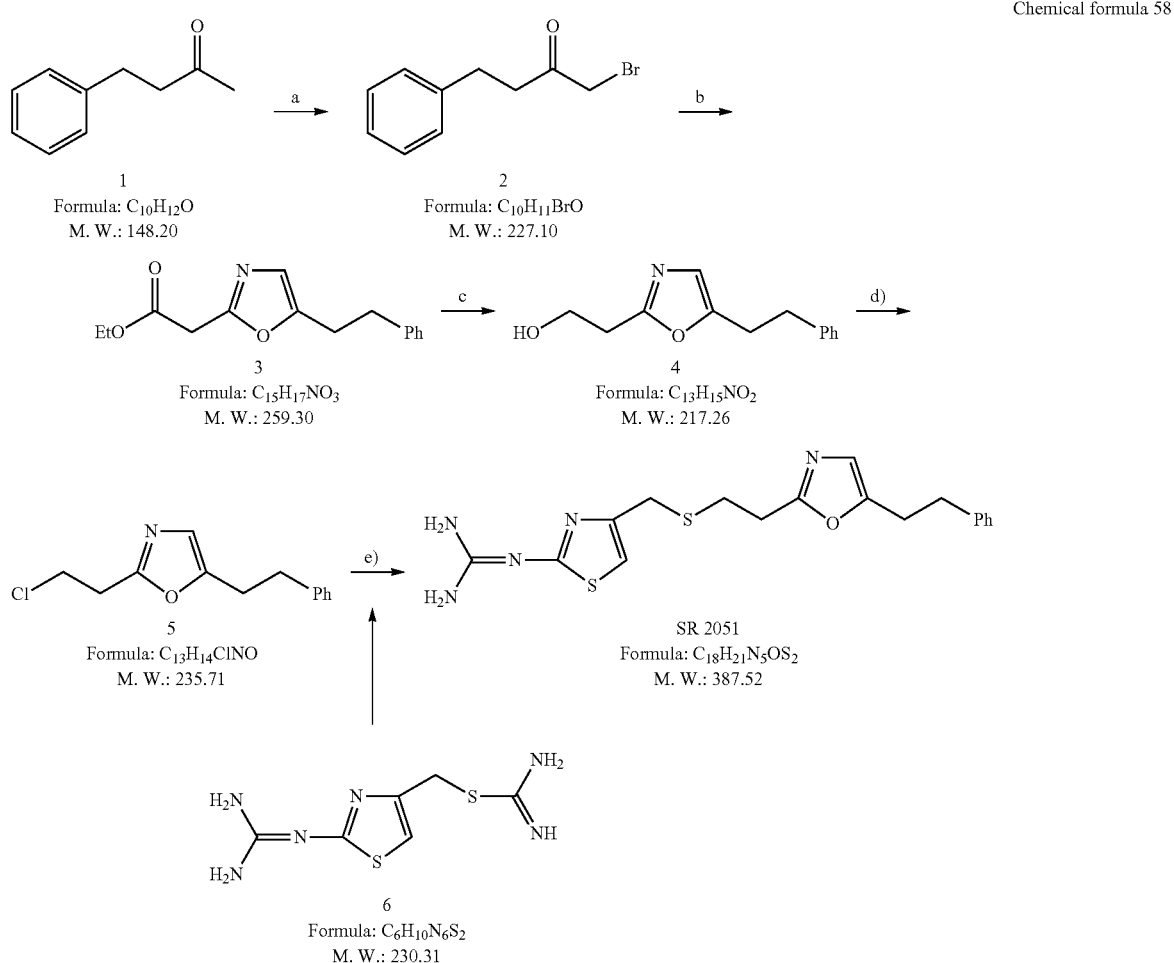

Chemical formula 58

Reagent and Condition
a) bromine, MeOH, rt, 2 h;
b) ethyl 3-amino-3-oxopropanoate, EtOH, reflux;
c) NaBH$_4$, MeOH;
d) SOCl$_2$, Et$_3$N, DCM;
e) NaOH, MeOH/H$_2$O Experiment Section 1-bromo-4-phenylbutan-2-one (2)[1]

To a solution of ketone 1 (4.52 g, 30 mmol) 240 ml in methanol, a solution of bromine (1.5 ml, 30 mmol) in 30 ml methanol was added in one portion at room temperature. The orange reaction mixture was then stirred at room temperature for 2 h. After the ketone 1 has been consumed, the reaction was quenched by adding a 0.3M sodium thiosulfate solution (18 ml) and diluted with EA (450 ml). The resulting mixture was washed with 450 ml water, then the organic phase was concentrated under reduce pressure to give a residue that was purified by chromatography (PE/EA, 10/1) to give the compound 2 (1.43 g, 21%). $^1$H-NMR (CDCl$_3$, 400 MHz): δ2.98 (t, 2H); 3.02 (t, 2H); 3.88 (s, 2H); 7.19~7.24 (m, 3H); 7.18~7.33 (m, 2H). M.W.: 226, 228) ESI-MS: 227, 229 (M+H).

Ethyl 2-(5-phenethyloxazol-2-yl)acetate (3)[5]

A solution of compound 2 (4.3 g, 19 mmol) and ethyl 3-amino-3-oxopropanoate (4.3 g, 33 mmol) in 50 ml EtOH was refluxed under nitrogen atmosphere for 48 h. After cooled at room temperature, the mixture was concentrated under reduce pressure to give a residue that was purified by chromatography (PE/EA, 10/1) to give the compound 3 (345 mg, 7%). $^1$H-NMR (CDCl$_3$, 300 MHz): δ1.25 (m, 3H); 2.73 (m, 2H); 3.49 (s, 2H); 4.21 (m, 2H); 4.66 (s, 2H); 7.08~7.35 (m, 6H).
M.W.: 259; ESI-MS: 260 (M+H).

2-(5-phenethyloxazol-2-yl)ethanol (4)

A solution of compound 3 (0.1 g, 0.38 mmol) and NaBH$_4$ (0.1 g, 2.6 mmol) in methanol (3 ml) was stirred 1 h at rt. Then the mixture was concentrated under reduce pressure to give a residue that was purified by chromatography (PE/EA, 2/1) to give the compound 4 (46 mg, 56%). $^1$H-NMR (CDCl$_3$, 300 MHz): δ2.61~2.78 (m, 2H); 2.81~2.95 (m, 4H); 3.56 (br, 1H); 3.95 (m, 2H); 7.08~7.35 (m, 6H). M.W.: 217; ESI-MS: 218 (M+H).

2-(2-chloroethyl)-5-phenethyloxazole(5): A solution of compound 4 (0.16 g, 0.74 mmol) and Et$_3$N (0.15 g, 1.5 mmol) in anhydrous DCM (3 ml) was cooled to 0~10° C., then dry SOCl$_2$ (0.8 ml, 11 mmol) was added. The mixture was stirred 2 h at rt. After that, the mixture was concentrated under reduce pressure to give a residue that was purified by chromatography (PE/EA, 25/1) to give the compound 5 (140 mg, 80%). $^1$H-NMR (CDCl$_3$, 300 MHz): δ2.68-2.80 (m, 2H); 2.81~2.97 (m, 2H); 3.18~3.24 (m, 2H); 3.95 (m, 2H); 7.08~7.35 (m, 6H). M.W.: 235; ESI-MS: 236 (M+H).

SR 2051[3]

A mixture of compound 5 (0.283 g, 1.2 mmol), NaOH (1.2 g, 3.0 mmol) and compound 6[4] (0.276 g, 1.2 mmol) in methanol/H$_2$O (10/10 ml) was stirred at room temperature under nitrogen atmosphere for 1 h. Then the solvent was removed under reduced pressure and the residue was purified by chromatography (DCM/Methanol, 50/1) to give compound SR 2051 (150 mg, 33%). $^1$H-NMR (d$^6$-DMSO, 400 MHz): δ2.71 (m, 2H); 2.81~2.88 (m, H); 2.96~3.00 (m, 2H); 3.60 (s, 2H); 6.50 (s, 1H); 6.85 (br, 2H); 7.15~7.28 (m, 5H); 7.65 (s, 1H). M.W.: 387; ESI-MS: 388 (M+H).

REFERENCES

1. *Bioorganic and Medicinal chemistry;* 2007, 3225~3234
2. *J. Med. Chem.* 1971, 1075~1077
3. U.S. Pat. No. 4,362,736
4. Detailed synthesis methods as shown in the report of SR 3155

Example 14

Example Relates to SR2216(OK-016)

Target Compound

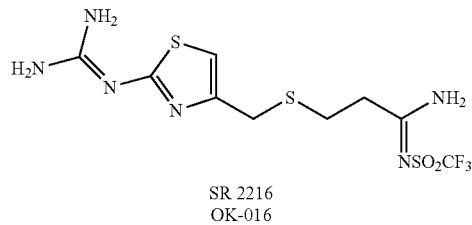

Chemical formula 59

SR 2216
OK-016

Synthesis Route

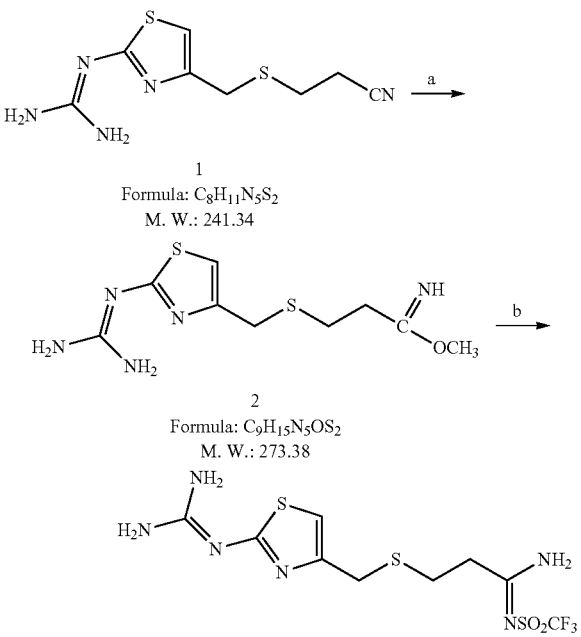

Chemical formula 60

Reagent and Condition a) dry HCl, MeOH/CHCl$_3$; b) c) CF$_3$SO$_2$NH$_2$, dry MeOH.

Experiment Section

SR 2216 (OK-016)[1]

A solution of 2-(4-((2-cyanoethylthio)methyl)thiazol-2-yl)guanidine 1[2] (0.48 g, 2 mmol) in anhydrous methanol/chloroform (10 ml/20 ml) was cooled to 0° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give to give compound 2. This intermediate was dissolved in the 5 ml methanol and trifluoromethanesulfonamide (0.447 g, 3 mmol) was added to the solution. The reaction mixture was stirred at the room temperature for 12 h, when TLC showed no starting material remained, the solvent was removed under reduced pressure and the residue was purified by chromatography (DCM/MeOH, 30/1) to give compound SR 2216 (OK-016) (0.27 g, 36%). $^1$H-NMR (d$^6$-DMSO, 300 MHz): δ2.48 (b, 4H); 3.57 (b, 2H); 3.66 (br, 3H, NH); 6.47 (s, 1H); 6.85 (br, 3H, NH); $^{13}$C-NMR (d$^6$-DMSO, 75 MHz): 27.9; 31.2; 35.7; 104.8; 147.6; 157.1; 157.2; 172.6; 175.4. M.W.: 390; ESI-MS: 391 (M+H).

REFERENCE 1. a) U.S. Pat. No. 4,362,736A; b) J. Med. Chem. 2004, 47, 2935
2. Detailed synthesis methods as shown in the report of SR 3203

Example 15

Example Relates to SR3203

Target Compound

Chemical formula 61

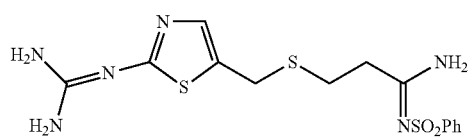

SR 3203

Synthesis Route

Chemical formula 62

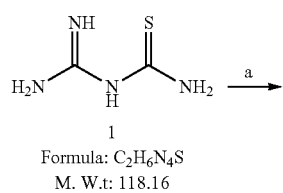

1
Formula: C$_2$H$_6$N$_4$S
M. W.t: 118.16

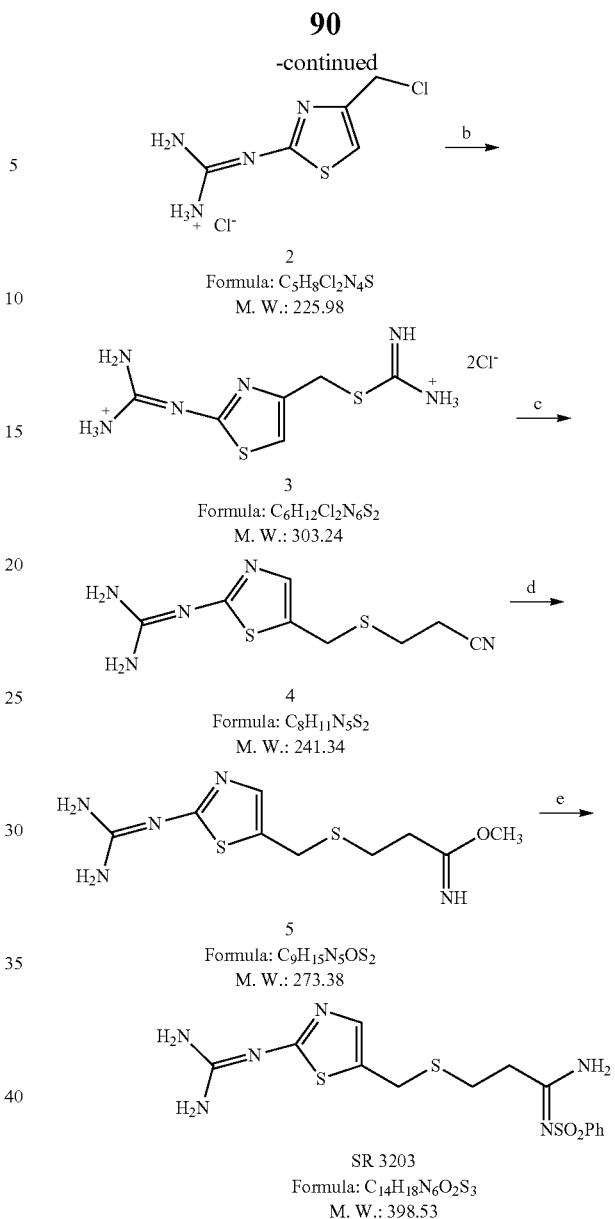

2
Formula: C$_5$H$_8$Cl$_2$N$_4$S
M. W.: 225.98

3
Formula: C$_6$H$_{12}$Cl$_2$N$_6$S$_2$
M. W.: 303.24

4
Formula: C$_8$H$_{11}$N$_5$S$_2$
M. W.: 241.34

5
Formula: C$_9$H$_{15}$N$_5$OS$_2$
M. W.: 273.38

SR 3203
Formula: C$_{14}$H$_{18}$N$_6$O$_2$S$_3$
M. W.: 398.53

Reagent and Condition a) CH$_2$ClCOCH$_2$Cl, actone, rt, 12 h; b) thiourea, EtOH, 80° C., 3 h; c) BrCH$_2$CH$_2$CN, EtOH, NaOH, 0° C.; d) dry HCl gas, MeOH/CHCl$_3$, 0~10° C.; e) benzenesulfonamide, dry MeOH, rt, 12 h Experiment Section 2-(5-(Chloromethyl)thiazol-2-yl)guanidine (2)[1]

A suspension of amidinothiourea 1 (118 g, 1 mol) in acetone (600 ml) was treated with 1,3-dichloroacetone (126 g, 1 mol). After stirring overnight at room temperature, the solid was filtered off and washed with acetone. Crystallization from ethanol gave the compound 2 (122 g, 54%). $^1$H-NMR (d$^6$-DMSO, 200 MHz): δ3.44 (br, 4H, NH); 4.76 (s, 2H); 7.43 (s, 1H); 8.41 (br, 1H, N$_3$+H). M.W.: 226 (hydrochloride); ESI-MS: 191 (M+H).

(2-(Diaminomethyleneamino)thiazol-5-yl)methyl carbamimidothioate (3)[2]

A solution of compound 2 (56.5 g, 0.25 mol) and thiourea (19 g, 0.25 mol) in 200 ml EtOH was stirred at 80° C. under nitrogen atmosphere for 3 h. After cooled at room temperature, the mixture was filtered and the residue washed with EtOH. Crystallization from 95% ethanol gave the compound 3 (61.9 g, 82%). $^1$H-NMR (d$^6$-DMSO, 300 MHz): δ3.42 (br, 7H, NH); 4.58 (s, 2H); 7.34 (s, 1H); 8.45 (br, 2H, N$_3$+H). M.W.: 302 (hydrochloride); ESI-MS: 231 (M+H).

2-(5-((2-Cyanoethylthio)methyl)thiazol-2-yl)guanidine (4)[3]

A solution of compound 3 (30.2 g, 0.1 mol) and BrCH$_2$CH$_2$CN (14.1 g, 0.1 mol) in ethanol/water (100 ml/100 ml) was cooled at 0° C., then aq. NaOH (0.4 mol, 16 g in 80 ml water) was added dropwise. After stirring 1 h at 0° C. and another 3 h at room temperature the mixture was filtered and the residue was washed with water. Crystallization from ethanol gave the compound 4 (19.2 g, 80%). $^1$H-NMR (d$^6$-DMSO, 300 MHz): δ2.74 (m, 2H); 2.83 (m, 2H); 3.41 (br, 3H, NH); 3.68 (s, 2H); 6.53 (s, 1H); 6.98 (br, 1H, NH). M.W.: 241; ESI-MS: 242 (M+H).

Methyl 3-((2-(diaminomethyleneamino)thiazol-5-yl)methylthio)propanimidate (5)[4]

A solution of compound 4 (12 g, 0.05 mol) in anhydrous methanol/chloroform (60 ml/120 ml) was cooled to 0~10° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate. The mixture was filtered and the residue washed with EtOH to give compound 5 (crude product, 13 g, 95.6%). 1H-NMR (d$^6$-DMSO, 300 MHz): δ2.60~2.64 (br, 4H); 3.45 (br, 4H, NH); 3.62 (s, 3H); 3.67 (s, 2H); 6.53 (s, 1H); 6.92 (br, 1H, NH). M.W.: 273; ESI-MS: 274 (M+H).

SR 3203[4]

A mixture of compound 5 (0.82 g, 3 mmol) and benzenesulfonamide (0.56 g, 3.6 mmol) in 5 ml dry methanol was stirred at room temperature under nitrogen atmosphere for 12 h. When TLC showed no starting material remained, the solvent was removed under reduced pressure and the residue was purified by chromatography (DCM/Methanol, 50/1) to give compound SR 3203 (530 mg, 44.4%). $^1$H-NMR (d$^6$-DMSO, 200 MHz): δ 2.54 (d, 2H); 2.62 (d, 2H); 3.42 (br, 6H, NH); 3.56 (s, 2H); 6.44 (s, 1H); 6.87 (br, 1H), 7.53 (d, 2H); 7.83 (d, 2H). M.W.: 398; ESI-MS: 399 (M+H).

REFERENCE

1. J. Med. Chem. 2004, 47, 2935-2938
2. WO 2005009986
3. Yiyao Gongye (1987) 18(6), 250-2.
4. U.S. Pat. No. 4,362,736A Example 16

Example Relates to SR2045

Target Compound

Chemical formula 63

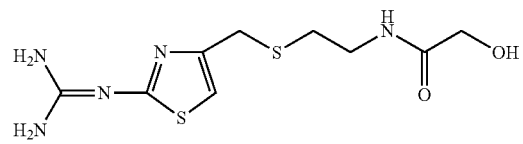

SR 2045

Synthesis Route

Chemical formula 64

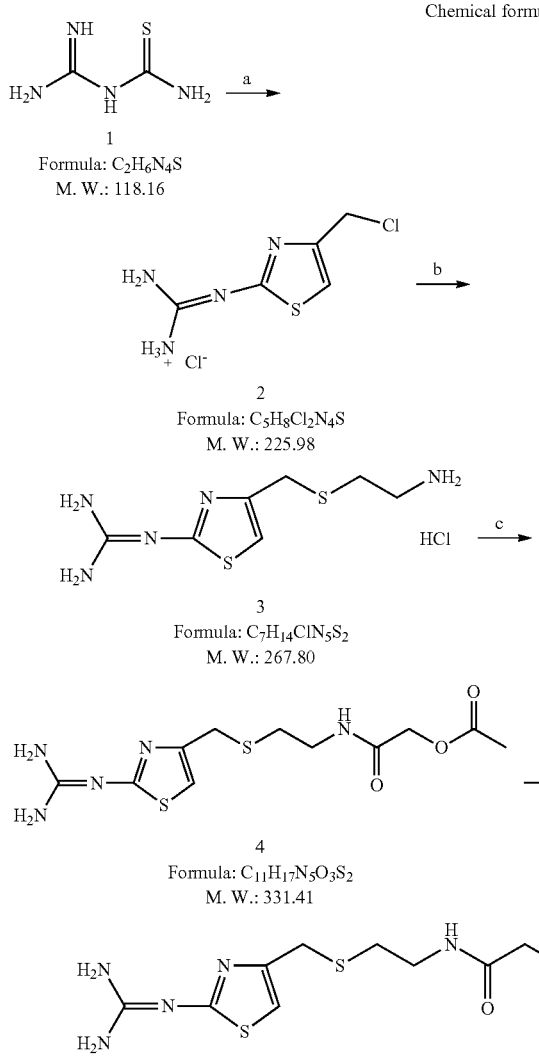

Reagent and Condition a) $CH_2ClCOCH_2Cl$, actone, rt, 12 h; b) 2-aminoethiol hydrochloride, EtONa, EtOH, 0° C., rt; c) 2-acetoxy-actyl-chloride, $Et_3N$, THF; d) NaOH, MeOH, $H_2O$ Experiment Section 2-(2-((2-(diaminomethyleneamino)thiazol-4-yl)methyl-thio)ethylamino)-2-oxoethyl acetate (4)[1] A solution of compound 3[2] (1.82 g, 6 mmol) and $Et_3N$ 5 ml in THF (100 ml) was cooled at 0° C., then 2-acetoxy-actylchloride (0.983 g, 7.2 mmol) was added dropwise. After stirring 2 h at rt the solvent was removed under reduced pressure and the residue was purified by chromatography (DCM/Methanol, 50/1) to give compound 4 (990 mg, 50%). $^1$H-NMR ($d^6$-DMSO, 300 MHz): δ 2.06 (s, 3H); 3.08 (m, 2H); 3.68 (s, 2H); 4.50 (s, 2H); 6.70 (s, 1H); 7.62 (br, 2H), 8.28 (br, 1H).

SR-2045[1]

A solution of compound 4 (0.66 g, 2 mmol) and NaOH (0.4 g, 10 mmol) in MeOH/H2O (30/30 ml) was stirred 1 h at rt, and then the solvent was removed under reduced pressure and the residue was purified by chromatography (DCM/Methanol, 20/1) to give compound SR 2045 (490 mg, 85%). $^1$H-NMR ($d^6$-DMSO, 400 MHz): δ1.92 (s, 1H); 2.55 (d, 2H); 3.10 (m, 1H); 3.30 (m, 2H); 3.62 (m, 2H); 3.80 (s, 2H); 6.50 (s, 1H); 6.80 (br, 3H), 7.80 (br, 1H). $^{13}$C-NMR ($d^6$-DMSO, 75 MHz): 174.478, 171.857, 156.766, 147.774, 104.784, 61.693, 31.013, 30.452, 21.131. M.W.: 289; ESI-MS: 290 (M+H).

REFERENCES

1. J. Med. Chem. 1988, 31, 1479-1486
2. Detailed synthesis methods as shown in the report of SR 2044

Example 17

Example Relates to SR2203(OK-003)

Target Compound

Chemical formula 65

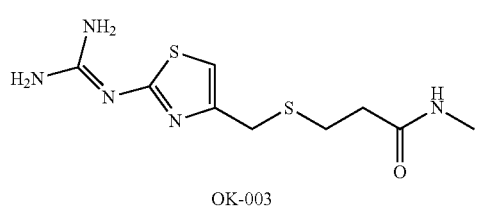

OK-003

SR 2203

Synthesis Route

Chemical formula 66

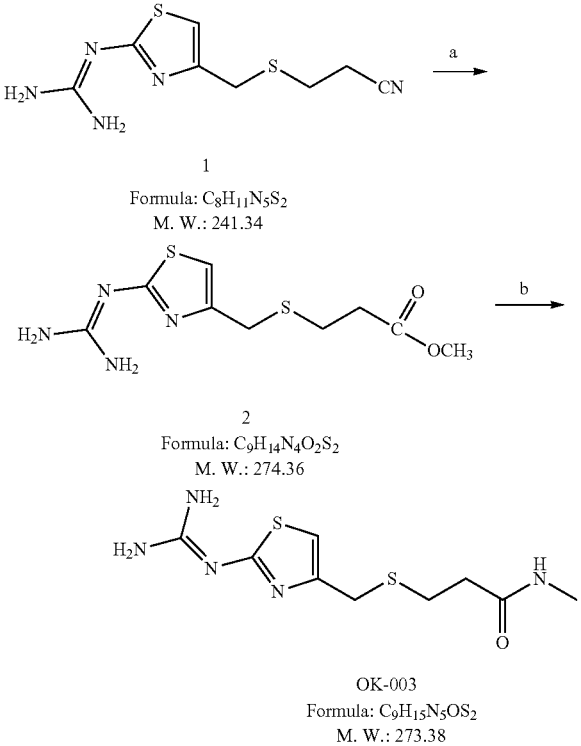

Reagent and Condition a) HCl(g), $CHCl_3/MeOH/H_2O$; b) $CH_3NH_2$, MeOH

Experiment Section

Methyl 3-((2-(diaminomethyleneamino)thiazol-4-yl) methylthio)propanoate (2)[1]

A solution of 2-(4-((2-cyanoethylthio)methyl)thiazol-2-yl)guanidine 1[2] (0.48 g, 2 mmol) in chloroform/methanol/$H_2O$ (20 ml/10 ml/5 ml) was cooled to 0° C., then HClgas was bubbled for 3 h under this temperature. After that, the mixture was allowed to stand at room temperature for 20 h and then concentrated under reduced pressure to afford oil crude product, the residue was purified by chromatography (DCM/MeOH, 50/1) to give the ester compound 2 (0.48 g, 87.6%). M.W.: 274, ESI-MS: 275 (M+H).

SR 2203 (OK-003)[3]

The compound methyl 3-((2-(diaminomethyleneamino) thiazol-4-yl) methylthio) propanoate 2 (0.41 g, 1.5 mmol) was added in 10 ml of 40% methanol solution of methyl amine, the reaction mixture was stirred at room temperature for 12 h, when TLC showed no starting material remained, the solvent was removed under reduced pressure and the residue was purified by chromatography (DCM/MeOH, 25/1) to give compound SR 2203 (OK-003) (0.33 g, 80.6%). $^1$H-NMR ($d^6$-DMSO, 400 MHz): δ2.33 (t, 2H); 2.54 (s, 3H); 2.63 (t, 2H); 3.32 (br, 4H, NH); 3.55 (s, 2H); 6.56 (s, 1H); 6.82 (br, 1H, NH), M.W.: 273, ESI-MS: 274 (M+H).

REFERENCES

1. U.S. Pat. No. 4,362,736A
2. Detailed synthesis methods as shown in the report of SR 3203
3. J. Med. Chem. 2004, 47, 2935

Example 18

Example Relates to SR2225(OK-025)

Target Compound

Chemical formula 67

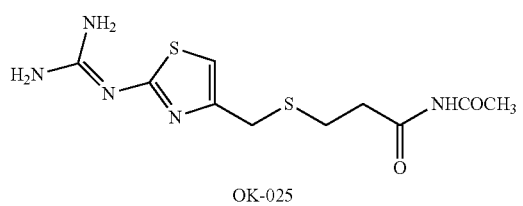

OK-025

Synthesis Route

Chemical formula 68

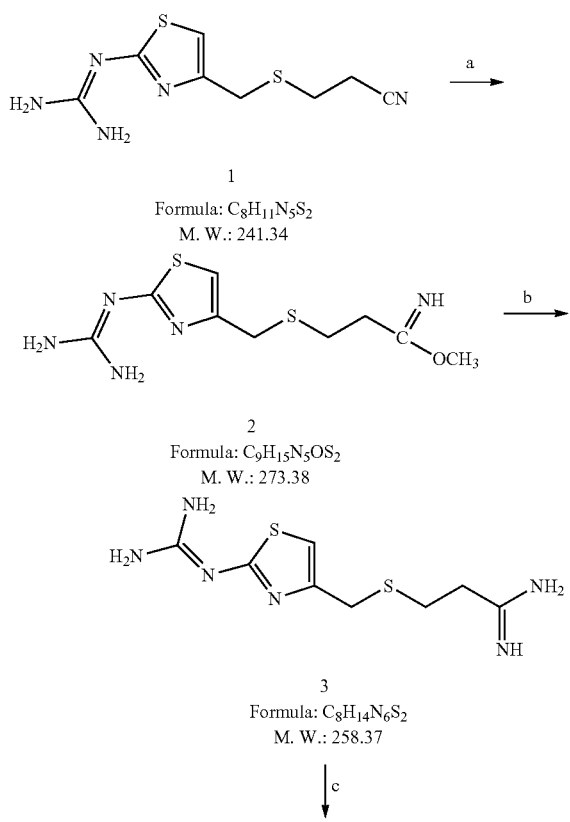

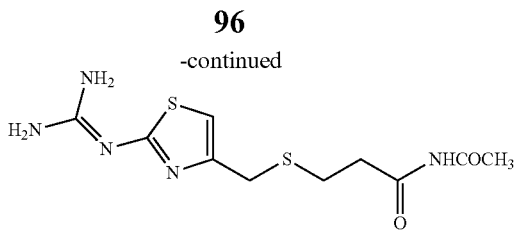

OK-025
Formula: $C_{10}H_{15}N_5O_2S_2$
M. W.: 301.39

Reagent and Condition a) dry HCl, MeOH/CHCl$_3$; b) NH$_4$Cl, dry MeOH; c) CH$_3$COCl, Et$_3$N, DMF Experiment Section

SR 2225 (OK-025)[1]

A solution of compound 3[2] (0.48 g, 2 mmol) and Et$_3$N (0.51 g, 5 mmol) were added into 20 ml anhydrous DMF at 0° C., then the acetyl chloride (0.24 g, 3 mmol) was added into mixture, and the reaction mixture was stirred for 12 h under room temperature. When TLC showed no starting material remained, the solvent was removed under reduced pressure and the residue was purified by chromatography (DCM/MeOH, 50/1) to give compound SR 2225 (OK-025) (0.37 g, 61%). $^1$H-NMR (d$^6$-DMSO, 300 MHz): δ2.15 (s, 3H); 2.73 (m, 4H); 3.37 (br, 4H, NH); 3.62 (s, 2H); 6.60 (s, 1H); 7.12 (br, 1H, NH). M.W.: 301; ESI-MS: 302 (M+H).

REFERENCES 1. a) J. Med. Chem. 1983, 26, 140; b) J. Med. Chem. 1990, 33, 1721; c) J. Am. Chem. Soc. 1949, 71; 616
2. a) U.S. Pat. No. 4,362,736A; b) J. Med. Chem. 2004, 47, 2935; c) Detailed synthesis methods as shown in the report of SR 3203; d) J. Med. Chem. 1983, 26, 140; e) J. Med. Chem. 1990, 33, 1721; f) J. Am. Chem. Soc. 1949, 71, 616; g) Detailed synthesis methods as shown in the report of SR 2076

Example 19

Example Relates to SR2226(OK-026)

Target Compound

Chemical formula 69

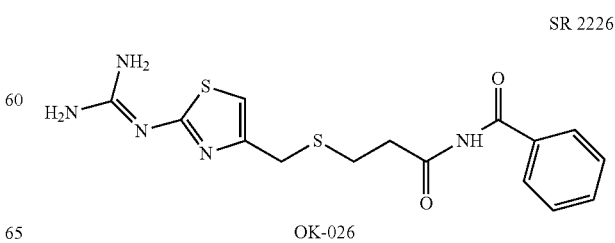

OK-026

Synthesis Route

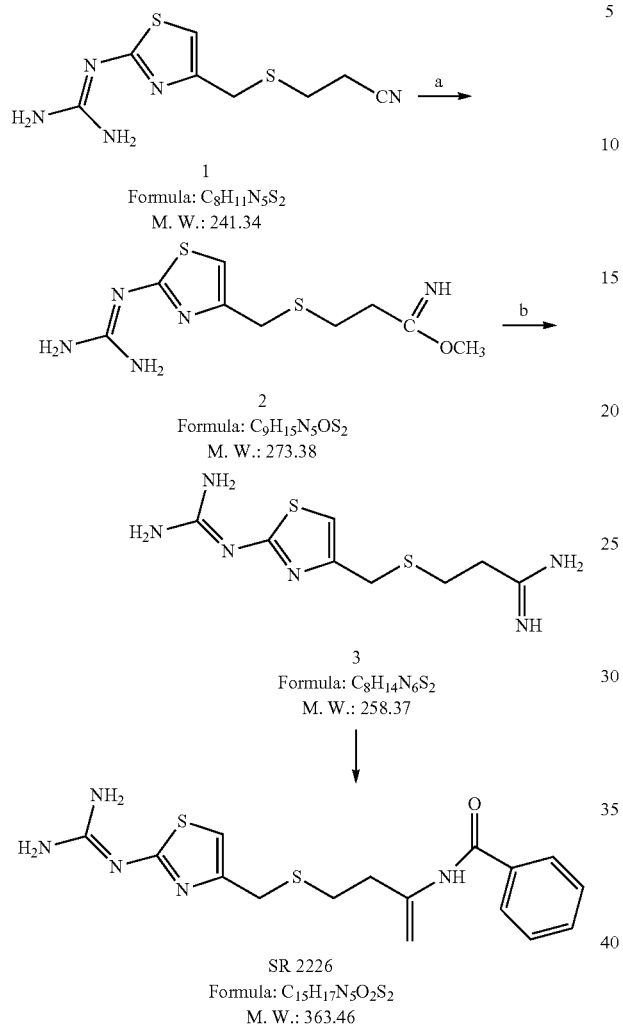

Reagent and Condition
c) dry HCl, MeOH/CHCl₃; b) NH₄Cl, dry MeOH; c) benzoyl chloride, Et₃N, DMF

Experiment Section

SR 2226 (OK-026)[1]

A solution of compound 3[2] (0.48 g, 2 mmol) and Et₃N (0.51 g, 5 mmol) were added into in 20 ml anhydrous DMF at 0° C., then the benzoyl chloride (0.42 g, 3 mmol) was added into mixture, and the reaction mixture was stirred for 12 h under room temperature. When TLC showed no starting material remained, the solvent was removed under reduced pressure and the residue was purified by chromatography (DCM/MeOH, 50/1) to give compound SR 2226 (OK-026) (0.43 g, 59%). $^1$H-NMR (d$^6$-DMSO, 300 MHz): δ2.74 (m, 2H); 3.01 (m, 2H); 3.35 (br, 4H, NH); 3.71 (s, 2H); 6.84 (s, 1H); 7.52 (br, 1H, NH); 7.62 (m, 3H); 7.92 (m, 2H). M.W.: 363; ESI-MS: 364 (M+H).

REFERENCES 1. a) J. Med. Chem. 1983, 26, 140; b) J. Med. Chem. 1990, 33, 1721; c) J. Am. Chem. Soc. 1949, 71; 616
2. a) U.S. Pat. No. 4,362,736A; b) J. Med. Chem. 2004, 47, 2935; c) synthesis methods as shown in the report of SR 3203; d) J. Med. Chem. 1983, 26, 140; e) J. Med. Chem. 1990, 33, 1721; f) J. Am. Chem. Soc. 1949, 71, 616; g) synthesis methods as shown in the report of SR 2076

Example 20

Example Relates to SR2044

Target Compound

Reagent and Condition a) CH$_2$ClCOCH$_2$Cl, actone, rt, 12 h; b) 2-aminoethiol hydrochloride, EtONa, EtOH, 0° C., rt; c) (E)-N-methyl-1-(methylthio)-2-nitroethenamine, NaOH, Et$_3$N Experiment Section 2-(5-(Chloromethyl)thiazol-2-yl)guanidine (2)[1]

A suspension of amidinothiourea 1 (118 g, 1 mol) in acetone (600 ml) was treated with 1,3-dichloroacetone (126 g, 1 mol). After stirring overnight at room temperature, the solid was filtered off and washed with acetone, Crystallization from ethanol gave the compound 2 (122 g, 54%, Rf=0.4, DCM/Methanol, 5/1). $^1$H-NMR (d$^6$-DMSO, 300 MHz): δ3.44 (b, 4H); 4.76 (s, 2H); 7.43 (s, 1H); 8.41 (b, 1H). M.W.: 226 (hydrochloride); ESI-MS: 191 (M+H).

2-(4-((2-aminoethylthio)methyl)thiazol-2-yl)guanidine hydrochloride salt (3)[1]

A solution of 2-aminoethiol hydrochloride (4.52 g, 40 mmol) in ethanol (40 ml) was added dropwise to a solution of sodium ethoxide in ethanol (60 ml) under nitrogen atmosphere at 0° C. After stirring for 2 hours at 0° C., a solution of compound 2 (4.54 g, 0.024 mol) in ethanol (35 ml) was added dropwise over 15 minutes while the temperature was maintained at 0° C. The mixture was then stirred at room temperature for 16 hours. The mixture was filtered and the filtrate was acidified with concentrated hydrochloric acid. Compound 3 was precipitated as a white crystalline solid (5.8 g, 79.5%, Rf=0.3, DCM/Methanol, 1/1). $^1$H-NMR (d$^6$-DMSO, 300 MHz): δ2.72 (t, 2H); 2.97 (b, 2H); 3.80 (s, 2H); 7.23 (s, 1H); 8.21 (b, 2H); 8.37 (s, 3H); 12.77 (b, 1H). M.W.: 304.30 (hydrochloride salt); ESI-MS: 232 (M+H).

SR 2044 m: To a solution of compound 3 (1.82 g, 6 mmol) in H$_2$O (20 ml) was added NaOH (0.48 g, 12 mmol) until pH=7. The water was removed under reduced pressure and the residue was dissolved in 30 ml methanol. To this solution was added (E)-N-methyl-1-(methylthio)-2-nitroethenamine (1.34 g, 9 mmol) and Et3N (5 ml). Then the mixture was refluxed at 55° C. for 4 h. After that the solvent was removed under reduced pressure and the residue was purified by chromatography (DCM/Methanol, 50/1) to give compound SR 2044 (597 mg, 30%). $^1$H-NMR (d$^6$-DMSO, 400 MHz): δ2.64 (s, 3H); 2.82 (m, 2H); 3.12 (m, 1H); 3.65-3.72 (m, 4H); 6.40 (m, 1H); 6.92 (s, 1H); 7.41 (b, 1H); 7.86 (b, 3H). $^{13}$C-NMR (d$^6$-DMSO, 75 MHz): δ173.020, 156.389, 156.157, 147.659, 105.187, 96.858, 31.137; 30.090, 28.765, 28.05; M.W.: 331; ESI-MS: 332 (M+H).

REFERENCES

1. J. Med. Chem. 2004, 47, 2935-2938
2. PCT Int. Appl., 2004069817, 19 Aug. 2004; Faming Zhuanli Shenqing Gongkai Shuomingshu, 1962626, 16 May 2007

Example 21

Example Relates to SR2204 (OK-004)

Target Compound

Chemical formula 73

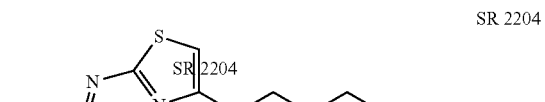

Synthesis Route

Chemical formula 74

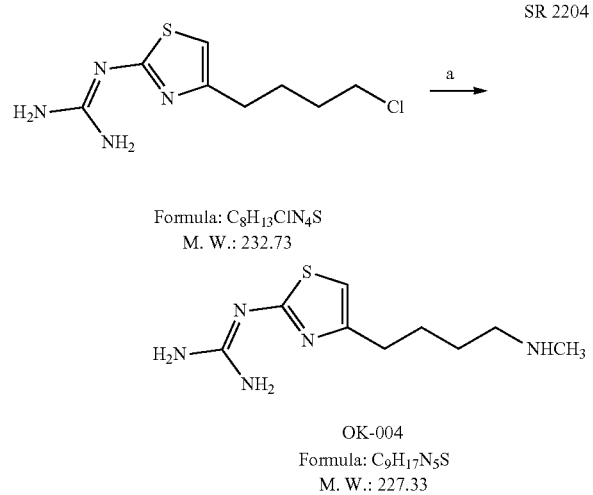

Reagent and Condition a) CH$_3$NH$_2$, MeOH

Experiment Section

SR 2204 (OK-004)[1]

The compound 2-(4-(4-chlorobutyl)thiazol-2-yl)guanidine[2] (0.46 g, 2 mmol) was added in 20 ml of 40% methanol solution of methyl amine. The reaction mixture was stirred at room temperature for 48 h, when TLC showed no starting material remained, the solvent was removed under reduced pressure and the residue was purified by chromatography (DCM/MeOH, 20/1) to give compound SR 2204 (OK-004) (0.31 g, 68.3%). $^1$H-NMR (d$^6$-DMSO, 300 MHz): δ1.57-1.59 (m, 4H); 2.48 (m, 2H); 2.78 (t, 2H); 3.59 (br, 4H, NH$_2$); 6.25 (s, 1H); 6.83 (br, 1H, NH). M.W.: 227; ESI-MS: 228 (M+H).

REFERENCES

1. U.S. Pat. No. 4,362,736A
2. Detailed synthesis methods as shown in the report of SR 2071

Example 22

Example Relates to SR2071

Target Compound

Chemical formula 75

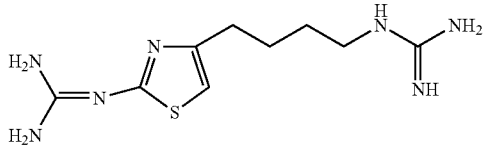

SR 2071

Synthesis Route

Chemical formula 76

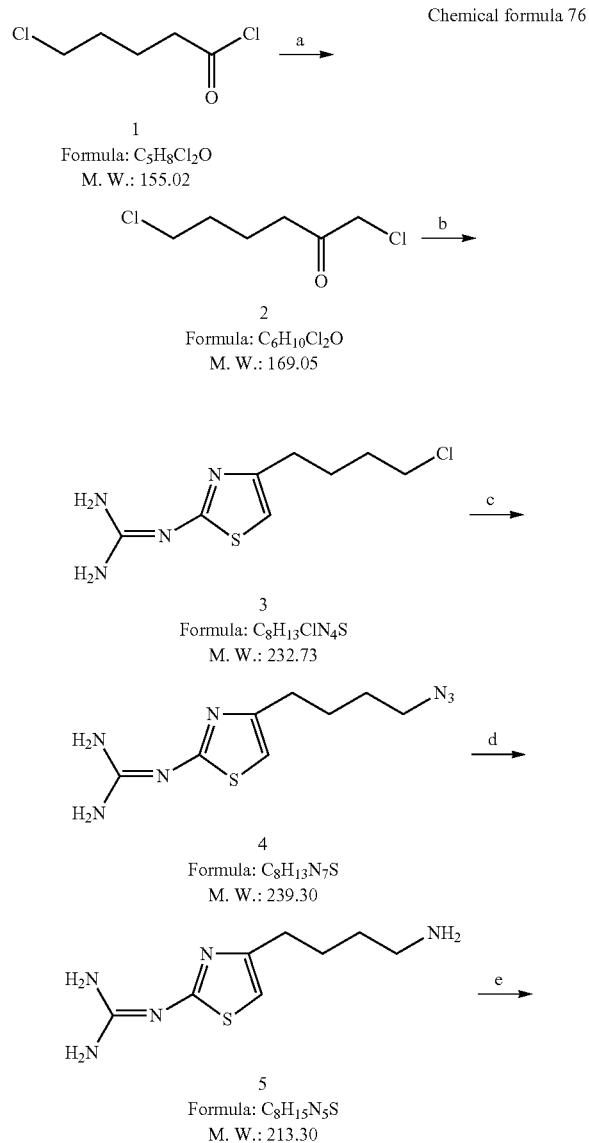

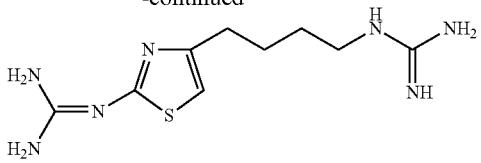

SR 2071
Formula: $C_9H_{17}N_7S$
M. W.: 255.34

Reagent and Condition a) $CH_2N_2$, ether, 0° C. b) guanylthiourea, acrtone, 70° C. c) $NaN_3$, DMSO, 70° C. d) $PPh_3$, $THF/H_2O$ e) 1,3-Bis(tert-butoxycarbonyl-2-(trifluoromethanesulfonyl)guanidine, dry MeOH

Experiment Section 1,6-dichlorohexan-2-one (2)[1]

To 200 ml of ether solution of diazomethane prepared from KOH (80 g, 1.43 mol), chloroform (48 g, 0.41 mol) and $NH_2NH_2.H_2O$ (11.76 g, 85%, 0.2 mol) was added under stirring 30 ml of ether solution of 5-chlorovalerylchloride (6 g, 39 mmol) dropwise at 0° C., and the solution was allowed to stand the same temperature for 2 h. Hydrogen chloride gas was passed through the reaction solution for 0.5 h. To the solution was added 100 ml of 1M NaOH and the ether layer was separated. The ether was washed twice with water, dried with magnesium sulfate and removed by distillation. The residue was distilled under reduced pressure to provide 1,6-dichlorohexan-2-one 2 (4.8 g, 73.3%).

2-(4-(4-chlorobutyl)thiazol-2-yl)guanidine (3)[1]

The suspension of 1,6-dichlorohexan-2-one (4.7 g, 28 mmol) and guanylthiourea (3.3 g, 28 mmol) in 80 ml acetone was stirred and refluxed at 75° C. over night. When TLC showed no starting material remained, the solvent was removed under reduced pressure and the residue was purified by chromatography (DCM/Methanol, 50/1) to give compound 3 (3.77 g, 58%). $^1$H-NMR (d$^6$-DMSO, 300 MHz): δ1.71 (br, 2H); 1.92 (br, 2H); 2.53 (br, 2H); 3.34 (br, 2H, NH); 3.66 (br, 2H); 6.35 (s, 1H); 6.94 (br, 2H, NH). M.W.: 232, ESI-MS: 233 (M+H).

2-(4-(4-azidobutyl)thiazol-2-yl)guanidine (4)[2]

To 30 ml of dimethylsulfoxide was added 2-(4-(4-chlorobutyl)thiazol-2-yl)guanidine 3 (1.16 g, 5 mmol) and sodium azide (0.36 g, 5.5 mmol), and the mixture was stirred and heated at 75° C. over night. When TLC showed no starting material remained, the reaction solution was removed under reduced pressure and the residue was purified by chromatography (DCM/Methol, 50/1) to give compound 3 (1.17 g, 98%). $^1$H-NMR (d$^6$-DMSO, 300 MHz): δ1.76 (br, 4H); 2.54 (br, 2H); 3.34 (br, 2H, NH); 3.71 (br, 2H); 6.38 (s, 1H); 7.05 (br, 2H, NH).

2-(4-(4-aminobutyl)thiazol-2-yl)guanidine (5)[2]

To the solution of 2-(4-(4-azido butyl)thiazol-2-yl)guanidine 4 (0.96 g, 4 mmol) in the 30 ml $THF/H_2O$ solution (v/v, 2/1), the triphenylphosphine (1.25 g, 4.8 mmol) was added. The reaction mixture was stirred at room temperature for 4 h, when TLC showed no starting material remained, the solvent was removed under reduced pressure and the residue was crystallized from ethanol to give 2-(4-(4-aminobutyl)thiazol-2-yl)guanidine (0.77 g, 90%) (5). M.W.: 213; ESI-MS: 214 (M+H).

SR 2071[3]

A mixture of compound 5 (0.213 g, 1 mmol) and 1,3-Bis(tert-butoxycarbonyl-2-(trifluoromethanesulfonyl)guanidine (0.128 g, 1 mmol) in 10 ml dry methanol was stirred at room temperature under nitrogen atmosphere for 1 h, when TLC showed no starting material remained, the solvent was removed under reduced pressure and the residue was crystallized from ethanol to give compound SR 2071 (210 mg, 82%). $^1$H-NMR (CD$_3$OD, 300 MHz): δ1.64 (m, 2H); 1.78 (m, 2H); 2.74 (t, 2H); 2.84 (t, 2H); 4.88 (br, 8H, NH); 6.85 (s, 1H). $^{13}$C-NMR (CD$_3$OD, 75 MHz): δ26.99, 29.48, 31.80, 42.38, 108.84, 154.12, 156.36, 158.79, 161.26; M.W.: 255; ESI-MS: 256 (M+H).

REFERENCES 1. a) U.S. Pat. No. 4,362,736A; b) J. Med. Chem. 2004, 47, 2935
2. a) Macromol. Rapid Commun. 2006, 27, 1739; b) J. Org. Chem. 1982, 47, 4327; c) J. Org. Chem. 1998, 63, 2796; d) Tetrahedron Letters, 1997, 38, 1065.
3. a) Bull. Chem. Soc. Jpn. 2009, 82, 1175; b) Chem. Pap. 2007, 61 507.

Example 23

Example Relates to SR2072

Target Compound

Chemical formula 77

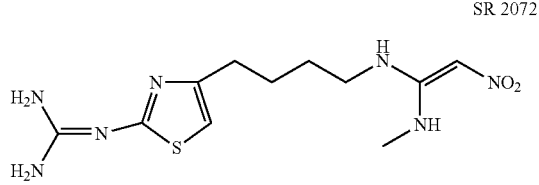

SR 2072

Synthesis Route

Chemical formula 78

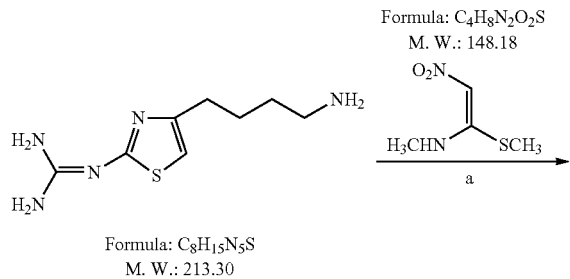

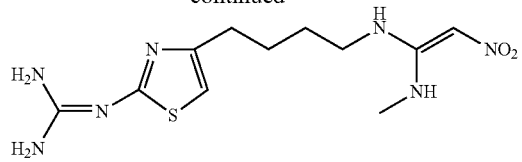

SR 2072
Formula: C$_{11}$H$_{19}$N$_7$O$_2$S
M. W.: 313.38

Reagent and Condition a) N-methyl-1-(methylthio)-2-nitroethenamine, Et$_3$N, MeOH.

Experiment Section

SR 2072[1]

A mixture of 2-(4-(4-aminobutyl)thiazol-2-yl)guanidine [2] (0.213 g, 1 mmol), N-methyl-1-(methylthio)-2-nitroethenamine (0.148 g, 1 mmol) and triethylamine (0.202 g, 2 mmol) in 10 ml dry methanol was stirred at room temperature under nitrogen atmosphere for 12 h, when TLC showed no starting material remained, the solvent was removed under reduced pressure and the residue was purified by chromatography (DCM/MeOH, 20/1) to give compound SR 2072 (0.21 g, 67%). $^1$H-NMR (d$^6$-DMSO, 300 MHz): δ1.61 (br, 4H); 2.72 (br, 4H); 3.08 (br, 3H); 3.38 (br, 6H); 6.31 (s, 1H); 6.87 (br, 1H). $^{13}$C-NMR (d$^6$-DMSO, 75 MHz): δ25.7, 28.1, 28.6, 31.1, 39.9, 95.0, 103.3, 151.7, 156.3, 156.5, 173.0; M.W.: 313, ESI-MS: 314 (M+H).

REFERENCES 1. a) J. Med. Chem. 2004, 47, 2935; b) J. Med. Chem. 1992, 35, 1102; c) J. Med. Chem. 1992, 35, 3141.
2. a) Detailed synthesis methods as shown in the report of SR 2071; b) Macromol. Rapid Commun. 2006, 27, 1739; c) J. Org. Chem. 1982, 47, 4327; d) J. Org. Chem. 1998, 63, 2796; d) Tetrahedron Letters, 1997, 38, 1065.

Example 24

Example Relates to SR2075

Target Compound

Chemical formula 79

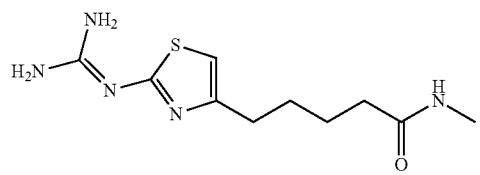

SR 2075

Synthesis Route

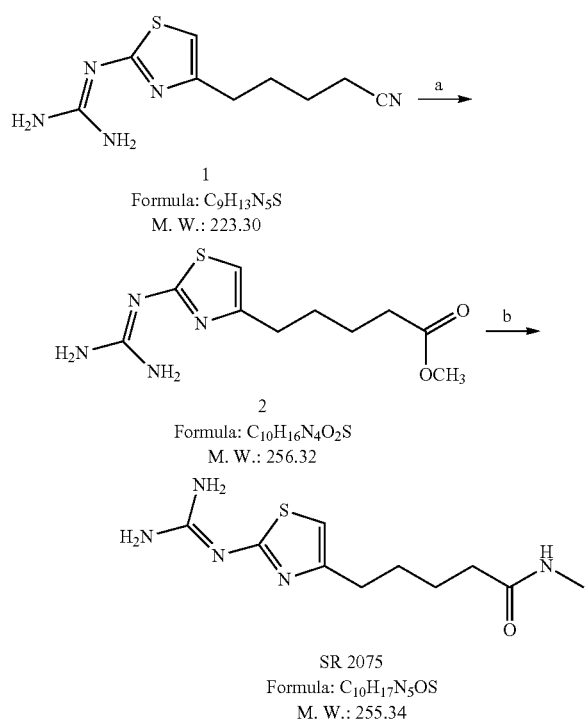

Reagent and Condition:
a) HCl(g), CHCl$_3$/MeOH/H$_2$O; b) CH$_3$NH$_2$, MeOH

Experiment Section

Methyl 5-(2-(diaminomethyleneamino)thiazol-4-yl)pentanoate (2)[1]

A solution of 2-(4-(4-cyanobutyl)thiazol-2-yl)guanidine 1[2] (0.45 g, 2 mmol) in chloroform/methanol/H$_2$O (20 ml/10 ml/5 ml) was cooled to 0° C., then dry HClgas was bubbled for 3 h under this temperature. After that, the mixture was allowed to stand at room temperature for 20 h and then concentrated under reduced pressure to afford crude product. The residue was purified by chromatography (DCM/MeOH, 50/1) to give the compound 2 (0.43 g, 83%).
M.W.: 256, ESI-MS: 257 (M+H).

SR 2075[3]

Compound 2 (0.39 g, 1.5 mmol) was added to 10 ml of 40% methanol solution of methyl amine, and then the reaction mixture was stirred at room temperature for 12 h. When TLC showed no starting material remained, the solvent was removed under reduced pressure and the residue was purified by chromatography (DCM/MeOH, 25/1) to give compound SR 2075 (0.29 g, 76%). $^1$H-NMR (CD$_3$OD, 300 MHz): δ 1.29 (br, 2H); 1.63 (br, 3H); 2.20 (br, 2H); 2.70 (br, 4H); 4.93 (br, 5H, NH); 6.56 (s, 1H). M.W.: 255, ESI-MS: 256 (M+H).

REFERENCES

1. U.S. Pat. No. 4,362,736A
2. Detailed synthesis methods as shown in the report of SR 2068
3. J. Med. Chem. 2004, 47, 2935

Example 25

Example Relates to SR3136

Target Compound

Chemical formula 81

SR 3136

Formula: C$_{13}$H$_{16}$FN$_5$S
M. W.: 293.36

Synthesis Route

Chemical formula 82

1
Formula: C$_5$H$_8$Cl$_2$N$_4$S
M. W.: 227.11

SR 3136
Formula: C$_{13}$H$_{16}$FN$_5$S
M. W.: 293.36

Reagent and Condition:
a) 4-Fluorophenethylamine, KI, DMF

Experiment Section

SR 3136:[1]

A mixture of compound 2-(5-(Chloromethyl)thiazol-2-yl)guanidinem (hydrochloride, 0.226 g, 1 mmol), 4-Fluorophenethylamine (1.39 g, 10 mmol), and some KI (catalysis) in dry DMF 5 ml was stirred at room temperature under nitrogen atmosphere for 12 h. When TLC showed no starting material remained, the solvent was removed under reduced pressure and the residue was purified by chromatography (DCM/MeOH, 50/1) to give compound SR 3136 (184 mg, 62.8%). 1H-NMR (d$^6$-DMSO, 300 MHz): δ2.93-2.99 (b, 4H); 3.85-3.95 (br, 6H); 6.56 (s, 1H); 6.92 (br, 1H), 7.13 (m, 2H); 7.25 (m, 2H). M.W.: 293, ESI-MS: 332 (M+K).

REFERENCES

1. J. Am. Chem. Soc. 1988, 110, 5524.
2. Detailed synthesis methods as shown in the report of SR 2044

Example 26

Example Relates to SR3131

Target Compound

Chemical formula 83

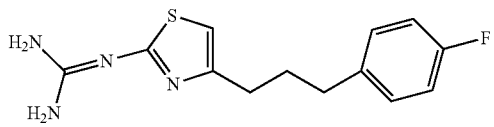

SR 3131

Synthesis Route

Chemical formula 84

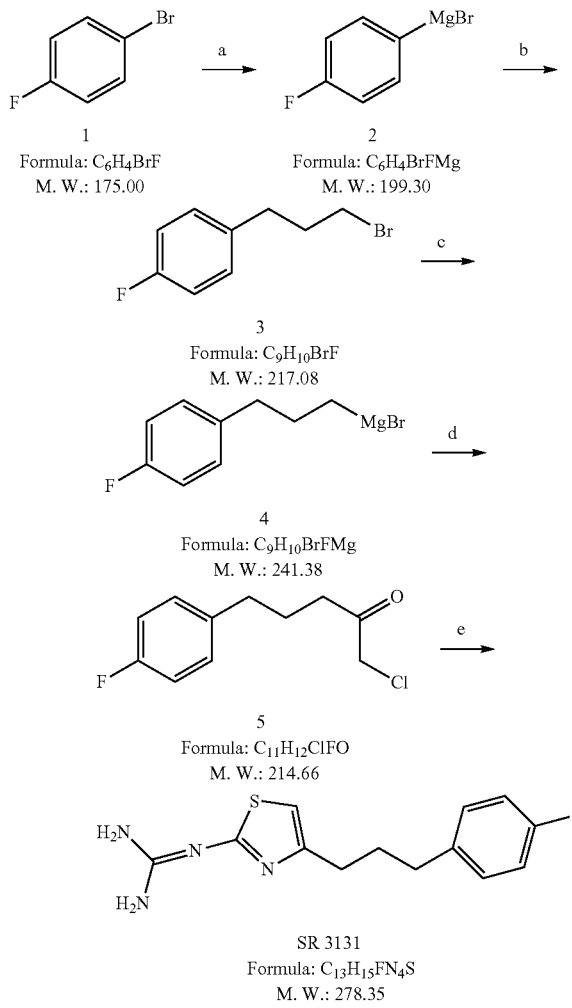

1
Formula: C$_6$H$_4$BrF
M. W.: 175.00

2
Formula: C$_6$H$_4$BrFMg
M. W.: 199.30

3
Formula: C$_9$H$_{10}$BrF
M. W.: 217.08

4
Formula: C$_9$H$_{10}$BrFMg
M. W.: 241.38

5
Formula: C$_{11}$H$_{12}$ClFO
M. W.: 214.66

SR 3131
Formula: C$_{13}$H$_{15}$FN$_4$S
M. W.: 278.35

Reagent and Condition a) Mg, THF, 40° C., 3 h; b) 1,3-dibromopropane, CuBr, LiBr, THF, 0° C., 3 h; c) Mg, THF, 50° C., 3 h; d) 2-chloro-N-methylacetamide, toulene/THF, 0~5° C.; e)amidinothiourea, 50° C., 12 h.

Experiment Section (4-flourophenyl) magnesium bromide (2): To a mixture of Mg (1.65 g, 68.75 mmol) in dry THF (10 ml), 1-bromo-4-fluorobenzene (1.75 g, 10 mmol) was added 40° C. When the temperature raised to 55° C., which meant that the reaction started, the solution of 1-bromo-4-fluorobenzene (8.25 g, 47.15 mmol) in THF (47 ml) was slowly added the mixture at 40° C. The solution was stirred for an additional 1 hour while maintaining the temperature at 40° C. by external heating, which gave the solution (4-flourophenyl) magnesium bromide (57.14 mmol) in THF.

1-(3-bromopropyl)-4-fluorobenzene (3)[1]

Copper(I)bromide (1.40 g, 9.76 mmol) and anhydrous lithium bromide (1.67 g, 19.2 mmol) were added to 100 ml THF, after shaking the mixture, we gave a greenish homogeneous solution. And then 1, 3-dibromopropane (34.6 g, 164 mmol) was added to the solution, and the mixture was warmed to 50° C. After which a solution of (4-flourophenyl) magnesium bromide 1 (57.14 mmol) of THF was added dropwise over about 1 hour, the rate of addition was adjusted such that the temperature of the reaction mixture remained between 50 and 55° C. The mixture was stirred for an additional 1 hour at 50° C. The solution was cooled to room temperature and subsequently quenched by a solution of ammonium chloride (30 g in 100 ml of ice water). The aqueous layer was extracted with EA (50 ml×2). The combined organic solutions were dried with MgSO$_4$ and concentrated under reduced pressure. The excessive 1,3-dibromopropane was removed under reduced pressure, and the remained liquid was 1-(3-bromopropyl)-4-fluorobenzene (6.80 g, 55%), $^1$H-NMR (CDCl$_3$, 300 MHz): δ2.15 (m, 2H); 2.75 (t, 2H); 3.37 (t, 2H); 7.11 (m, 2H); 7.45 (m, 2H).

(3-(4-fluorophenyl)propyl) magnesium bromide (4): To a mixture of Mg (0.66 g, 27.5 mmol) in dry THF (5 ml), 1-(3-bromopropyl)-4-fluorobenzene (1.5 g, 6.9 mmol) was added at 40° C. When the temperature raised to 55° C., which meant that the reaction started, then a solution of 1-(3-bromopropyl)-4-fluorobenzene (4.5 g, 20.7 mmol) in THF (20 ml) was added slowly into this mixture at 40° C. The reaction mixture was stirred for an additional 1 hour at the same temperature to give the solution of (3-(4-fluorophenyl)propyl) magnesium bromide (23.0 mmol).

1-chloro-5-(4-fluorophenyl)pentan-2-one (5)[2]

A solution of 2-chloro-N-methyl acetamide (2.54 g, 18.4 mmol) in 5 ml toluene was diluted with 10 ml dry THF, and the mixture was cooled to 0° C. And then a solution of the (3-(4-fluorophenyl)propyl) magnesium bromide 4 (23.0 mmol) in THF was added dropwise to the mixture (over 30 min, <5° C.), the reaction mixture was stirred another 1 h at the same temperature. The reaction was quenched by 30 ml 3N HCl, and the aqueous layer was extracted two times with EA (50 ml×2). The combined organic solutions were dried with MgSO$_4$ and concentrated under reduced pressure, the residue was purified by chromatography (PE/EA, 100/1) to give compound 1-chloro-5-(4-fluorophenyl)pentan-2-one 5

(3.5 g, 71%) $^1$H-NMR (CDCl_3, 300 MHz): δ1.93 (m, 2H); 2.59 (m, 4H); 4.14 (s, 2H); 7.00 (m, 2H); 7.12 (m, 2H).

SR 3131[3]

A mixture of compound 5 (1.07 g, 5 mmol) and amidinothiourea (0.59 g, 5 mmol) in acetone (50 ml) was stirred at 50° c. under nitrogen atmosphere for 12 h. When TLC showed no starting material remained, the solvent was removed under reduced pressure and the residue was purified by chromatography (DCM/Methanol, 60/1) to give compound SR 3131 (690 mg, 49.6%). $^1$H-NMR (CD_3OD, 300 MHz): δ 2.01 (m, 2H); 2.66 (m, 4H); 4.93 (br, 4H, NH); 6.78 (s, 1H); 7.01 (m, 2H); 7.20 (m, 2H). M.W.: 278, ESI-MS: 279 (M+H).

REFERENCES

1. Synthetic Communications, 20(15), 2349-51; 1990
2. Synlett, (3), 225-226; 1996
3. J. Med. Chem. 2004, 47, 2935-2938

Example 27

Example Relates to SR3123

Target Compound

Chemical formula 85

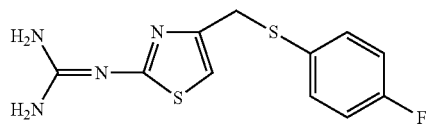

SR 3123

Synthesis Route

Chemical formula 86

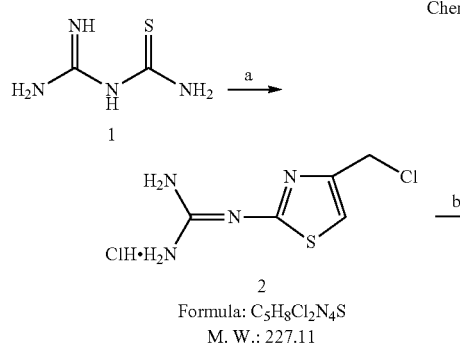

Reagent and Condition a) CH_2ClCOCH_2Cl, actone, rt, 12 h; b) 4-fluorobenzenethiol, NaOH, NaH, rt;

Experiment Section

SR 3123[1]

A mixture of compound 2[2] (1.13 g, 5 mmol), 4-fluorobenzenethiol (0.768 g, 6 mmol) and NaOH (0.8 g, 20 mmol) in 20 ml H_2O was stirred at room temperature for 1 h. The solvent was removed and the residue was purified by chromatography (DCM/Methanol, 100/1, Rf=0.5, DCM/Methanol, 5/1) to give compound SR 3123 (847 mg, 60%). $^1$H-NMR (d[6]-DMSO, 400 MHz): δ2.66 (m, 2H); 2.76 (m, 2H); 3.58 (s, 2H); 6.47 (s, 1H); 6.81 (br, 2H), 7.05 (m, 2H); 7.21 (m, 2H). M.W.: 282; ESI-MS: 283 (M+H).

REFERENCES

1. J. Med. Chem. 1984, 27849-857
2. Detailed synthesis methods as shown in the report of SR 2044

Example 28

Example Relates to SR3154

Target Compound

Chemical formula 87

SR 3154

Synthesis Route

Chemical formula 88

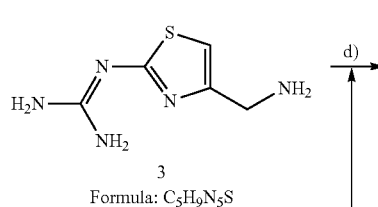
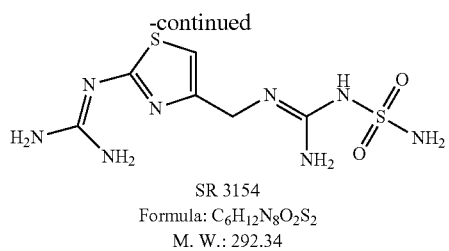

3
Formula: C₅H₉N₅S
M. W.: 171.22

SR 3154
Formula: C₆H₁₂N₈O₂S₂
M. W.: 292.34

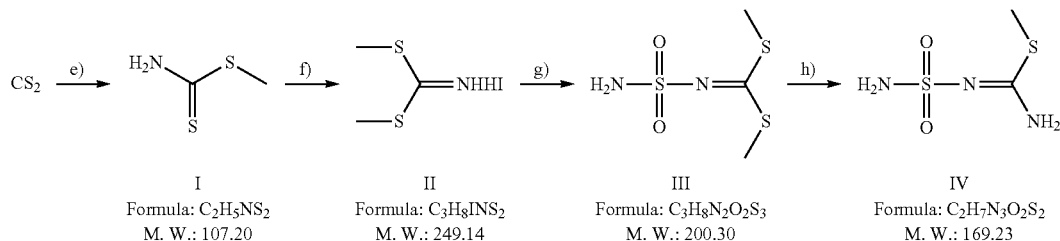

| I | II | III | IV |
|---|---|---|---|
| Formula: C₂H₅NS₂ | Formula: C₃H₈INS₂ | Formula: C₃H₈N₂O₂S₃ | Formula: C₂H₇N₃O₂S₂ |
| M. W.: 107.20 | M. W.: 249.14 | M. W.: 200.30 | M. W.: 169.23 |

Reagent and Condition
a) $CH_2ClCOCH_2Cl$, actone, rt, 12 h; b) DMF, $NaN_3$, rt; c) $THF/H_2O$, $Ph_3P$, rt; d) $Et_3N$, MeOH, Methyl N'-sulfamoyl-carbamimidothioate (IV), reflux; e)$NH_3$, THF; $(MeO)_2SO_2$, f) MeI, MeCN, rt; g) MeCN, $Et_3N$, $H_2NSO_2Cl$; h) Toluene, $NH_3$, reflux;

Experiment Section 2-(4-(azidomethyl)thiazol-2-yl)guanidine(2): A solution of 2-(4-(chloromethyl)thiazol-2-yl)guanidine hydrochloride 1[1] (3.66 g, 16 mmol) and $NaN_3$ (1.37 g, 21 mmol) in 25 ml DMF was stirred overnight at room temperature. Then the DMF was removed under reduced pressure to give compound 2 (3.19 g). It was used without further purification.

2-(4-(aminomethyl)thiazol-2-yl)guanidine(3): A solution of compound 2 (3.19 g, 16 mmol) and $Ph_3P$ (5.09 g, 19 mmol) in $THF/H_2O$ (40 ml/20 ml) was stirred overnight at room temperature. The solvent was removed under reduced pressure and the residue was purified by chromatography (DCM/MeOH, 5/1) to give compound 3 (dry 2.04 g, yield of two steps 74%). M.W.: 171; ESI-MS: 172.1 (M+H).

Methyl Dithiocarbamate(I)[2]

In a 500 mL three-necked flask, provided with a gas-inlet tube, a stirrer, and a gas outlet combined with a thermometer, are placed dry THF (140 mL) and carbon disulfide (16.7 g, 0.22 mol). Ammonia is then introduced with continuous stirring, the flow of ammonia being adjusted in such a way that a slow stream is leaving the flask. The temperature is allowed to rise to 40-45° C. and is kept at that level by occasional cooling. When, after 1 h, no more heat is evolved and the temperature has dropped to 35° C., the flask is evacuated (rotary evaporator) to remove some dissolved ammonia. Water (25 mL) is then added to dissolved the white precipitate. To the resultant mixture of THF and aqueous ammonium dithiocarbamate, dimethylsulfate (25.2 g, 0.2 mol) is added with vigorous stirring. During the addition (which requires 30 min), the temperature of the mixture is allowed to rise to 45-50° C. and is maintained at that level for 15 min by occasional cooling. Then, concentrated aqueous ammonia (5 mL) is added to destroy excess dimethyl sulfate and stirring is continued for 15 min. The upper layer is separated and dried with magnesium sulfate (without being washed). The aqueous layer is extracted with EA (3×20 mL) and the organic phases are combined. The solution is concentrated in a water-pump vacuum and the last traces of solvent are removed at 0.5-1 torr by means of an oil pump to leave nearly pure methyl dithiocarbamate(I); yield: 20 g (93%, calculated on dimethyl sulfate).

S,S-Dimethyliminodithiocarbonate hydroiodide (II)[2]

9.96 g (0.07 mol, 4.40 ml) of methyl iodide were added to a solution of 5.00 g (0.05 mol) of methyl dithiocarbamate in 10 ml of acetonitrile. Reaction mixture was stirred at room temperature overnight. The precipitate was filtered off, washed with small amount of acetonitrile, and dried in vacuum. Yield: 10 g.

Dimethyl sulfamoylcarbonimidodithioate (III)[3]

1.1 g (4 mmol) of S,S-dimethyliminodithiocarbamate hydroiodide was placed into three necked flask, and 30 ml of acetonitrile were added. The resulting suspension was cooled to 0° C. at inert gas (Ar) atmosphere, followed by the addition of 0.45 g (4 mmol) of triethylamine. Reaction mixture was stirred for 15 min at 0° C. The second portion of triethylamine (4 mmol) was added at this temperature, followed by the solution of 0.62 g (4 mmol) of $H_2NSO_2Cl$[4] in 5 ml of acetonitrile. Resulting solution was stirred for 2 h at 0° C., warmed slowly to room temperature, and stirred for an additional 10 h. All volatiles were removed in vacuum, and the residue treated with 5% solution of $Na_2SO_3$. The precipitate was filtered off, dissolved in ether, and dried over $MgSO_4$. Ether was evaporated in vacuum resulting in compound 4 (0.6 g, 75% yield) as a colorless solid.

Methyl N'-sulfamoylcarbamimidothioate (IV)[3]

$NH_3$ was passed through the solution of 0.60 g of dithiocarbonate (III) in 30 ml of toluene at 60° C. The end of the reaction was monitored by TLC. All volatiles were removed in vacuum and the residue crystallized from toluene and benzene in a ratio of 3:1 mixture resulting in compound 5 (0.4 g, 78% yield) as pale yellow crystals.

SR 3154[5]

A mixture of compound IV (Methyl N'-sulfamoylcarbamimidothioate) (0.4 g, 2.4 mmol) and 2-(4-(aminomethyl)thiazol-2-yl)guanidine 3 (0.4 g, 2.4 mmol) in 30 ml dry methanol was heated to reflux under nitrogen atmosphere for 12 h. When TLC showed no starting material remained, the solvent was removed under reduced pressure and the residue was purified by chromatography (DCM/Methanol, 3/1) to give compound SR 3154 (0.15 g, 24%). $^1$H-NMR (d$^6$-DMSO, 300 MHz): δ3.76 (s, 2H); 6.60 (s, 1H); 6.89 (t, NH). M.W.: 292.05; ESI-MS: 293 (M+H).

REFERENCES

1. Detailed synthesis methods as shown in the report of SR 2044
2. Synthesis, 1985, 948-949
3. Journal of Fluorine Chemistry 124 (2003) 151-158
4. Detailed synthesis methods as shown in the report of SR 3155
5. Chemische Berichte (1958), 91, 1339-41.

Example 29

Example Relates to SR3155

Target Compound

Chemical formula 89

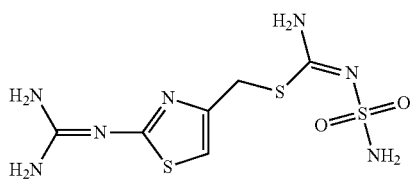

Chemical formula 90

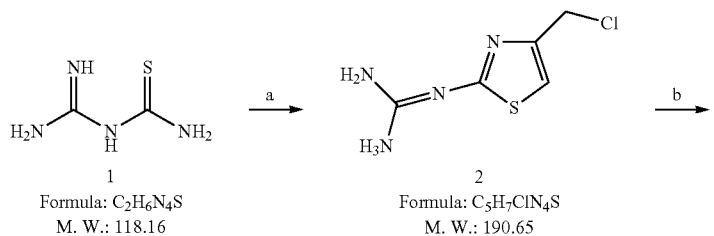

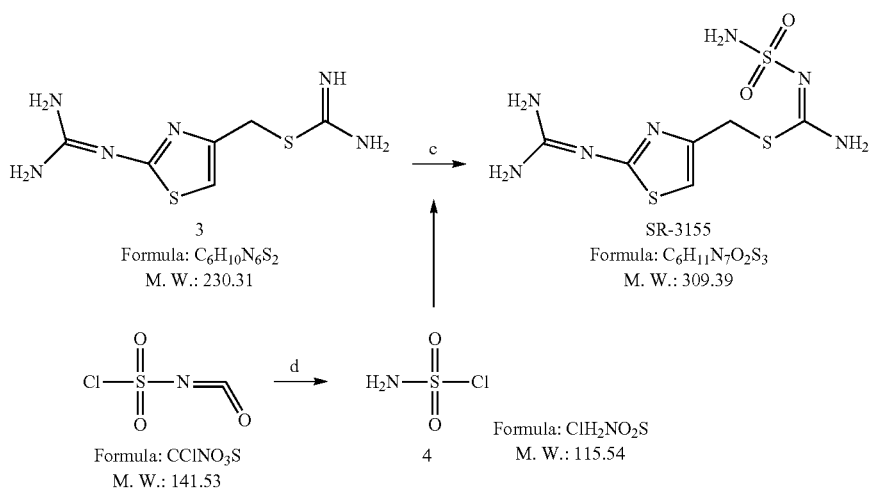

Reagent and Condition a) CH$_2$ClCOCH$_2$Cl, actone, rt, 12 h; b) thiourea, EtOH, 80° C., 3 h; c) NH$_2$SO$_2$Cl, CH$_3$CN, 0° C.; d) HCO$_2$H Experiment Section 2-(5-(Chloromethyl)thiazol-2-yl)guanidine (2)[1]; A suspension of amidinothiourea 1 (118 g, 1 mol) in acetone (600 ml) was treated with 1,3-dichloroacetone (126 g, 1 mol). After stirring overnight at room temperature, the solid was filtered off and washed with acetone, Crystallization from ethanol gave the compound 2 (122 g, 54%). $^1$H-NMR (d$^6$-DMSO, 300 MHz): δ3.44 (br, 4H); 4.76 (s, 2H); 7.43 (s, 1H); 8.41 (br, 1H). M.W.: 190.01; ESI-MS: 191 (M+H).

(2-(Diaminomethyleneamino)thiazol-5-yl)methyl carbamimidothioate (3)[2]

A solution of compound 2 (56.5 g, 0.25 mol) and thiourea (19 g, 0.25 mol) in 200 ml EtOH was stirred at 80° C. under nitrogen atmosphere for 3 h. After cooled at room temperature, the mixture was filtered and the residue was washed with EtOH. Crystallization from 95% ethanol gave the compound 3 (61.9 g, 82%). $^1$H-NMR (d$^6$-DMSO, 300 MHz): δ3.42 (br, 7H); 4.58 (s, 2H); 7.34 (s, H); 8.45 (br, 2H). M.W.: 230.04; ESI-MS: 231 (M+H).

Sulfamoyl chloride (4)[3]

ClSO$_2$NCO (83 g, 0.586 mol) was treated dropwise with 27 g of dry HCO$_2$H at 5° C. Then the mixture was kept at room temperature until gas evolution ceased. After that, the mixture was dissolved in benzene and filtered the solid. The filtrate was removed under reduced pressure to give 62 g sulfamoyl chloride 4 (92%), mp 40° C.

SR 3155

A solution of (2-(Diaminomethyleneamino)thiazol-5-yl) methyl carbamimidothioate (3) (0.8 g, 3 mmol) and Et$_3$N (0.6 g, 6 mmol) in 50 mL dry CH$_3$CN was cooled at −10° C. under nitrogen atmosphere. Then sulfamoyl chloride 4 (0.34 g, 3 mmol) and Et$_3$N (0.3 g, 3 mmol) were added slow at the same time. The mixture was stirred room temperature under nitrogen atmosphere at −10° C. for 1 h. When TLC showed no starting material remained, the solvent was removed under reduced pressure and the residue was purified by chromatography (DCM/Methanol, 1/1) to give compound SR 3155. $^1$H-NMR (d$^6$-DMSO, 300 MHz): δ4.563 (s, 2H); 7.321 (s, 1H); 8.401 (s, 4H—NH); 9.364 (d, 4H—NH); 12.787 (s, 1H—NH). M.W.: 309.01; ESI-MS: 310 (M+H).

REFERENCES

1. J. Med. Chem. 2004, 47, 2935-2938
2. WO 2005009986
3. Chemische Berichte (1958), 91, 1339-41.

Example 30

Example Relates to SR3159

Target Compound

Chemical formula 91

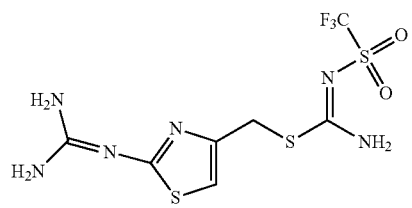

SR 3159

Synthesis Route

Chemical formula 92

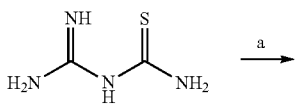

Formula: C$_2$H$_6$N$_4$S
M. W.: 118.16

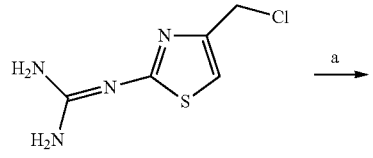

2
Formula: C$_5$H$_7$ClN$_4$S
M. W.: 190.65

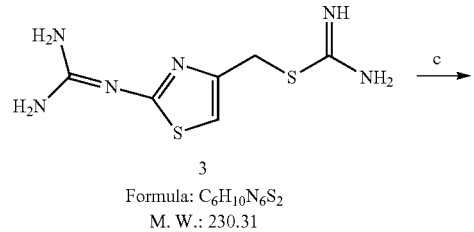

3
Formula: C$_6$H$_{10}$N$_6$S$_2$
M. W.: 230.31

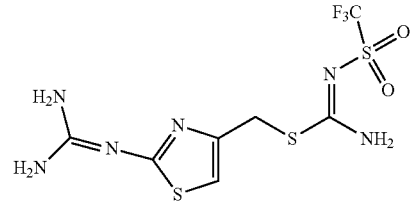

SR 3159
Formula: C$_7$H$_9$F$_3$N$_6$O$_2$S$_3$
M. W.: 362.38

Reagent and Condition a) CH$_2$ClCOCH$_2$Cl, actone, rt, 12 h; b) thiourea, EtOH, 80° C., 3 h; c) CF$_3$SO$_2$Cl, DMF, 0° C.

Experiment Section

SR 3159

A solution of (2-(Diaminomethyleneamino)thiazol-5-yl) methyl carbamimidothioate (3)[1] (0.8 g, 3 mmol) and Et$_3$N (0.6 g, 6 mmol) in 15 mL dry DMF was cooled at −10° C. under nitrogen atmosphere. Then CF$_3$SO$_2$Cl (0.5 g, 3 mmol) and Et$_3$N (0.3 g, 3 mmol) were added slow at the same time. The mixture was stirred room temperature under nitrogen atmosphere at −10° C. for 1 h. When TLC showed no starting material remained, the solvent was removed under reduced pressure and the residue was purified by HPLC separation (MeOH: 0.1% TFA=20:80~80:20) to give SR 3159 (0.16 g, 15.7%). $^1$H-NMR (d$^6$-DMSO, 300 MHz): δ4.54 (s, 2H); 7.31 (s, 1H); 8.37 (s, 2H); 9.34 (s, 2H). M.W.: 361.99; ESI-MS: 363 (M+H).

REFERENCES

1. Detailed synthesis methods as shown in the report of SR 3155

Example 31

Example Relates to 2232 (OK-032)

Target Compound

Chemical formula 93

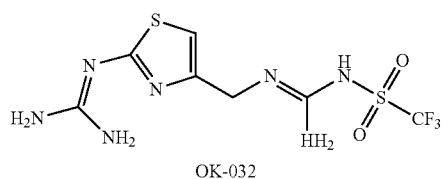

SR 2232

OK-032

Synthesis Route

Reagent and Condition a) CH$_2$ClCOCH$_2$Cl, actone, rt, 12 h; b) DMF, NaN$_3$, rt; c) THF/H$_2$O, Ph$_3$P, rt; d) Et$_3$N, MeOH, reflux; e)NH$_3$, THF; (MeO)$_2$SO$_2$, f) MeI, MeCN, rt; g) CH$_2$Cl$_2$, Et$_3$N, Tf$_2$O; h) Toluene, NH$_3$, reflux

Experiment Section 2-(5-(Chloromethyl)thiazol-2-yl)guanidine hydrochloride (1)[1]

A suspension of amidinothiourea (118 g, 1 mol) in acetone (600 ml) was treated with 1,3-dichloroacetone (126 g, 1 mol). After stirring overnight at room temperature, the solid was filtered off and washed with acetone, crystallization from ethanol gave the compound 2 (122 g, 54%). $^1$H-NMR (d$^6$-DMSO, 300 MHz): δ3.44 (br, 4H); 4.76 (s, 2H); 7.43 (s, 1H); 8.41 (br, 1H). M.W.: 226; ESI-MS: 191 (M−HCl+H).

2-(4-(azidomethyl)thiazol-2-yl)guanidine(2): A solution of compound 1 (3.66 g, 16 mmol) and NaN$_3$ (1.37 g, 21 mmol) in 25 mL of DMF was stirred overnight at room temperature. Then the solvent was removed under reduced pressure to give compound 2. (3.19 g). It was used in next step without purification.

2-(4-(aminomethyl)thiazol-2-yl)guanidine(3): A solution of compound 2 (3.19 g, 16 mmol) and Ph$_3$P (5.09 g, 19 mmol) in THF/H$_2$O (40 ml/20 ml) was stirred overnight at room temperature. Then the solvent was removed under reduced pressure and the residue was purified by chromatography (DCM/MeOH, 5/1) to give compound 3 (2.04 g, two steps 74%). M.W.: 171; ESI-MS: 172.1 (M+H).

Methyl Dithiocarbamate(I)[2]

In a 500 mL three-necked flask, provided with a gas-inlet tube, a stirrer, and a gas outlet combined with a thermometer, are placed dry THF (140 mL) and carbon disulfide (16.7 g, 0.22 mol). Ammonia is then introduced with continuous stirring, the flow of ammonia being adjusted in such a way Chemical formula 94

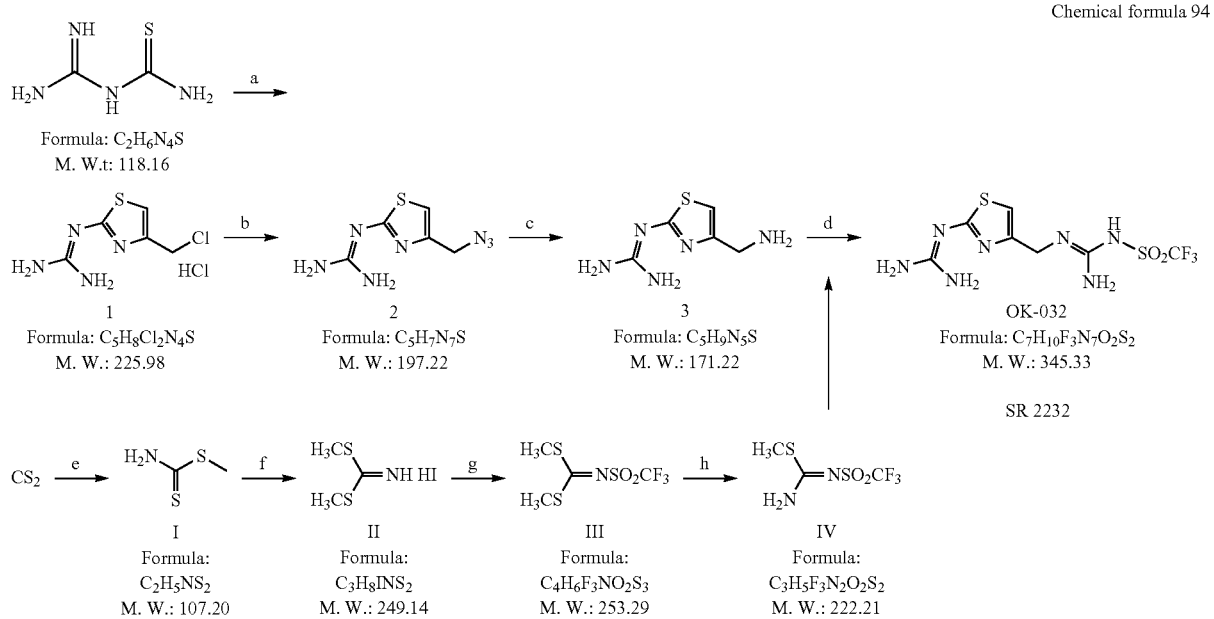

that a slow stream is leaving the flask. The temperature is allowed to rise to 40-45° C. and is kept at that level by occasional cooling. When, after 1 h, no more heat is evolved and the temperature has dropped to 35° C., the flask is evacuated (rotary evaporator) to remove some dissolved ammonia. Water (25 mL) is then added to dissolved the white precipitate. To the resultant mixture of THF and aqueous ammonium dithiocarbamate, dimethylsulfate (25.2 g, 0.2 mol) is added with vigorous stirring. During the addition (which requires 30 min), the temperature of the mixture is allowed to rise to 45-50° C. and is maintained at that level for 15 min by occasional cooling. Then, concentrated aqucous ammonia (5 mL) is added to destroy excess dimethyl sulfate and stirring is continued for 15 min. The upper layer is separated and dried with magnesium sulfate (without being washed). The aqueous layer is extracted with EA (3×20 mL) and the organic phases are combined. The solution is concentrated in a water-pump vacuum and the last traces of solvent are removed at 0.5-1 torr by means of an oil pump to leave nearly pure methyl dithiocarbamate(I); yield: 20 g (93%, calculated on dimethyl sulfate).

S,S-Dimethyliminodithiocarbonate hydroiodide (II)[2]

9.96 g (0.07 mol, 4.40 ml) of methyl iodide were added to a solution of 5.00 g (0.05 mol) of methyl dithiocarbamate in 10 ml of acetonitrile. Reaction mixture was stirred at room temperature overnight. The precipitate was filtered off, washed with small amount of acetonitrile, and dried in vacuum. Yield: 10 g.

N-Bis(methylthio)methylenetrifluoromethanesulfonylamide (III)[2]

11.00 g (0.04 mol) of S,S-dimethyliminodithiocarbamate-hydroiodide was placed into three necked flask, and 15 ml of dichloromethane were added. The resulting suspension was cooled to −20° C. at inert gas (Ar) atmosphere, followed by the addition of 4.47 g (6.16 ml, 0.04 mol) of triethylamine. Reaction mixture was stirred for 15 min at −20° C., and cooled to −78° C. The second portion of triethylamine (0.04 mol) was added at this temperature, followed by the solution of 12.46 g (7.43 ml, 0.04 mol) of $Tf_2O$ in 5 ml of dichloromethane. Resulting solution was stirred for 1 h at −78° C., warmed slowly to room temperature, and stirred for an additional 10 h. All volatiles were removed in vacuum, and the residue treated with 5% solution of $Na_2SO_3$. The precipitate was filtered off, dissolved in ether, and dried over $MgSO_4$. Ether was evaporated in vacuum resulting in compound 4 (9.50 g, 85% yield) as a colorless solid. Melting point 66-67° C.

N-Trifluoromethylsulfonyl-S-methylthiourea (IV)[3]

$NH_3$ was passed through the solution of 0.30 g of dithiocarbonate III in 3 ml of toluene at 60° C. The end of the reaction was monitored by TLC. All volatiles were removed in vacuum and the residue crystallized from toluene and benzene in a ratio of 3:1 mixture resulting in compound 5 (0.2 g, 81% yield) as pale yellow crystals, mp 61-63° C.

SR 2232 (OK-032)[3]

A mixture of compound IV (0.2 g, 1 mmol) and 2-(4-(aminomethyl)thiazol-2-yl)guanidine(3) (0.17 g, 1 mmol) in 10 ml dry methanol was heated to reflux under nitrogen atmosphere for 12 h. When TLC showed no starting material remained, the solvent was removed under reduced pressure and the residue was purified by chromatography (DCM/Methanol, 10/1) to give compound SR 2232 (OK-032) (0.28 g, 85%). M.W. 345.03; ESI-MS: 346.0 (M+H). $^1$H-NMR ($d^6$-DMSO, 300 MHz): δ4.26 (s, 2H); 6.64 (s, 1H); δ7.38-7.96 (br, 6H).

REFERENCES

1. J. Med. Chem. 2004, 47, 2935-2938
2. Synthesis, 1985, 948-949
3. Journal of Fluorine Chemistry 124 (2003) 151-158

Example 32

Example Relates to SR2236 (OK-036)

Target Compound

Chemical formula 95

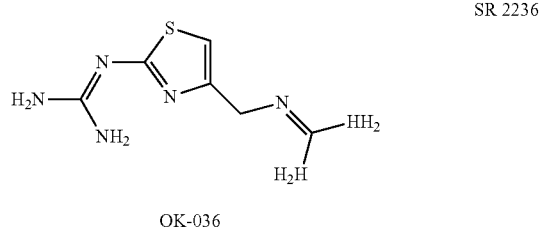

OK-036

Chemical formula 96

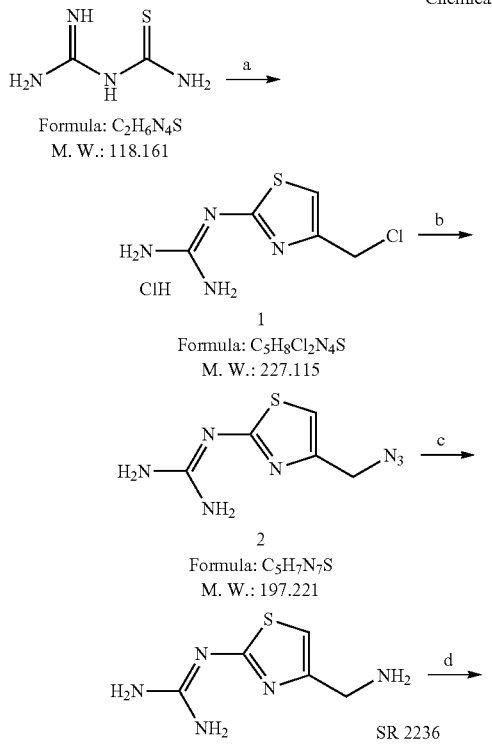

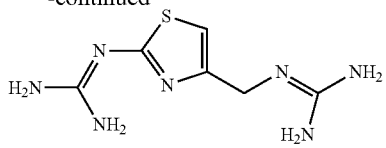

OK-036
Formula: C₆H₁₁N₇S
M. W.: 213.262

Reagent and Condition a) CH₂ClCOCH₂Cl, actone, rt, 12 h; b) DMF, NaN₃, rt; c) THF/H₂O, Ph₃P, rt; d) NH₂CN, 130° C.

Experiment Section 2-(5-(Chloromethyl) thiazol-2-yl) guanidine (1)[1]

A suspension of amidinothiourea 1 (118 g, 1 mol) in acetone (600 ml) was treated with 1,3-dichloroacetone (126 g, 1 mol). After stirring overnight at room temperature, the solid was filtered off and washed with acetone, Crystallization from ethanol gave the compound 2 (122 g, 54%). ¹H-NMR (d⁶-DMSO, 300 MHz): δ3.44 (br, 4H); 4.76 (s, 2H); 7.43 (s, 1H); 8.41 (br, 1H). M.W.: 190; ESI-MS: 191 (M+H).

2-(4-(azidomethyl)thiazol-2-yl)guanidine(2): A solution of 2-(4-(chloromethyl)thiazol-2-yl)guanidine hydrochloride 1 (3.66 g, 16 mmol) and NaN₃ (1.37 g, 21 mmol) in 25 mL of DMF was stirred overnight at room temperature. The DMF was removed under reduced pressure to give compound 2 (3.19 g).

2-(4-(aminomethyl)thiazol-2-yl)guanidine(3): A solution of compound 2 (3.19 g, 16 mmol) and Ph₃P (5.09 g, 19 mmol) in THF/H₂O (40 mL/20 mL) was stirred overnight at room temperature. The solvent was removed under reduced pressure and the residue was purified by chromatography (DCM/MeOH, 5/1) to give compound 3 (dry 2.04 g, two steps 74%). M.W.: 171.1; ESI-MS: 172.1 (M+H).

SR 2236 (OK-036)

A mixture of compound 3 (0.194 g, 1.1 mmol) and NH₂CN (0.191 g, 4.5 mol) was melted and rapid stirred under Ar for 15 min at 130° C. Then the mixture was cooled to room temperature. The residue was purified by chromatography (DCM/MeOH, 5/1) to give SR 2236 (OK-036) (dry 54 mg, 23%). ¹H-NMR (d⁶-DMSO, 300 MHz): δ2.58 (s, 2H); 7.34 (s, 1H). M.W.: 213; ESI-MS: 214.1 (M+H)

REFERENCES

1. J. Med. Chem. 2004, 47, 2935-2938

Example 33

Example Relates to SR2064

Target Compound

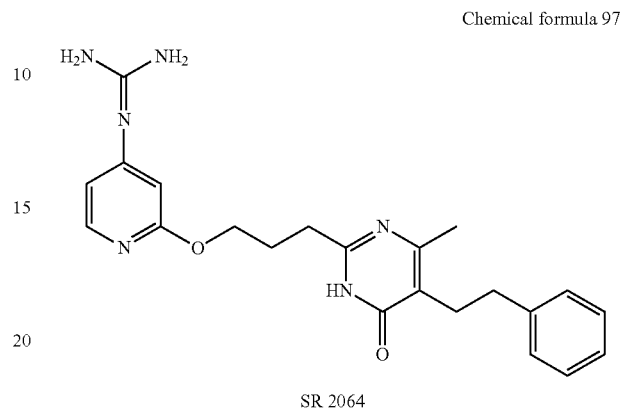

Chemical formula 97

SR 2064

Synthesis Route

Chemical formula 98

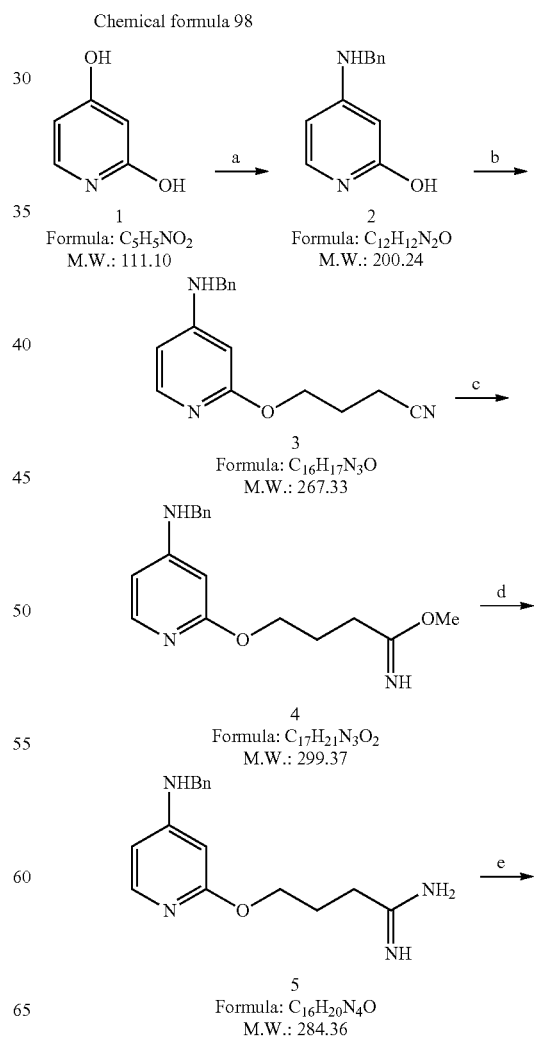

-continued

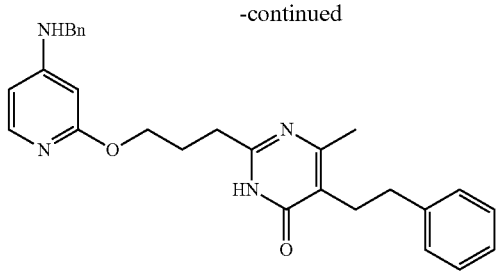

6
Formula: C₂₈H₃₀N₄O₂
M.W.: 454.56

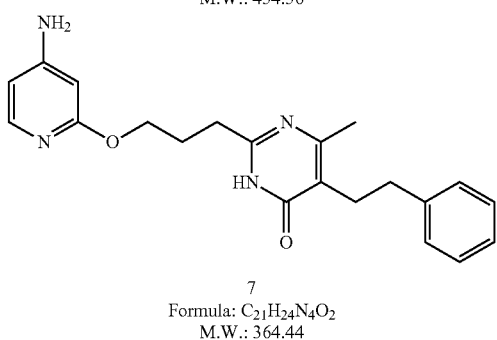

7
Formula: C₂₁H₂₄N₄O₂
M.W.: 364.44

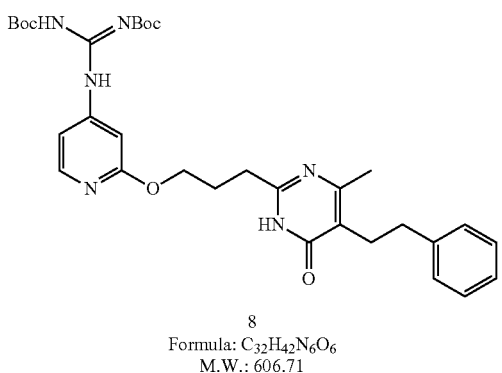

8
Formula: C₃₂H₄₂N₆O₆
M.W.: 606.71

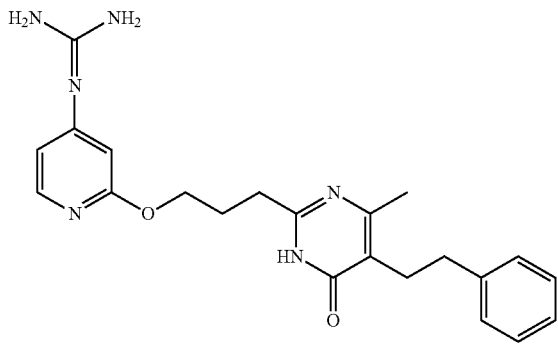

SR 2064
Formula: C₂₂H₂₆N₆O₂
M.W.: 406.48

Reagent and Condition a) benzylamine, 170° C., 3 h; b) 4-Chlorobutyronitrile, AgCO₃, DMF, reflux, 3 h; c) dry HCl gas, MeOH/DCM, 0~5° C.; d)NH₄Cl, MeOH, rt; e) CH₃Ona; f) MeOH, Pd/C, H₂, HCO₂NH₄, 60° C.; g) 1,3-di-Boc-2-methyl isothiourea, HgCl, Et₃N, DMF; h) TFA/DCM Experiment Section 4-(benzylamino)pyridin-2-ol (2)[1]

A mixture of compound 1 (50 g, 0.45 mol) and benzylamine (460 ml, 4.05 mol) was stirred 170° C. for 3 hs, and then the solvent was removed under reduced pressure. The residue was washed with water to gave the compound 2 (45 g, 50%). ¹H-NMR (d⁶-DMSO, 300 MHz): δ4.21 (s, 2H); 5.03 (s, 1H); 5.74 (d, 1H); 6.98 (d, 1H); 7.10 (s, 1H); 7.25-7.35 (m, 5H). M.W.: 199; ESI-MS: 201 (M+H).

4-(4-(benzylamino)pyridin-2-yloxy)butanenitrile (3)[2]

A mixture of compound 2 (1 g, 5 mmol), 4-Chlorobutyronitrile (1.03 g, 10 mmol) and AgCO₃ (2.7 g, 10 mol) in 20 ml DMF was stirred at 150° C. for 3 h, and then the solvent was removed under reduced pressure and the residue was crystallized from PE/EA=1/1 to give the compound 3 (0.4 g, 30%). ¹H-NMR (CDCl₃, 300 MHz): δ2.09 (m, 2H); 2.51 (t, 2H); 4.33 (m, 4H); 4.50 (br, 1H); 5.86 (d, 1H); 6.17 (m, 1H); 7.29-7.36 (m, 5H); 7.76 (d, 1H). M.W.: 267; ESI-MS: 268 (M+H).

Methyl 4-(4-(benzylamino)pyridin-2-yloxy)butanimidate(4)[3]

A solution of compound 3 (0.5 g, 1.87 mmol) in anhydrous methanol/DCM (1 ml/20 ml) was cooled to 0~10° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give crude compound 4 (0.56 g, 100%). ¹H-NMR (d⁶-DMSO, 300 MHz): δ2.05 (m, 2H); 4.20 (t, 2H); 4.40 (s, 2H); 5.76 (s, 1H); 6.45 (d, 1H); 7.25-7.41 (m, 5H); 7.29-7.36 (m, 5H); 7.59 (br, 1H); 7.69 (d, H); 8.82-9.18 (br, 3H). M.W.: 299; ESI-MS: 300 (M+H).

4-(4-(benzylamino)pyridin-2-yloxy)butanimidamide (5)[3]

A solution of compound 4 (0.56 g, 1.87 mmol) and NH₄Cl (0.15 g, 2.85 mmol) in 10 ml MeOH was stirred at room temperature for 1 h, then the solvent was removed under reduced pressure and the residue was purified by chromatography (DCM/Methanol, 50/1) to give compound 5 (0.2 g, 37.6%).

2-(3-(4-(benzylamino)pyridin-2-yloxy)propyl)-6-methyl-5-phenethylpyrimidin-4(3H)-one(6)[4]

A mixture of compound 5 (0.2 g, 0.7 mmol), ethyl 3-oxo-2-(2-phenylethyl)butanoate (EOPEB) (0.16 g, 0.7 mmol) and CH₃ONa (0.06 g, 1.4 mmol) in 10 ml dry MeOH was stirred at room temperature for 10 h, then the solvent was removed under reduced pressure and the residue was purified by chromatography (DCM/Methanol, 20/1) to give compound 6 (0.16 g, 50%). M.W.: 454; ESI-MS: 455 (M+H).

2-(3-(4-aminopyridin-2-yloxy)propyl)-6-methyl-5-phenethylpyrimidin-4(3H)-one(7): A solution of compound 6 (0.2 g, 0.4 mmol), Pd/C (0.3 g) and ammonium formate (0.12 g, 2 mmol) in 50 ml MeOH was stirred at 80° C. under hydrogen atmosphere for 5 h. After cooled at room temperature, the mixture was filtered and the solvent was removed under reduced pressure. The residue was purified by chromatography (DCM/Methanol, 10/1) to give compound 7 (0.064 g, 40%). M.W.: 364; ESI-MS: 365 (M+H).

(E)-tert-butyl (tert-butoxycarbonylamino) (2-(3-(4-methyl-6-oxo-5-phenethyl-1,6-dihydro-pyrimidin-2-yl)propoxy)pyridin-4-ylamino)methylenecarbamate (8)[5]

A solution of compound 7 (0.06 g, 0.16 mmol), 1,3-di-Boc-2-methylisothiourea (0.06 g, 0.19 mmol), HgCl (0.06 g, 0.24 mmol) and Et$_3$N (0.05 g. 0.48 mmol) in 5 ml DMF was stirred at room temperature for 5 h, then the solvent was removed under reduced pressure and the residue was purified by chromatography (DCM/Methanol, 50/1) to give compound 8 (0.082 g, 81%). M.W.: 606; ESI-MS: 607 (M+H).

SR 2064[5]

A solution of compound 8 (0.06 g, 0.1 mmol) and TFA (6 ml, 0.08 mol) in 30 ml DCM was stirred at room temperature for 12 h, then the solvent was removed under reduced pressure and the residue was purified by chromatography (DCM/Methanol, 10/1) to give compound SR 2064 (0.022 g, 55%). $^1$H-NMR (CD$_3$OD, 400 MHz): δ1.29 (m, 2H); 1.97 (s, 3H); 2.76-2.88 (m, 4H); 2.90 (m, 4H); 3.88 (m, 2H); 6.90 (d, 1H); 7.90 (t, 1H); 7.13-7.24 (m, 6H). M.W.: 406; ESI-MS: 407 (M+H).

REFERENCES

1 Synthesis; English; 9; 1984; 765-766
2 Synthesis, (16), 2725-2728; 2009
3 Journal of Medicinal Chemistry; English; 30; 10; 1987; 1787-1793
4 Journal of the American Chemical Society; 71; 1949; 616
5 Org. Lett., 2004, 6, 3675-3678; PCT Int. Appl., 2006095159, 14 Sep. 2006

Example 34

Example Relates to SR2020

Target Compound

Chemical formula 99

SR 2020

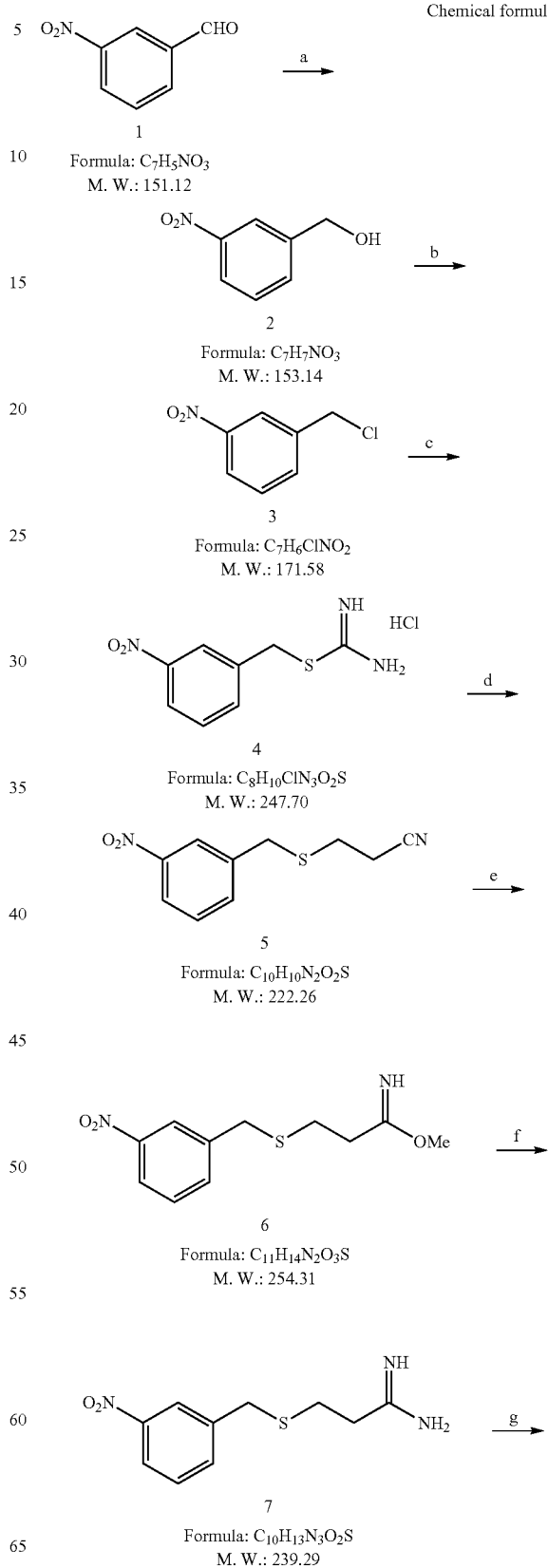

Synthesis Route

Chemical formula 100

-continued

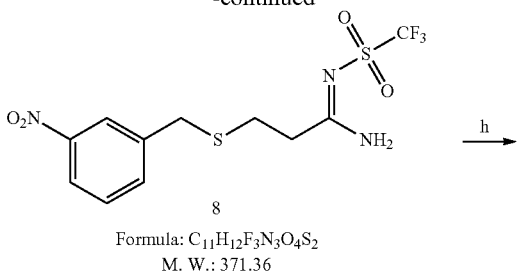

8
Formula: C₁₁H₁₂F₃N₃O₄S₂
M. W.: 371.36

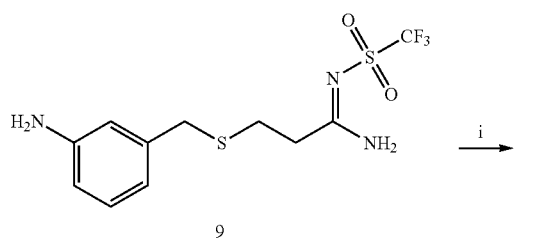

9
Formula: C₁₁H₁₄F₃N₃O₂S₂
M. W.: 341.37

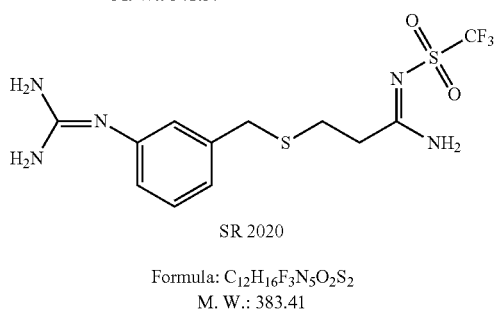

SR 2020
Formula: C₁₂H₁₆F₃N₅O₂S₂
M. W.: 383.41

Reagent and Condition
a) MeOH, NaBH$_4$, rt, 1 h; b) Et$_3$N, SOCl$_2$, rt, 1 h; c) thiourea, EtOH, 80° C.; d) BrCH$_2$CH$_2$CN, EtOH—H$_2$O, NaOH, 0° C.; e) dry HCl gas, MeOH/DCM, 0~5° C.; f) MeOH, NH$_4$Cl, rt, 1 h; g) dry THF, Trifluoromethanesulfonyl chloride, Et$_3$N, 0~5° C.; h) MeOH, Pd/C, H$_2$; i) Cyanamide, 80° C.

Experiment Section (3-nitrophenyl)methanol (2): A suspension of 3-nitrobenzaldehyde 1 (15.11 g, 0.1 mol) in MeOH (130 ml) was treated with NaBH$_4$ (2.4 g, 0.063 mol) at room temperature for 1 h. Then 1000 ml water was added into the mixture. Extracted by EA 1500 ml*3 and then concentrated under reduced pressure to afford the compound 2 without purification (13.78 g, 90%). $^1$H-NMR (CDCl$_3$, 300 MHz): δ2.97 (s, 1H); 4.78 (s, 2H); 7.50 (t, 1H); 7.66 (d, 1H); 8.08 (d, 1H); 8.19 (s, 1H).

1-(chloromethyl)-3-nitrobenzene (3): A mixture of compound 2 (7.65 g, 0.05 mol) and Et$_3$N (15.18 g, 0.15 mol) and SOCl$_2$ (8.92 g, 0.075 mol) was stirred at room temperature for 1 h. When TLC showed no starting material remained, the solvent was removed under reduced pressure to give the compound 3 (8.57 g, 100%). It was used directly in next step without further purification.

3-nitrobenzyl carbamimidothioate hydrochloride (4)[1]

A solution of compound 3 (10.6 g, 0.061 mol) and thiourea (3.08 g, 0.04 mol) in 50 ml EtOH was stirred at 80° C. under nitrogen atmosphere for 0.5 h. When TLC showed no starting material remained, the mixture was cooled at room temperature. Then the solvent was removed under reduced pressure and the residue was crystallized to give compound 4 (3.8 g, 25%). $^1$H-NMR (d$^6$-DMSO, 300 MHz): δ4.75 (s, 2H); 7.70 (t, 1H); 7.94 (d, 1H); 8.18 (d, 1H); 8.38 (d, 1H); 9.46 (d, 3H). M.W.: 247 (hydrochloride salt); ESI-MS: 212 (M+H).

3-(3-nitrobenzylthio)propanenitrile (5)[1]; A solution of compound 4 (1.23 g, 5 mmol) and BrCH$_2$CH$_2$CN (0.7 g, 5.2 mmol) in ethanol/water (5 ml/5 ml) was cooled at 0° C., then aq. NaOH (0.5 g in 8 ml water) was added dropwise. After stirring 1 h at 0° C. and another 3 h at room temperature the mixture was filtered and the residue was washed with water. Crystallization from ethanol gave the compound 5 (0.96 g, 86%). $^1$H-NMR (CDCl$_3$, 300 MHz): δ2.63 (m, 2H); 2.70 (m, 2H); 3.93 (s, 2H); 7.54 (t, 1H); 7.71 (d, 1H); 8.15 (d, 1H); 8.22 (d, 1H). M.W.: 222; ESI-MS: 223 (M+H).

Methyl 3-(3-nitrobenzylthio)propanimidate(6)[2]

A solution of compound 5 (1 g, 4.5 mmol) in anhydrous methanol/DCM (1 ml/20 ml) was cooled to 0~10° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give crude compound 6 (1 g, 87%).

3-(3-nitrobenzylthio)propanimidamide (7)[2]

A solution of crude compound 6 (0.8 g, 3.1 mmol) and NH$_4$Cl (0.25 g, 4.72 mmol) in 50 ml MeOH was stirred at room temperature for 1 h. When TLC showed no starting material remained the solvent was removed under reduced pressure and the residue was purified by chromatography (DCM/Methanol, 50/1) to give compound 7 (0.7 g, 95%). $^1$H-NMR (d$^6$-DMSO, 300 MHz): δ2.82 (m, 4H); 4.06 (s, 2H); 7.66 (t, 1H); 7.90 (d, 1H); 8.14 (d, 1H); 8.27 (s, 1H); 8.80-9.60 (br, 4H). M.W.: 239; ESI-MS: 240 (M+H).

(Z)-3-(3-nitrobenzylthio)-N'-(trifluoromethylsulfonyl)propanimidamide (8)[3]

A solution of compound 7 (3.19 g, 13 mmol) and trifluoromethanesulfonylchloride (2.70 g, 16 mmol) in anhydrous THF was cooled to 0~5° C., then Et$_3$N (2.7 ml, 20 mmol) was added dropwise. After stirring 1 h at 0° C. and another 12 h at room temperature the solvent was removed under reduced pressure and the residue was purified by chromatography (DCM/Methanol, 30/1) to give compound 8 (2.1 g, 42%). $^1$H-NMR (CDCl$_3$, 300 MHz): δ2.69 (m, 2H); 2.78 (m, 2H); 3.85 (s, 2H); 7.23 (br, 1H); 7.52 (t, 1H); 7.69 (d, 1H); 8.11 (d, 1H); 8.16 (br, 1H); 8.19 (s, 1H). M.W.: 371; ESI-MS: 372 (M+H).

(Z)-3-(3-aminobenzylthio)-N'-(trifluoromethylsulfonyl) propanimidamide (9): A mixture of compound 8 (0.8 g, 2.1 mmol) and Pd/C (0.3 g) in methanol was stirred at room temperature under hydrogen atmosphere for 1 h. When TLC showed no starting material remained, the mixture was filtered and the solvent was removed under reduced pressure. The residue was purified by chromatography (DCM/Methanol, 20/1) to give compound 9 (0.335 g, 46%). $^1$H-NMR (CDCl$_3$, 300 MHz): δ2.45 (t, 2H); 2.69 (t, 2H);

3.59 (s, 2H); 3.65 (br, 2H); 6.55 (d, 1H); 6.62 (s, 1H); 6.65 (d, 1H); 7.08 (t, 1H); 7.36 (br, 1H). M.W.: 341; ESI-MS: 342 (M+H).

SR2020[4]

A mixture of compound 9 (1 g, 2.93 mmol) and cyanamide (0.2 g, 4.76 mmol) was melted and stirred at 80° C. under nitrogen atmosphere for 15 min. Then the residue was purified by chromatography (DCM/Methanol, 50/1) to give compound SR 2020 (220 mg, 20%). $^1$H-NMR (d$^6$-DMSO, 300 MHz): δ2.65-2.72 (m, 4H); 3.76 (s, 2H); 7.04 (d, 1H); 7.08 (s, 1H); 7.16-7.23 (m, 2H); 7.34-7.39 (br, 3H).

M.W.: 383; ESI-MS: 384 (M+H).

REFERENCES

1 U.S. Pat. No. 4,362,736
2 J. Med. Chem. 2004, 47, 2935-2938
3 WO9840367
4 Chemical Papers, 61(6), 507-511; 2007

Example 35

Example Relates to SR2208 (OK-008)

Target Compound

Chemical formula 101

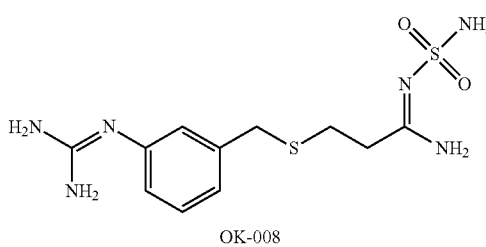

SR 2208

OK-008

Synthesis Route

Chemical formula 102

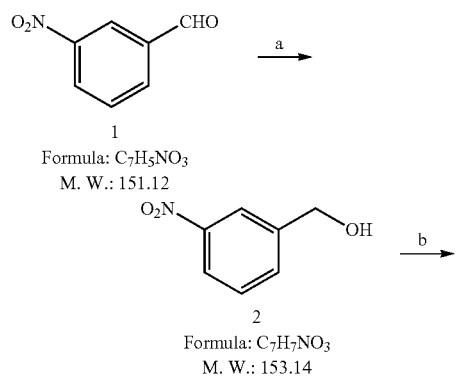

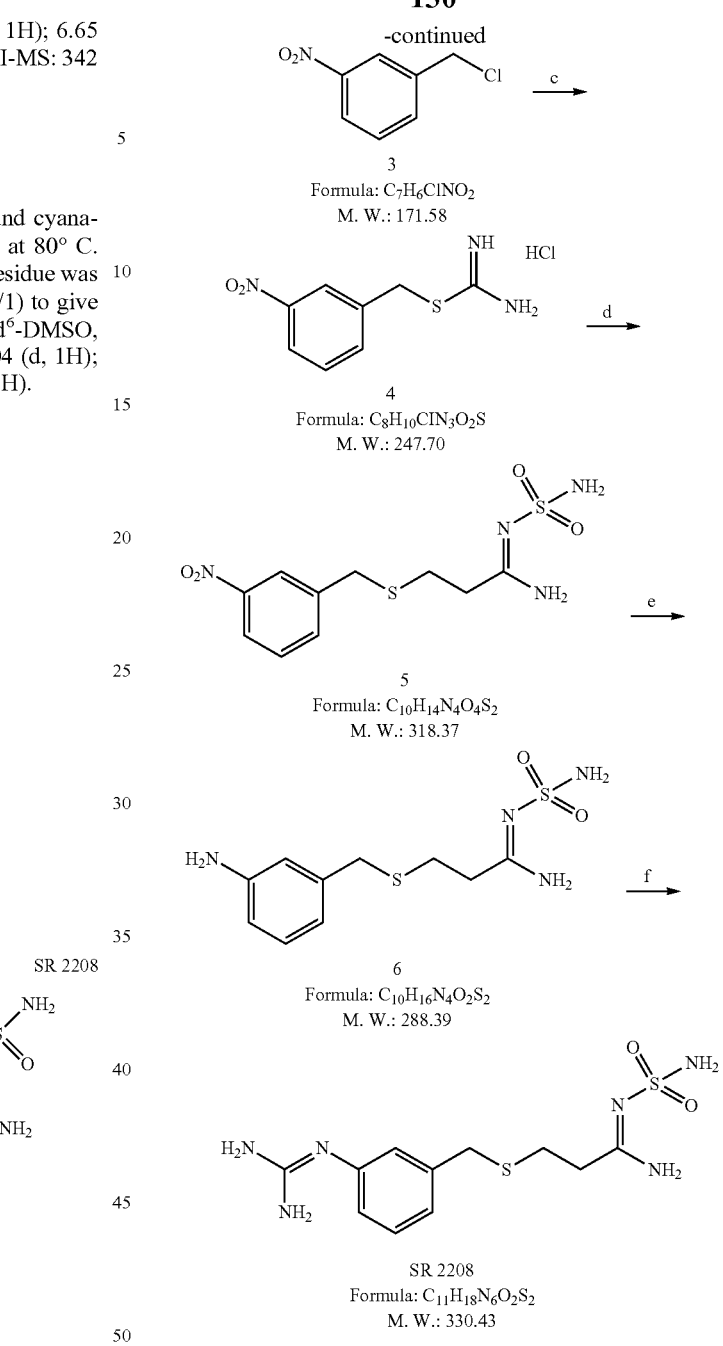

Reagent and Condition a) MeOH, NaBH$_4$, rt, 1 h; b) Et$_3$N, SOCl$_2$, rt, 1 h; c) thiourea, EtOH, 80° C.; d) (Z)-3-chloro-N'-sulfamoylpropanimidamide, EtOH—H$_2$O, NaOH, 0° C.; e) MeOH, Pd/C, H$_2$; f) Cyanamide, 80° C.

Experiment Section (3-nitrophenyl) methanol (2): A suspension of 3-nitrobenzaldehyde 1 (15.11 g, 0.1 mol) in MeOH (130 ml) was treated with NaBH$_4$ (2.4 g, 0.063 mol) at room temperature for 1 h then the reaction was quenched by saturated potassium carbonate solution. The solvent was removed under reduced pressure to give the crude compound 2. It was used directly without further purification. $^1$H-NMR (CDCl$_3$, 200 MHz): δ 2.97 (s, 1H); 4.78 (s, 2H); 7.50 (t, 1H); 7.66 (d, 1H); 8.08 (d, 1H); 8.19 (s, 1H)

1-(chloromethyl)-3-nitrobenzene (3): A mixture of compound 2 (7.65 g, 0.05 mol), Et$_3$N (15.18 g, 0.15 mol) and SOCl$_2$ (8.92 g, 0.075 mol) was stirred at room temperature for 1 h. When TLC showed no starting material remained, the solvent was removed under reduced pressure to give the compound 3 (8.57 g, 100%). It was used directly in next step without further purification.

3-nitrobenzyl carbamimidothioate hydrochloride (4)[1]

A solution of compound 3 (10.6 g, 0.061 mol) and thiourea (3.08 g, 0.04 mol) in 50 ml EtOH was stirred at 80° C. under nitrogen atmosphere for 0.5 h. When TLC showed no starting material remained, the mixture was cooled at room temperature. Then the solvent was removed under reduced pressure and the residue was crystallized to give compound 4 (3.8 g, 25%). $^1$H-NMR (d$^6$-DMSO, 300 MHz): δ4.75 (s, 2H); 7.70 (t, 1H); 7.94 (d, 1H); 8.18 (d, 1H); 8.38 (d, 1H); 9.46 (d, 3H). M.W.: 247.7 (hydrochloride salt); ESI-MS: 212 (M+H).

(Z)-3-(3-nitrobenzylthio)-N'-sulfamoylpropanimidamide (5) m: A solution of compound 4 (1 g, 4 mmol) and (Z)-3-chloro-N'-sulfamoylpropanimidamide (0.805 g, 4.2 mmol) in ethanol/water (5 ml/5 ml) was cooled at 0° C., then aq. NaOH (0.4 g in 2 ml water) was added dropwise. After stirring 1 h at 0° C. and another 3 h at room temperature the mixture was filtered and the residue was washed with water. Crystallization from ethanol gave the compound 5 (0.79 g, 62%).

2-(5-((2-Cyanoethylthio)methyl)thiazol-(Z)-3-(3-aminobenzylthio)-N'-sulfamoylpropanimidamide (6): A mixture of compound 5 (0.3 g, 0.94 mmol) and Pd/C (0.1 g) in methanol was stirred 65° C. under hydrogen atmosphere for 2 h. When TLC showed no starting material remained, the solvent was removed under reduced pressure. The residue was purified by chromatography (DCM/Methanol, 20/1) to give compound 6 (97 mg, 36%).

SR 2208 (OK-008)[3]

A mixture of compound 6 (0.2 g, 0.7 mmol) and cyanamide (0.1 g, 2.4 mmol) was melted and stirred at 80° C. under nitrogen atmosphere for 15 min. After cooled to the temperature, the mixture was purified by chromatography (DCM/Methanol, 5/1) to give compound SR 2208 (OK-008) (50 mg, 22%). $^1$H-NMR (d$^6$-DMSO, 300 MHz): δ2.46-2.51 (m, 4H); 2.61-2.64 (m, 2H); 3.81 (s, 2H); 6.41 (s, 1H); 6.53 (s, 2H); 7.08 (m, 1H); 7.36 (br, 2H); 7.63 (br, 1H); 8.46 (br, 1H). M.W.: 330; ESI-MS: 331 (M+H).

REFERENCES

1 U.S. Pat. No. 4,362,736
2 J. Med. Chem. 2004, 47, 2935-2938
3 Chemical Papers, 61(6), 507-511; 2007

Example 36

Example Relates to SR3209

Target Compound

Chemical formula 103

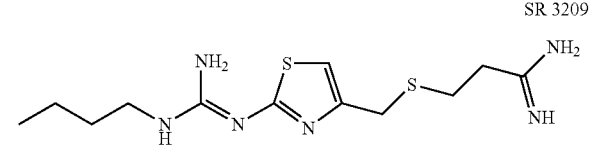

SR 3209

Synthesis Route

Chemical formula 104

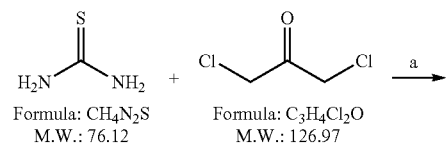

Formula: CH$_4$N$_2$S
M.W.: 76.12

Formula: C$_3$H$_4$Cl$_2$O
M.W.: 126.97

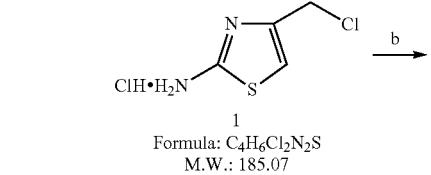

1
Formula: C$_4$H$_6$Cl$_2$N$_2$S
M.W.: 185.07

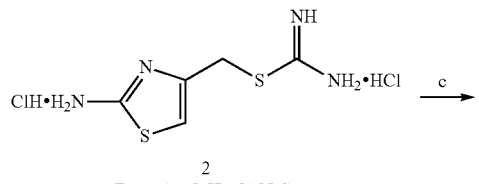

2
Formula: C$_5$H$_{10}$Cl$_2$N$_4$S$_2$
M.W.: 261.20

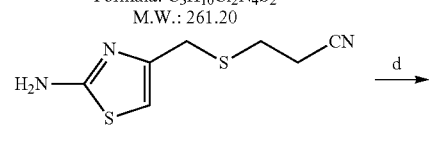

3
Formula: C$_7$H$_9$N$_3$S$_2$
M.W.: 199.30

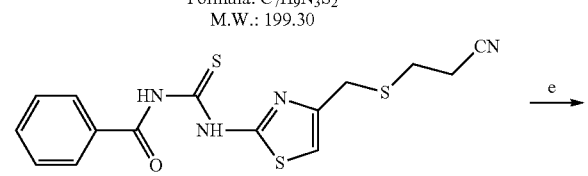

4
Formula: C$_{15}$H$_{14}$N$_4$OS$_3$
M.W.: 362.49

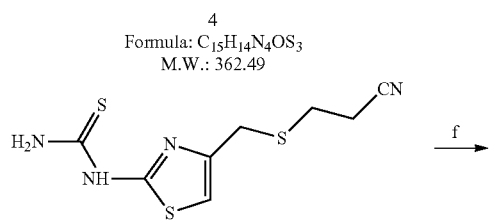

5
Formula: C$_8$H$_{10}$N$_4$S$_3$
M.W.: 258.39

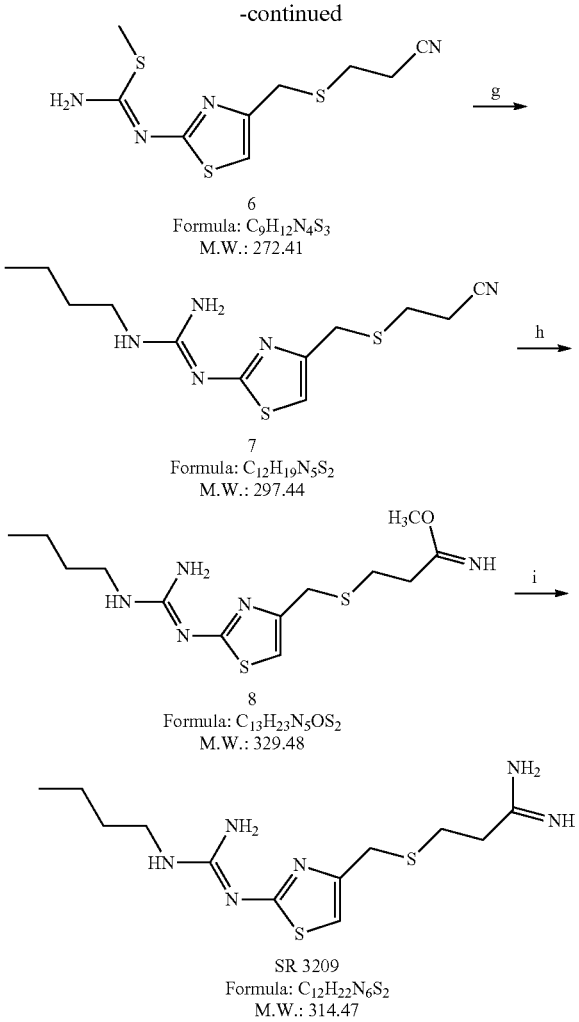

a) CH$_2$ClCOCH$_2$Cl, actone, 12 h; b) thiourea, EtOH, 80° C., 3 h; c) BrCH$_2$CH$_2$CN, EtOH, NaOH, 0° C.; d) Benzoyl isothiocyanate, dry HCl gas, MeOH/CHCl$_3$, 0~10° C.; e) K$_2$CO$_3$ potassium carbonate, dry MeOH, rt, 12 h; f)CH$_3$I, ethanol; g) butan-1-amine, reflux; h) dry HCl(g), MeOH/CHCl$_3$; i)NH$_4$Cl, dry MeOH.

Experiment Section 4-(chloromethyl)thiazol-2-amine (1)[1]

A suspension of thiourea (76 g, 1 mol) in acetone (500 ml) was treated with 1,3-dichloroacetone (126 g, 1 mol). After stirring overnight at room temperature, the solid was filtered off and washed with acetone. Crystallization from ethanol gave the compound 2 (112 g, 61%).

(2-aminothiazol-4-yl)methyl carbamimidothioate (2)[2]

A solution of compound 1 (110 g, 0.6 mol) and thiourea (46 g, 0.6 mol) in 300 ml EtOH was stirred at 80° C. under nitrogen atmosphere for 3 h. After cooled at room temperature, the mixture was filtered and the residue washed with EtOH. Crystallization from 95% ethanol gave the compound 2 (111 g, 71%). $^1$H-NMR (d$^6$-DMSO, 300 MHz): δ4.62 (s, 2H); 7.00 (s, 1H); 9.52 (br, 7H, NH); M.W.: 260 (hydrochloride), ESI-MS: 189 (M+H).

3-((2-aminothiazol-4-yl)methylthio)propanenitrile (3)[3]

A solution of compound 2 (104 g, 0.4 mol) and BrCH$_2$CH$_2$CN (56.4 g, 0.4 mol) in ethanol/water (200 ml/200 ml) was cooled at 0° C., then aq. NaOH (64 g in 200 ml water) was added dropwise to the mixture. After stirring 1 h at 0° C. and another 3 h at room temperature the mixture was filtered and the residue was washed with water. Crystallization from ethanol gave the compound 3 (50.2 g, 63%). $^1$H-NMR (d$^6$-DMSO, 300 MHz): δ2.73-2.80 (m, 2H); 3.13 (m, 2H); 3.34 (br, 1H, NH); 3.59 (s, 2H); 6.37 (s, 1H); 6.91 (b, 1H, NH). M.W.: 199, ESI-MS: 222 (M+Na).

N-(4-((2-cyanoethylthio)methyl)thiazol-2-ylcarbamothioyl)benzamide(4)[3]

To a solution of 3-((2-aminothiazol-4-yl)methylthio)propanenitrile 3 (49.8 g, 0.25 mol) in 500 ml acetone, benzoyl isothiocyanate (45 g, 0.276 mol) was added. The mixture was refluxed for 5 hs. Then the solvent was removed under reduced pressure to give the crude products 4. Further purification by chromatography (DCM/Methanol, 200/1) to give compound 4 (55.4 g, 61%). $^1$H-NMR (CDCl$_3$, 300 MHz): δ2.68 (m, 2H); 2.84 (m, 2H); 3.86 (s, 2H); 3.34 (br, 1H, NH); 6.88 (s, 1H); 7.56-7.58 (m, 3H); 7.90~7.92 (m, 2H); 9.16 (br, 1H, NH). M.W.: 362, ESI-MS: 363 (M+H).

1-(4-((2-cyanoethylthio)methyl)thiazol-2-yl)thiourea (5)[3]

To a solution of compound 4 (40 g, 0.11 mol) in 500 ml acetone and 120 ml methanol, aq. potassium carbonate (10 g in 150 ml water) was added. The mixture was stirred for 5 h at 50° C., and then the solvent was removed under reduce pressure. The residue formed was added to 1000 ml of ice water followed by stirring for 24 h, and the crystals deposited were collected by filtration to provide compound 5 (26.7 g, 94%). M.W.: 258, ESI-MS: 259 (M+H).

Methyl N'-4-((2-cyanoethylthio)methyl)thiazol-2-ylcarbamimidothioate (6)[3]

To a solution of compound 5 (15 g, 58.1 mmol) in 200 ml of ethanol was added iodomethane (12.4 g, 88 mmol) dropwises. The mixture was refluxed for 1 h. Then, the solvent was removed under reduce pressure, and the crystals deposited were collected by filtration to give compound 6 (11.2 g, 71%). M.W.: 272, ESI-MS: 273 (M+H).

(E)-1-butyl-2-(4-((2-cyanoethylthio)methyl)thiazol-2-yl)guanidine(7)[3]

The solution of compound 6 (10.9 g, 40 mmol) in 50 ml butan-1-amine was refluxed under N$_2$ atmosphere for 12 hs. Then, the solvent was removed under reduce pressure, and the residue was purified by chromatography (DCM/Methanol, 100/1) to give compound 7 (2.73 g, 23%). $^1$H-NMR (d$^6$-DMSO, 400 MHz): δ0.88 (t, 3H); 1.32-1.45 (m, 4H); 2.71-2.76 (m, 4H); 3.13 (m, 2H); 3.34 (br, 3H, NH); 3.67 (s, 2H); 6.52 (s, 1H). M.W.: 297, ESI-MS: 298 (M+H).

SR 3209[3]

A solution of compound 7 (1.49 g, 5 mmol) in anhydrous methanol/chloroform (20 ml/40 ml) was cooled to 0~10° C., then dry HCl gas was bubbled for 3 h under this temperature. After that, the mixture was allowed to stand at 0~4° C. for 20 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give intermediate 8. This intermediate was dissolved in the 10 ml methanol and ammonium chloride (0.40 g, 7.5 mmol) was added to the solution. The reaction mixture was stirred at the room temperature for 12 h, when TLC showed no starting material remained, the solvent was removed under reduced pressure and the residue was purified by chromatography (DCM/MeOH/NH$_3$H$_2$O, 200/20/1) to give compound SR 3209 (0.82 g, 52%). $^1$H-NMR (d$^6$-DMSO, 400 MHz): δ1.31 (t, 3H); 1.48 (m, 2H); 1.51 (m, 2H); 2.75 (br, 4H); 3.34 (br, 6H, NH); 3.82 (s, 2H); 6.82 (s, 1H). M.W.: 314, ESI-MS: 315 (M+H).

REFERENCES

1. J. Med. Chem. 2004, 47, 2935-2938
2. WO 2005009986
3. U.S. Pat. No. 4,362,736A Example 37

Example Relates to SR 2213 (OK-013)

Target Compound

Chemical formula 105

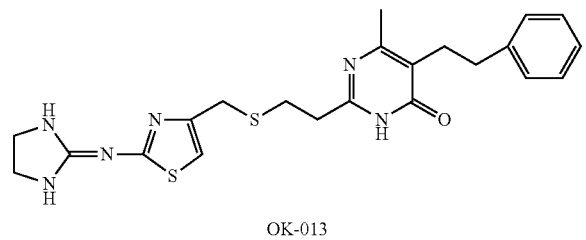

OK-013

Synthesis Route

Chemical formula 106

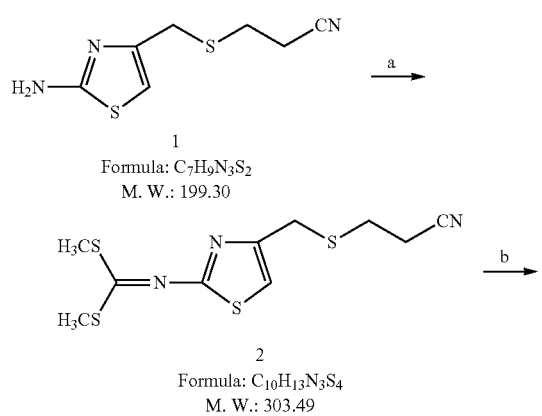

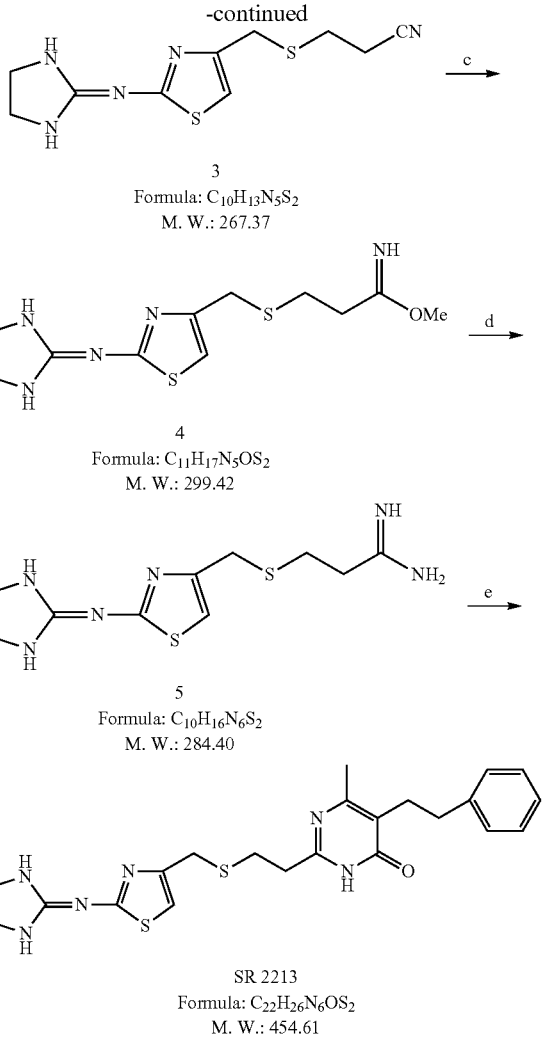

Reagent and Condition a) DMF, NaOH, CS$_2$, CH$_3$I; b) DMF, Ethylenediamine; c) MeOH, DCM, HCl; d) NH$_4$Cl, MeOH; e) Ethyl 3-oxo-2-(2-phenylethyl)butanoate (EOPEB), CH$_3$ONa, MeOH Experiment Section Dimethyl 4-((2-cyanoethylthio)methyl)thiazol-2-ylcarbonimidodithioate (2)[1]

A suspension of compound 1 (1 g, 5 mmol) in 6 ml DMF was treated with 20M NaOH (0.22 g, 5.5 mmol) for 10 min. Then CS$_2$ (0.21 g, 2.75 mmol) was added to the reaction vessel. After 10 min, an additional 0.12 g (3 mmol) of the 20M NaOH and 0.11 g (1.5 mnol) of the CS$_2$ were added and the solution stirred for 10 min longer. A third portion of the 20M NaOH (0.12 g, 3 mmol) and CS$_2$ (0.11 g, 1.5 mmol) were added to the reaction vessel and the solution stirred for 30 min. After cooled at 0° C., the mixture was treated with CH$_3$I (1.42 g, 10 mmol) and the solution stirred for 2 h longer. Then the mixture was extracted with DCM, dried with Na$_2$SO$_4$ and the solvent was removed under reduced pressure. The residue was purified by chromatography (PE/EA, 20/1) to give compound 2 (0.38 g, 25%). $^1$H-NMR ($d^6$-DMSO, 200 MHz): δ2.77-2.81 (m, 6H); 2.97 (t, 2H); 3.67 (t, 2H); 4.69 (s, 2H); 7.40 (s, 1H); M.W.: 303; ESI-MS: 304 (M+H).

3-((2-(imidazolidin-2-ylideneamino)thiazol-4-yl)methylthio)propanenitrile (3)[2]

A solution of compound 2 (1.67 g, 5.5 mmol) and ethylenediamine (0.66 g, 11 mmol) in 20 ml DMF was stirred at 110° C. under nitrogen atmosphere for 9 h. After cooled at room temperature, The mixture was extracted with DCM, dried with $Na_2SO_4$ and the solvent removed under reduced pressure. The residue was purified by chromatography (DCM/MeOH, 50/1) to give compound 3 (0.74 g, 50%). $^1$H-NMR ($d^6$-DMSO, 300 MHz): δ2.70~2.86 (m, 4H); 3.50 (m, 4H); 3.62 (m, 2H); 6.58 (s, 1H); 7.62 (br, 1H). ESI-MS: 268 (M+H).

Methyl 3-((2-(imidazolidin-2-ylideneamino)thiazol-4-yl)methylthio)propanimidate (4)[3]

A solution of compound 3 (0.2 g, 0.7 mmol) in anhydrous methanol/DCM (5 ml/10 ml) was cooled to 0~10° C., then dry HClgas was bubbled for 3 h under this temperature. After that, the mixture was allowed to stand at 0~4° C. for 10 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give crude compound 4 (0.3 g, above 100%). ESI-MS: 300 (M+H). It was used in next step without further purification.

3-((2-(imidazolidin-2-ylideneamino)thiazol-4-yl)methylthio)propanimidamide(5)[3]

A solution of crude compound 4 (0.3 g, 1 mmol) and $NH_4Cl$ (0.1 g, 1.5 mmol) in 5 ml MeOH was stirred at room temperature for 1 h, the solvent was removed under reduced pressure and the residue was purified by chromatography (DCM/Methanol, 15/1) to give compound 5 (0.17 g, 60%). $^1$H-NMR ($d^6$-DMSO, 300 MHz): δ2.80 (m, 2H); 3.43 (m, 6H); 3.67 (s, 2H); 7.18 (s, 1H); 7.35~7.54 (br, 1H); 8.90 (br, 1H); 9.29 (br, 1H). M.W.: 284; ESI-MS: 285 (M+H).

SR 2213 (OK-013)[4]

A solution of crude compound 5 (0.1 g, 0.35 mmol) and ethyl 3-oxo-2-(2-phenylethyl)butanoate (EOPEB) (0.08 g, 0.35 mmol) and $CH_3ONa$ (0.05 g, 1 mmol) in 5 ml MeOH was stirred at room temperature for 5 h, then the solvent was removed under reduced pressure and the residue was purified by chromatography (DCM/Methanol, 10/1) to give compound SR 2213 (OK-013) (0.08 g, 50%). $^1$H-NMR ($d^6$-DMSO, 300 MHz): δ2.61 (m, 2H); 2.61-2.69 (m, 4H); 2.82 (s, 3H); 3.49 (m, 4H); 3.61 (m, 2H); 3.71 (m, 2H); 6.54 (s, 1H); 7.17-7.29 (m, 5H); 7.58-7.71 (m, 4H). M.W.: 454; ESI-MS: 455 (M+H).

REFERENCES

1. JACS, 1996, 6355-6369; Journal of the Chemical Society; 1956; 1644
2. Arzneimittel Forschung; German; 35; 3; 1985; 573-577
3. Journal of Medicinal Chemistry; English; 30; 10; 1987; 1787-1793
4. Journal of the American Chemical Society; 71; 1949; 616

Example 38

Example Relates to SR3208

Target Compound

Chemical formula 107

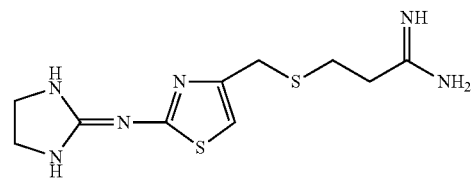

SR 3208

Synthesis Route

Chemical formula 108

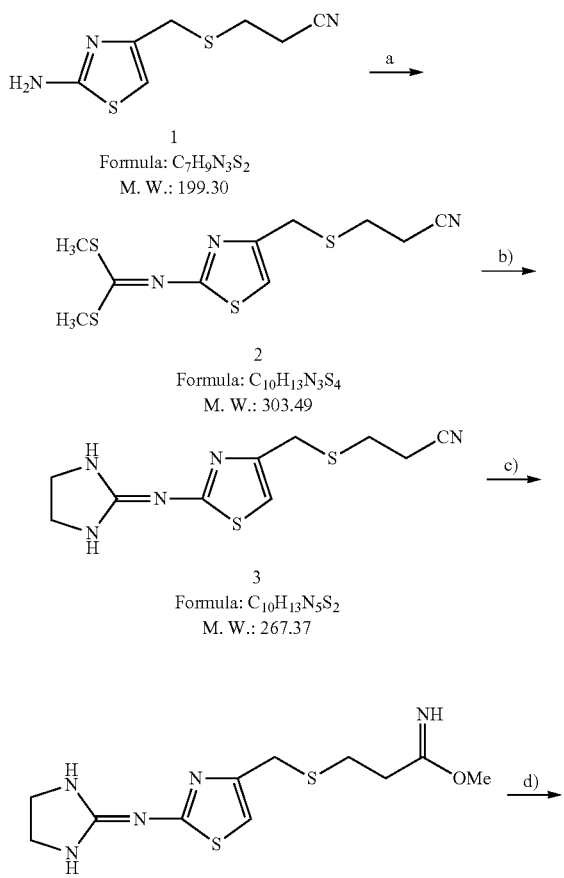

-continued

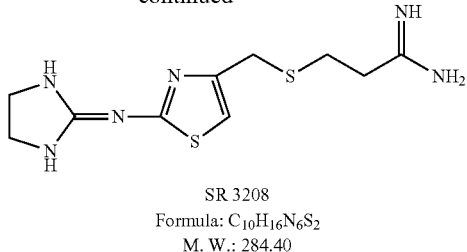

SR 3208
Formula: $C_{10}H_{16}N_6S_2$
M. W.: 284.40

Reagent and Condition
a) DMF, NaOH, $CS_2$, $CH_3I$; b) DMF, Ethylenediamine; c) MeOH, DCM, HCl; d) $NH_4Cl$, MeOH Experiment Section Dimethyl 4-((2-cyanoethylthio)methyl)thiazol-2-ylcarbonimidodithioate (2)[1]

A suspension of compound 1[2] (1 g, 5 mmol) in 6 ml DMF was treated with 20M NaOH (0.22 g, 5.5 mmol) for 10 min. Then $CS_2$ (0.21 g, 2.75 mmol) was added to the reaction vessel. After 10 min, an additional of 20M NaOH (0.12 g, 3 mmol) and $CS_2$ (0.11 g, 1.5 mmol) were added and the solution stirred for 10 min longer. After that a third portion of the 20M NaOH (0.12 g, 3 mmol) and $CS_2$ (0.11 g, 1.5 mmol) were added to the reaction vessel and the solution stirred for 30 min. After cooled at 0° C., the mixture was treated with $CH_3I$ (1.42 g, 10 mmol) and the solution stirred for 2 h longer. The mixture was extracted with DCM, the solvent was removed under reduced pressure and the residue was purified by chromatography (PE/EA, 20/1) to give compound 2 (0.38 g, 25%). $^1$H-NMR (d$^6$-DMSO, 300 MHz): δ 2.77-2.81 (m, 6H); 2.97 (t, 2H); 3.67 (t, 2H); 4.69 (s, 2H); 7.40 (s, 1H); M.W.: 303; ESI-MS: 304 (M+H).

3-((2-(imidazolidin-2-ylideneamino)thiazol-4-yl)methylthio)propanenitrile (3)[3]

A solution of compound 2 (1.67 g, 5.5 mmol) and ethylenediamine (0.66 g, 11 mmol) in 20 ml DMF were stirred at 110° C. under nitrogen atmosphere for 9 h. After cooled at room temperature, The mixture was extracted with DCM, the solvent removed under reduced pressure and the residue was purified by chromatography (DCM/MeOH, 50/1) to give compound 3 (0.74 g, 50%). $^1$H-NMR (d$^6$-DMSO, 200 MHz): δ2.70~2.86 (m, 4H); 3.50 (m, 4H); 3.62 (m, 2H); 6.58 (s, 1H); 7.62 (br, 1H). M.W.: 267; ESI-MS: 268 (M+H).

Methyl 3-((2-(imidazolidin-2-ylideneamino)thiazol-4-yl)methylthio)propanimidate (4)[4]

A solution of compound 3 (0.2 g, 0.7 mmol) in anhydrous methanol/DCM (5 ml/10 ml) was cooled to 0~10° C., then dry HClgas was bubbled for 3 h under this temperature. After that, the mixture was allowed to stand at 0~4° C. for 10 h and then concentrated under reduced pressure to afford imidate hydrochlorides as a crystalline solid. Free imidates were obtained by adding the reaction mixture into ice-cooled water containing excess potassium carbonate and the mixture was filtered and the residue washed with EtOH to give crude compound 4 (0.21 g, 93%). M.W.: 299; ESI-MS: 300 (M+H).

SR 3208: A solution of crude compound 4[3] (0.3 g, 1 mmol) and $NH_4Cl$ (0.1 g, 1.5 mmol) in 5 ml MeOH was stirred at room temperature for 1 h, then the solvent was removed under reduced pressure and the residue was purified by chromatography (DCM/Methanol, 15/1) to give compound SR 3208 (0.17 g, 60%). $^1$H-NMR (d$^6$-DMSO, 300 MHz): δ2.80 (m, 2H); 3.43 (m, 6H); 3.67 (s, 2H); 7.18 (s, 1H); 7.35~7.54 (br, 1H); 8.90 (br, 1H); 9.29 (br, 1H). M.W.: 284; ESI-MS: 285 (M+H).

REFERENCES

1. JACS, 1996, 6355-6369; Journal of the Chemical Society; 1956; 1644
2. Detailed synthesis methods as shown in the report of SR 3209
3. Arzneimittel Forschung; German; 35; 3; 1985; 573-577
4. Journal of Medicinal Chemistry; English; 30; 10; 1987; 1787-1793

Example 39

Example Relates to SR3021

Target Compound

Chemical formula 109

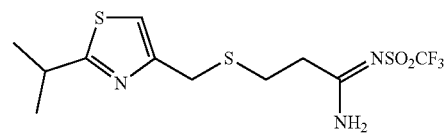

SR 3021

Synthesis Route

Chemical formula 110

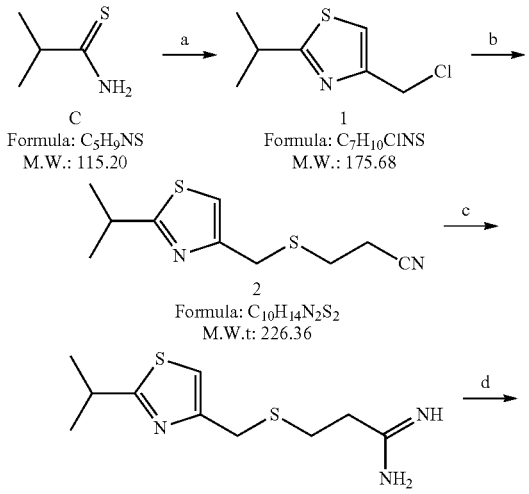

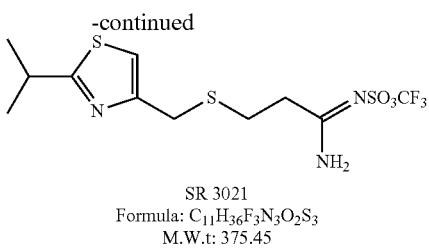

SR 3021
Formula: C₁₁H₃₆F₃N₃O₂S₃
M.W.t: 375.45

Reagent and Condition
a) CH₂ClCOCH₂Cl, actone, b) thiourea, EtOH/H₂O, 80° C.; BrCH₂CH₂CN/NaOH; c) dry HCl gas, EtOH/CHCl₃, 0° C.; NH₃/MeOH; d) trifluoromethanesulfonyl chloride, chloroform, 0° C., 5 h;

Experiment Section

The Preparation of Compound C[1]

A mixture of isobutyramide (50 g, 0.57 mol) and phosphorus pentasulfide (27 g, 0.12 mol) in 1 L ethyl ether stirred at room temperature over night. The mixture was filtered and the ethyl ether was concentrated to give a light yellow oil A (52.8 g, 90%). ¹H-NMR (d⁶-DMSO, 300 MHz): δ 1.08 (d, 6H); 2.78 (m, 1H); 9.08 (d, 2H); 9.29 (s, 1H).

4-(chloromethyl)-2-isopropylthiazole 1M A solution of 2-methylpropanethioamide (73 g, 0.71 mol) and 1,3-dichloropropan-2-one (90 g, 0.71 mol) in 600 ml acetone was refluxed for 8 hours, cooled and filtered to give compound 1 (30 g, 25%). ¹H-NMR (d⁶-DMSO, 300 MHz): δ 1.40 (d, 6H); 3.32 (m, 1H); 4.68 (s, 2H); 7.16 (s, 1H).

3-((2-isopropylthiazol-4-yl)methylthio)propanenitrile 2[2]

A mixture of 4-(chloromethyl)-2-isopropylthiazole 1 (0.63 g, 3.6 mmol) and thiourea (0.27 g, 3.6 mmol) was dissolved in 10 ml ethyl alcohol (95%). The mixture was refluxed for 5 hours, then concentrated to 5 ml. After that 5 ml water and 3-bromoethyl cyanide 0.72 g (044 ml, 5.4 mmol) was added in one portion. Cooled the mixture to 0° C., 6 ml NaOH (2M) was added dropwise. Stirred at this temperature for 1 hours, the mixture was extracted with EA (20 ml×4), dried and filtered. The solvent was removed under vacuo to give impure product 2 (0.25 g, 31%). ¹H-NMR (CDCl₃, 300 MHz): δ 1.35 (d, 6H); 2.80 (m, 4H); 3.32 (m, 1H); 3.70 (s, 1H); 7.10 (s, 1H). M.W.: 226.36; ESI-MS: 227 (M+H).

3-((2-isopropylthiazol-4-yl) methylthio) propanimidamide 3[3][4]

Compound 2 (1.0 g, 4.4 mmol) and dry ethyl alcohol (0.3 g, 6.6 mmol) were dissolved in 50 ml dry ethyl ether. Cooled the mixture to 0° C. and the dry hydrogen chloride gas was bubbled to the solution. After 3 hours, the mixture was concentrated and dissolved in 20 ml dry methol. Cooled to 0° C. again, NH₃ gas was bubbled to the mixture for 1 hours. After that the mixture was concentrated and purified by chromatographic column to give 3 (620 mg, 58%). ¹H-NMR (d⁶-DMSO, 300 MHz): δ 1.31 (d, 6H); 2.60 (m, 4H); 3.34 (m, 1H); 3.75 (s, 1H); 7.04 (s, 1H), 8.51 (s, 2H); M.W: 243.39; ESI-MS: 244 (M+H).

SR 3021[5]

To a solution of compound 3 (0.5 g, 2 mmol) and 0.2 ml triethylamine in 50 ml chloroform and trifluoro-methanesulfonyl chloride (0.25 ml, 2.4 mmol) was added dropwise below 0° C. The reaction mixture was stirred for 5 h under the room temperature until TLC showed no starting material remained. Then the solvent was removed under reduced pressure and the residue was purified by chromatography (DCM/Methanol, 50/1) to give compound SR 3021 (150 mg, 20%). ¹H-NMR (d⁶-DMSO, 400 MHz): δ 1.30 (d, 6H); 2.76 (s, 4H); 3.24 (m, 1H); 3.83 (m, 2H); 7.30 (s, 1H). M.W: 375.4; ESI-MS: 376 (M+H).

REFERENCES 1. huaxue yanjiu yu yingyong, 2006, 18(2), 186-188.
2. hubei huagong, 2000, 5, 19-20,
3. J. Org. Chem. 1989, 54, 1256-1264
4. J. Org. Chem. 1981, 46, 2455-2465
5. U.S. Pat. No. 4,362,736A Example 40

Example Relates to SR2207 (OK-007)

Target Compound

Chemical formula 111

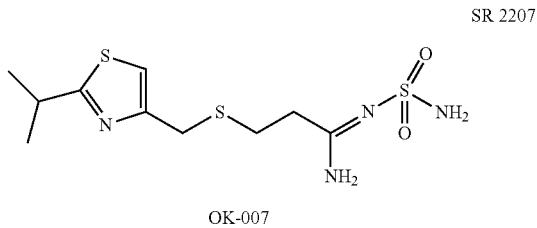

SR 2207

OK-007

Synthesis Route

Chemical formula 112

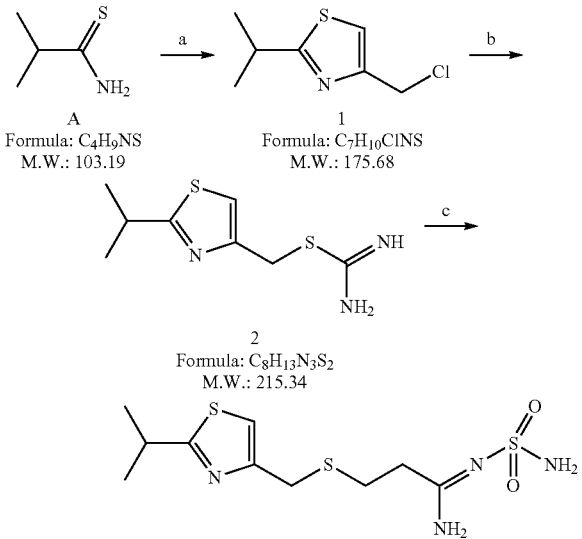

A
Formula: C₄H₉NS
M.W.: 103.19

1
Formula: C₇H₁₀ClNS
M.W.: 175.68

2
Formula: C₈H₁₃N₃S₂
M.W.: 215.34

SR 2207
Formula: C₁₀H₁₈N₄O₂S₃
M.W.: 322.47

Reagent and Condition
a) CH$_2$ClCOCH$_2$Cl, actone, 8 h; b) thiourea, EtOH, 80° C., 10 h; c) (Z)-3-chloro-N'-sulfamoylpropanimidamide, NaOH;

Experiment Section (2-isopropylthiazol-4-yl)methyl carbamimidothioate 2[1]

A mixture of 4-(chloromethyl)-2-isopropylthiazole 1[3] (6.3 g, 36 mmol) and thiourea (2.7 g, 36 mmol) was dissolved in 20 ml ethanol (95%). The reaction mixture was refluxed for 3 hours. When TLC showed no starting material remained, the solvent was concentrated under reduced pressure. The residue was washed with ethanol to give compound 2 (7.2 g, 93.5%).

(Z)-3-((2-isopropylthiazol-4-yl)methylthio)-N'-sulfamoylpropanimidamide SR 2207 (OK-007)[2]

A solution of compound 2 (3.0 g, 13.9 mmol) and (Z)-3-chloro-N'-sulfamoyl propanimidamide (2.59 g, 14 mmol) in 60 ml combined solvent (H$_2$O/EtOH, 2/1, v/v), the mixture was cooled to 0° C., and 10 ml NaOH (2M) was added dropwise to the solution. The reaction mixture was stirred at this temperature for 2 hours. When TLC showed no starting material remained, the solvent was removed under reduced pressure to give the crude product. The residue was purified by chromatographic column (DCM/MeOH, 25/1) to give SR 2207 (OK-007) (700 mg, 15.6%). $^1$H-NMR (d$^6$-DMSO, 300 MHz): δ1.32 (d, 6H); 2.59 (m, 2H); 2.80 (m, 2H); 3.25 (m, 1H); 3.83 (s, 2H); 5.89 (s, 1H); 7.64 (d, 2H). $^{13}$C-NMR (d$^6$-DMSO, 75 MHz): 178.8, 167.0, 151.9, 114.6, 36.7, 32.9, 31.1, 28.4, 23.1. M.W: 322.4; ESI-MS: 323 (M+H).

REFERENCES 1. huaxue yanjiu yu yingyong, 2006, 18(2), 186;
2. a) hubei huagong, 2000, 5, 19; b) J. Heter. Chem., 1986, 23, 577
3. a) huaxue yanjiu yu yingyong, 18(2), 186-188, 2006; b) hubei huagong, 5, 19-20, 2000; c) J. Org. Chem. 1989, 54, 1256-1264; d) J. Org. Chem. 1981, 46, 2455-2465; e) Journal, De cat, Van Dormael, BSCBAG, Bulletin des Societes Chimiques Belges, 59, 1950, 573, 583, ISSN: 0037-9646; f) Journal, Allen et al., JOCEAH, Journal of Organic Chemistry, 24, 1959, 787, 792; g) Journal, Antaki, Petrow, JCSOA9, Journal of the Chemical Society, 1951, 551, 554

Example 41

Example Relates to SR2011

Target Compound

Chemical formula 113

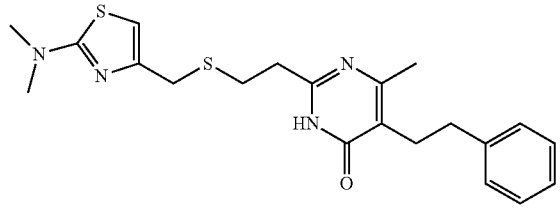

SR 2011

Synthesis Route

Chemical formula 114

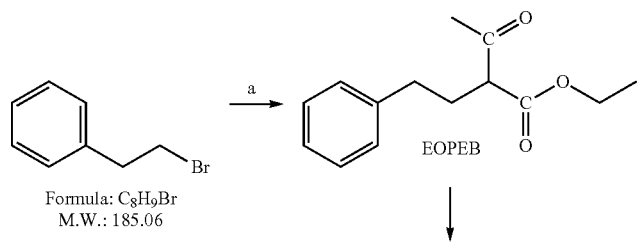

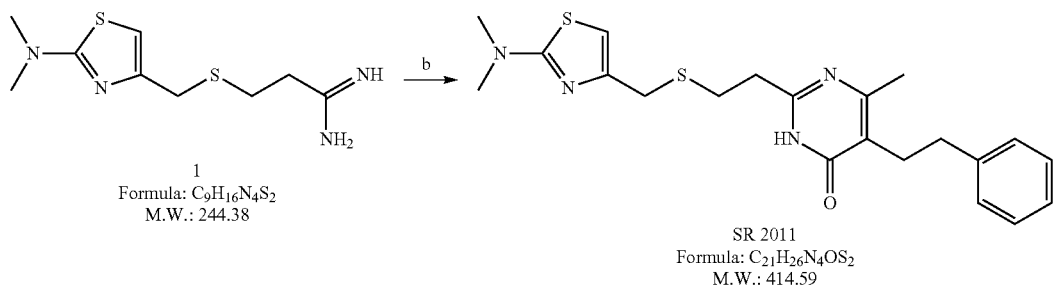

Reagent and Condition
a) Ethyl 3-oxo-butanoate, NaOMe, reflux 20 h; b) B, NaOMe, reflux, 2 h;

Experiment Section

SR 2011[2]

To a solution of 3-(2-(dimethylamino)thiazol-4-yl)methylthio-propanimidamide 1[3] (0.5 g, 2 mmol) and MeONa (0.26 g, 0.48 mmol) in 20 ml anhydrous methanol at room temperature, ethyl 3-oxo-2-(2-phenylethyl)butanoate (EOPEB) B (0.53 g, 2.4 mmol) was added. The mixture was stirred for 12 h under this temperature until TLC showed no starting material remained. Then the solvent was removed under reduced pressure and the residue was purified by chromatography (DCM/MeOH, 50/1) to give compound SR 2011 (0.21 g, 25.3%). $^1$H-NMR (d$^6$-DMSO, 400 MHz): δ 2.03 (s, 4H); 2.64 (d, 3H); 2.83 (d, 4H); 3.05 (s, 6H); 3.61 (d, 2H); 6.63 (s, 1H); 7.15-7.26 (m, 5H). M.W: 414.5; ESI-MS: 415 (M+H).

REFERENCES 1. a) J. Am. Chem. Soc., 1946, 68 (12), 2492; b) J. Am. Chem. Soc., 1949, 71 (6), 1922;
2. a) Bulletin des Societes Chimiques Belges; 1950, 59; 57; b) J. Org. Chem. 1959, 24, 787; c) J. Chem. Soc. 1951, 551.
3. a) Detailed synthesis methods as shown in the report of SR 2005, b) J. Org. Chem. 1989, 54, 1256-1264; c) J. Org. Chem. 1981, 46, 2455-2465; d) U.S. Pat. No. 4,362,736A.

Example 42

Example Relates to SR2005

Target Compound

Chemical formula 115

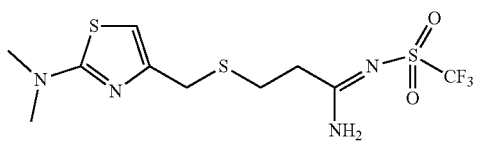
SR 2005

Synthesis Route

Chemical formula 116

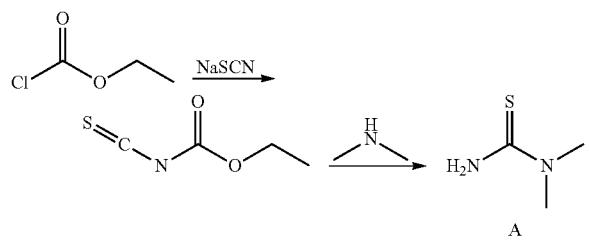

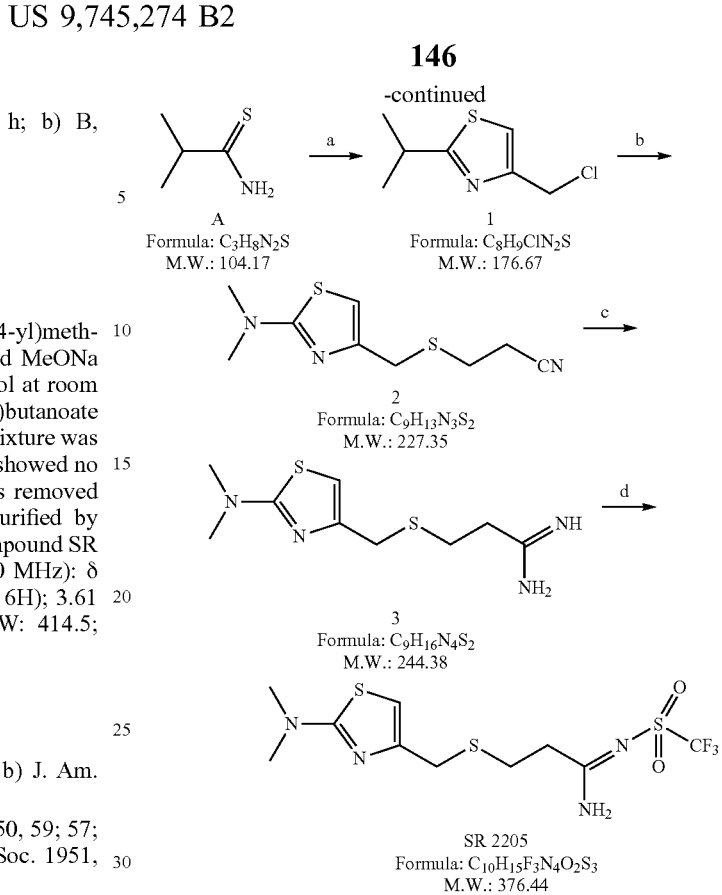

Reagent and Condition
a) CH$_2$ClCOCH$_2$Cl, acetone, 5 h; b) thiourea, EtOH, 80° C., 3 h; BrCH$_2$CH$_2$CN/NaOH; c) dry HCl gas, EtOH/CHCl$_3$, 0° C.; NH$_3$/MeOH; d) trifluoromethanesulfonyl chloride, chloroform, 5 h.

Experiment Section 3-((2-(dimethylamino)thiazol-4-yl)methylthio)propanenitrile 2[2]

A mixture of 2-dimethylamino-4-chloromethyl-thiazole 1 (7 g, 39 mmol) and thiourea (3 g, 39 mmol) was dissolved in 100 ml ethanol (95%). The reaction mixture was refluxed for 3 hours. When TLC showed no starting material remained, the solvent was concentrated under reduced pressure, until a half of solvent was removed, and 3-bromopropanenitrile (4 g, 2.4 ml) was added in one portion. The mixture was cooled to 0° C., and NaOH (2M, 64 ml) was added dropwise to the solution, the reaction mixture was stirred at this temperature for 1 hour. When TLC showed no starting material remained, the mixture was extracted with EA (4×50 ml), and the organic layer was dried and filtered. The solvent was removed under vacuo to give the oiled product, and the impure product was crystallize from ethanol to give compound 2 (2.6 g, 29%). $^1$H-NMR (d$^6$-DMSO, 300 MHz): δ 2.78 (s, 4H); 3.05 (s, 6H); 3.70 (s, 2H); 6.48 (s, 1H). M.W: 227.3; ESI-MS: 228 (M+H).

3-((2-(dimethylamino)thiazol-4-yl)methylthio)propanimidamide 3[3]

Compound 2 (0.62 g, 2.7 mmol) and dry ethyl alcohol (0.23 ml, 4.1 mmol) were dissolved in 20 ml dry chloroform.

The mixture was cooled to 0° C. and the dry hydrogen chloride gas was bubbled into the reaction mixture. After 3 hours, the mixture was concentrated and dissolved in 20 ml dry methanol. And then the mixture was cooled to 0° C. and the ammonia gas was bubbled to the mixture for 1 h. After that the solvent was removed under reduced pressure and the residue was purified by chromatography (DCM/Methanol, 25/1) to give compound 3 (470 mg, 71%). M.W: 244.3; ESI-MS: 245 (M+H)

SR 2005[4]

A solution of compound 3 (1.0 g, 4 mmol) and 0.4 ml triethylamine in 50 ml chloroform was cooled to 0° C., and trifluoro-methanesulfonyl chloride (0.4 ml, 4 mmol) was added dropwise to the mixture. The reaction mixture was stirred for 5 h under the room temperature, when TLC showed no starting material remained, a The solvent was removed under reduced pressure and the residue was purified by chromatography (DCM/Methanol, 50/1) to give compound SR 2005 (250 mg, 16%). $^1$H-NMR (d$^6$-DMSO, 400 MHz): δ 2.74 (s, 4H); 2.97 (s, 6H); 3.58 (s, 2H); 6.48 (s, 1H). $^{13}$C-NMR (d$^6$-DMSO, 75 MHz): 172.698, 170.801, 149.761, 121.813, 103.460, 35.763, 30.954, 28.066; M.W.: 376; ESI-MS: 377 (M+H).

REFERENCES 1. huaxue yanjiu yu yingyong, 2006, 18(2), 186-188
2. a) hubei huagong, 2000, 5, 19-20; b) J. Heterocyclic Chem., 1986, 23, 577
3. a) J. Org. Chem. 1989, 54, 1256-1264; b) J. Org. Chem. 1981, 46, 2455-2465
4. U.S. Pat. No. 4,362,736A Example 43

Example Relates to SR2208 (OK-008)

Target Compound

Chemical formula 117

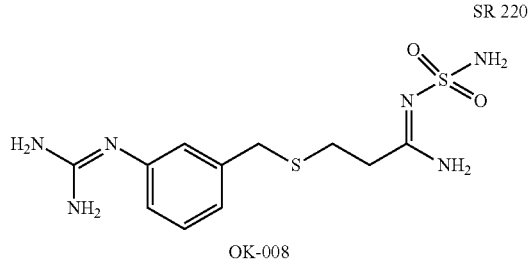

OK-008

Synthesis Route

Chemical formula 118

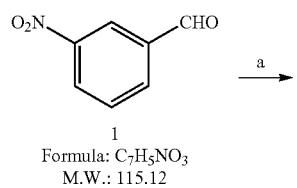

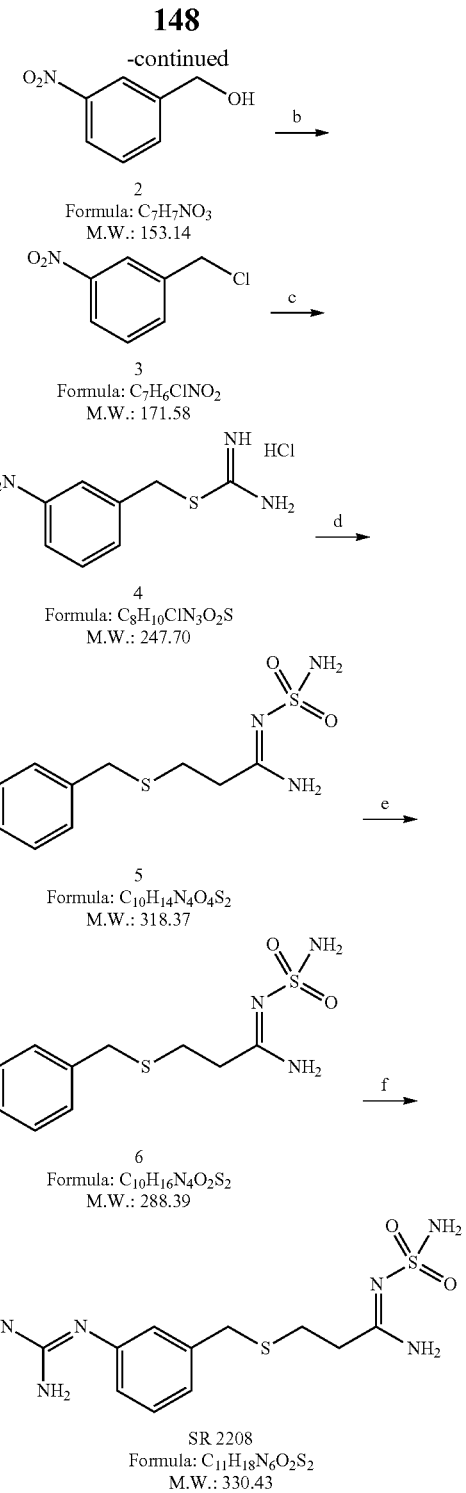

Reagent and Condition
a) MeOH, NaBH$_4$, rt, 1 h; b) Et$_3$N, SOCl$_2$, rt, 1 h; c) thiourea, EtOH, 80° C.; d) (Z)-3-chloro-N'-sulfamoylpropanimidamide, EtOH—H$_2$O, NaOH, 0° C.; e) MeOH, Pd/C, H$_2$; f) Cyanamide, 80° C.

Experiment Section (3-nitrophenyl) methanol (2): A suspension of 3-nitrobenzaldehyde 1 (15.11 g, 0.1 mol) in MeOH (130 ml) was treated with NaBH$_4$ (2.4 g, 0.063 mol) at room temperature for 1 h then the reaction was quenched by saturated potassium carbonate solution. The solvent was removed under reduced pressure to give the crude compound 2. It was used directly without further purification. $^1$H-NMR (CDCl$_3$, 200 MHz): δ 2.97 (s, 1H); 4.78 (s, 2H); 7.50 (t, 1H); 7.66 (d, 1H); 8.08 (d, 1H); 8.19 (s, 1H).

1-(chloromethyl)-3-nitrobenzene (3): A mixture of compound 2 (7.65 g, 0.05 mol), Et$_3$N (15.18 g, 0.15 mol) and SOCl$_2$ (8.92 g, 0.075 mol) was stirred at room temperature for 1 h. When TLC showed no starting material remained, the solvent was removed under reduced pressure to give the compound 3 (8.57 g, 100%). It was used directly in next step without further purification.

3-nitrobenzyl carbamimidothioate hydrochloride (4)[1]

A solution of compound 3 (10.6 g, 0.061 mol) and thiourea (3.08 g, 0.04 mol) in 50 ml EtOH was stirred at 80° C. under nitrogen atmosphere for 0.5 h. When TLC showed no starting material remained, the mixture was cooled at room temperature. Then the solvent was removed under reduced pressure and the residue was crystallized to give compound 4 (3.8 g, 25%). $^1$H-NMR (d$^6$-DMSO, 300 MHz): δ 4.75 (s, 2H); 7.70 (t, 1H); 7.94 (d, 1H); 8.18 (d, 1H); 8.38 (d, 1H); 9.46 (d, 3H). M.W.: 247.7 (hydrochloride salt); ESI-MS: 212 (M+H).

(Z)-3-(3-nitrobenzylthio)-N'-sulfamoylpropanimidamide (5)[2]

A solution of compound 4 (1 g, 4 mmol) and (Z)-3-chloro-N'-sulfamoylpropanimidamide (0.805 g, 4.2 mmol) in ethanol/water (5 ml/5 ml) was cooled at 0° C., then aq. NaOH (0.4 g in 2 ml water) was added dropwise. After stirring 1 h at 0° C. and another 3 h at room temperature the mixture was filtered and the residue was washed with water. Crystallization from ethanol gave the compound 5 (0.79 g, 62%).

2-(5-((2-Cyanoethylthio)methyl)thiazol-(Z)-3-(3-aminobenzylthio)-N'-sulfamoylpropanimidamide (6): A mixture of compound 5 (0.3 g, 0.94 mmol) and Pd/C (0.1 g) in methanol was stirred 65° C. under hydrogen atmosphere for 2 h. When TLC showed no starting material remained, the solvent was removed under reduced pressure. The residue was purified by chromatography (DCM/Methanol, 20/1) to give compound 6 (97 mg, 36%).

SR 2208 (OK-008)[3]

A mixture of compound 6 (0.2 g, 0.7 mmol) and cyanamide (0.1 g, 2.4 mmol) was melted and stirred at 80° C. under nitrogen atmosphere for 15 min. After cooled to the temperature, the mixture was purified by chromatography (DCM/Methanol, 5/1) to give compound SR 2208 (OK-008) (50 mg, 22%). $^1$H-NMR (d$^6$-DMSO, 300 MHz): δ2.46-2.51 (m, 4H); 2.61-2.64 (m, 2H); 3.81 (s, 2H); 6.41 (s, 1H); 6.53 (s, 2H); 7.08 (m, 1H); 7.36 (br, 2H); 7.63 (br, 1H); 8.46 (br, 1H). M.W.: 330; ESI-MS: 331 (M+H).

REFERENCES

1. U.S. Pat. No. 4,362,736
2 J. Med. Chem. 2004, 47, 2935-2938
3 Chemical Papers, 61(6), 507-511; 2007

Example 44

Example Relates to SR3003

Target Compound

Chemical formula 119

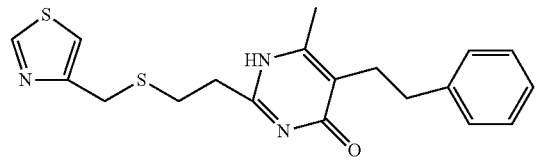

Synthesis Route

Chemical formula 120

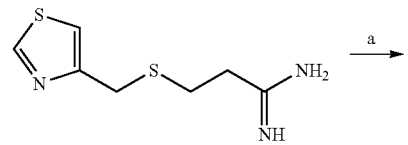

1
Formula: C$_7$H$_{11}$N$_3$S$_2$
M.W.: 201.31

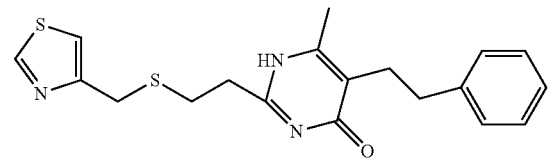

SR 3003
Formula: C$_{19}$H$_{21}$N$_3$OS$_2$
M.W. 371.52

Reagent and Condition a) NaOH, ethyl 3-oxo-2-(2-phenylethyl)butanoate (EOPEB), 65° C.

Experiment Section

SR-3003[1]

To a solution of 3-(thiazol-4-ylmethylthio)propanimidamide 1[2] (1.1 g, 5.5 mmol) and ethyl 3-oxo-2-(2-phenylethyl)butanoate (EOPEB)[3] (1.25 g, 5.3 mmol) in 15 ml methanol, NaOH (1.5 g, 38 mmol) was added. The mixture was stirred for 0.5 h at 65° C. When TLC showed no starting material remained, the solvent was removed under reduced pressure and the residue was purified by chromatography (DCM/MeOH, 50/1) to give compound SR 3003 as a white solid (550 mg, 27%). $^1$H-NMR (d$^6$-DMSO, 400 MHz): δ 1.95 (s, 2H); 2.35 (S, 3H); 2.43 (m, 2H); 3.91 (s, 2H); 7.10-7.25 (m, 5H); 7.50 (s, 1H); 9.04 (s, 1H); 12.37 (s, 1H). $^{13}$C-NMR (d$^6$-DMSO, 75 MHz): 162.4, 159.6, 156.6, 154.2, 128.3, 125.8, 120.9, 115.9, 34.0, 30.3, 28.4, 27.6; M.W: 371.5; ESI-MS: 372 (M+H).

REFERENCES 1. a) Bulletin des Societes Chimiques Belges; 1950, 59; 57; b) J. Org. Chem. 1959, 24, 787; c) J. Chem. Soc. 1951, 551.
2. Detailed synthesis methods as shown in the report of SR 3002
3. Detailed synthesis methods as shown in the report of SR 2011

Example 45

Example Relates to SR3002

Target Compound

Chemical formula 121

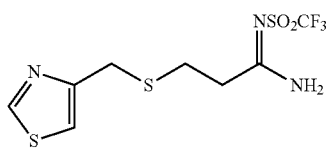

SR 3002

Synthesis Route

Chemical formula 122

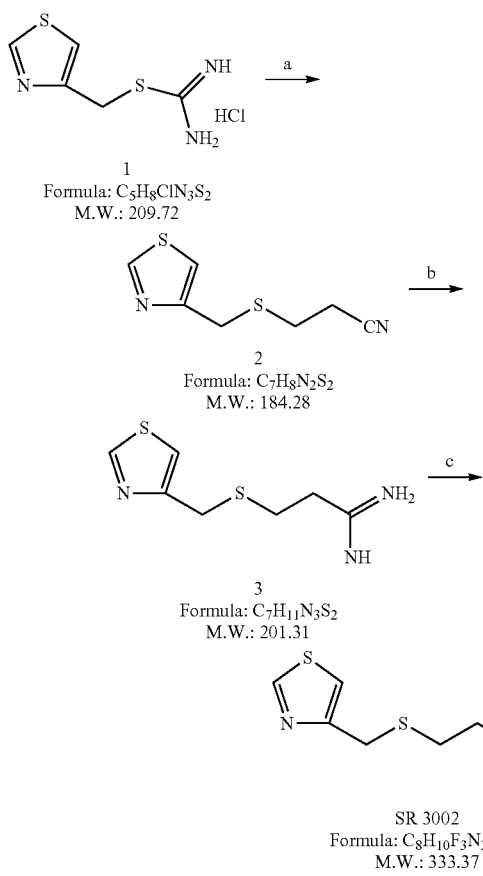

Reagent and Condition a) $BrCH_2CH_2CN$, NaOH; b) $HCl/CH_3OH$, $NH_3/CH_3OH$; c) $CF_3SO_2Cl$, $DCM/CH_3CN/THF$, 0° C. 0.5 h Experiment Section 3-(thiazol-4-ylmethylthio)propanenitrile 2[1]

To a solution of thiazol-4-ylmethyl carbamimidothioate 1[2] (5.5 g, 26.2 mmol) and 3-bromopropanenitrile (3.5 g, 26.2 mmol) in 30 ml combined solvent ($H_2O$/EtOH, 2/1, v/v), 11 ml NaOH (4M) was added dropwise below 0° C. The reaction mixture was stirred at this temperature for 2 hours. When TLC showed no starting material remained the solvent was removed under reduced pressure and the residue was purified by chromatographic column (DCM/MeOH, 25/1) to give compound 2 (2.73 g, 55%). $^1$H-NMR ($CDCl_3$, 300 MHz): δ2.62 (m, 2H); 2.78 (m, 2H); 3.68 (s, 2H); 5.16 (s, 1H); 6.35 (s, 1H). M.W: 184.2; ESI-MS: 185 (M+H).

3-(thiazol-4-ylmethylthio)propanimidamide 3[3] 3-(thiazol-4-ylmethylthio)propanenitrile 2 (2.73 g, 14.8 mmol) was dissolved in 20 ml dry chloroform and 7.5 ml the dry ethyl alcohol. The mixture was cooled to 0° C. and the dry hydrogen chloride gas was imported. After 3 hours, the mixture was concentrated and dissolved in 20 ml dry methanol. And then the mixture was cooled to 0° C. and the ammonia gas was imported to the mixture for 1 h. The solvent was removed under reduced pressure and the residue was purified by chromatography (DCM/Methanol, 25/1) to give compound 3 (2 g, 46%). $^1$H-NMR ($d^6$-DMSO, 300 MHz): δ 2.79 (m, 4H); 3.60 (s, 2H); 6.46 (s, 1H); 7.02 (s, 1H); 8.86 (s, 1H); 9.25 (s, 1H).

SR 3002[4]

To a solution of 3-(thiazol-4-ylmethylthio)propanimidamide 3 (0.5 g, 2.5 mmol) and 0.3 ml triethyl-amine in 30 ml solvent ($DCM/CH_3CN$/THF=2:5:7), trifluoromethanesulfonyl chloride (0.7 g, 4.2 mmol) was added dropwise below 0° C. The reaction mixture was stirred for 0.5 h under the room temperature until TLC showed no starting material remained. The solvent was removed under reduced pressure and the residue was purified by chromatography (DCM/Methanol, 50/1) to give compound SR 3002 (200 mg, 24.1%). $^1$H-NMR ($CD_3OD$, 400 MHz): δ 2.74 (m, 4H); 3.92 (s, 2H); 7.43 (s, 1H); 8.95 (s, 1H). $^{13}$C-NMR ($CD_3OD$, 75 MHz): 174.3, 155.7, 154.8, 123.2, 118.9, 37.6, 31.3, 28.9; M.W: 333.3; ESI-MS: 334 (M+H).

REFERENCES 1. huaxue yanjiu yu yingyong, 2006, 18(2), 186-188.
2. Detailed synthesis methods as shown in the report of SR 3001
3. a) J. Org. Chem. 1989, 54, 1256-1264; b) J. Org. Chem. 1981, 46, 2455-2465;
4. U.S. Pat. No. 4,362,736A

Example 46

Example Relates to SR3001

Target Compound

Chemical formula 123

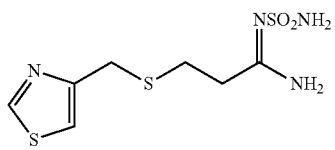

SR 3001

Synthesis Route

Chemical formula 124

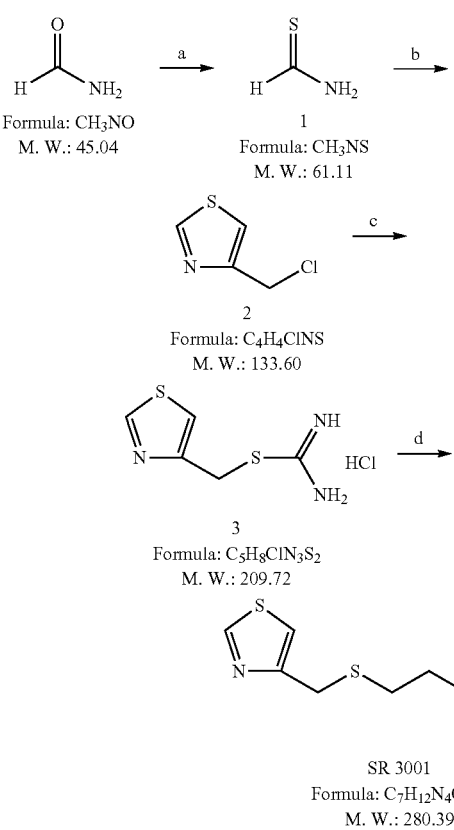

Reagent and Condition a) $P_2S_5$, $Et_2O$; b) $CH_2ClCOCH_2Cl$, acetone; c) thiourea, EtOH, 80° C., 3 h; d) (Z)-3-chloro-N'-sulfamoyl-propa-nimidamide, NaOH.

Experiment Section

Methanethioamide 1[1]

To a suspension of phosphorus pentasulfide (133 g, 0.6 mol) in 500 ml ethyl ether the formamide (61 ml, 1.53 mol) was added at room temperature. After stirred 2 h, the solid was filtered off and washed with ethyl ether. The organic layer was combined and the solvent was removed under reduced pressure to give compound 1 as a yellow oil (50 g, 55%), the product was used without further purification.

4-(chloromethyl)thiazole 2[2]

A suspension of methanethioamide 1 (13 g, 0.21 mol) and 1,3-dichloroacetone(12.6 g, 0.1 mol) in 400 ml aceton was heated 75° C. for 5 h. When TLC showed no starting material remained, the solvent was concentrated under reduced pressure, and the residue was purified by chromatographic column (PE/EA, 25/1) to give 2 (10.76 g, 84%). $^{1}$H-NMR (CDCl$_3$, 300 MHz): δ 4.62 (s, 2H); 7.30 (s, 1H); 8.90 (s, 1H).

Thiazol-4-ylmethyl carbamimidothioate 3[2]

A solution of 4-(chloromethyl)thiazole 2 (5.11 g, 38.4 mmol) and thiourea (2.9 g, 38.4 mmol) in 50 ml ethanol was refluxed for 2-3 h. When TLC showed no starting material remained, the solvent was removed under reduced pressure to give the yellow oil. The crude product was crystallized from acetone to give compound 3 (6.16 g, 93%).

SR 3001

To a solution of thiazol-4-ylmethyl carbamimidothioate 3 (1.5 g, 7.2 mmol) and (Z)-3-chloro-N'-sulfamoyl propanimidamide (1.46 g, 7.9 mmol) in 30 ml combined solvent ($H_2O$/EtOH, 2/1, v/v), 8 ml NaOH (2M) was added dropwise below 0° C. The reaction mixture was stirred at this temperature for 2 hours until TLC showed no starting material remained. The solvent was removed under reduced pressure and the residue was purified by chromatographic column (DCM/MeOH, 25/1) to give SR 3001 (600 mg, 46.5%). $^{1}$H-NMR (CD$_3$OD, 300 MHz): δ 2.59 (m, 2H); 2.59 (m, 2H); 2.79 (m, 2H); 3.83 (s, 2H); 7.47 (d, 1H); 8.96 (s, 1H); $^{13}$C-NMR(CD$_3$OD, 75 MHz): 167.9, 155.7, 154.7, 117.4, 37.5, 31.4, 29.6.

M.W: 280.3; ESI-MS: 303 (M+Na).

REFERENCES 1. huaxue yanjiu yu yingyong. 2006, 18(2), 186;
2. a) hubei huagong, 2000, 5, 19-20, b) J. Heterocyclic Chem., 1986, 23, 577.

Example 47

Example Relates to SR2239 (OK-039)

Target Compound

Chemical formula 125

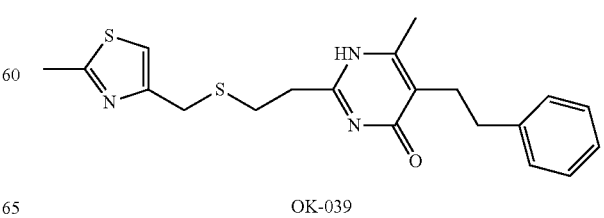

SR 2239

OK-039

Synthesis Route

Chemical formula 126

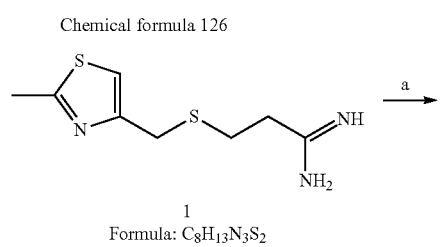

1
Formula: C_8H_13N_3S_2
M.W.: 215.34

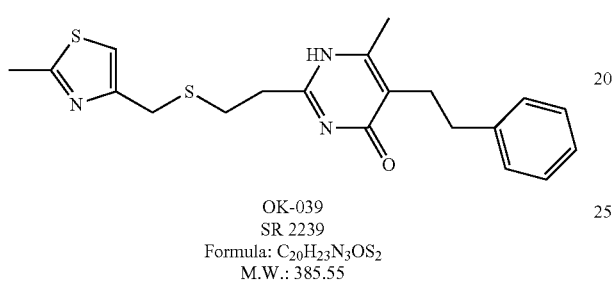

OK-039
SR 2239
Formula: C_20H_23N_3OS_2
M.W.: 385.55

Reagent and Condition
Reagents and Conditions:
a) NaOH, ethyl 3-oxo-2-(2-phenylethyl)butanoate (EOPEB);

Experiment Section

SR 2239 (OK-039)[1]

A solution of 3-((2-methylthiazol-4-yl)methylthio)propanimidamide 1[2] (0.5 g, 2.3 mmol) and ethyl 3-oxo-2-(2-phenylethyl)butanoate (EOPEB) (0.54 g, 2.3 mmol) in 15 ml methanol, NaOH (0.6 g, 15 mmol) was added into mixture and stirred for 3 h at 65° C. When TLC showed no starting material remained, the solvent was removed under reduced pressure and the residue was purified by chromatography (DCM/MeOH, 50/1) to give compound SR 2239 (OK-039) as a white solid (200 mg, 23%) as a white solid. $^1$H-NMR (CD_3OD, 300 MHz): δ1.99 (s, 2H); 2.64 (s, 2H); 2.74 (s, 3H); 2.85 (s, 3H); 3.80 (s, 2H); 7.12-7.22 (m, 6H); $^{13}$C-NMR (CD_3OD, 75 MHz): 168.7, 153.7, 142.7, 129.6, 129.3, 126.9, 116.8, 35.5, 35.0, 31.8, 29.9, 28.9, 18.7. M.W: 385.5; ESI-MS: 408 (M+Na).

REFERENCES 1. a) J. Org. Chem. 1989, 54, 1256-1264; b) J. Org. Chem. 1981, 46, 2455-2465;
2. Detailed synthesis methods as shown in the report of SR 2238 (OK-038)

Example 48

Example Relates to SR2238 (OK-038)

Chemical formula 127

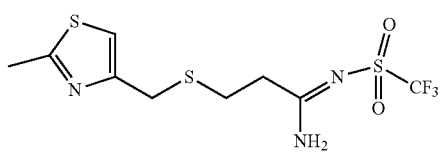

SR 2238

OK-038

Synthesis Route

Chemical formula 128

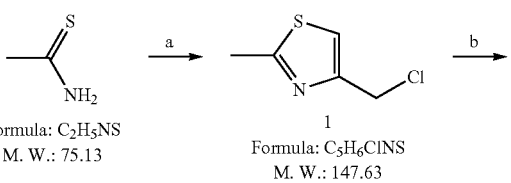

Formula: C_2H_5NS
M. W.: 75.13

1
Formula: C_5H_6ClNS
M. W.: 147.63

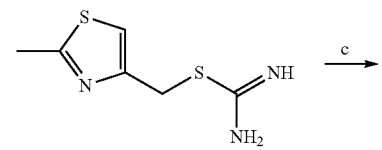

2
Formula: C_6H_9N_3S_2
M. W.: 187.29

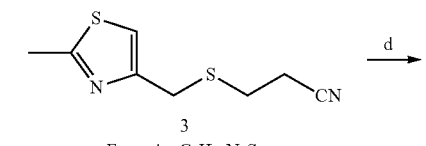

3
Formula: C_8H_10N_2S_2
M. W.: 198.31

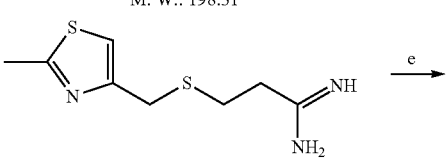

4
Formula: C_8H_13N_3S_2
M. W.: 215.34

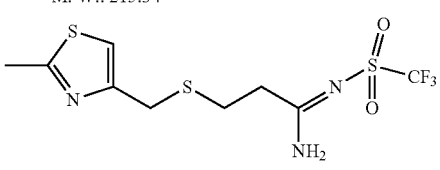

OK-038
Formula: C_9H_12F_3N_3O_2S_3
M. W.: 347.40

Reagent and Condition a) $CH_2ClCOCH_2Cl$, EtOH, reflux; b) thiourea, EtOH, 80° C., 3 h; c) $BrCH_2CH_2CN$/NaOH; d) dry HCl gas, MeOH/$CHCl_3$, 0° C.; $NH_3$/MeOH; d) trifluoromethanesulfonyl chloride, 0° C.;

Experiment Section 3-((2-methylthiazol-4-yl)methylthio)propanenitrile 3[1]

A mixture of (2-methylthiazol-4-yl) methyl carbamimidothioate 2[2] (2.6 g, 13.9 mmol) and 3-bromopropanenitrile (1.58 g, 13.9 mmol) was added in one portion. The mixture was cooled to 0° C., and NaOH (2M, 35 ml) was added dropwise to the solution, the reaction mixture was stirred at this temperature for 1 hour. When TLC showed no starting material remained, the mixture was extracted with EA (4×50 ml), the organic layer was dried and filtered. The solvent was concentrated to give the oiled product, and the impure product was crystallize from ethanol to give compound 3 (1.5 g, 54.5%). $^1$H-NMR (d$^6$-DMSO, 300 MHz): δ2.70 (m, 2H); 2.74 (m, 2H); 2.82 (s, 3H); 3.70 (s, 2H); 7.04 (s, 1H).

3-((2-methylthiazol-4-yl)methylthio)propanimidamide 4[3]; 3-((2-methylthiazol-4-yl) methyl thio) propanenitrile 3 (1.5 g, 7.6 mmol) was dissolved in 30 ml dry chloroform, and the 1 ml dry ethyl alcohol was added. The mixture was cooled to 0° C. and the dry hydrogen chloride gas was bubbled. After 3 hours, the mixture was concentrated and dissolved in 20 ml dry methanol. And then the mixture was cooled to 0° C. and the ammonia gas was bubbled to the mixture for 2 h. The solvent was removed under reduced pressure and the residue was purified by chromatography (DCM/Methanol, 25/1) to give compound 4 (850 mg, 52%).

SR 2238 (OK-038)[4]

A solution of 3-((2-methylthiazol-4-yl)methylthio)propanimidamide 4 (0.5 g, 2.3 mmol) and 0.47 g triethylamine in 50 ml chloroform was cooled to 0° C., and trifluoromethanesulfonyl chloride (0.39 g, 2.3 mmol) was added dropwise to the mixture. The reaction mixture was stirred for 5 h under the room temperature, when TLC showed no starting material remained, the solvent was removed under reduced pressure. The residue was purified by chromatography (DCM/Methanol, 50/1) to give compound SR 2238 (OK-038) (150 mg, 19%). $^1$H-NMR (CD$_3$OD, 300 MHz): δ2.74 (s, 3H); 2.77 (m, 2H); 2.92 (m, 2H); 3.81 (s, 2H); 6.97 (s, 1H); 8.26 (s, 1H); 9.00 (s, 1H). $^{13}$C-NMR (DMSO, 75 MHz): 173.3, 167.4, 152.3, 115.4, 43.5, 36.9, 31.5, 29.5, 18.9. M.W.: 347.4; ESI-MS: 348 (M+H).

REFERENCES 1. huaxue yanjiu yu yingyong, 2006, 18(2), 186-188.
2. Detailed synthesis methods as shown in the report of SR 2228 (OK-028)
3. a) hubei huagong, 2000, 5, 19-20; b) J. Heterocyclic Chem., 1986, 23, 577;
4. a) J. Org. Chem. 1989, 54, 1256-1264; b) J. Org. Chem. 1981, 46, 2455-2465;

Example 49

Example Relates to SR2228 (OK-028)

Target Compound

Chemical formula 129

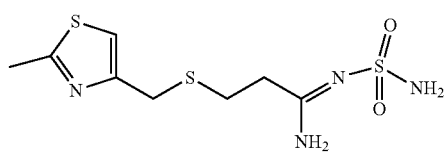

OK-028

Synthesis Route

Chemical formula 130

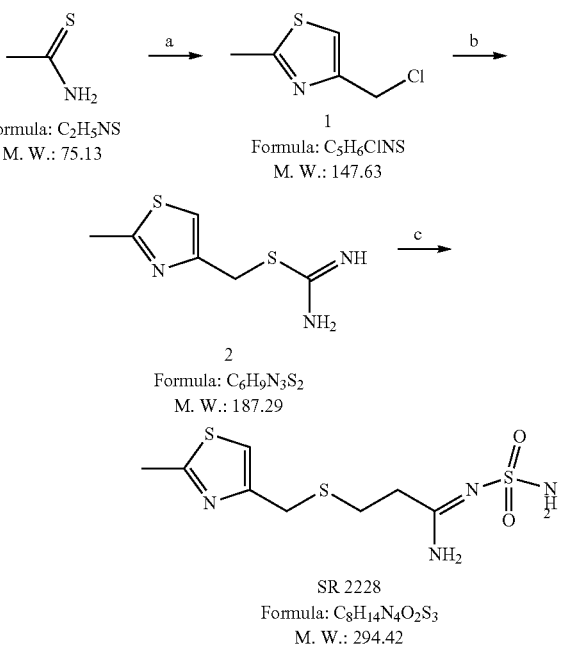

Reagent and Condition a) $CH_2ClCOCH_2Cl$, EtOH, reflux; b) thiourea, EtOH, 80° C., 3 h; c) (Z)-3-chloro-N'-sulfamoylpropanimidamide NaOH;

Experiment Section 4-(chloromethyl)-2-methylthiazole 1[1]

A solution of ethanethioamide (15 g, 0.2 mol) and 1,3-dichloropropan-2-one (25.4 g, 0.2 mol) in 150 ml EtOH was refluxed for 10 hs, when TLC showed no starting material remained, the solvent was removed under reduced pressure and the residue was crystallized from acetone to give compound 1 (14.7 g, 50%). $^1$H-NMR (d$^6$-DMSO, 300 MHz): δ 2.85 (s, 1H); 4.70 (s, 2H); 7.04 (s, 1H).

(2-methylthiazol-4-yl)methyl carbamimidothioate 2: A mixture of 4-(chloromethyl)-2-methyl thiazole 1 (2.94 g, 20 mmol) and thiourea (1.52 g, 20 mmol) was dissolved in 20 ml ethanol (95%). The reaction mixture was refluxed for 3 hours. When TLC showed no starting material remained, the solvent was concentrated under reduced pressure to give some solid. The solid was washed with ethanol to give compound 2 as a white solid (1.58 g, 91%).

SR 2228 (OK-028)[2]

A solution of (2-methylthiazol-4-yl)methyl carbamimidothioate 2 (3.36 g, 18 mmol) and (Z)-3-chloro-N'-sulfamoyl propanimidamide (3.47 g, 20 mmol) in 50 ml combined solvent (H$_2$O/EtOH, 2/1, v/v), the mixture was cooled to 0° C., and 40 ml NaOH (2M) was added dropwise to the solution. The reaction mixture was stirred at this temperature for 2 hours. When TLC showed no starting material remained, the solvent was removed under reduced pressure to give the crude product. The residue was purified by chromatographic column (DCM/MeOH, 25/1) to give SR 2228 (OK-028) (2.1 g, 40%). $^1$H-NMR (d$^6$-DMSO, 300 MHz): δ 2.50 (m, 2H); 2.55 (s, 3H); 2.67 (m, 2H); 3.80 (s, 2H); 6.52 (s, 2H); 7.30 (s, 1H); 8.26 (s, 1H). $^{13}$C-NMR (d$^6$-DMSO, 75 MHz): 165.5, 164.9, 152.6, 115.6, 36.1, 30.5, 27.9, 18.9. M.W: 294.4; ESI-MS: 295 (M+H).

REFERENCES 1. huaxue yanjiu yu yingyong. 2006, 18(2), 186;
2. a) hubei huagong, 2000, 5, 19-20, b) J. Heterocyclic Chem., 1986, 23, 577.

Example 50

Example Relates to SR3012

Target Compound:

Chemical formula 131

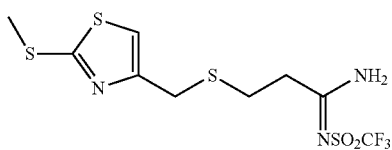

SR 3012

Synthesis Route

Chemical formula 132

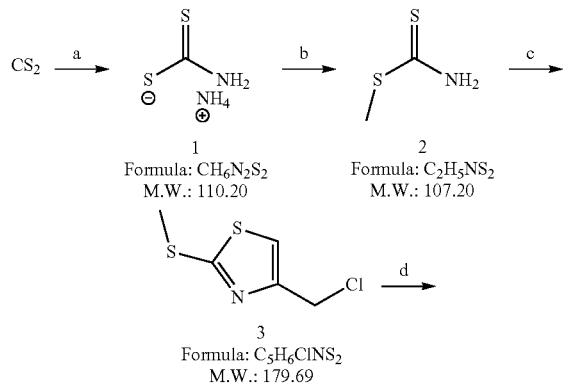

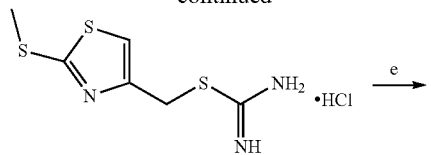

4
Formula: C$_6$H$_{10}$ClN$_3$S$_3$
M.W.: 255.81

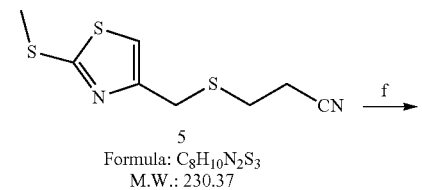

5
Formula: C$_8$H$_{10}$N$_2$S$_3$
M.W.: 230.37

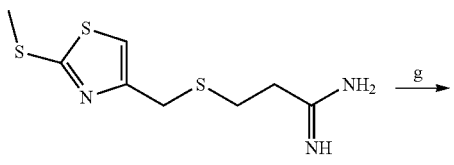

6
Formula: C$_8$H$_{13}$N$_3$S$_3$
M.W.: 247.40

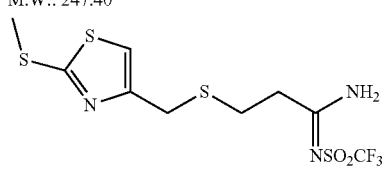

SR 3012
Formula: C$_9$H$_{12}$F$_3$N$_3$O$_2$S$_4$
M.W.: 379.47

Reagent and Condition
a) NH$_3$, THF, 1.5 h; b) (CH$_3$)$_2$SO$_4$, H$_2$O; c) CH$_2$ClCOCH$_2$Cl, ethanol, 3 h; d) thiourea, ethanol, 80° C., 5 h; e) BrCH$_2$CH$_2$CN/NaOH; f) dry HCl gas, EtOH/CHCl$_3$, 0° C.; NH$_3$/MeOH; g) trifluoromethanesulfonyl chloride, chloroform, 0° C., 5 h.

Experiment Section

Ammonium Carbamodithioate 2[1]

Ammonia gas was pumped into the solution CS$_2$ (8 ml, 0.13 mol) in 70 ml dry THF, and the temperature rised to 40~50° C. in this period. After 1.5 h, the temperature was cooled to room temperature. Then the solvent was removed under reduced pressure and the residue was dissolved in 50 ml water. To this solution dimethyl sulfate (11 ml, 116 mmol) was added dropwise at room temperature. After stirred for 40 min, 10 ml ammonium hydroxide was added into the mixture. The reaction mixture was stirred for another 15 min, then the mixture was extracted with DCM (3×20 ml). The organic phase was dried with MgSO$_4$ and concentrated to give product 2 (10 g, 71%), the product was used without further purification.

4-(chloromethyl)-2-(methylthio)thiazole 3[2]

A solution of ammonium carbamodithioate 2 (5 g, 50 mmol), 1,3-dichloropropan-2-one (6 g, 50 mmol), MgSO4 (5.6 g, 50 mmol) in 120 ml ethanol was refluxed for 3 h. When TLC showed no starting material remained, the mixture was cooled and filtered. The filtrate was concentrated under reduced pressure, then the residue was purified by chromatographic column (PE/EA, 25/1) to give compound 3 (4.5 g, 54%). 1H-NMR (d6-DMSO, 300 MHz): δ2.70 (s, 3H); 4.77 (s, 2H); 7.65 (s, 1H). M.W: 179.6; ESI-MS: 180 (M+H)

(2-(methylthio)thiazol-4-yl)methyl carbamimidothioate hydrochloride 4[3]

A mixture of 4-(chloromethyl)-2-(methylthio)thiazole 3 (2.0 g, 12 mmol) and thiourea (0.9 g, 12 mmol) was dissolved in 60 ml ethanol. The reaction mixture was refluxed for 5 h until TLC showed no starting material remained. The mixture was cooled and filtered, and the solid was collected and wash with ethanol (3×20 ml) to give product 4 (2 g, 66%)

3-((2-(methylthio)thiazol-4-yl)methylthio)propanenitrile 5[3]

To a solution of (2-(methylthio)thiazol-4-yl)methyl carbamimidothioate hydrochloride 4 (1.2 g, 5 mmol) and 3-bromopropanenitrile (1.22 g, 5 mmol) in 30 ml combined solvent ($H_2O$/EtOH, 2/1, v/v), 20 ml NaOH (2M) was added dropwise below 0° C. The reaction mixture was stirred at this temperature for 2 hours. When TLC showed no starting material remained, the solvent was removed under reduced pressure and the residue was purified by chromatographic column (DCM/MeOH, 25/1) to give compound 4 (1.0 g, 83%). $^1$H-NMR (CDCl$_3$, 300 MHz): δ 2.73 (s, 3H); 2.80 (m, 4H); 7.25 (s, 1H). M.W: 230.3; ESI-MS: 231 (M+H).

3-((2-(methylthio)thiazol-4-yl)methylthio)propanimidamide 6[4]

To a solution of 3-((2-(methylthio)thiazol-4-yl) methylthio)propanenitrile 5 (1 g, 4.4 mmo) in 20 ml dry chloroform and 0.3 ml dry ethyl alcohol, the dry hydrogen chloride gas was imported below 0° C. After 3 hours, the mixture was concentrated and dissolved in 20 ml dry methanol. And then the mixture was cooled to 0° C. and the ammonia gas was imported to the mixture for 1 h. When TLC showed no starting material remained the solvent was removed under reduced pressure to give compound 5 (1.2 g, 100%). It was used without further purification.

SR 3012[5]; To a solution of 3-((2-(methylthio)thiazol-4-yl)methylthio)propanimidamide 6 (1.2 g, 5 mmol) and 0.5 ml triethylamine in 30 ml CHCl$_3$, (0.8 g, 5 mmol) trifluoromethanesulfonyl chloride was added dropwise below 0° C. The reaction mixture was stirred for 1 h under the room temperature until TLC showed no starting material remained. Then the solvent was removed under reduced pressure and the residue was purified by chromatography (DCM/Methanol, 50/1) to give compound SR 3012 (500 mg, 26%). $^1$H-NMR (d$^6$-DMSO, 300 MHz): δ 2.73 (m, 2H); 2.76 (m, 2H); 3.16 (s, 3H); 3.81 (s, 2H); 7.35 (s, 1H); 9.00 (s, 1H); 9.60 (s, 1H). $^{13}$C-NMR (d$^6$-DMSO, 75 MHz): 172.4, 165.4, 153.2, 121.6, 117.4, 115.6, 48.6, 35.6, 30.1, 27.9, 16.1 M.W: 379.4; ESI-MS: 402 (M+Na).

REFERENCES

1. Synthesis Communications, 1985, 948;
2. huaxue yanjiu yu yingyong, 2006, 18(2), 186;
3. a) hubei huagong, 2000, 5, 19; b) J. Heterocyclic Chem., 1986, 23, 577; c) J. Org. Chem. 1989, 54, 1256-1264
4. J. Org. Chem. 1981, 46, 2455;
5. U.S. Pat. No. 4,362,736A

Example 51

Example Relates to SR2227(OK-027)

Target Compound

Chemical formula 133

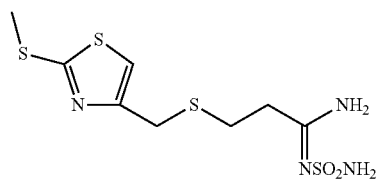

OK-027

Synthesis Route

Chemical formula 134

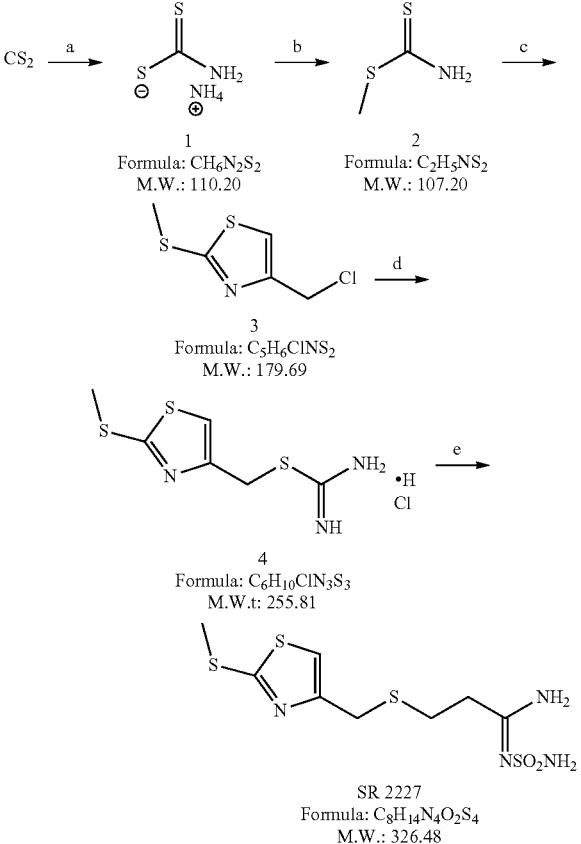

Reagent and Condition a) NH$_3$, THF, 1.5 h; b) (CH$_3$)$_2$SO$_4$, H$_2$O; c) CH$_2$ClCOCH$_2$Cl, ethanol, 3 h; d)thiourea, ethanol, 80° C., 5 h; e) (Z)-3-chloro-N'-sulfamoylpropanimidamide, NaOH.

Experiment Section (2-(methylthio)thiazol-4-yl)methyl carbamimidothioate hydrochloride 4[1]: 4-(chloromethyl)-2-(methylthio)thiazole 3[2] (2.0 g, 11 mmol) and thiourea (0.9 g, 12 mmol) were dissolved in 60 ml ethanol, then the mixture was refluxed for 5 h. When TLC showed no starting material remained, the mixture was cooled and filtered, the solid was collected and wash with ethanol (3×20 ml) to give product 4 (2 g, 71%).

SR 2227 (OK-027)[3]

A solution of compound 4 (2.0 g, 7.8 mmol) and (Z)-3-chloro-N'-sulfamoyl propanimidamide (1.6 g, 9.1 mmol) in 30 ml combined solvent ($H_2O$/EtOH, 2/1, v/v) was cooled to 0° C., then 20 ml NaOH (2M) was added dropwise to the Chemical formula 136

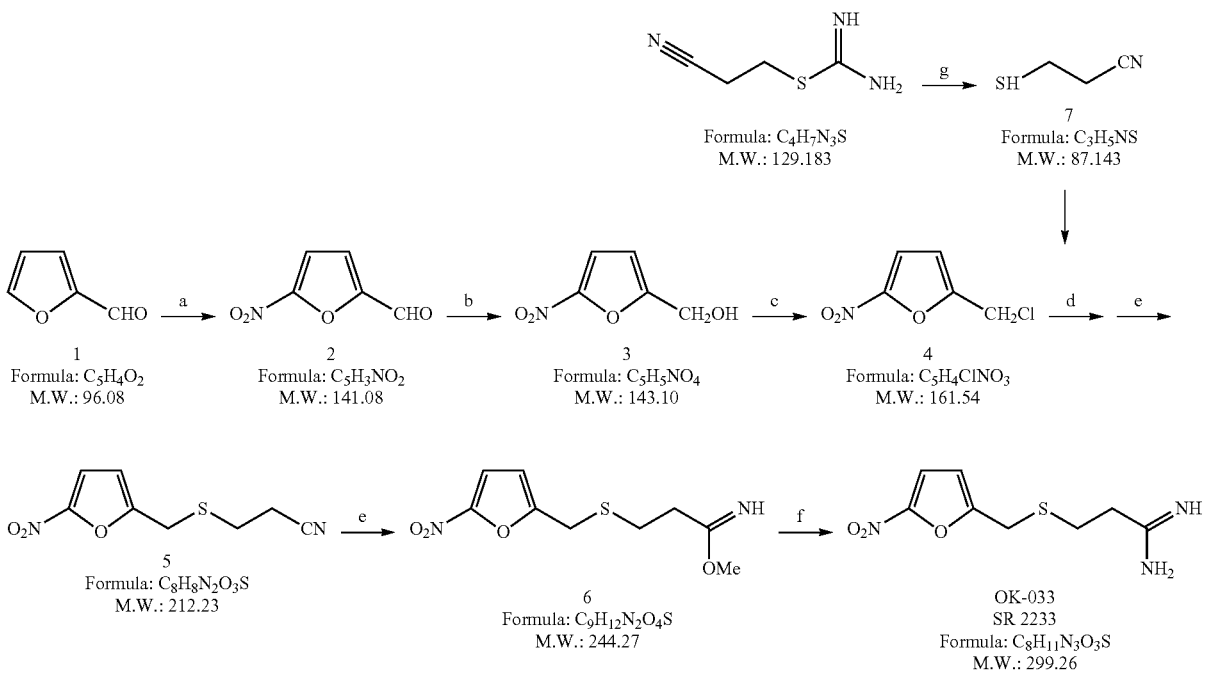

solution. The reaction mixture was stirred at this temperature for 2 hours. When TLC showed no starting material remained, the solvent was removed under reduced pressure to give the crude product. The residue was purified by chromatographic column (DCM/MeOH, 25/1) to give SR 2227 (OK-027) (0.95 g, 38%). $^1$H-NMR (d$^6$-DMSO, 300 MHz): δ 2.65 (m, 2H); 3.42 (s, 3H); 3.59 (s, 2H); 3.78 (s, 2H); 6.23 (s, 1H); 6.51 (s, 1H); 7.33 (s, 1H); 7.38 (s, 1H); 8.26 (s, 1H). $^{13}$C-NMR (d$^6$-DMSO, 75 MHz): 166.1, 165.0, 153.5, 115.6, 36.2, 30.5, 28.0, 16.3; M.W.: 326.4; ESI-MS: 327 (M+H).

REFERENCES 1. huaxue yanjiu yu yingyong. 2006, 18(2), 186;
2. Detailed synthesis method was shown in report SR 3012
3. a) hubei huagong, 2000, 5, 19-20, b) J. Heterocyclic Chem., 1986, 23, 577.

Example 52

Example Relates to SR2233(OK-033)

Target Compound

Chemical formual 135

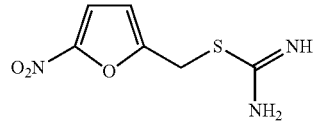

OK-033

Synthesis Route

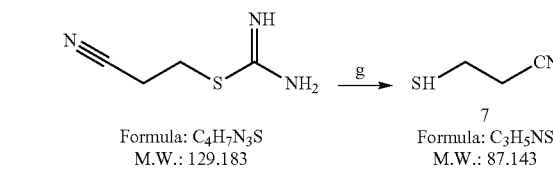

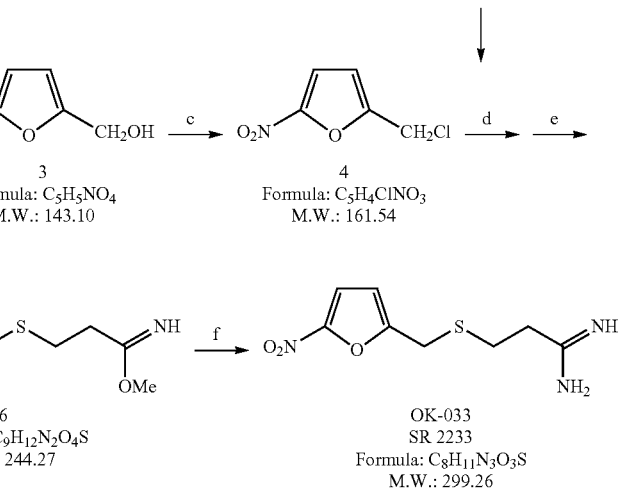

Reagent and Condition
a) $Ac_2O$, $HNO_3$, 2 h, −30° C.; b) $NaBH_4$, THF/$H_2O$, rt, 30 min;
c) $SOCl_2$, rt; d) $Et_3N$; d) e) MeOH, DCM, dry HCl gas, rt;
f) MeOH, $NH_4Cl$, rt, 12 h; g) NaOH, 45° C.

Experiment Section 5-nitrofuran-2-carbaldehyde (2)[1][2]

13 mL of nitric acid (68%) was added slowly to 83 ml of acetic anhydride between 15-25° C. with rapid stirring. After the addition was complete, the nitration reagent was added slowly to the solution of furan-2-carbaldehyde (1) (9.6 g, 0.1 mol) in acetic anhydride (100 ml) cooled to −30° C. in advance. When TLC showed no starting material remained, the mixture was poured on ice water and extracted with ethyl acetate. The organic layer was dried and purified by chromatography (PE/DCM, 3/1) to give compound 2 (3.1 g, 22%).

(5-nitrofuran-2-yl)methanol (3)

A solution of compound 2 (4.24 g, 0.03 mol) in 30 ml THF was stirred at room temperature. Then NaBH$_4$ (0.3 g, 0.06 mol) was added in several times. When TLC showed no starting material remained, the mixture was poured into 30 ml water and extracted with DCM. The organic layer was dried and removed in vacuo to give compound 3 (3.5 g, 81.5%).

2-(chloromethyl)-5-nitrofuran (4)

A solution of compound 3 (3.5 g, 25 mmol) in 5 mL SOCl$_2$ was stirred at room temperature. When TLC showed no starting material remained, ice was added to the solution. Extracted with DCM, then the organic layer was dried and removed in vacuo. The residue was purified by chromatography (PE/DCM, 10/1) to give compound 4 (2.8 g, 71%). $^1$H-NMR (CDCl$_3$, 300 MHz): δ 4.598 (s, 2H); 6.628 (d, 1H); 7.280 (d, 1H).

3-mercaptopropanenitrile (7)

NaOH solution (11.3 M, 1.71 g/5.6 mL H$_2$O) was slowly injected to the solution of 2-Cyanoethyl carbamimidothioate (4 g, 0.031 mol) in 40 mL H$_2$O under nitrogen atmosphere, keeping the internal temperature below 25° C. The reaction mixture was heated at 45° C. for 45 min, then cooled to 20° C. After that, 6 M H$_2$SO$_4$ solution was slowly added under nitrogen until the pH was to 6. The mixture was extracted with dichloromethane under nitrogen by means of injector.

3-((5-nitrofuran-2-yl)methylthio)propanenitrile (5)[3]

Compound 7 was injected into the solution of compound 4 (1.6 g, 10 mmol) at 0° C. under nitrogen atmosphere, then 1.1 g of Et$_3$N was added. The reaction mixture was stirred for 1 h at 0° C. and another 1 h at room temperature. When TLC showed no starting material remained the solvent was removed under reduced pressure and the residue was purified by chromatography (PE/EA, 120/1) to give compound 5 (68 g, 32%). $^1$H-NMR (CDCl$_3$, 300 MHz): δ 2.681 (t, 2H); 2.900 (t, 1H); 3.881 (s, 2H); 6.527 (d, 1H); 7.278 (d, 1H).

Methyl 3-((5-nitrofuran-2-yl)methylthio)propanimidate (6)

A solution of compound 5 (0.58 g, 2.7 mmol) in anhydrous methanol/dichloromethane (1 ml/5 ml) was cooled to 0~10° C., then dry HClgas was bubbled for 6 h under this temperature. Free imidates were obtained by adding the reaction mixture into ice-cooled water containing excess potassium carbonate (0.6 g) and the solution was extractive with (DCM:MeOH=3:1). The organic layer was dried by MgSO$_4$, then the solution was removed in vacuo to give compound 6 (0.59 g, 88%).

SR 2233 (OK-033)

A mixture of compound 6 (0.59 g, 0.0024 mol) and NH$_4$Cl (0.56 g, 3.6 mmol) in 5 ml dry methanol was stirred at room temperature under nitrogen atmosphere for 12 h. When TLC showed no starting material remained, the solvent was removed under reduced pressure and the residue was purified by chromatography (DCM/Methanol, 20/1) to give compound SR2233 (OK-033). $^1$H-NMR (CDCl$_3$, 300 MHz): δ 2.799 (t, 2H); 2.856 (t, 2H); 4.083 (s, 2H); 6.912 (d, 1H); 7.669 (d, 1H); 8.903 (s, 2H); 9.384 (s, 2H). M.W.: 229; ESI-MS: 230 (M+H).

REFERENCES

1. JACS, 82, 3588-3598, 1960.
2. JACS, 11, 282-285, 1968.
3. Organic Syntheses, Coll. Vol. 10, p. 234(2004); Vol. 77, p. 186 (2000).

Example 53

Example Relates to SR2234(OK-034)

Target Compound

Chemical formual 137

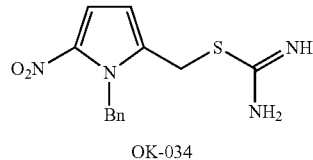

OK-034

Synthesis Route

Chemical formula 138

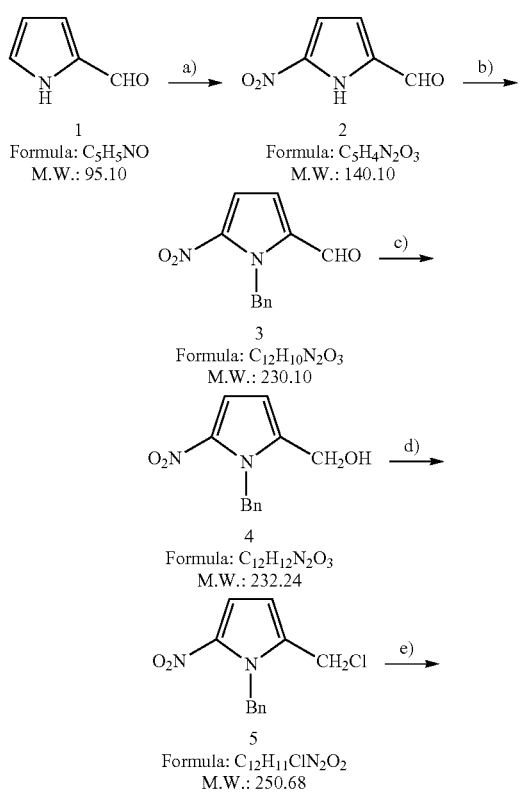

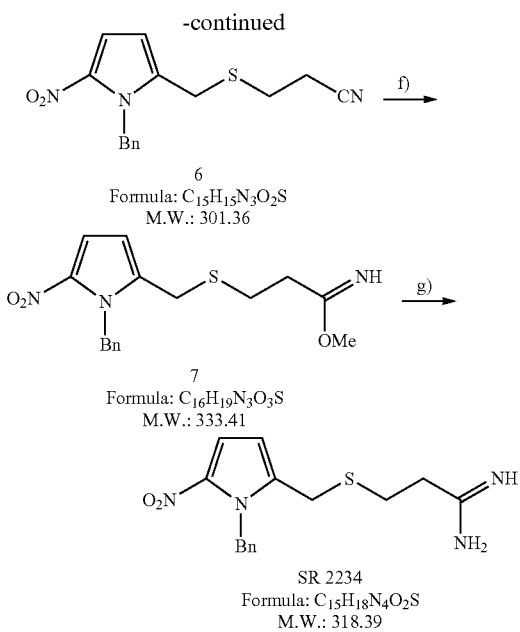

6
Formula: C₁₅H₁₅N₃O₂S
M.W.: 301.36

7
Formula: C₁₆H₁₉N₃O₃S
M.W.: 333.41

SR 2234
Formula: C₁₅H₁₈N₄O₂S
M.W.: 318.39

Reagent and Condition
a) Ac₂O, HNO₃, 2 h, −30° C.; b) i: Na, EtOH, THF, rt, 20 min, ii: Benzyl chloride, DMF, 90° C., 36 h; c) NaBH₄, THF/H₂O, rt, 30 min; d) SOCl₂, rt; e) i: 2-Cyanoethyl carbamimidothioate, NaOH, 45° C., ii: Et₃N; f) MeOH, DCM, dry HCl gas, −10° C.; g) MeOH, NH₄Cl, rt, 12 h Experiment Section 5-nitro-1H-pyrrole-2-carbaldehyde (2)[1][2]

19 mL of nitric acid (68%) was added slowly to 126 ml of acetic anhydride between 15-25° C. with rapid stirring. After the addition was complete, the nitration reagent was added slowly to the solution of 1H-pyrrole-2-carbaldehyde (1) (15 g, 0.158 mol) in acetic anhydride (150 ml) cooled to −30° C. in advance. When TLC showed no starting material remained, the mixture was poured on ice water and extracted with ethyl acetate. The organic layer was dried and removed in vacuo. The residue was purified by chromatography (PE/DCM, 3/1) to give compound 2 (4.6 g, 21%). ¹H-NMR (CDCl₃, 200 MHz): δ 6.98 (d, 1H); 7.14 (d, 1H); 9.78 (s, 1H).

1-benzyl-5-nitro-1H-pyrrole-2-carbaldehyde(3)[2]

The sodium salt of 5-nitro-1H-pyrrole-2-carbaldehyde was prepared from 49 mmol of NaOEt (from 1.13 g of Na and 50 mL of EtOH) and 4.6 g (33 mmol) of 5-nitro-1H-pyrrole-2-carbaldehyde (2) in 83.5 ml of dry THF. The reaction was allowed to proseed for 20 min at room temperature, and the dry sodim salt was isolated by removing the solvent at 65° C. in vacuo. The salt in 80 mL of DMF was treated rapidly with 8.3 g (66 mmol) of benzyl chloride in 41 ml of DMF. The mixture was heated under N₂ for 21 h at 90° C. The DMF was removed under reduced pressure and the residue was purified by chromatography (PE/EA, 100/1) to give compound 3 (4.5 g, 60%). ¹H-NMR (CDCl₃, 300 MHz): δ6.16 (s, 2H); 6.99 (d, 2H); 7.18 (d, 2H); 7.19 (d, 1H); 7.27 (m, 1H); 7.33 (d, 1H); 9.83 (s, 1H).

(1-benzyl-5-nitro-1H-pyrrol-2-yl)methanol (4): NaBH₄ (0.69 g, 0.018 mol) was added to the solution of compound 3 (3.44 g, 0.015 mol) in THF/H₂O (40 mL/20 mL) at room temperature. When TLC showed no starting material remained, the mixture was poured into 20 ml water and extracted with ethyl acetate. The organic layer was dried and removed in vacuo give crude compound 4 (3.48 g). It was used in next step without further purification. M.W.: 232; ESI-MS: 233.1 (M+H), 255.1 (M+Na).

1-benzyl-2-(chloromethyl)-5-nitro-1H-pyrrol(5): A solution of compound 4 (3.48 g, 0.015 mol) in 15 ml of SOCl₂ was stirred at room temperature. When TLC showed no starting material remained, the mixture was poured on ice water and extracted with ethyl acetate. The solvent was removed under reduced pressure and the residue was purified by chromatography (PE/EA, 120/1) to give compound 5 (2.04 g, yield of two steps 55%). ¹H-NMR (CDCl₃, 200 MHz): δ 4.50 (s, 2H); 5.77 (s, 2H); 6.98 (d, 1H); 6.99 (d, 1H); 7.25-7.35 (m, 5H).

3-((1-benzyl-5-nitro-1H-pyrrol-2-yl)methylthio)propanenitrile(6)[3]

3-mercaptopropanenitrile[4] was injected into the solution of compound 5 (2.34 g, 9 mmol) at 0° C. under nitrogen atmosphere, then 1.04 g of Et₃N was added. The reaction mixture was stirred for 1 h at 0° C. then overnight at room temperature. The solvent was removed under reduced pressure and the residue was purified by chromatography (PE/EA, 120/1) to give compound 6 (2.58 g, 92%). ¹H-NMR (d⁶-DMSO, 300 MHz): δ2.70 (t, 4H); 3.74 (s, 2H); 5.78 (s, 2H); 6.27 (d, 1H); 6.95 (d, 1H); 7.26-7.33 (m, 5H).

Methyl 3-((1-benzyl-5-nitro-1H-pyrrol-2-yl) methylthio)propanimidate(7)

A solution of compound 6 (1.66 g, 0.0055 mol) in anhydrous methanol/dichloromethane (1 ml/18 ml) was cooled to 0~10° C., then dry HCl gas was bubbled for 6 h under this temperature. Then the solvent were removed under reduced pressure and the mixture was added into ice-cooled K₂CO₃ aq., extracted with dichloromethane. The organic layer was dried over MgSO₄, and evaporated to dryness in vacuo to give compound 7 (1.84 g). It was used in next step without further purification

SR 2234 (OK-034)

A mixture of compound 7 (1.84 g, 5.5 mmol) and NH₄Cl (0.885 g, 16.5 mmol) in 30 ml dry methanol was stirred at room temperature for 12 h under nitrogen atmosphere. When TLC showed no starting material remained, the solvent was removed under reduced pressure and the residue was purified by chromatography (DCM/MeOH, 50/1) to give compound SR 2234 (OK-034) (0.948 g, two steps 54%). ¹H-NMR (d⁶-DMSO, 300 MHz): δ2.75 (t, 4H); 3.98 (s, 2H); 5.67 (s, 2H); 6.52 (d, 1H); 6.92 (d, 1H); 6.95-7.36 (m, 5H), 8.77 (s, 1H), 9.19 (s, 2H). M.W.: 318; ESI-MS: 319.1 (M+H)

REFERENCES

1. JACS, 82, 3588-3598, 1960.
2. JACS, 11, 282-285, 1968.
3. Organic Syntheses, Coll. Vol. 10, p. 234(2004); Vol. 77, p. 186(2000).
4. Detailed synthesis method was shown in report SR 2233 (OK-033)

Example 54

Example Relates to SR2235(OK-035)

Target Compound

Chemical formula 139

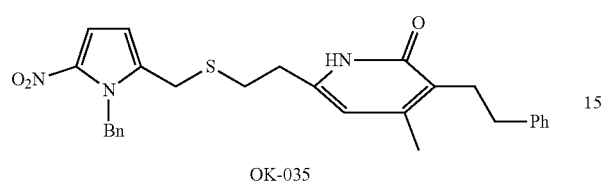

OK-035

Synthesis Route

Chemical formula 140

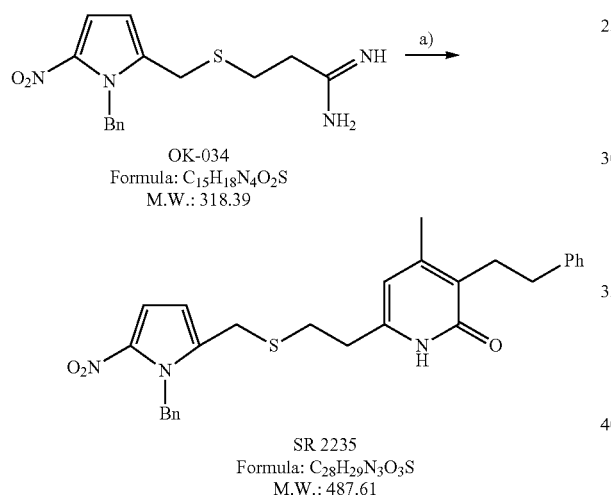

Reagent and Condition
a) Ethyl 3-oxo-2-(2-phenylethyl)butanoate (EOPEB), Na, MeOH

Experiment Section

SR 2235 (OK-035)

A solution of SR 2234 (OK-034)[1] (0.5 g, 1.6 mmol) and ethyl 3-oxo-2-(2-phenylethyl)butanoate (EOPEB) (0.368 g, 1.6 mmol) in 6.2 mL of NaOMe/MeOH (from 0.036 g of Na and 6.2 mL of MeOH) was stirred at room temperature overnight under nitrogen atmosphere. When TLC showed no starting material remained, the solvent was removed under reduced pressure and the residue was purified by chromatography (PE/DCM, 3/1) to give compound SR 2235 (OK-035) (128 mg, 17%). $^1$H-NMR (CDCl$_3$, 300 MHz): δ2.16 (s, 3H); 2.77 (t, 2H); 2.84 (t, 2H); 2.94 (t, 2H); 3.48 (t, 2H); 3.70 (s, 2H); 6.26 (d, 1H); 6.88 (d, 1H); 7.15-7.26 (m, 10H). M.W.: 487.6; ESI-MS: 489.2 (M+H).

REFERENCES

1. Detailed synthesis methods as shown in the report of SR 2023.

Example 55

Example Relates to SR2240(OK-040)

Chemical formula 141

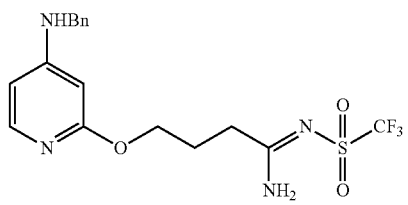

OK-040

Synthesis Route

Chemical formula 142

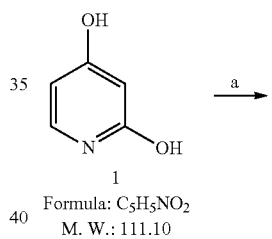

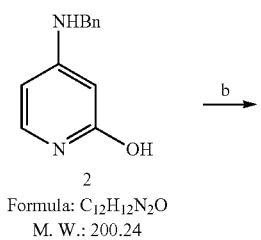

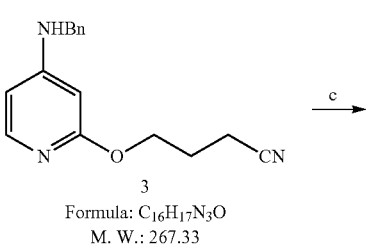

-continued

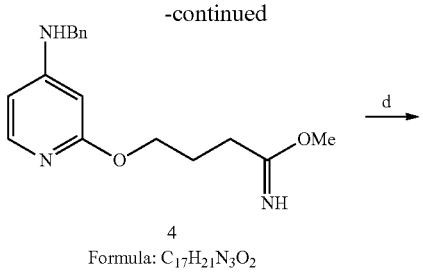

4
Formula: C$_{17}$H$_{21}$N$_3$O$_2$
M. W.: 299.37

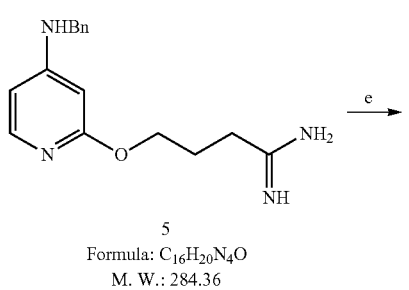

5
Formula: C$_{16}$H$_{20}$N$_4$O
M. W.: 284.36

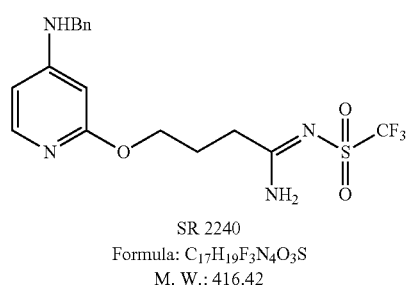

SR 2240
Formula: C$_{17}$H$_{19}$F$_3$N$_4$O$_3$S
M. W.: 416.42

Reagent and Condition
a) benzylamine, 170° C., 3 h; b) 4-Chlorobutyronitrile, AgCO$_3$, DMF, reflux, 3 h; c) dry HCl gas, MeOH/DCM, 0~5° C.; d)NH$_4$Cl, MeOH, rt; e) DCM/acetonitrile, Trifluoromethanesulfonyl chloride, Et3N, 0~5° C.

Experiment Section 4-(benzylamino)pyridin-2-ol (2)[1]

A solution of compound 1 (50 g, 0.45 mol) in benzylamine (460 ml, 4.05 mol) was reflux at 170° C. for 3 h, then the solvent was removed under reduced pressure and the residue was washed with water to give the compound 2 (45 g, 50%). $^1$H-NMR (d$^6$-DMSO, 300 MHz): δ 4.21 (s, 2H); 5.03 (s, 1H); 5.74 (d, 1H); 6.98 (d, 1H); 7.10 (s, 1H); 7.25-7.35 (m, 5H). M.W.: 200; ESI-MS: 201 (M+H).

4-(4-(benzylamino)pyridin-2-yloxy)butanenitrile (3)[2]

A solution of compound 2 (1 g, 5 mmol), 4-Chlorobutyronitrile (1.03 g, 10 mmol) and AgCO$_3$ (2.7 g, 10 mol) in DMF was stirred at 150° C. for 3 h, then the solvent was removed under reduced pressure and the residue was crystallized from PE/EA=1/1 to give the compound 3 (0.4 g, 30%). $^1$H-NMR (CDCl$_3$, 300 MHz): δ 2.09 (m, 2H); 2.51 (t, 2H); 4.33 (m, 4H); 4.50 (br, 1H); 5.86 (d, 1H); 6.17 (m, 1H); 7.29-7.36 (m, 5H); 7.76 (d, 1H). M.W.: 267; ESI-MS: 268 (M+H).

methyl 4-(4-(benzylamino)pyridin-2-yloxy)butanimidate(4)[3]

A solution of compound 3 (0.5 g, 1.87 mmol) in anhydrous methanol/DCM (1 ml/20 ml) was cooled to 0~10° C., then dry HClgas was bubbled for 3 h under this temperature. After that, the mixture was allowed to stand at 0~4° C. for 20 h and then concentrated under reduced pressure to afford imidate hydrochlorides as a crystalline solid. Free imidates 4 were obtained by adding the reaction mixture into ice-cooled water containing excess potassium carbonate and the mixture was filtered and the residue washed with EtOH to give compound 4 (0.56 g, 100%). $^1$H-NMR (d$^6$-DMSO, 300 MHz): δ 2.05 (m, 2H); 4.20 (t, 2H); 4.40 (s, 2H); 5.76 (s, 1H); 6.45 (d, 1H); 7.25-7.41 (m, 5H); 7.29-7.36 (m, 5H); 7.59 (br, 1H); 7.69 (d, H); 8.82-9.18 (br, 3H).

M.W.: 299; ESI-MS: 300 (M+H).

4-(4-(benzylamino)pyridin-2-yloxy)butanimidamide (5)[3]

A solution of compound 4 (0.56 g, 1.87 mmol) and NH$_4$Cl (0.15 g, 2.85 mmol) in 10 ml MeOH was stirred at room temperature for 1 h, the solvent was removed under reduced pressure and the residue was purified by chromatography (DCM/Methanol, 50/1) to give compound 5 (0.2 g, 40%).

SR 2240 (OK-040)[4]

A solution of compound 5 (2 g, 7 mmol) and trifluoromethanesulfonylchloride (3.54 g, 21 mmol) in DCM/acetonitrile (200 ml/100 ml) was cooled to 0~5° C., then Et$_3$N (7.5 ml, 52 mmol) was added dropwise. After stirring 1 h at 0° C. and another 12 h at room temperature the solvent was removed under reduced pressure and the residue was purified by chromatography (DCM/Methanol, 30/1) to give compound SR 2240 (OK-040) (0.58 g, 20%). $^1$H-NMR (d$^6$-DMSO, 300 MHz): δ2.05 (m, 2H); 4.17 (m, 2H); 4.37 (m, 2H); 5.95 (s, 1H); 6.40 (d, 1H); 7.26-7.35 (m, 5H); 7.66 (d, 1H); 8.89-9.24 (d, 2H). M.W.: 416; ESI-MS: 417 (M+H).

REFERENCES

1 Synthesis; English; 9; 1984; 765-766
2 Synthesis, (16), 2725-2728; 2009
3 Journal of Medicinal Chemistry; English; 30; 10; 1987; 1787-1793
4 U.S. Pat. No. 4,362,736

Example 56

Physical property of the obtained compound was assessed in a manner similar to Example 12. The results are shown in the following tables.

TABLE 3-1

| # | ID | Structure | MW (Integer Mass) | Histamine Incorporation Rate to Control (%) | OCT3 Inhibition Rate (%) | Property |
|---|---|---|---|---|---|---|
| 2 | SR-2051 | 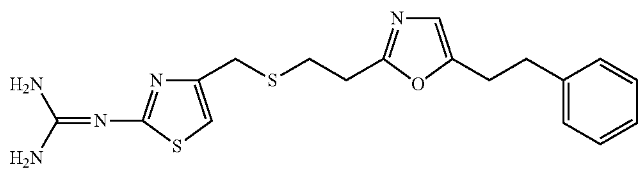 [SMILES: NC(N)=Nc1nc(CSCCc2ncc(CCc3ccccc3)o2)cs1] | 387 | 61.2 | 38.8 | Colorless oil |
| 3 | SR-3137 | 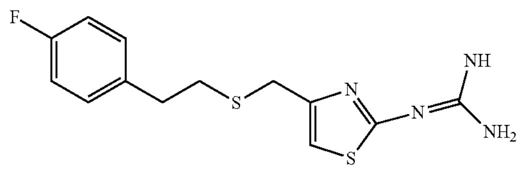 [SMILES: NC(N)=Nc1nc(CSCCc2ccc(F)cc2)cs1] | 310 | 66.7 | 33.3 | Yellow, powder |
| 4 | SR-2216 | 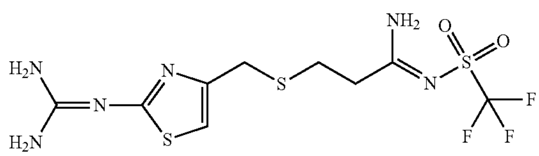 [SMILES: NC(N)=Nc1nc(CSCC/C(N)=N/S(=O)(=O)C(F)(F)F)cs1] | 390 | 38.5 | 61.5 | White, powder |

TABLE 3-2

| # | ID | Structure | MW (Integer Mass) | Histamine Incorporation Rate to Control (%) | OCT3 Inhibition Rate (%) | Property |
|---|---|---|---|---|---|---|
| 5 | SR-3203 | 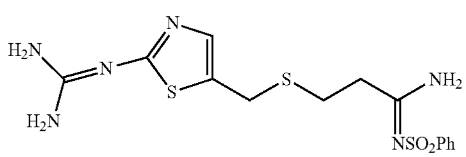 | 398 | 77.8 | 22.2 | Yellow, powder |
| 6 | SR-2045 | 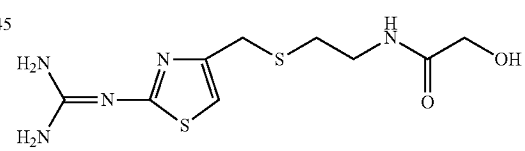 | 289 | 35.2 | 64.8 | Yellow, powder |
| 7 | SR-2203 | 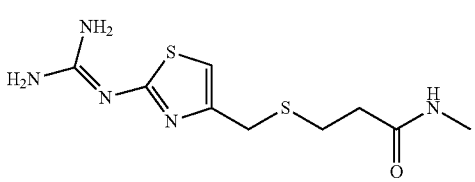 [SMILES: CNC(=O)CCSCc1csc(N=C(N)N)n1] | 273 | 83.7 | 16.3 | Yellow, powder |
| 8 | SR-2225 | 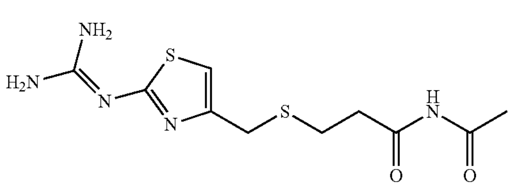 [SMILES: CC(=O)NC(=O)CCSCc1csc(N=C(N)N)n1] | 301 | 69.6 | 30.4 | White, oil |

TABLE 3-3

| # | ID | Structure | MW (Integer Mass) | Histamine Incorporation Rate to Control (%) | OCT3 Inhibition Rate (%) | Property |
|---|----|-----------|-------------------|---------------------------------------------|--------------------------|----------|
| 9 | SR-2226 | 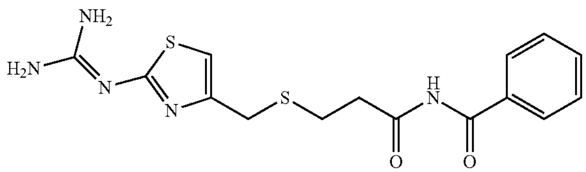 [SMILES: NC(N)=Nc1nc(CSCCC(=O)NC(=O)c2ccccc2)cs1] | 353 | 78.2 | 21.8 | White, powder |
| 10 | SR-2044 | 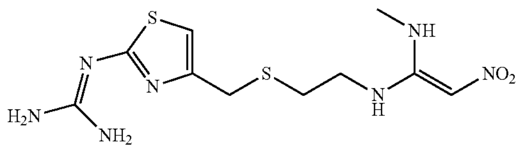 [SMILES: CN/C(=C\[N+](=O)[O-])NCCSCc1csc(N=C(N)N)n1] | 331 | 92.1 | 7.9 | White, powder |
| 11 | SR-2076 | 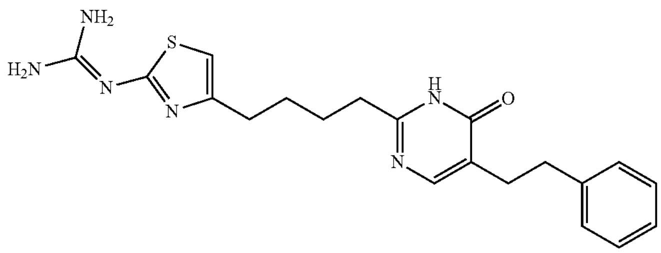 [SMILES: NC(N)=Nc1nc(CCCCc2ncc(CCc3ccccc3)c(=O)[nH]2)cs1] | 410 | 11.8 | 88.2 | White, powder |
| 12 | SR-2073 | 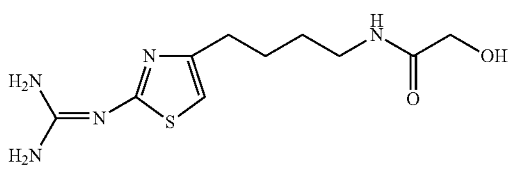 [SMILES: NC(N)=Nc1nc(CCCCNC(=O)CO)cs1] | 271 | 52.9 | 47.1 | Yellow, powder |

TABLE 3-4

| # | ID | Structure | MW (Integer Mass) | Histamine Incorporation Rate to Control (%) | OCT3 Inhibition Rate (%) | Property |
|---|----|-----------|-------------------|---------------------------------------------|--------------------------|----------|
| 13 | SR-2068 | 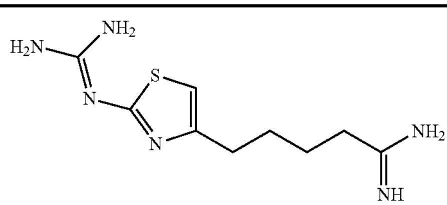 | 240 | 71.5 | 28.5 | Yellow, powder |
| 14 | SR-2204 | 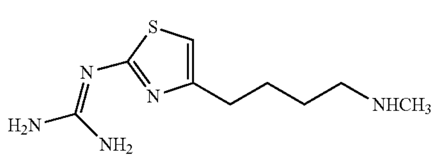 [SMILES: CNCCCCc1csc(N=C(N)N)n1] | 227 | 96.6 | 3.4 | White, powder |
| 15 | SR-2069 | 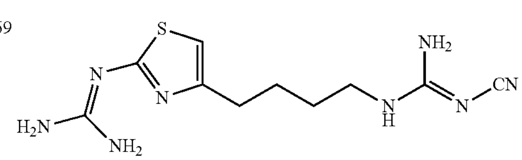 | 280 | 48.6 | 51.4 | Yellow, liquid |

TABLE 3-4-continued

| # | ID | Structure | MW (Integer Mass) | Histamine Incorporation Rate to Control (%) | OCT3 Inhibition Rate (%) | Property |
|---|----|-----------|-------------------|---------------------------------------------|--------------------------|----------|
| 16 | SR-2071 | 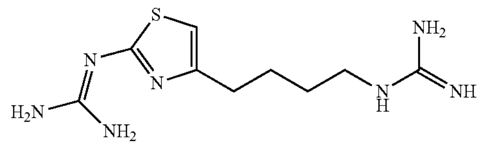 [SMILES: N=C(N)NCCCCc1csc(N=C(N)N)n1] | 255 | 73.0 | 27.0 | White, powder |

TABLE 3-5

| # | ID | Structure | MW (Integer Mass) | Histamine Incorporation Rate to Control (%) | OCT3 Inhibition Rate (%) | Property |
|---|----|-----------|-------------------|---------------------------------------------|--------------------------|----------|
| 17 | SR-2072 | 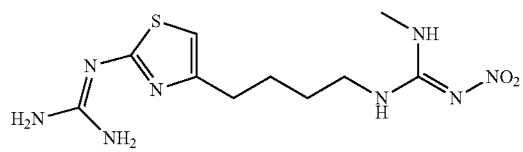 [SMILES: CN/C(=N\[N+](=O)[O-])NCCCCc1csc(N=C(N)N)n1] | 314 | 84.1 | 15.9 | Yellow, powder |
| 18 | SR-2075 | 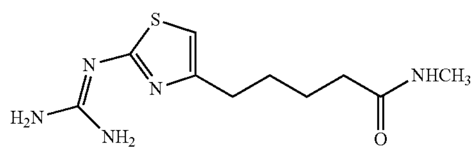 [SMILES: CNC(=O)CCCCc1csc(N=C(N)N)n1] | 255 | 76.1 | 23.9 | White, powder |
| 19 | SR-2065 | 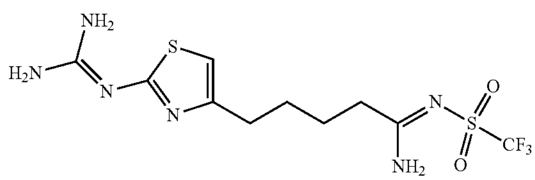 [SMILES: NC(N)=Nc1nc(CCCC/C(N)=N/S(=O)(=O)C(F)(F)F)cs1] | 372 | 41.5 | 58.5 | Yellow, oil |
| 20 | SR-2066 | 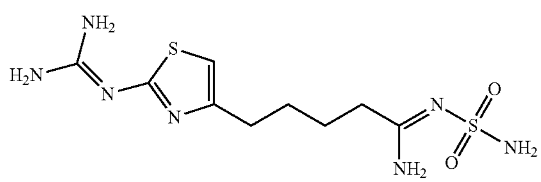 [SMILES: NC(N)=Nc1nc(CCCC/C(N)=N/S(N)(=O)=O)cs1] | 319 | 58.1 | 41.9 | White, powder |

TABLE 3-6

| # | ID | Structure | MW (Integer Mass) | Histamine Incorporation Rate to Control (%) | OCT3 Inhibition Rate (%) | Property |
|---|----|-----------|-------------------|---------------------------------------------|--------------------------|----------|
| 21 | SR-3136 | 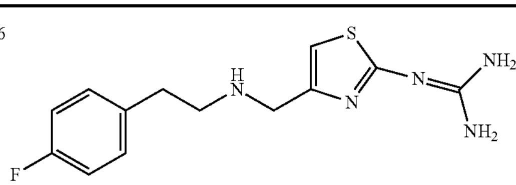 | 293 | 71.4 | 28.6 | White, powder |

TABLE 3-6-continued

| # | ID | Structure | MW (Integer Mass) | Histamine Incorporation Rate to Control (%) | OCT3 Inhibition Rate (%) | Property |
|---|---|---|---|---|---|---|
| 22 | SR-3131 | 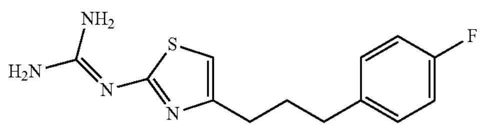 [SMILES: NC(N)=Nc1nc(CCCc2ccc(F)cc2)cs1] | 278 | 77.7 | 22.3 | Yellow, oil |
| 23 | SR-3129 | 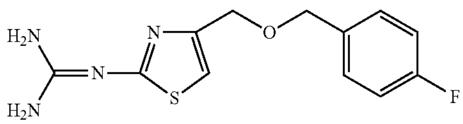 [SMILES: NC(N)=Nc1nc(COCc2ccc(F)cc2)cs1] | 280 | 79.4 | 20.6 | White, powder |
| 24 | SR-3123 | 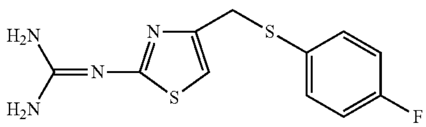 [SMILES: NC(N)=Nc1nc(CSc2ccc(F)cc2)cs1] | 282 | 52.8 | 47.2 | Yellow, powder |

TABLE 3-7

| # | ID | Structure | MW (Integer Mass) | Histamine Incorporation Rate to Control (%) | OCT3 Inhibition Rate (%) | Property |
|---|---|---|---|---|---|---|
| 25 | SR-3154 | 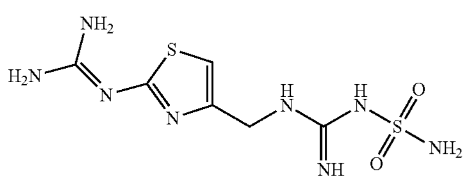 [SMILES: N=C(NCc1csc(N=C(N)N)n1)NS(N)(=O)=O] | 292 | 111.5 | −11.5 | Yellow, solid |
| 26 | SR-3155 | 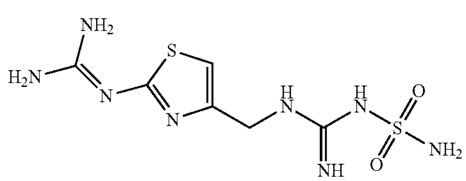 [SMILES: N=C(NCc1csc(N=C(N)N)n1)NS(N)(=O)=O] | 309 | 110.3 | −10.3 | White, solid |
| 27 | SR-3159 | 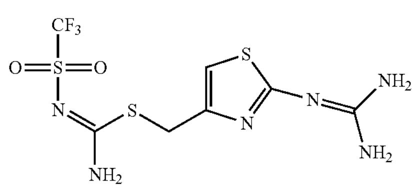 [SMILES: NC(N)=Nc1nc(CS/C(N)=N\S(=O)(=O)C(F)(F)F)cs1] | 362 | 93.8 | 6.2 | White, powder |
| 28 | SR-2232 | 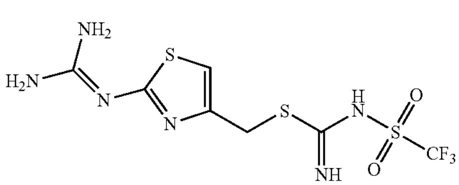 [SMILES: N=C(NS(=O)(=O)C(F)(F)F)SCc1csc(N=C(N)N)n1] | 345 | 87.5 | 12.5 | Yellow, solid |

TABLE 3-8
| # | ID | Structure | MW (Integer Mass) | Histamine Incorporation Rate to Control (%) | OCT3 Inhibition Rate (%) | Property |
|---|---|---|---|---|---|---|
| 29 | SR-2236 | 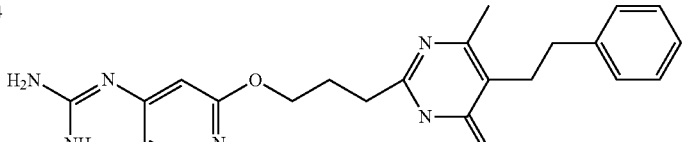 | 213 | 101.4 | −1.4 | White, solid |
| 30 | SR-2023 | 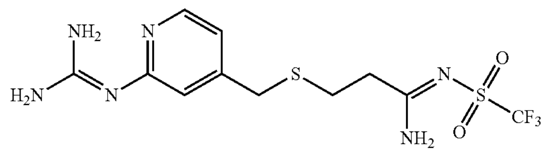 [SMILES: NC(N)=Nc1cc(CSCC/C(N)=N/S(=O)(=O)C(F)(F)F)ccn1] | 384 | 15.0 | 85.0 | Yellow, oil |
| 31 | SR-2219 | 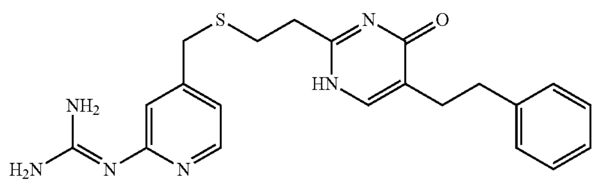 [SMILES: NC(N)=Nc1cc(CSCCc2nc(=O)c(CCc3ccccc3)c[nH]2)ccn1] | 422 | 22.6 | 77.4 | Yellow, powder |
| 32 | SR-2229 | 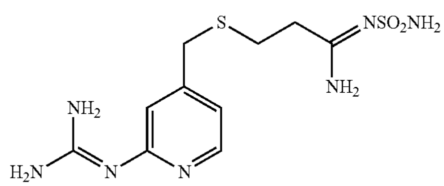 | 331 | 55.8 | 44.2 | White, powder |
TABLE 3-9
| # | ID | Structure | MW (Integer Mass) | Histamine Incorporation Rate to Control (%) | OCT3 Inhibition Rate (%) | Property |
|---|---|---|---|---|---|---|
| 33 | SR-2064 | 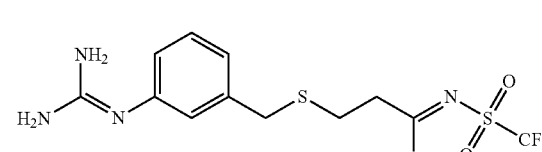 | 406 | 82.5 | 17.5 | Yellow, oil |
| 34 | SR-2020 | 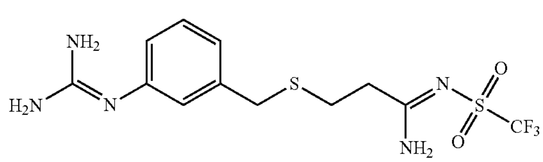 [SMILES: NC(N)=Nc1cccc(CSCC/C(N)=N/S(=O)(=O)C(F)(F)F)c1] | 383 | 74.6 | 25.4 | Colorless oil |
| 35 | SR-2208 | 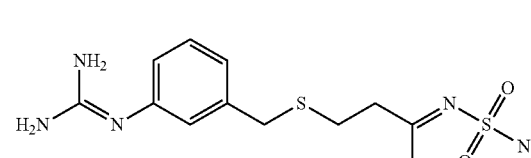 | 330 | 96.5 | 3.5 | Yellow, solid |

TABLE 3-9-continued

| # | ID | Structure | MW (Integer Mass) | Histamine Incorporation Rate to Control (%) | OCT3 Inhibition Rate (%) | Property |
|---|---|---|---|---|---|---|
| 36 | SR-2022 | 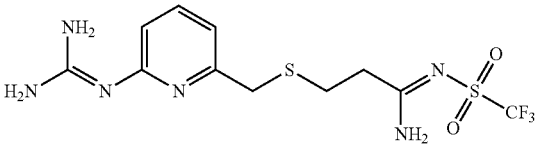 | 384 | 21.0 | 79.0 | Yellow, oil |

TABLE 3-10

| # | ID | Structure | MW (Integer Mass) | Histamine Incorporation Rate to Control (%) | OCT3 Inhibition Rate (%) | Property |
|---|---|---|---|---|---|---|
| 37 | SR-2036 | 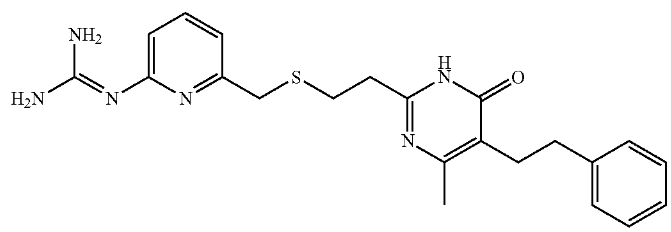 [SMILES: Cc1nc(CCSCc2cccc(N=C(N)N)n2)[nH]c(=O)c1CCc1ccccc1] | 422 | 15.4 | 84.6 | White, powder |
| 38 | SR-2230 | 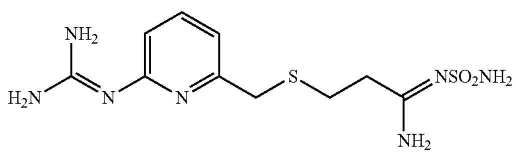 | 331 | 41.4 | 58.6 | White, powder |
| 39 | SR-3209 | 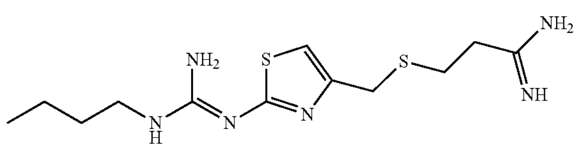 [SMILES: CCCCN/C(N)=N/c1nc(CSCCC(=N)N)cs1] | 314 | 57.0 | 43.0 | Yellow, powder |
| 40 | SR-2213 | 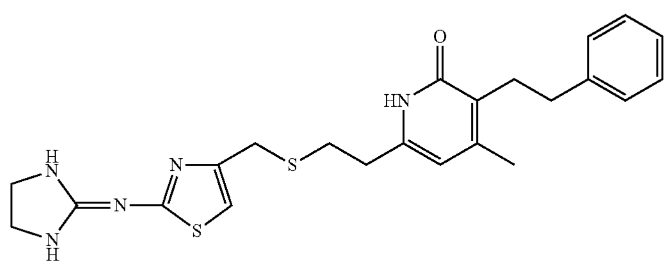 [SMILES: Cc1cc(CCSCc2csc(N=C3NCCN3)n2)[nH]c(=O)c1CCc1ccccc1] | 454 | 54.2 | 45.8 | Yellow, solid |

TABLE 3-11

| # | ID | Structure | MW (Integer Mass) | Histamine Incorporation Rate to Control (%) | OCT3 Inhibition Rate (%) | Property |
|---|---|---|---|---|---|---|
| 41 | SR-3208 | 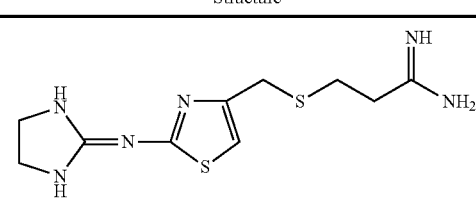 | 284 | 91.3 | 8.7 | White, powder |

TABLE 3-11-continued
| # | ID | Structure | MW (Integer Mass) | Histamine Incorporation Rate to Control (%) | OCT3 Inhibition Rate (%) | Property |
|---|---|---|---|---|---|---|
| 42 | SR-2205 | 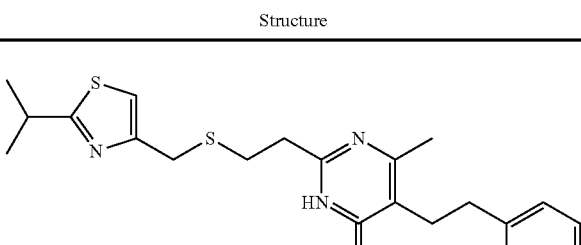 | 413 | 76.8 | 23.2 | Yellow, powder |
| 43 | SR-3021 | 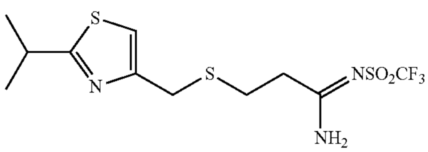 | 375 | 104.0 | −4.0 | Yellow, oil |
| 44 | SR-2207 | 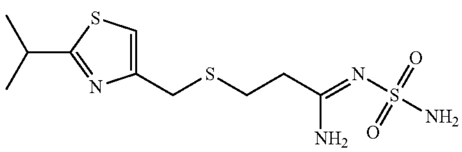 [SMILES: CC(C)c1nc(CSCC/C(N)=N/S(N)(=O)=O)cs1] | 322 | 93.3 | 6.7 | Yellow, oil |
TABLE 3-12
| # | ID | Structure | MW (Integer Mass) | Histamine Incorporation Rate to Control (%) | OCT3 Inhibition Rate (%) | Property |
|---|---|---|---|---|---|---|
| 45 | SR-2011 | 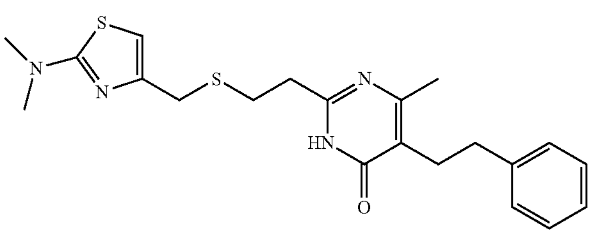 [SMILES: Cc1nc(CCSCc2csc(N(C)C)n2)[nH]c(=O)c1CCc1ccccc1] | 415 | 62.1 | 37.9 | White, powder |
| 46 | SR-2005 | 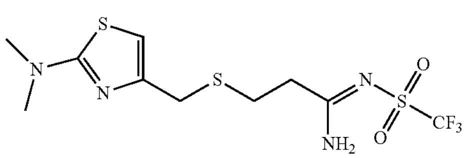 [SMILES: CN(C)c1nc(CSCC/C(N)=N/S(=O)(=O)C(F)(F)F)cs1] | 376 | 107.8 | −7.8 | Yellow, liquid |
| 47 | SR-2208 | 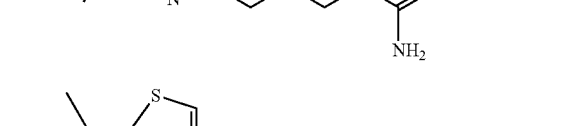 | 323 | 96.5 | 3.5 | Yellow, oil |

TABLE 3-12-continued

| # | ID | Structure | MW (Integer Mass) | Histamine Incorporation Rate to Control (%) | OCT3 Inhibition Rate (%) | Property |
|---|---|---|---|---|---|---|
| 48 | SR-3003 | 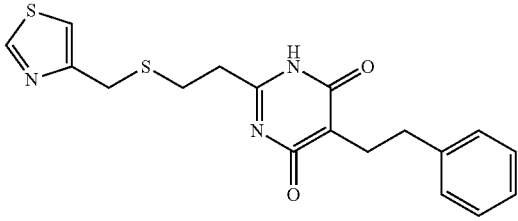 | 371 | 59.4 | 40.6 | White, powder |

TABLE 3-13

| # | ID | Structure | MW (Integer Mass) | Histamine Incorporation Rate to Control (%) | OCT3 Inhibition Rate (%) | Property |
|---|---|---|---|---|---|---|
| 49 | SR-3002 | 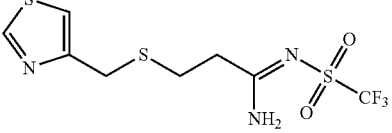 | 333 | 100.2 | −0.2 | Yellow, oil |
| 50 | SR-3001 | 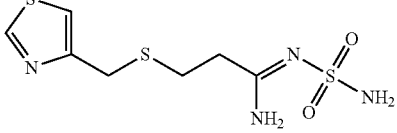 | 280 | 114.7 | −14.7 | Yellow, oil |
| 51 | SR-2239 | 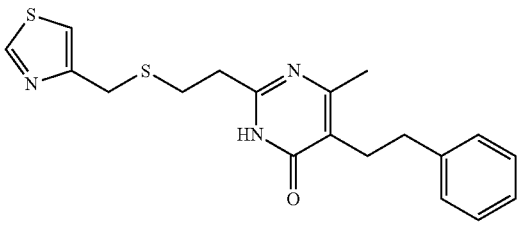 [SMILES: Cc1nc(CCSCc2cscn2)[nH]c(=O)c1CCc1ccccc1] | 385 | 66.8 | 33.2 | White, solid |
| 52 | SR-2238 | 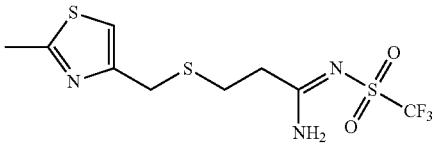 [SMILES: Cc1nc(CSCC/C(N)=N/S(=O)(=O)C(F)(F)F)cs1] | 347 | 107.4 | −7.4 | Yellow, solid |

TABLE 3-14

| # | ID | Structure | MW (Integer Mass) | Histamine Incorporation Rate to Control (%) | OCT3 Inhibition Rate (%) | Property |
|---|---|---|---|---|---|---|
| 53 | SR-2228 | 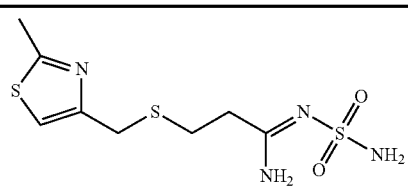 | 294 | 82.4 | 17.6 | White, powder |

TABLE 3-14-continued

| # | ID | Structure | MW (Integer Mass) | Histamine Incorporation Rate to Control (%) | OCT3 Inhibition Rate (%) | Property |
|---|---|---|---|---|---|---|
| 54 | SR-3012 | 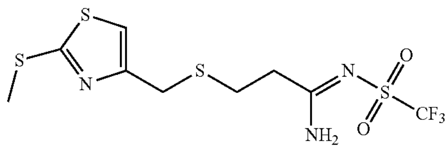 [SMILES: CSc1nc(CSCC/C(N)=N/S(=O)(=O)C(F)(F)F)cs1] | 379 | 108.1 | −8.1 | Yellow, oil |
| 55 | SR-2227 | 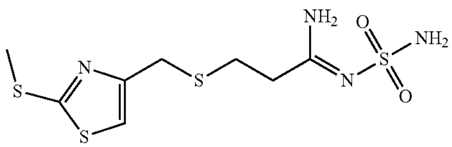 [SMILES: CSc1nc(CSCC/C(N)=N/S(N)(=O)=O)cs1] | 326 | 86.2 | 13.8 | White, powder |
| 56 | SR-2233 | 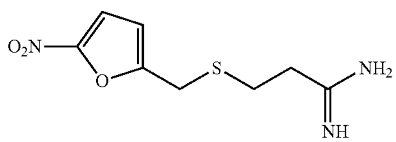 [SMILES: N=C(N)CCSCc1ccc([N+](=O)[O-])o1] | 229 | 95.3 | 4.7 | Red, solid |

TABLE 3-15

| # | ID | Structure | MW (Integer Mass) | Histamine Incorporation Rate to Control (%) | OCT3 Inhibition Rate (%) | Property |
|---|---|---|---|---|---|---|
| 57 | SR-2234 | 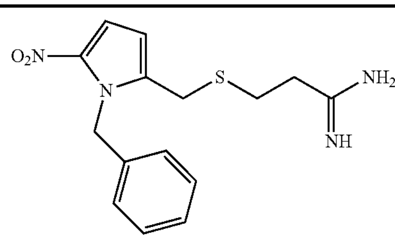 | 318 | 49.8 | 50.2 | Yellow, solid |
| 58 | SR-2235 | 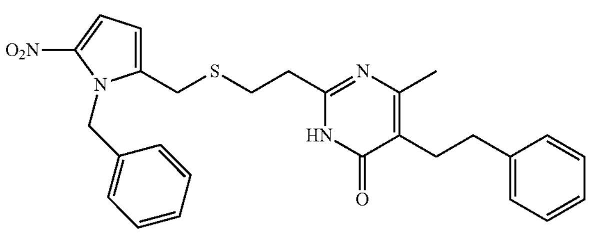 [SMILES: Cc1nc(CCSCc2ccc([N+](=O)[O-])n2Cc2ccccc2)[nH]c(=O)c1CCc1ccccc1] | 488 | 91.3 | 8.7 | Red, solid |
| 59 | SR-2240 | 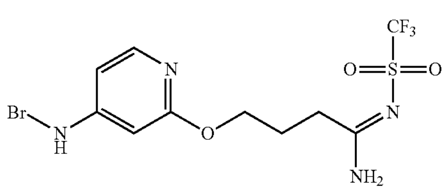 [SMILES: N/C(CCCOc1cc(NBr)ccn1)=N/S(=O)(=O)C(F)(F)F] | 406 | 80.9 | 19.1 | Yellow, oil |

Example 57

Example 57 relates to an evaluation method of antidepressant action and anti-depressant-like symptoms. Currently, the forced swimming test developed by Porsolt et al. is the most generally used evaluation method of antidepressant action (Porsolt R D. et al, Arch Int Pharmacodyn. 1977; 229: 327-336). In the forced swimming test, forced swimming is loaded on a mouse or rat as a test animal in a test tank from which the mouse or rat cannot escape. Then, after an escape behavior of the test animal, an akinesis (a state in which the test animal is floating with only its face out over the surface of the water and without moving legs) is confirmed. When the test animal is put in the test tank again after 24 or more hours later, the akinesis is expressed earlier than the first test. Duration of the akinesis within a predetermined time period (generally about 5 minutes) is reproduced relatively accurately.

It is known that existing antidepressants, of which effectiveness have been clinically guaranteed, specifically and significantly reduce the duration of the akinesis induced by the forced swimming test, and it is believed that the existing antidepressants are useful for detecting antidepressant action. Moreover, since this method requires very simple testing operations, this method is widely used in preclinical evaluation of candidates of new antidepressants and analysis of phenotypes of genetically modified animals (Nichiyakurishi, v 130, p 97-104, 2007).

A method as described below is usually used as a test design using the present method. A typical antidepressant (for example, tricyclic antidepressant and the like) as a positive control drug and a buffer solution and the like not containing drugs as a negative control are administered to different bodies of animals respectively, and test conditions of the forced swimming test is set so that "specifically arisen changes in behavior" can be detected. Subsequently, a test substance is administered in accordance with a similar schedule to that of the positive control drug. If induction of changes in behavior is confirmed similar to the administration of the positive control drug, it is possible to conclude that the test substance can be expected to have the antidepressant action as the clinical effect similar to that of the positive control drug (Yutaka Nakagawa, Jissen Koudou Yakurigaku, Kinpoudou, 2010, p 35-42).

Note that consideration is required to obtain stable experimental results by setting experimental conditions always constantly. The experimental conditions include body weight of the mouse, diameter of the cylindrical test tank, depth of water in the test tank and the like. Further, since it is known that expression time of the akinesis changes depending on the water temperature in the test tank, it is required to keep the water temperature constantly (normally at about 24° C.) during the test, and it is effective and general to set the water temperature to a temperature higher than the room temperature by about 1.0 to 1.5° C. (Yutaka Nakagawa, Jissen Koudou Yakurigaku, Kinpoudou, 2010, p 35-42).

It is also known that the akinesis is apparently suppressed even in a state that locomotor activity is facilitated by administration of central stimulant. Accordingly, it is required to confirm that the locomotor activity of the test animal is not changed by not only suppression of the akinesis in the forced swimming but also administration of antidepressant candidate, in order to confirm antidepressant activity certainly (Nichiyakurishi, v 130, p 97-104, 2007).

Example 58

Example 58 relates to confirmation of an antidepressant effect of OCT3 inhibitor and a combined effect of OCT3 inhibitor and antidepressant imipramine.

The antidepressant action of OCT3 and the combined effect of OCT3 inhibitor and antidepressant imipramine can be confirmed as disclosed in the prior art document (Kitaichi et al, Neurosci Lett. 2005 Jul. 1-8; 382(1-2): 195-200). Specifically, a test is performed as follows.

Male ddY-strain mice (Japan SLC, Inc.) having body weights of 28 to 33 g are used for an experiment. Note that the ddY-strain mice are outbred, have high reproductive ability, and favorably develop, and the name of "ddY-strain mouse" is a representative strain name of laboratory mice widely used for various experimental works including drug effect test, pharmacological test, toxicity test and the like. After obtaining the mice, the mice are raised in a room having controlled temperature (22 to 24° C.), humidity (50 to 60%), and lighting (switched on from 8 a.m. to 8 p.m.) for three days or more. In the first forced swimming test, all of the laboratory mice are made to swim in a glass cylinder (diameter 15.5 cm, depth 17 cm, depth of water 12 cm, temperature of water 25° C.) for 300 seconds, the akinesis time are measured, and the mice are divided into experimental groups (OCT3 inhibitor administration group, positive control group, and negative control group) so that average values of these groups are almost identical. A mouse, of which expressed akinesis time is different from the average value by 60 seconds or more (longer case and shorter case), is removed from the experiment. In addition, in order to avoid an influence of a pheromone and the like of a mouse used for the experiment on subsequent mice, the water in the test tank is replaced for each mouse. With respect to the OCT3 inhibitor administration group, next day of the swimming, OCT3 inhibitor dissolved in physiological buffer (140 mM NaCl, 3.0 mM KCl, 1.5 mM $NaH_2PO_4$, 1.2 mM $MgCl_2$, 1.2 mM $CaCl_2$, pH7.4) is continuously injected into the third ventricle by an osmotic pump, in accordance with a method previously reported (J. Chem. Neuroanat. 2000, 20:375-87). After one week from the injection, the mice are made to swim in the cylinder again for 300 seconds, and the akinesis time is measured for each of the mice. With respect to the positive control group, antidepressant imipramine dissolved in saline (three types having final concentrations of 4, 8, and 16 mg/kg are prepared) is administered into abdominal cavity of each mouse (drugs having different concentrations are administered to groups included in the positive group respectively) 30 minutes before the start of the second forced swimming test. With respect to the negative control group, only physiological buffer instead of the OCT3 inhibitor is continuously injected into the third ventricle in accordance with an administration method and an experimental schedule similar to those of the OCT3 inhibitor administration group, and the forced swimming test is performed.

In the forced swimming test, results similar to those disclosed in the prior art document (Kitaichi. et al, Neurosci Lett. 2005 Jul. 1-8; 382(1-2): 195-200) are expected. Namely, in the negative control group, it is expected that the depression-like symptoms are induced and the akinesis state is expressed for most of the 300 seconds of swimming (average of the akinesis time is about 200 seconds). With respect to the mice to which sufficient OCT3 inhibitor for $IC_{50}$ concentration is continuously injected (0.25 μl/hr), significant shortening of the akinesis time is expected (average of the akinesis time is about 70 seconds). In a case of administering low dose of antidepressant imipramine (4 mg/kg) or low dose of OCT3 inhibitor (0.25 μl/hr) independently, it is estimated that the akinesis time in the forced swimming test has no difference as compared with that of the negative control group (each average of the akinesis time is about 200 seconds). However, in a case of using antidepressant imipramine and OCT3 inhibitor simultaneously, significant shortning of the akinesis time as compared with that of the negative control group is expected (average of the akinesis time is about 100 seconds). If the above results are obtained, then the antidepressant action of OCT3 inhibitor is confirmed and the combined effect of OCT3 inhibitor and antidepressant imipramine can be confirmed.

Example 59

Confirmation of change of locomotor activity before and after administration of OCT3 inhibitor In order to remove possibility that "the locomotor activity is facilitated and the akinesis is apparently suppressed (no antidepressant action) by administration of OCT3 inhibitor", the locomotor activity before and after administration of OCT3 inhibitor is determined in a manner similar to that disclosed in the prior art document (Kitaichi. et al, Neurosci Lett. 2005 Jul. 1-8; 382(1-2): 195-200).

Male ddY-strain mice are used for an experiment. The mice raised for three days or more from a purchase are divided into two groups, and OCT3 inhibitor is continuously injected into the third ventricle of each mouse included in one group by an osmotic pump, based on a method previously reported (J. Chem. Neuroanat. 2000, 20:375-87). Sham operation is performed for each mouse included in another group and physiological buffer instead of the OCT3 inhibitor is injected into the third ventricle as a negative control. After one week from the injection, the mice are put in a plastic cage (30 cm×35 cm×17 cm), and determination of locomotor activity is performed before and after administration of stimulant methamphetamine (1 mg/kg) into a vein of each of the mice. The locomotor activities are automatically counted by an infrared sensor (Melquest Ltd, SCANET SV-10) attached to a wall surface. From 120 minutes before to just before the administration of stimulant methamphetamine, the locomotor activities of the negative control group and the OCT3 inhibitor administration group are determined, and from immediately after to 180 minutes after the administration of methamphetamine, stimulant-induced locomotor activities of each group are determined. After the determinations, significance test is performed by using Scheffe method in relation to the number of count of the locomotor activities, and judgement is made as to whether the locomotor activities are statistically significantly (p value is less than 0.05) changed.

In the locomotor activity test, results similar to those disclosed in the prior art document (Kitaichi. et al, Neurosci Lett. 2005 Jul. 1-8; 382(1-2): 195-200) are expected. Namely, before administration of stimulant methamphetamine, it is estimated that the number of count of the locomotor activities in the negative control group is the same extent as that in the OCT3 inhibitor administration group, and after administration of stimulant methamphetamine, it is estimated that the number of count in OCT3 inhibitor non-administration group is about twice as much as that in the negative group and the number of count in OCT3 inhibitor administration group is about five times as much as that in the negative group. Then, by performing the significance test in relation to the number of count, it is expected that no significant difference between the negative control group and the OCT3 inhibitor administration group is confirmed before administration of stimulant methamphetamine, namely no change of the locomotor activities due to administration of OCT3 inhibitor is confirmed. Further, since it is expected that the locomotor activities after administration of stimulant methamphetamine are statistically significantly facilitated as compared with before administration, it is expected that the test system is confirmed to function effectively. If the above results are obtained, then no locomotor activity of OCT3 inhibitor is confirmed and shortening of the akinesis time confirmed by the forced swimming test is the basis indicating the antidepressant action.

INDUSTRIAL APPLICABILITY

The present invention can be utilized in the fields of Chemical industry and pharmaceutical industry.

The invention claimed is:

1. A compound represented by the following formula (A), a pharmaceutically acceptable salt thereof, or a pharmaceutically acceptable solvate thereof, $$R^1\text{-}R^2\text{-}R^3\text{-}R^4 \quad (A)$$

wherein, $R^1$ represents a group represented by $(H_2N)_2C=N-$ $-R^2-$ represents a group represented by

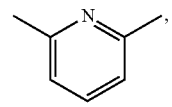

$-R^3-$ represents
a group represented by $-R^{36}\text{-}R^{37}\text{-}R^{38}-$, wherein
$-R^{36}-$ represents a methylene group,
$-R^{37}-$ represents $-O-$ or $-S-$, and
$-R^{38}-$ represents an ethylene group, and
$-R^4$ represents
a group represented by $-R^{41}\text{-}R^{42}$,
a group represented by $-C(NH_2)=NR^{43}$,
a group represented by $-NHC(NH(R^{46}))=R^{44}R^{45}$, or
a group represented by $-NHR^{48}$, wherein
$-R^{41}-$ represents a group represented by

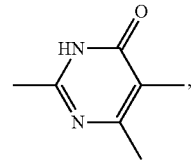

$-R^{42}-$ represents a $C_{7\text{-}10}$ aralkyl group,
$R^{43}$ represents $-SO_2-R^{431}$, wherein
$R^{431}$ represents an amino group or a trifluoromethyl group,
$R^{44}$ represents a nitrogen atom,
$R^{45}$ represents a cyano group,
$R^{46}$ represents a hydrogen atom, and
$R^{48}$ represents $-CO-CH_2-O-H$.

2. A pharmaceutical composition comprising a compound of claim 1 and a pharmaceutically acceptable carrier.

* * * * *